US012735444B2

(12) United States Patent
Robillard et al.

(10) Patent No.: US 12,735,444 B2
(45) **Date of Patent: *Sep. 15, 2026**

(54) CHEMICALLY CLEAVABLE GROUP

(71) Applicant: TAGWORKS PHARMACEUTICALS B.V., Eindhoven (NL)

(72) Inventors: Marc Stefan Robillard, Eindhoven (NL); Ronny Mathieu Versteegen, Eindhoven (NL); Wolter Ten Hoeve, Eindhoven (NL); Raffaella Rossin, Eindhoven (NL)

(73) Assignee: Tagworks Pharmaceuticals B.V., Nijmegen (NL)

( * ) Notice: Subject to any disclaimer, the term of this patent is extended or adjusted under 35 U.S.C. 154(b) by 335 days.

This patent is subject to a terminal disclaimer.

(21) Appl. No.: 17/023,343

(22) Filed: Sep. 16, 2020

(65) Prior Publication Data

US 2021/0002320 A1 Jan. 7, 2021

Related U.S. Application Data

(63) Continuation of application No. 14/646,619, filed as application No. PCT/NL2013/050850 on Nov. 22, 2013, now Pat. No. 10,927,139.

(30) Foreign Application Priority Data

Nov. 22, 2012 (EP) .................................... 12193911

(51) Int. Cl.

| | |
|---|---|
| ***C07C 209/62*** | (2006.01) |
| ***A61K 47/54*** | (2017.01) |
| ***A61K 47/60*** | (2017.01) |
| ***A61K 47/68*** | (2017.01) |
| ***B82Y 5/00*** | (2011.01) |
| ***C07C 29/10*** | (2006.01) |
| ***C07C 37/50*** | (2006.01) |
| ***C07C 45/61*** | (2006.01) |
| ***C07C 205/20*** | (2006.01) |
| ***C07C 205/57*** | (2006.01) |
| ***C07H 15/252*** | (2006.01) |
| ***G01N 33/543*** | (2006.01) |
| ***G01N 33/60*** | (2006.01) |

(52) U.S. Cl.

CPC ......... *C07H 15/252* (2013.01); *A61K 47/555* (2017.08); *A61K 47/60* (2017.08); *A61K 47/6897* (2017.08); *B82Y 5/00* (2013.01); *C07C 29/10* (2013.01); *C07C 37/50* (2013.01); *C07C 45/61* (2013.01); *C07C 205/20* (2013.01); *C07C 205/57* (2013.01); *C07C 209/62* (2013.01); *G01N 33/54353* (2013.01); *G01N 33/60* (2013.01)

(58) Field of Classification Search

CPC .. A61K 47/555; A61K 47/60; A61K 47/6897; B82Y 5/00; C07C 29/10; C07C 37/50; C07C 45/61; C07C 205/20; C07C 205/57; C07C 209/62; G01N 33/54353; G01N 33/60

USPC .......................................................... 568/309

See application file for complete search history.

(56) References Cited

U.S. PATENT DOCUMENTS

| | | | |
|---|---|---|---|
| 4,486,414 | A | 12/1984 | Pettit et al. |
| 4,486,444 | A | 12/1984 | Shepard et al. |
| 4,879,278 | A | 11/1989 | Pettit et al. |
| 4,986,988 | A | 1/1991 | Ettit et al. |
| 5,138,036 | A | 8/1992 | Pettit et al. |
| 5,198,560 | A | 3/1993 | Kadow |
| 5,410,024 | A | 4/1995 | Pettit et al. |
| 5,504,191 | A | 4/1996 | Pettit et al. |
| 5,521,284 | A | 5/1996 | Pettit et al. |
| 5,530,097 | A | 6/1996 | Pettit et al. |
| 5,599,902 | A | 2/1997 | Pettit et al. |
| 5,635,483 | A | 6/1997 | Pettit et al. |
| 5,663,149 | A | 9/1997 | Pettit et al. |
| 5,665,860 | A | 9/1997 | Pettit et al. |
| 5,780,588 | A | 7/1998 | Pettit et al. |
| 6,034,065 | A | 3/2000 | Pettit et al. |
| 6,239,104 | B1 | 5/2001 | Pettit et al. |
| 6,323,315 | B1 | 11/2001 | Pettit et al. |
| 7,005,132 | B2 | 2/2006 | Cubicciotti |
| 9,421,274 | B2 | 8/2016 | Robillard et al. |
| 9,427,482 | B2 | 8/2016 | Rossin et al. |
| 9,463,256 | B2 | 10/2016 | Lub et al. |

(Continued)

FOREIGN PATENT DOCUMENTS

| | | | |
|---|---|---|---|
| WO | 2010051530 | A2 | 5/2010 |
| WO | 2010119382 | A1 | 10/2010 |

(Continued)

OTHER PUBLICATIONS

Ajay et al., "Diversity-Oriented Synthesis of cis-3,4-Dihydroxylated Piperidine and Its Higher Saturated and Unsaturated Homologues from d-Ribose and Their Glycosidase-Inhibition Study", SYNLETT, 2016, Vo. 27, No. 19, pp. 2721-2725.

(Continued)

*Primary Examiner* — Ana Z Muresan

(74) *Attorney, Agent, or Firm* — Foley & Lardner LLP

(57) ABSTRACT

Disclosed is the use of the reactive components of the inverse electron-demand Diels Alder reaction for chemical masking and unmasking in vitro. This can be applied in complex chemical reactions and, particularly in the synthesis of biomolecules, e.g. on solid supports. The reactice components are a dienophile, particularly a trans-cyclooctene, and a diene, particularly a tetrazine.

20 Claims, 6 Drawing Sheets

(56) References Cited

U.S. PATENT DOCUMENTS

| | | | |
|---|---|---|---|
| 9,913,921 | B2 | 3/2018 | Robillard et al. |
| 9,931,408 | B2 | 4/2018 | Robillard et al. |
| 10,004,810 | B2 | 6/2018 | Robillard et al. |
| 10,376,594 | B2 | 8/2019 | Robillard et al. |
| 10,927,139 | B2 | 2/2021 | Robillard et al. |
| 10,967,069 | B2 | 4/2021 | Robillard et al. |
| 2009/0023916 | A1 | 1/2009 | Fox et al. |
| 2015/0297741 | A1 | 10/2015 | Robillard |

FOREIGN PATENT DOCUMENTS

| | | | |
|---|---|---|---|
| WO | 2010119389 | A2 | 10/2010 |
| WO | 2012012612 | A2 | 1/2012 |
| WO | 2012049624 | A1 | 4/2012 |
| WO | 2012085789 | A1 | 6/2012 |
| WO | 2012/156919 | | 11/2012 |
| WO | 2012156918 | A1 | 11/2012 |
| WO | 2014/065860 | | 5/2014 |
| WO | 2014/081301 | | 5/2014 |
| WO | 2014/081303 | | 5/2014 |
| WO | 2016/025480 | | 2/2016 |
| WO | 2018/004338 | | 1/2018 |

OTHER PUBLICATIONS

Alley, S; Okeley N; Senter, PD; et al. "Antibody-drug conjugates: targeted drug delivery for cancer." Current Opinion in Chemical Biology, (2010), 14:529-537.

Banker, G.S. et al., "B. Prodrugs", Modern Pharmaceutics, 3ed, Marcel Dekker, New York, 1996, p. 451 and 596.

Haun, Jered B. et al, "Bioorthogonal Chemistry Amplifies Nanoparticle Binding and Enhances the Sensitivity of Cell Detection", Nature Nanotechnology, vol. 5, Sep. 2010, pp. 660-665.

International Search Report and Written Opinion for Corresponding International Application No. PCT/NL2019/050271 (10 Pages) ( Oct. 23, 2019).

International Search Report and Written Opinion for Corresponding International Application No. PCT/NL2019/050272 (9 Pages) (Oct. 9, 2019).

International Search Report and Written Opinion for Corresponding International Application No. PCT/NL2020/050386 (17 Pages) (Nov. 5, 2020).

International Search Report and Written Opinion for Corresponding International Application No. PCT/NL2020/050387 (9 Pages) (Aug. 25, 2020).

International Search Report and Written Opinion for Corresponding International Application No. PCT/NL2020/050388 (9 Pages) (Aug. 19, 2020).

Rossin et al., "Highly Reactive trans-Cyclooctene Tags with Improved Stability for Diels-Alder Chemistry in Living Systems", Bioconjugate Chemistry, 2013, vol. 24, No. 7, pp. 1210-1217.

Rossin et al., "Triggered Drug Release from an Antibody-Drug Conjugate Using Fast "Click-to-Release" Chemistry In Mice", Bioconjugate Chemistry, 2016, vol. 27, No. 7, pp. 1697-1706.

Rossin, R. et al. "In vivo chemistry for pretargeted tumor imaging in live mice". Angewandte Chemie International Edition, (2010), 49, 3375-3378.

Thalhammer, F. et al. Reaktivitat Einfacher Offenkettiger Und Cyclischer Dienophile Bei Diels-alder-reaktionen mil inversem elektronenbedarf. Tetrahedron Letters (1990), 31 (47), 6851-6854. (See English abstract.).

Van Brakel, R. et al. "A doxorubicin prodrug activated by the staudinger reaction". Bioconjugate Chem. (2008), 19, 714-718.

White et al., "Synthesis of Polyhydroxylated Pyrrolizidine Alkaloids of the Alexine Family by Tandem Ring-Closing Metathesis-Transannular Cyclization. (+)-Australine", Journal of Organic Chemistry, 2000, vol. 65, No. 26, pp. 9129-9142.

Whitham, G.H. et al. "trans-Cycloalkenes. Part I. (1 RS,2RS)-Irans-Cyclo-oct-2-en-1-ol". Journal Chem. Society, (1971), 883-886.

Whitham, G.H. et al. "trans-Cycloalkenes. Part II. Application of the Dioxolan Olefin Synthesis to the Stereospecific Formation of trans-Cyclo-octene Derivatives. (1 SR,2RS)-Irans-Cyclo-oct-2-en-1-ol". Journal Chem. Society, (1971), 886-890.

Whitham, G.H. et al. "trans-Cycloalkenes. Part III. Stereochemistry and mechanism of some reactions of diastereoisomeric 3-substituted trans-cyclo-octenes". Journal Chem. Society, (1971), 891-896.

Wiessler, Manfred; et al. "Extension of the PNA world by functionalized PNA monomers eligible candidates for Inverse Diels Alder Click Chemistry", Int. Journal of Medical Science, Jun. 27, 2010, 7(4):213-223.

Xia,Y. et al. "Shape-Controlled Synthesis of Metal Nanocrystals: Simple Chemistry Meets Complex Physics?", Angewandte Chemie International Edition (2009), 48, 1-5.

U.S. Appl. No. 13/877,725, filed Apr. 4, 2013, U.S. Pat. No. 9,463,256, Oct. 11, 2016, Pretargeting Kit, Method and Agents Used Therein.

U.S. Appl. No. 13/994,783, filed Jun. 17, 2013, U.S. Pat. No. 9,427,482, Aug. 30, 2016, Agents for Clearing Biomolecules From Circulation.

U.S. Appl. No. 14/115,455, filed Nov. 4, 2013, U.S. Pat. No. 9,913,921, Mar. 13, 2018, Pretargeting Kit for Imaging or Therapy Comprising a Trans-Cyclooctene Dienophile and a Diene.

U.S. Appl. No. 14/117,246, filed Nov. 12, 2013, U.S. Pat. No. 9,421,274, Aug. 23, 2016, Bio-Orthogonal Drug Activation.

U.S. Appl. No. 15/233,283, filed Nov. 23, 2016, U.S. Pat. No. 10,004,810, Jun. 26, 2018, Bio-Orthogonal Drug Activation.

U.S. Appl. No. 14/117,655, filed Nov. 15, 2013, U.S. Pat. No. 9,931,408, Apr. 3, 2018, Bio-Orthogonal Drug Activation.

U.S. Appl. No. 14/983,858, filed Dec. 30, 2015, U.S. Pat. No. 10,376,594, Aug. 13, 2019, Bio-Orthogonal Drug Activation.

U.S. Appl. No. 16/512,038, filed Jul. 15, 2019, U.S. Pat. No. 10,967,069, Apr. 6, 2021, Bio-Orthogonal Drug Activation.

U.S. Appl. No. 17/169,217, filed Feb. 5, 2021, Bio-Orthogonal Drug Activation.

U.S. Appl. No. 14/646,619, filed May 21, 2015, U.S. Pat. No. 10,927,139, Feb. 23, 2021, Chemically Cleavable Group.

U.S. Appl. No. 17/052,925, filed Nov. 4, 2020, Compounds Comprising a Linker for Increasing Transcyclooctene Stability.

U.S. Appl. No. 17/052,928, filed Nov. 4, 2020, Tetraines for High Click Conjugation Yield in Vivo and High Click Release Yield.

U.S. Appl. No. 17/619,791 filed Dec. 16, 2021, Compunds for Fast and Efficient Click Release.

U.S. Appl. No. 17/619,794, filed Dec. 16, 2021, Tetrazines for High Click Release Speed and Yield.

U.S. Appl. No. 17/619,796, filed Dec. 16, 2021, Agents for Cleaving Labels from Biomolecules in Vivo.

Senter, P .D. et al. "Antibody-drug conjugates: targeted drug delivery for cancer." Current Opinion in Chemical Biology, (2010), 14:529-537.

Klopman, G. et al. "Computer automated log P calculations based on an extended group contribution approach". Joumal Chem. Inf. Comput. Sci. (1994), 34, 752-781.

Thakur, A. et al. "Cancer therapy with bispecific antibodies: Clinical experience". Current Opinion in Molecular Therapeutics, (2010), 12(3), 340-349.

Thalhammer, F. et al. Reaktivitat Einfacher Offenkettiger Und Cyclischer Dienophile Bei Diels-alder-reaktionen mil inversem elektronenbedarf. Tetrahedron Letters (1990), 31 (47), 6851-6854.

Wijnen, J.W. et al. "Substitute effects on an inverse electron demand hetero diels-alder reaction in aqueous solution and organic solvents: cycloaddition of substituted styrenes to Di(2-pyridyl)-1,2,4,5-tetrazine". Journal of Organic Chemistry, (1996), 61, 2001-2005.

Blackman, M.L. et al. "The tetrazine ligation: fast bioconjugation based on inverse-electron-demand Diels-Alder reactivity". Journal of American Chemical Society, (2008), 130(41), 13518-13519.

International Preliminary Report on Patentability for International Application No. PCT/IB2012/052446, Nov. 19, 2013, 10 Pages.

Devaraj, N.K. et al. "Fast and sensitive pretargeted labeling of cancer cells via tetrazine/trans-cyclooctene cycloaddition". Angewandte Chemie International Edition, (2009), 48(38): 7013-1016.

Xia. et al. Angewandte Chemie International Edition (2009), 48, 1-5.

(56) References Cited

OTHER PUBLICATIONS

Tranoy-Opalinski, I. et al. "Design of self-Immolative linkers for tumour activated prodrug therapy". Anti-Cancer Agents in Medicinal Chemistry, (2008), 8, 618-637.
Greenwald, R.B. et al. "Drug delivery systems employing 1,4-or 1,6-elimination: Poly(ethylene glycol) prodrugs of amine-containing compounds". Journal Med. Chem. (1999), 42, 3657-3667.
Blencowe, C.A. et al. "Self-immolative linkers in polymeric delivery systems". Polymer Chemistry, (2011 ), 2, 773-790.
Cere, V. et al. "Olefin Inversion. Protection of the sulfide function in the stereospecific synthesis of trans-Thiacyclooct-4-ene". Journal of Organic Chemistry, (1980), 45, 261-264.
Prevost, M. et al. "Insertions of silylenes into vinyl epoxides: Diastereoselective synthesis of functionalized, optically active trans-Dioxasilacyclooctenes". Journal of the American Chemical Society, (2009), 131, 14182-14182.
Devaraj, N.K. et al. "Tetrazine-based cycloadditions: Application to Pretargeted live cell imaging",Bioconjugate Chem., (2008), 19(12), 2297-2299.
Geldard, J.F. et al. "The organic chemistry of a new weak field tridentate chelating agent. 3,5-Di(2-pyridyl)-1,2,4-triazole". Journal Organic Chemistry. (1965), 30, 318-319.
Grakauskas, V.A. et al. "Some 3,6-unsymmetrically disubstituted 1,2,4,5-Tetrazines". Journal American Chemical Society, (1958), 80, 3155-3159.
Audebert, P. et al. "Synthesis of new substituted tetrazines: electrochemical and spectroscopic properties". New Journal Chem. (2004), 28, 387-392.
Kaim, W. et al. "The new tetrafunctional (pi) acceptor ligand 3,6-Bis(2'-pyrimidyl)-1,2,4,5-tetrazine(bmtz): Diruthenium complexes of bmtz and of its 1,4-Dihydro form". Z. Naturforsch, 50b, 123-127 (1995).
Choe, Y.H. et al. "Anticancer drug delivery systems: multi-loaded N4-acyl poly(ethylene glycol) prodrugs of ara-C. II. Efficacy in ascites and solid tumors". Journal of Controlled Release, (2002), 79, 55-70.
Haba, K. et al. "Single-triggered trimeric prodrugs". Angewandte Chemie International Edition. (2005), 44, 726-730.
Ingold, C.K. et al. "The Nature of the Alternating effect in carbon chains. Part XXII. An attempt further to define the probable mechanism of orientation in aromatic substitution". Journal Chem. Society. (1927), 2918-2926.
Mohsin, H. et al. "Radiolanthanide-labeled monoclonal antibody CC49 for radioimmunotherapy of cancer: biological comparison of DOTA conjugates and 149Pm, 166Ho, and 177Lu". Bloconjugate Chem. (2006), 17, 485-492.
Thompson, S. et al. "The construction and in vitro testing of photo-activalable cancer targeting folaled anti-CD3 conjugates". Biochemical and Biophysical Research Communications, (2008), 366, 526-531.
Brakel, van, R. et al. "A doxorubicin prodrug activated by the staudinger reaction". Bioconujugate Chem. (2008), 19, 714-718.
Viswanadhan, V.N. et al. "Atomic physicochemical parameters for three dimensional structure directed quantitative structure-activity relationships. 4. Additional parameters for hydrophobic and dispersive interactions and their application for an automated superposition of certain naturally occuring nucleoside antibiotics". Journal Chem. Inf. Comput. Sci. (1989), 29, 163-172.
International Search Report and Written Opinion for International Application No. PCT/IB2012/052446, Oct. 23, 2012, 14 Pages.
Wolff, Manfred E. "Burgers Medicinal Chemistry", 5ed, Part 1 John Wiley & Sons, 1995, pp. 975-977.
Banker, G.S. et al., Modem Pharmaceutices, 3ed Marcel Dekker, New York, 1996, p. 451 and 596.
Atfah, M., "Diels-Alder Reactions of 3,6-Diphenyl-1,2,3,4,5-Tetrazinenad 3,6-Di(2-Pyridyl)-1,2,4,5,-tetrazine with some 1-Morpholinocycloalkenes," J. Heterocyclic Chem, 26, 717 (1989).
Rossin, R. et al., "In Vivo Chemistry for Pretargeted Tumor Imaging in Live Mice," Angew Chem In led 2010, 49.375-3378.
Thomas, J., et al., "Proligands with protease-regulated binding activity identified from cell-displayed prodomain libraries," Protein Science 2009, vol. 18:2053-2059.
International Search Report and Written Opinion for Corresponding International Application No. PCT/NL2013/050850 (9 Pages) (Feb. 11, 2014).

1 +
2 +
3 +
4 ++
5 +++
6 +++
7 ++
8 +++
9 +++
10 ++
11 +++
12 +++
13 +++
14 +++
15 ++
16 ++
17 +++
18 +++

CHEMICALLY CLEAVABLE GROUP

CROSS-REFERENCE TO RELATED APPLICATIONS

This application is a continuation of U.S. application Ser. No. 14/646,619, filed May 21, 2015, which in turn is a 371 of PCT/NL2013/050850, filed Nov. 22, 2013, which claims the benefit of priority from European Patent Application No. 12193911.0, filed Nov. 22, 2012, the contents of each of which are hereby incorporated by reference.

FIELD OF THE INVENTION

The invention pertains to the field of provoked chemical cleavage. Particularly, the invention pertains to providing chemical substances with a functional group cappable of acting as a Trigger for release of an entity attached to said chemical group. This plays a role, e.g., in solid phase synthesis, biomolecule interactions, modification of surfaces (including cell surfaces), and modification of molecules under physiological conditions (e.g., in a cellular environment).

BACKGROUND OF THE INVENTION

The current state of the art in organic chemistry enables the preparation of highly complex molecular structures, by application of a wide toolbox of synthetic transformations. Unfortunately, the vast majority of chemical techniques is executed under strictly defined conditions, requiring toxic solvents, stoichiometric reagents, extreme temperatures, exclusion of moisture or oxygen, and with carefully designed protective group protocols. One of the most difficult challenges in synthetic chemistry remains the ability to have precise control over chemical reactivity and selectivity. These demands are amplified when it is necessary to perform selective reactions in chemically complex environments, such as those found in biology. Unfortunately, only a few chemical transformations are so mild and precise that they can be used to selectively modify biochemical structures, such as proteins or nucleic acids, which typically proceed in water and at near-ambient temperature. Moreover, such biomolecular modification must be highly chemospecific in the sense that only a single functionality of interest is selectively modified in the presence of a plethora of other functional groups. Even more challenging is to apply a chemical reaction on or in living cells or whole organisms. Selective chemical reactions that are orthogonal to the diverse functionality of biological systems are called bioorthogonal reactions and occur between two abiotic groups with exclusive mutual reactivity. Truly bioorthogonal reactions are not yet available as each reaction so far is orthogonal to a subset of the functionalities found in biological systems. Thus, extremely selective and high-yielding bioorthogonal coupling chemistry reactions continue to receive interest.

Examples of such reactions, and with a relatively high degree of bioorthogonality, include the Staudinger ligation [Saxon et al. Science 2000; 287:2007-10], the copper-catalyzed azide acetylene cycloaddition [Hein et al. Pharm Res 2008; 25:2216-30, the strain-promoted cycloaddition reaction between azides and cyclooctyne or oxanorbornadiene derivatives [Debets et al. Acc Chem Res 2011; 44:805-15; van Berkel et al. ChemBioChem 2007; 8:1504-8], and between nitrone and cyclooctyne derivatives [Ning et al. Angew Chem Int Ed 2010; 49:3065-8], and the strain-promoted cycloaddition reaction between tetrazines and trans-cyclooctene derivatives [Blackman et al. J Am Chem Soc 2008; 130:13518-9.].

Bioorthogonal reactions are broadly useful tools with applications that span synthesis, materials science, chemical biology, diagnostics, and medicine. They are generally used in coupling reactions of small molecules, peptides, proteins, oligonucleotides, other types of polymers, glycans, nanoparticles, and on surfaces (e.g., glass slides, gold, resins). Further examples include: compound library synthesis, protein engineering, functional proteomics, activity-based protein profiling, target guided synthesis of enzyme inhibitors, chemical remodeling of cell surfaces, tracking of metabolite analogues, and imaging tagged biomolecules in live cells and animals.

Analogous to selective coupling reactions, chemoselective cleavable linkers and protective groups have widespread application in the manipulation of conjugates and derivatives of: small molecules, polymers, and biomolecules such as peptides, proteins and DNA within the context of chemical synthesis, materials science, chemical biology, diagnostics, and medicine.

For example, linker systems that allow mild cleavage under conditions ideally orthogonal to functionalities present in the biological system at hand have found application in activity-based protein profiling. Protease substrates linked to a biotin tag through a cleavable linker have been used to capture and isolate specific enzymes by the binding of the biotin tag to avidin coated resin or beads. Subsequently the captured complex can then be released under mild conditions by cleavage of the linker instead of having to break the biotin-avidin interaction. Also, chemically cleavable linkers have emerged as powerful tools in solid-phase organic synthesis, especially for the rapid production of highly diverse organic compound libraries created through combinatorial or parallel chemistry methods. Other examples include drug delivery agents for pharmaceuticals applications, as well as various reversible bioconjugates and sophisticated spectroscopic bioprobes for applications in the field of biological analysis.

Examples of linker types include linkers that contain a (reductively or thiol mediated) cleavable disulfide (Finn, F. M., Stehle, C. J., and Hofmann, K. (1985) Biochemistry 24, 1960-1965; Shimkus, M., Levy, J., and Herman, T. (1985) Proc. Natl. Acad. Sci. USA 82, 2593-2597), an acid-sensitive moiety (van der Veken, P., Dirksen, E. H. C., Ruijter, E., Elgersma, R. C., Heck, A. J. R., Rijkers, D. T. S., Slijper, M., and Liskamp, R. M. J. (2005) ChemBioChem 6, 2271-2280), base-sensitive moiety (Ball, H. L., and Mascagni, P. (1997)

J. Pept. Sci. 3, 252-260), nucleophile-sensitive moiety (Lin, W. C., and Morton, T. H. (1991)

J. Org. Chem. 56, 6850-6856), reductive moiety (Verhelst, S. H. L., Fonovic, M., and Bogyo, M. (2007) Angew. Chem. Int. Ed. Engl. 46, 1284-1286). Other examples use an acylhydrazone unit which is cleaved with acylhydrazides, aniline-labile hydrazones (Dirksen, A., Yegneswaran, S., and Dawson, P. E. (2010) Angew. Chem. Int. Ed. 49, 2023-2027), diazobenzene cleavable by dithionite (Verhelst, S. H. L., Fonovic', M., and Bogyo, M. (2007) Angew. Chem. Int. Ed. 46, 1284-1286), and the hydrazine-labile levulinoyl group (Geurink, P. P., Florea, B. I., Li, N., Witte, M. D., Verasdonck, J., Kuo, C. L., Van der Marel, G. A.; Overkleeft., H. S. (2010) Angew. Chem., Int. Ed., 38, 6802-6905).

However, the foregoing examples have a limited orthogonality compared to the relatively highly bioorthogonal coupling reactions listed above (Staudinger ligation, azide-alkyne/cyclooctyne cycloaddition, azide-oxanorbadiene, nitrone-cyclooctyne, and the tetrazines-trans-cyclooctene cycloaddition) and with respect to the wide range of functionalities present in the complex environments encountered in e.g. biological media, biomolecules, or complex materials. For example, cleavage of a disulfide linker in a peptide substrate may also affect a cysteine disulfide functionality elsewhere in the molecule. A pH cleavable linker or protective group may severely limit the pH range at which chemical transformations are conducted on a biomolecule. As a result, the optimal linker or protective group needs to be selected and optimized on a case-by-case basis, if suitable at all.

A wider and more uniform application scope may be achieved for chemoselective linkers and protecting groups if the aforementioned bioorthogonal coupling reactions could be adapted to effect selective release instead of selective conjugation. From this class, only the Staudinger ligation and the parent Staudinger reaction have been applied in selective cleavage.

With respect to the Staudinger reaction, it has been proposed in Tetrahedron Letters 47 (2006) 2147-2150 to make use of the Staudinger reaction for the chemoselective release of synthesized DNA from the solid-phase release in solid-phase synthesis. Further, it has been proposed in Bioconjugate Chem 2008, 19, 714-718, to make use of the Staudinger reaction to provoke activation of a prodrug. Briefly, in the introduced concept, the prodrug is a conjugate of a drug and a trigger, and this drug-trigger conjugate is not activated endogeneously by e.g. an enzyme or a specific pH, but by a controlled administration of the activator, i.e. a species that reacts with the trigger moiety in the prodrug, to induce release of the drug from the trigger. The presented Staudinger approach for this concept, however, has turned out not to work well, and its area of applicability is limited in view of the specific nature of the release mechanism imposed by the Staudinger reaction. Other drawbacks for use of Staudinger reactions are their limited reaction rates, and the oxidative instability of the phosphine components of these reactions.

Therefore, it is desired to provide reactants for an abiotic, bio-orthogonal reaction that are stable in biological environments, that are more reactive towards each other, and that are capable of inducing release of a bound construct by means of a variety of mechanisms, thus offering a greatly versatile construct release method.

SUMMARY OF THE INVENTION

In order to better address one or more of the aforementioned desires, and as a further advancement in provoked chemical cleavage, the invention provides, in one aspect, the use of a dienophile, particularly of formula 1a defined below, as a chemically cleavable group attached to a Construct, and provoking the release, preferably the in vitro release of the Construct by allowing the dienophile to react with a diene capable of undergoing an rDA reaction, as defined below, with the dienophile.

DETAILED DESCRIPTION OF THE INVENTION

Figure 1:
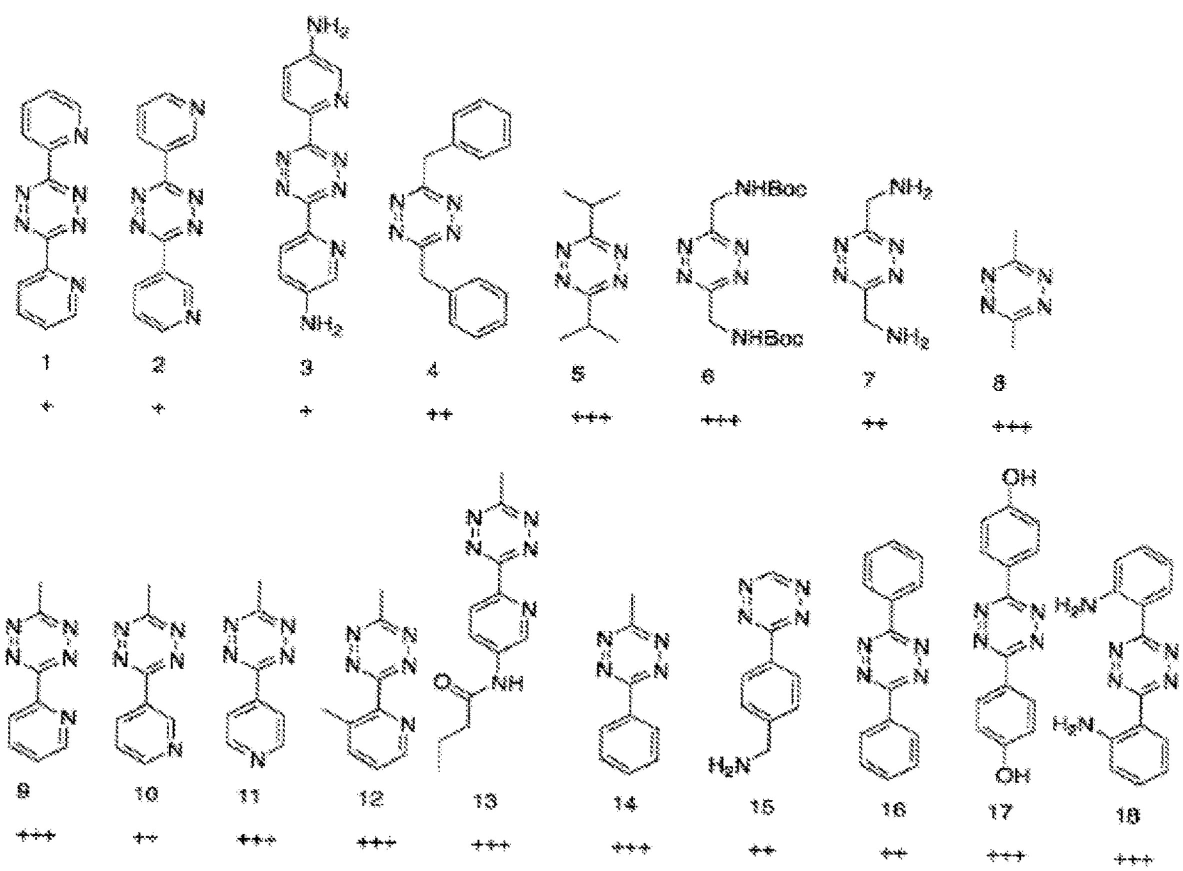
FIG. 1 presents tetrazines and the relative doxorubicin release yield when reacted with TCO-2-Doxorubicin.

The invention provides a tool for the controlled release of a bound substance (bound to any carrier or any other chemical group) for a diverse range of applications, including but not limited to drug delivery, biological and chemical sensors, chemical biology, diagnostics, and chemistry.

The release can be particularly in a chemically complex environment (also including standard organic synthesis), particularly comprising biological surroundings, which include the synthesis and handling conditions of biomolecules. This includes, organic solvents, aqueous solvents and media, cell lysates; at ambient temperature. The invention preferably relates to in vitro release.

The invention is based on the judicious recognition that the rDA reaction (as defined below) enables the controlled manipulation of a wide range of substrates in relatively complex environments; in the presence of a range of other chemical functional groups. This control can be temporal and, optionally, also spatial. The manipulation can be versatile, e.g. for a variety of purposes including but not limited to activating, deactivating, releasing, trapping, or otherwise altering a Construct attached to said chemically cleavable group.

This invention provides an Activator that reacts with a construct-conjugated Trigger, resulting in the cleavage of the Trigger from the construct and optionally the cleavage of one construct from another construct.

In some embodiments, the Trigger is used as a reversible covalent bond between two molecular species.

The term Construct in this invention is used to indicate any substance, carrier, or chemical group, of which it is desired to have it first in a bound (or masked) state, and being able to provoke release from that state. The Construct may be present in the form of two or more Constructs, linked via a self-immolative linker.

Trigger

The Construct-Trigger conjugate comprises a Construct-A denoted as $C^A$ linked, directly or indirectly, to a Trigger moiety denoted as $T^R$, wherein the Trigger moiety is a dienophile. Optionally, the $T^R$ is furthermore linked, directly or indirectly, to a Construct-B denoted as $C^B$. The dienophile, in a broad sense, is an eight-membered non-aromatic cyclic alkenylene moiety (preferably a cyclooctene moiety, and more preferably a trans-cyclooctene moiety). Optionally, the trans-cyclooctene (TCO) moiety comprises at least two exocyclic bonds fixed in substantially the same plane, and/or it optionally comprises at least one substituent in the axial position, and not the equatorial position. The person skilled in organic chemistry will understand that the term "fixed in substantially the same plane" refers to bonding theory according to which bonds are normally considered to be fixed in the same plane. Typical examples of such fixations in the same plane include double bonds and strained fused rings. E.g., the at least two exocyclic bonds can be the two bonds of a double bond to an oxygen (i.e. C═O). The at least two exocyclic bonds can also be single bonds on two adjacent carbon atoms, provided that these bonds together are part of a fused ring (i.e. fused to the TCO ring) that assumes a substantially flat structure, therewith fixing said two single bonds in substantially one and the same plane. Examples of the latter include strained rings such as cyclopropyl and cyclobutyl. Without wishing to be bound by theory, the inventors believe that the presence of at least two exocyclic bonds in the same plane will result in an at least partial flattening of the TCO ring, which can lead to higher reactivity in the retro-Diels-Alder reaction.

The Retro Diels-Alder coupling chemistry generally involves a pair of reactants that couple to form an unstable intermediate, which intermediate eliminates a small molecule (depending on the starting compounds this may be e.g. $N_2$, $CO_2$, RCN), as the sole by-product through a retro Diels-Alder reaction to form the retro Diels-Alder adduct. The paired reactants comprise, as one reactant (i.e. one Bio-orthogonal Reactive Group), a suitable diene, such as a derivative of tetrazine, e.g. an electron-deficient tetrazine and, as the other reactant (i.e. the other Bio-orthogonal Reactive Group), a suitable dienophile, such as a strained cyclooctene (TCO).

The exceptionally fast reaction of e.g. electron-deficient (substituted) tetrazines with a TCO moiety results in a ligation intermediate that rearranges to a dihydropyridazine retro Diels-Alder adduct by eliminating $N_2$ as the sole by-product in a [4+2]Retro Diels-Alder cycloaddition. In aqueous environment, the initially formed 4,5-dihydropyridazine product may tautomerize to a 1,4-dihydropyridazine product.

The two reactive species are abiotic and do not undergo fast metabolism or side reactions in vivo. They are bio-orthogonal, e.g. they selectively react with each other in physiologic media. Thus, the compounds and the method of the invention can be used in a living organism. Moreover, the reactive groups are relatively small and can be introduced in biological samples or living organisms without significantly altering the size of biomolecules therein. References on the Inverse electron demand Diels Alder reaction, and the behavior of the pair of reactive species include: Thalhammer, F; Wallfahrer, U; Sauer, J, Tetrahedron Letters, 1990, 31 (47), 6851-6854; Wijnen, J W; Zavarise, S; Engberts, JBFN, Journal Of Organic Chemistry, 1996, 61, 2001-2005; Blackman, ML; Royzen, M; Fox, J M, Journal Of The American Chemical Society, 2008, 130 (41), 13518-19), R. Rossin, P. Renart Verkerk, Sandra M. van den Bosch, R. C. M. Vulders, 1. Verel, J. Lub, M. S. Robillard, Angew Chem Int Ed 2010, 49, 3375, N. K. Devaraj, R. Upadhyay, J. B. Haun, S. A. Hilderbrand, R. Weissleder, Angew Chem Int Ed 2009, 48, 7013, and Devaraj et al., Angew. Chem. Int. Ed., 2009, 48, 1-5.

It will be understood that, in a broad sense, according to the invention the aforementioned retro Diels-Alder coupling and subsequent construct release chemistry can be applied to basically any pair of molecules, groups, constructs. I.e. one of such a pair will comprise a construct linked to a dienophile (the Trigger). The other one will be a complementary diene for use in reaction with said dienophile.

The dienophile, defined in formula (1a) below, and the diene, also defined hereinbelow, are capable of reacting in said rDA reaction. The rDA reaction of the Trigger with the Activator leads to release of the Construct from the Trigger.

Below a reaction scheme is given for a [4+2]Diels-Alder reaction between the (3,6)-di-(2-pyridyl)-s-tetrazine diene and a trans-cyclooctene dienophile, followed by a retro Diels Alder reaction in which the product and dinitrogen is formed. The reaction product may tautomerize, and this is also shown in the scheme. Because the trans-cyclooctene derivative does not contain electron withdrawing groups as in the classical Diels Alder reaction, this type of Diels Alder reaction is distinguished from the classical one, and frequently referred to as an "inverse electron demand Diels Alder reaction". In the following text the sequence of both reaction steps, i.e. the initial Diels-Alder cyclo-addition (typically an inverse electron demand Diels Alder cyclo-addition) and the subsequent retro Diels Alder reaction will be referred to in shorthand as "retro Diels Alder reaction" or "retro-DA". It will sometimes be abbreviated as "rDA" reaction. The product of the reaction is then the retro Diels-Alder adduct, or the rDA adduct.

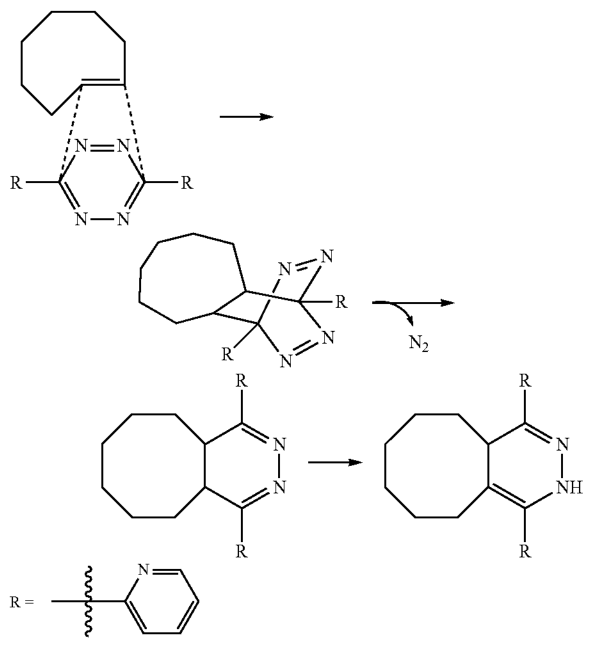

In a general sense, the invention is based on the recognition that a construct can be released from trans-cyclooctene derivatives satisfying formula (1a) upon cyclooaddition with compatible dienes, such as tetrazine derivatives. The dienophiles of formula (1a) have the advantage that they react (and effectuate construct release) with substantially any diene.

Without wishing to be bound by theory, the inventors believe that the molecular structure of the retro Diels-Alder adduct is such that a spontaneous elimination reaction within this rDA adduct releases the construct. Particularly, the inventors believe that appropriately modified rDA components lead to rDA adducts wherein the bond to the construct on the dienophile is destabilized by the presence of a lone electron pair on the diene. Alternatively, and without wishing to be bound by theory, the inventors believe that the molecular structure of the retro Diels-Alder adduct is such that a spontaneous elimination or cyclization reaction within this rDA adduct releases the construct. Particularly, the inventors believe that appropriately modified rDA components, i.e. according to the present invention, lead to rDA adducts wherein the bond to the construct on the part originating from the dienophile is broken by the reaction with a nucleophile on the part originating from the dienophile, while such an intramolecular reaction within the part originating from the dienophile is precluded prior to rDA reaction with the diene.

The general concept of using the retro-Diels Alder reaction in Construct release is illustrated in Scheme 1.

Scheme 1: general scheme of Construct release according to this invention

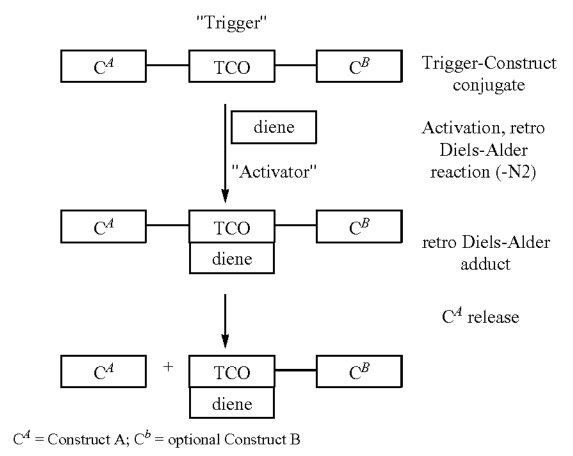

$C^A$ = Construct A; $C^b$ = optional Construct B

In this scheme "TCO" stands for trans-cyclooctene. The term trans-cyclooctene is used here as possibly including one or more hetero-atoms, and particularly refers to a structure satisfying formula (1a). In a broad sense, the inventors have found that—other than the attempts made on the basis of the Staudinger reaction—the selection of a TCO as the trigger moiety for a masked construct, provides a versatile tool to render Constructs into stable masked or linked Constructs. The construct release occurs through a powerful, abiotic, bio-orthogonal reaction of the dienophile (Trigger) with the diene (Activator), viz the aforementioned retro Diels-Alder reaction. The masked or bound construct is a construct-dienophile conjugate. Possibly the construct is linked to one or more additional constructs linked via a self-immolative linker.

It will be understood that in Scheme 1 in the retro Diels-Alder adduct as well as in the end product, the indicated TCO group and the indicated diene group are the residues of, respectively, the TCO and diene groups after these groups have been converted in the retro Diels-Alder reaction.

A requirement for the successful application of an abiotic bio-orthogonal chemical reaction is that the two participating functional groups have finely tuned reactivity so that interference with coexisting functionality is avoided. Ideally, the reactive partners would be abiotic, reactive under physiological conditions, or in other biological media, and reactive only with each other while ignoring their cellular/physiological/biological surroundings (bio-orthogonal). The demands on selectivity imposed by a biological environment preclude the use of most conventional reactions.

The inverse electron demand Diels Alder reaction, however, has proven utility in animals at low concentrations and semi-equimolar conditions (R. Rossin et al, Angewandte Chemie Int Ed 2010, 49, 3375-3378). The reaction partners subject to this invention are strained trans-cyclooctene (TCO) derivatives and suitable dienes, such as tetrazine derivatives. The cycloaddition reaction between a TCO and a tetrazine affords an intermediate, which then rearranges by expulsion of dinitrogen in a retro-Diels-Alder cycloaddition to form a dihydropyridazine conjugate. This and its tautomers is the retro Diels-Alder adduct.

Reflecting the suitability of the rDA reaction, the invention provides, in one aspect, the use of a tetrazine as an activator for the release, in a chemical, biological, or physiological environment, of a construct linked to a trans-cyclooctene. In connection herewith, the invention also pertains to a tetrazine for use as an activator for the release, in a chemical, biological, or physiological environment, of a substance linked to a trans-cyclooctene, and to a method for activating, in a chemical, biological, or physiological environment, the release of a substance linked to a trans-cyclooctene, wherein a tetrazine is used as an activator.

In this invention, the TCO satisfies the following formula (1a):

(1a)

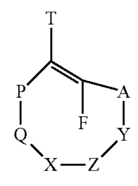

A and P each independently are $CR^a_2$ or $CR^aX^D$, provided that at least one is $CR^aX^D$. $X^D$ is $(O—C(O))_p-(L^D)_n-(C^A)$, $S—C(O)-(L^D)_n-(C^A)$, $O—C(S)-(L^D)_n-(C^A)$, $S—C(S)-(L^D)_n-(C^A)$, $O—S(O)-(L^D)_n-(C^A)$, wherein p=0 or 1. Preferably, $X^D$ is $(O—C(O))_p-(L^D)_n-(C^A)$, where p=0 or 1, preferably 1, and n=0 or 1.

In an interesting embodiment, Y, Z, X, Q each independently are selected from the group consisting of $CR^a_2$, $C{=}CR^a_2$, C═O, C=S, $C{=}NR^b$, S, SO, $SO_2$, O, $NR^b$, and $SiR^c_2$, with at most three of Y, Z, X, and Q being selected from the group consisting of $C{=}CR^a_2$, C═O, C=S, and $C{=}NR^b$, wherein two R moieties together may form a ring, and with the proviso that no adjacent pairs of atoms are present selected from the group consisting of O—O, $O—NR^b$, $S—NR^b$, O—S, O—S(O), $O—S(O)_2$, and S—S, and such that Si is only adjacent to $CR^a_2$ or O.

In another interesting embodiment, one of the bonds PQ, QX, XZ, ZY, YA is part of a fused ring or consists of $CR^a{=}CR^a$, such that two exocyclic bonds are fixed in the same plane, and provided that PQ and YA are not part of an aromatic 5- or 6-membered ring, of a conjugated 7-membered ring, or of $CR^a{=}CR^a$; when not part of a fused ring P and A are independently $CR^a_2$ or $CR^aX^D$, provided that at least one is $CR^aX^D$; when part of a fused ring P and A are independently $CR^a$ or $CX^D$, provided that at least one is $CX^D$; the remaining groups (Y, Z, X, Q) being independently from each other $CR^a_2$, C═$CR^a_2$, C═O, C═S, C═$NR^b$, S, SO, $SO_2$, O, $NR^b$, $SiR^c_2$, such that at most 1 group is C═$CR^a_2$, C═O, C═S, C═$NR^b$, and no adjacent pairs of atoms are present selected from the group consisting of O—O, O—$NR^b$, S—$NR^b$, O—S, O—S(O), O—$S(O)_2$, and S—S, and such that Si, if present, is adjacent to $CR^a_2$ or O, and the $CR^a_2$═$CR^a_2$ bond, if present, is adjacent to $CR^a_2$ or C═$CR^a_2$ groups;

In some embodiments fused rings are present that result in two exocyclic bonds being fixed in substantially the same plane. These are selected from fused 3-membered rings, fused 4-membered rings, fused bicyclic 7-membered rings, fused aromatic 5-membered rings, fused aromatic 6-membered rings, and fused planar conjugated 7-membered rings as defined below:

Fused 3-Membered Rings are:

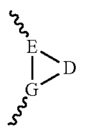

Therein E, G are part of the above mentioned 8-membered ring and can be fused to PQ, QP, QX, XQ, XZ, ZX, ZY, YZ, YA, AY, such that P, A are $CR^a$ or $CX^D$, and such that $CX^D$ can only be present in A and P.

E-G is $CR^a$—$CR^a$ or $CR^a$—$CX^D$, and D is $CR^a_2$, C═O, C═S, C═$NR^b$, $NR^b$, O, S; or E-G is $CR^a$—N or $CX^D$—N, and D is $CR^a_2$, C═O, C═S, C═$NR^b$, $NR^b$O, or S.

Fused 4-Membered Rings are:

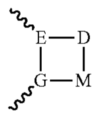

E-G is part of the above mentioned 8-membered ring and can be fused to PQ, QP, QX, XQ, XZ, ZX, ZY, YZ, YA, AY, such that P, A are C, $CR^a$ or $CX^D$, and such that $CX^D$ can only be present in A and P.

- E, G are $CR^a$, $CX^D$ or N, and D, M independently from each other are $CR^a_2$, C═O, C═S, C═$NR^b$, C═$CR^a_2$, S, SO, $SO_2$, O, $NR^b$ but no adjacent O—O or S—S groups; or
- E-D is C═$CR^a$ and G is N, $CR^a$, $CX^D$ and M is $CR^a_2$, S, SO, $SO_2$, O, $NR^b$; or E-D is C═N and G is N, $CR^a$, $CX^D$ and M is $CR^a_2$, S, SO, $SO_2$, O; or
- D-M is $CR^a$═$CR^a$ and E, G each independently are $CR^a$, $CX^D$ or N; or D-M is $CR^a$═N and E is $CR^a$, $CX^D$, N, and G is $CR^a$ or $CX^D$; or
- E is C, G is $CR^a$, $CX^D$ or N, and D, M are $CR^a_2$, S, SO, $SO_2$, O, $NR^b$, or at most one of C═O, C═S, C═$NR^b$, C═$CR^a_2$, but no adjacent O—O or S—S groups; or E and G are C, and D and M independently from each other are $CR^a_2$, S, SO, $SO_2$, O, $NR^b$ but no adjacent O—O, or S—S groups.

Fused Bicyclic 7-Membered Rings are:

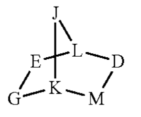

E-G is part of the above mentioned 8-membered ring and can be fused to PQ, QP, QX, XQ, XZ, ZX, ZY, YZ, YA, AY, such that P, A are C, $CR^a$ or $CX^D$, and such that $CX^D$ can only be present in A and P;

- E, G are C, $CR^a$, $CX^D$ or N; K, L are $CR^a$; D, M form a $CR^a$═$CR^a$ or $CR^a$=N, or D, M independently from each other are $CR^a_2$, C═O, C═S, C═$NR^b$, C═$CR^a_2$, S, SO, $SO_2$, O, $NR^b$ but no adjacent O—O, S—S, N—S groups; J is $CR^a_2$, C═O, C═S, C═$NR^b$, C═$CR^a_2$, S, SO, $SO_2$, O, $NR^b$; at most 2 N groups; or
- E, G are C, $CR^a$, $CX^D$; K is N and L is $CR^a$; D, M form a $CR^a$═$CR^a$ bond or D, M independently from each other are $CR^a_2$, C═O, C═S, C═$NR^b$, C═$CR^a_2$, $NR^b$ but no adjacent O—O, S—S, N—S groups; J is $CR^a_2$, C═O, C═S, C═$NR^b$, C═$CR^a_2$, S, SO, $SO_2$, O, $NR^b$; at most 2 N groups; or E, G are C, $CR^a$, $CX^D$; K and L are N; D, M, J independently from each other are $CR^a_2$, C═O, C═S, C═$NR^b$, C═$CR^a_2$ groups;

Fused Aromatic 5-Membered Rings are

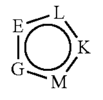

E, G are part of the above mentioned 8-membered ring and can be fused to QX, XQ, XZ, ZX, ZY, YZ.

E and G are C; one of the groups L, K, or M are O, $NR^b$, S and the remaining two groups are independently from each other $CR^a$ or N; or E is C and G is N; L, K, M are independently from each other $CR^a$ or N.

Fused aromatic 6-membered rings are:

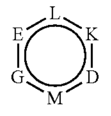

E, G are part of the above mentioned 8-membered ring and can be fused to QX, XQ, XZ, ZX, ZY, YZ.

E, G is C; L, K, D, M are independently from each other $CR^a$ or N

Fused Planar Conjugated 7-Membered Rings are

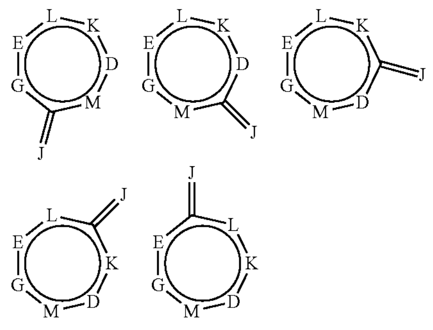

E, G are part of the above mentioned 8-membered ring and can be fused to QX, XQ, XZ, ZX, ZY, YZ E, G is C; L, K, D, M are $CR^a$; J is S, O, $CR^a_2$, $NR^b$.

$(L^D)_n$ is an optional linker, with n=0 or 1, preferably linked to $T^R$ via S, N, NH, or O, wherein these atoms are part of the linker, which may consist of multiple units arranged linearly and/or branched. $C^A$ is Construct $C^A$, preferably linked via S, N, NH, or O, wherein these atoms are part of $C^A$.

T, F each independently denotes H, or a substituent selected from the group consisting of alkyl, F, Cl, Br, or I.

Without wishing to be bound by theory, the inventors believe that in the foregoing embodiments, the rDA reaction results in a cascade-mediated release or elimination (i.e. cascade mechanism) of the Construct $C^A$.

In several alternative embodiments, with reference to formula (1a), said release or elimination is believed to be mediated by a strain release mechanism.

Therein, in Embodiment 1, one of the bonds PQ, QP, QX, XQ, XZ, ZX, ZY, YZ, YA, AY consists of —$CR^aX^D$—$CR^aY^D$—, the remaining groups (from A, Y, Z, X, Q, P) being independently from each other $CR^a_2$, S, O, $SiR^c_2$, such that P and A are $CR^a_2$, and no adjacent pairs of atoms are present selected from the group consisting of O—O, O—S, and S—S, and such that Si, if present, is adjacent to $CR^a_2$ or O.

$X^D$ is O—C(O)-$(L^D)_n$-$(C^A)$, S—C(O)-$(L^D)_n$-$(C^A)$, O—C(S)-$(L^D)_n$-$(C^A)$, S—C(S)-$(L^D)_n$-$(C^A)$, $NR^d$—C(O)-$(L^D)_n$-$(C^A)$, $NR^d$—C(S)-$(L^D)_n$-$(C^A)$, and then $Y^D$ is $NHR^d$, OH, SH; or $X^D$ is C(O)-$(L^D)_n$-$(C^A)$, C(S)-$(L^D)_n$-$(C^A)$; and then $Y^D$ is $CR^d_2NHR^d$, $CR^d_2OH$, $CR^d_2SH$, NH—$NH_2$, O—$NH_2$, NH—OH. Preferably $X^D$ is $NR^d$—C(O)-$(L^D)_n$-$(C^A)$, and $Y^D$ is $NHR^d$.

In this Embodiment 1, the $X^D$ and $Y^D$ groups may be positioned cis or trans relative to each other, where depending on the positions on the TCO, cis or trans are preferred: if PQ, QP, AY or YA is —$CR^aX^D$—$CR^aY^D$—, then $X^D$ and $Y^D$ are preferably positioned trans relative to each other; if ZX or XZ is —$CR^aX^D$—$CR^aY^D$—, then $X^D$ and $Y^D$ are preferably positioned cis relative to each other.

In Embodiment 2, A is $CR^aX^D$ and Z is $CR^aY^D$, or Z is $CR^aX^D$ and A is $CR^aY^D$, or P is $CR^aX^D$ and X is $CR^aY^D$, or X is $CR^aX^D$ and P is $CR^aY^D$, such that $X^D$ and $Y^D$ are positioned in a trans conformation with respect to one another; the remaining groups (from A, Y, Z, X, Q, P) being independently from each other $CR^a_2$, S, O, $SiR^c_2$, such that P and A are $CR^a_2$, and no adjacent pairs of atoms are present selected from the group consisting of O—O, O—S, and S—S, and such that Si, if present, is adjacent to $CR^a_2$ or O; $X^D$ is O—C(O)-$(L^D)_n$-$(C^A)$, S—C(O)-$(L^D)_n$-$(C^A)$, O—C(S)-$(L^D)_n$—$(C^A)$, S—C(S)-$(L^D)_n$-$(C^A)$, $NR^d$—C(O)-$(L^D)_n$-$(C^A)$, $NR^d$—C(S)-$(L^D)_n$-$(C^A)$, and then $Y^D$ is $NHR^d$, OH, SH, $CR^d_2NHR^d$, $CR^d_2OH$, $CR^d_2SH$, NH—$NH_2$, O—$NH_2$, NH—OH; or $X^D$ is $CR^d_2$—O—C(O)-$(L^D)_n$—$(C^A)$, $CR^d_2$—S—C(O)-$(L^D)_n$-$(C^A)$, $CR^d_2$—O—C(S)-$(L^D)_n$-$(C^A)$, $CR^d_2$—S—C(S)-$(L^D)_n$-$(C^A)$, $CR^d_2$—$NR^d$—C(O)-$(L^D)_n$-$(C^A)$, $CR^d_2$—$NR^d$—C(S)-$(L^D)_n$-$(C^A)$; and then $Y^D$ is $NHR^d$, OH, SH; or $X^D$ is C(O)-$(L^D)_n$—$(C^A)$, C(S)-$(L^D)_n$-$(C^A)$; and then $Y^D$ is $CR^d_2NHR^d$, $CR^d_2OH$, $CR^d_2SH$, NH—$NH_2$, O—$NH_2$, NH—OH. Preferably $X^D$ is $NR^d$—C(O)-$(L^D)_n$-$(C^A)$, and $Y^D$ is $NHR^d$.

In Embodiment 3, A is $CR^aY^D$ and one of P, Q, X, Z is $CR^aX^D$, or P is $CR^aY^D$ and one of A, Y, Z, X is $CR^aX^D$, or Y is $CR^aY^D$ and X or P is $CR^aX^D$, or Q is $CR^aY^D$ and Z or A is $CR^aX^D$, or either Z or X is $CR^aY^D$ and A or P is $CR^aX^D$, such that $X^D$ and $Y^D$ are positioned in a trans conformation with respect to one another; the remaining groups (from A, Y, Z, X, Q, P) being independently from each other $CR^a_2$, S, O, $SiR^c_2$, such that P and A are $CR^a_2$, and no adjacent pairs of atoms are present selected from the group consisting of O—O, O—S, and S—S, and such that Si, if present, is adjacent to $CR^a_2$ or O.

$X^D$ is $(O—C(O))_p$-$(L^D)_n$-$(C^A)$, S—C(O)-$(L^D)_n$-$(C^A)$, O—C(S)-$(L^D)_n$-$(C^A)$, S—C(S)-$(L^D)_n$-$(C^A)$; $Y^D$ is $CR^d_2NHR^d$, $CR^d_2OH$, $CR^d_2SH$, NH—$NH_2$, O—$NH_2$, NH—OH; p=0 or 1. Preferably $X^D$ is $(O—C(O))_p$-$(L^D)_n$-$(C^A)$, with p=1, and $Y^D$ is $CR^d_2NHR^d$.

In Embodiment 4, P is $CR^aY^D$ and Y is $CR^aX^D$, or A is $CR^aY^D$ and Q is $CR^aX^D$, or Q is $CR^aY^D$ and A is $CR^aX^D$, or Y is $CR^aY^D$ and P is $CR^aX^D$, such that $X^D$ and $Y^D$ are positioned in a trans conformation with respect to one another; the remaining groups (from A, Y, Z, X, Q, P) being independently from each other $CR^a_2$, S, O, $SiR^c_2$, such that P and A are $CR^a_2$, and no adjacent pairs of atoms are present selected from the group consisting of O—O, O—S, and S—S, and such that Si, if present, is adjacent to $CR^a_2$ or O.

$X^D$ is $(O—C(O))_p$-$(L^D)_n$-$(C^A)$, S—C(O)-$(L^D)_n$-$(C^A)$, O—C(S)-$(L^D)_n$-$(C^A)$, S—C(S)-$(L^D)_n$-$(C^A)$; $Y^D$ is $NHR^d$, OH, SH; p=0 or 1. Preferably $X^D$ is $(O—C(O))_p$-$(L^D)_n$-$(C^A)$, with p=1, and $Y^D$ is $NHR^d$.

In Embodiment 5, Y is $Y^D$ and P is $CR^aX^D$, or Q is $Y^D$ and A is $CR^aX^D$; the remaining groups (from A, Y, Z, X, Q, P) being independently from each other $CR^a_2$, S, O, $SiR^c_2$, such that P and A are $CR^a_2$, and no adjacent pairs of atoms are present selected from the group consisting of O—O, O—S, and S—S, and such that Si, if present, is adjacent to $CR^a_2$ or O.

$X^D$ is $(O—C(O))_p$-$(L^D)_n$-$(C^A)$, S—C(O)-$(L^D)_n$-$(C^A)$, O—C(S)-$(L^D)_n$-$(C^A)$, S—C(S)-$(L^D)_n$-$(C^A)$, $NR^d$—C(O)-$(L^D)_n$-$(C^A)$, $NR^d$—C(S)-$(L^D)_n$-$(C^A)$, C(O)-$(L^D)_n$-$(C^A)$, C(S)-$(L^D)_n$-$(C^A)$; $Y^D$ is NH; p=0 or 1. Preferably $X^D$ is $NR^d$—C(O)-$(L^D)_n$-$(C^A)$ or $(O—C(O))_p$-$(L^D)_n$-$(C^A)$, with p=0 or 1.

In Embodiment 6, Y is $Y^D$ and P or Q is $X^D$, or Q is $Y^D$ and A or Y is $X^D$; the remaining groups (from A, Y, Z, X, Q, P) being independently from each other $CR^a_2$, S, O, $SiR^c_2$, such that P and A are $CR^a_2$, and no adjacent pairs of atoms are present selected from the group consisting of O—O, O—S, and S—S, and such that Si, if present, is adjacent to $CR^a_2$ or O.

$X^D$ is N—C(O)-$(L^D)_n$-$(C^A)$, N—C(S)-$(L^D)_n$-$(C^A)$; $Y^D$ is NH. Preferably $X^D$ is N—C(O)-$(L^D)_n$-$(C^A)$ Also herein, $(L^D)_n$ is an optional linker, with n=0 or 1, preferably linked to $T^R$ via S, N, NH, or O, wherein these atoms are part of the linker, which may consist of multiple units arranged linearly and/or branched. $C^A$ is Construct $C^A$, preferably linked via S, N, NH, or O, wherein these atoms are part of $C^A$.

T, F each independently denotes H, or a substituent selected from the group consisting of alkyl, F, Cl, Br, or I.

It is preferred that when $C^A$ is bound to $T^R$ or $L^D$ via NH, this NH is a primary amine (—$NH_2$) residue from $C^A$, and when $C^A$ is bound via N, this N is a secondary amine (—NH—) residue from $C^A$. Similarly, it is preferred that when $C^A$ is bound via O or S, said O or S are, respectively, a hydroxyl (—OH) residue or a sulfhydryl (—SH) residue from $C^A$.

It is further preferred that said S, N, NH, or O moieties comprised in $C^A$ are bound to an aliphatic or aromatic carbon of $C^A$.

It is preferred that when $L^D$ is bound to $T^R$ via NH, this NH is a primary amine (—$NH_2$) residue from $L^D$, and when $L^D$ is bound via N, this N is a secondary amine (—NH—) residue from $L^D$. Similarly, it is preferred that when $L^D$ is bound via O or S, said O or S are, respectively, a hydroxyl (—OH) residue or a sulfhydryl (—SH) residue from $L^D$.

It is further preferred that said S, N, NH, or O moieties comprised in $L^D$ are bound to an aliphatic or aromatic carbon of $L^D$.

Where reference is made in the invention to a linker $L^D$ this can be self-immolative or not, or a combination thereof, and which may consist of multiple self-immolative units. It will be understood that if $L^D$ is not self-immolative, the linker equals a spacer $S^P$.

By way of further clarification, if p=0 and n=0, the species $C^A$ directly constitutes the leaving group of the elimination reaction, and if p=0 and n=1, the self-immolative linker constitutes the leaving group of the elimination. The position and ways of attachment of linkers $L^D$ and constructs $C^A$ are known to the skilled person (see for example Papot et al, *Anti-Cancer Agents in Medicinal Chemistry,* 2008, 8, 618-637). Nevertheless, typical but non-limiting examples of self-immolative linkers $L^D$ are benzyl-derivatives, such as those drawn below. On the right, an example of a self-immolative linker with multiple units is shown; this linker will degrade not only into $CO_2$ and one unit of 4-aminobenzyl alcohol, but also into one 1,3-dimethylimidazolidin-2-one unit.

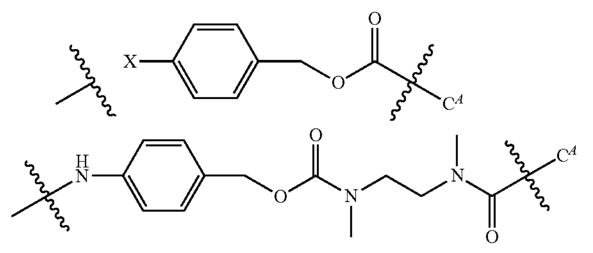

X = O or S or NH or NR with R = alkyl or aryl

By substituting the benzyl groups of aforementioned self-immolative linkers $L^D$ preferably on the 2- and/or 6-position, it may be possible to tune the rate of release of the construct $C^A$, caused by either steric and/or electronic effects on the intramolecular cyclization/elimination reaction. Synthetic procedures to prepare such substituted benzyl-derivatives are known to the skilled person (see for example Greenwald et al, *J. Med. Chem.,* 1999, 42, 3657-3667 and Thornthwaite et al, *Polym. Chem.,* 2011, 2, 773-790). Some examples of substituted benzyl-derivatives with different release rates are drawn below.

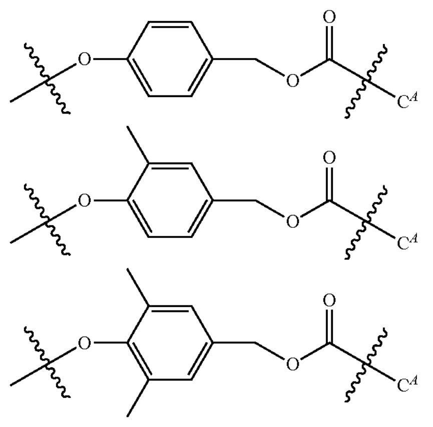

In a preferred embodiment, the TCO of formula (1a) is an all-carbon ring. In another preferred embodiment, the TCO of formula (1a) is a heterocyclic carbon ring, having of one to two oxygen atoms in the ring, and preferably a single oxygen atom.

Each $R^a$ as above-indicated can independently be H, alkyl, aryl, OR', SR', S(=O)R''', S(=O)$_2$R''', S(=O)$_2$NR'R'', Si—R''', Si—O—R''', OC(=O)R''', SC(=O)R''', OC(=S)R''', SC(=S)R''', F, Cl, Br, I, $N_3$, $SO_2H$, $SO_3H$, $SO_4H$, $PO_3H$, $PO_4H$, NO, $NO_2$, CN, OCN, SCN, NCO, NCS, $CF_3$, $CF_2$—R', NR'R'', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', OC(=O)NR'—R''', SC(=O)NR'—R''', OC(=S)NR'—R''', SC(=S)NR'—R''', NR'C(=O)NR''—R'', NR'C(=S)NR''—R'', CR'NR'', with each R' and each R'' independently being H, aryl or alkyl and R''' independently being aryl or alkyl;

Each $R^b$ as above indicated is independently selected from the group consisting of H, alkyl, aryl, O-aryl, O-alkyl, OH, C(=O)NR'R'' with R' and R'' each independently being H, aryl or alkyl, R'CO-alkyl with R' being H, alkyl, and aryl;

Each $R^c$ as above indicated is independently selected from the group consisting of H, alkyl, aryl, O-alkyl, O-aryl, OH;

Each $R^d$ as above indicated is independently selected from H, $C_{1-6}$ alkyl and $C_{1-6}$ aryl;

wherein two or more $R^{a,b,c,d}$ moieties together may form a ring;

Preferably, each $R^a$ is selected independently from the group consisting of H, alkyl, O-alkyl, O-aryl, OH, C(=O)O—R', C(=O)NR'R'', NR'C(=O)—R''', with R' and R'' each independently being H, aryl or alkyl, and with R''' independently being alkyl or aryl.

Optionally, in all of the above embodiments, one of A, P, Q, Y, X, and Z, or the substituents or fused rings of which they are part, or the self-immolative linker $L^D$, is bound, optionally via a spacer or spacers $S^P$, to construct $C^B$.

The synthesis of TCO's as described above is well available to the skilled person. This expressly also holds for TCO's having one or more heteroatoms in the strained cycloalkene rings. References in this regard include Cere et al. *Journal of Organic Chemistry* 1980, 45, 261 and Prevost et al. *Journal of the American Chemical Society* 2009, 131, 14182.

In a preferred embodiment, the trans-cyclooctene moiety satisfies formula (1b):

(1b)

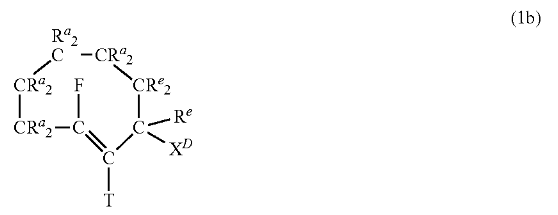

wherein, in addition to the optional presence of at most two exocyclic bonds fixed in the same plane, each $R^a$ independently denotes H, or, in at most four instances, a substituent selected from the group consisting of alkyl, aryl, OR', SR', S(=O)R''', S(=O)$_2$R''', S(=O)$_2$NR'R'', Si—R''', Si—O—R''', OC(=O)R''', SC(=O)R''', OC(=S)R''', SC(=S)R''', F, Cl, Br, I, $N_3$, $SO_2H$, $SO_3H$, $SO_4H$, $PO_3H$, $PO_4H$, NO, $NO_2$, CN, OCN, SCN, NCO, NCS, $CF_3$, $CF_2$—R', NR'R'', C(=O)R', C(=S)R', C(=O)O—R', C(=S)O—R', C(=O)S—R', C(=S)S—R', C(=O)NR'R'', C(=S)NR'R'', NR'C (=O)—R''', NR'C(=S)—R''', NR'C(=O)O—R''', NR'C(=S)O—R''', NR'C(=O)S—R''', NR'C(=S)S—R''', OC(=O)NR'—R''', SC(=O)NR'—R''', OC(=S)NR'—R''', SC(=S)NR'—R''', NR'C(=O)NR''—R'', NR'C(=S)NR''—R'', CR'NR'', with each R' and each R'' independently being H, aryl or alkyl and R''' independently being aryl or alkyl;

Each $R^c$ as above indicated is independently selected from the group consisting of H, alkyl, aryl, OR', SR', S(=O)R''', $S(=O)_2R'''$, Si—R''', Si—O—R''', OC(=O)R''', SC(=O)R''', OC(=S)R''', SC(=S)R''', F, Cl, Br, I, $N_3$, $SO_2H$, $SO_3H$, $PO_3H$, NO, $NO_2$, CN, $CF_3$, $CF_2$—R', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', NR'C(=O)NR''—R'', NR'C(=S)NR''—R'', CR'NR'', with each R' and each R'' independently being H, aryl or alkyl and R''' independently being aryl or alkyl;

wherein two $R^{a,e}$ moieties together may form a ring;

wherein optionally one $R^{a,e}$ or the self-immolative linker $L^D$, is bound, optionally via a spacer or spacers $S^P$, to $C^B$, and wherein T and F each independently denote H, or a substituent selected from the group consisting of alkyl, F, Cl, Br, and I, and $X^D$ is $(O—C(O))_p-(L^D)_n-(C^A)$, $S—C(O)-(L^D)_n-(C^A)$, $O—C(S)-(L^D)_n-(C^A)$, $S—C(S)-(L^D)_n-(C^A)$, $O—S(O)-(L^D)_n-(C^A)$, wherein p=0 or 1. Preferably, $X^D$ is $(O—C(O))_p-(L^D)_n-(C^A)$, where p=0 or 1, preferably 1, and n=0 or 1.

Preferably, each $R^a$ and each $R^c$ is selected independently from the group consisting of H, alkyl, O-alkyl, O-aryl, OH, C(=O)O—R', C(=O)NR'R'', NR'C(=O)—R''', with R' and R'' each independently being H, aryl or alkyl, and with R''' independently being alkyl or aryl.

In the foregoing dienophiles, it is preferred that the at least two exocyclic bonds fixed in the same plane are selected from the group consisting of (a) the single bonds of a fused cyclobutyl ring, (b) the hybridized bonds of a fused aromatic ring, (c) an exocyclic double bond to an oxygen, and (d) an exocyclic double bond to a carbon.

The TCO, containing one or two $X^D$ moieties, may consist of multiple isomers, also comprising the equatorial vs. axial positioning of substituents, such as $X^D$, on the TCO. In this respect, reference is made to Whitham et al. *J. Chem. Soc.* (C), 1971, 883-896, describing the synthesis and characterization of the equatorial and axial isomers of trans-cyclo-oct-2-en-ol, identified as (1RS, 2RS) and (1SR, 2RS), respectively. In these isomers the OH substituent is either in the equatorial or axial position.

In a preferred embodiment, with reference to formula (1a), for structures where the substituents of A and/or P, such as $X^D$ and $Y^D$, can be either in the axial or the equatorial position, the substituent is in the axial position.

Preferred dienophiles, which are optimally selected for $C^A$ release believed to proceed via a cascade elimination mechanism, are selected from the following structures:

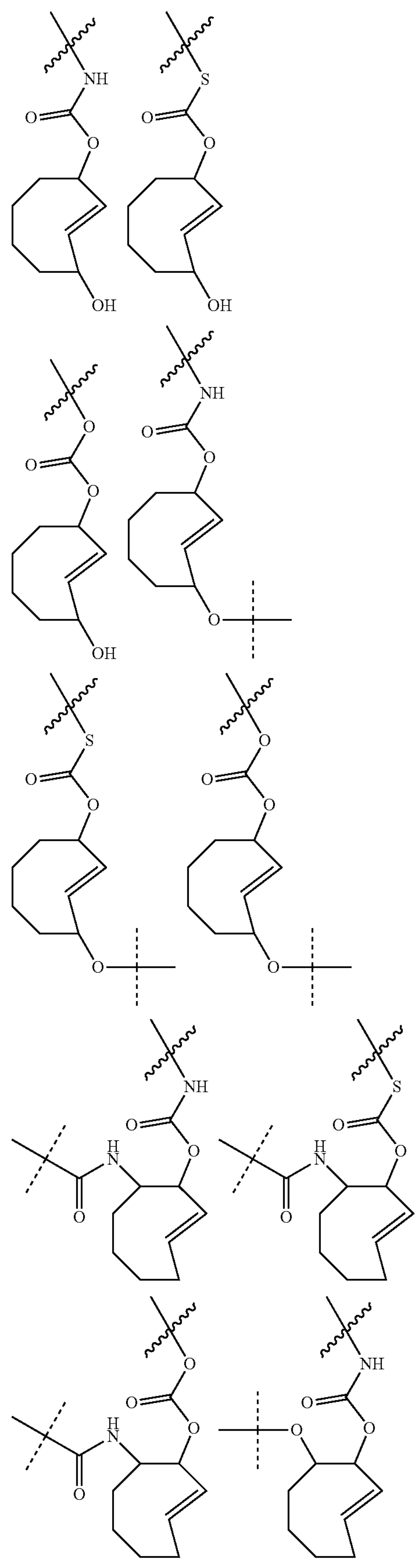

-continued
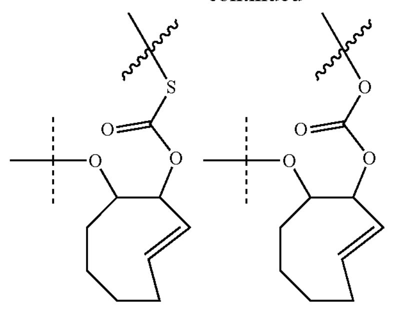
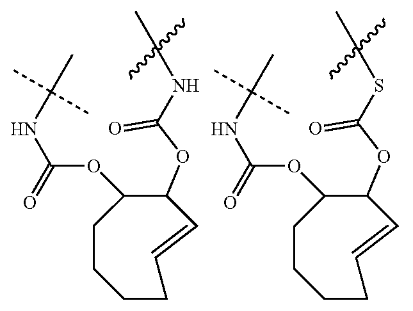
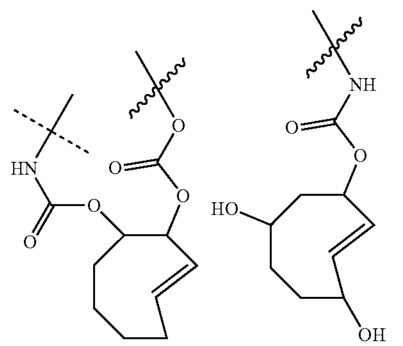
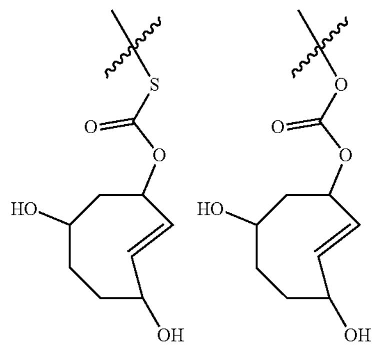
-continued
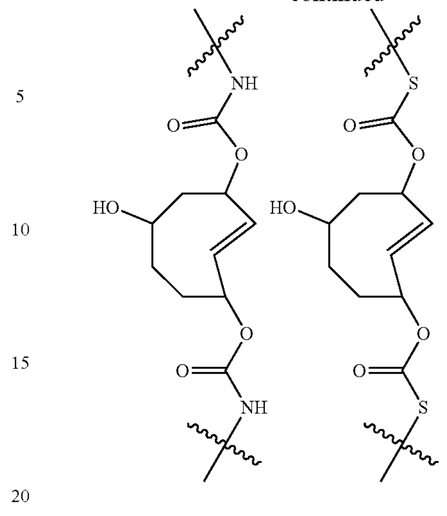
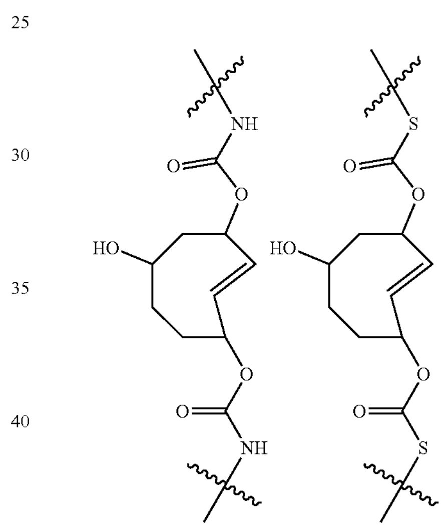
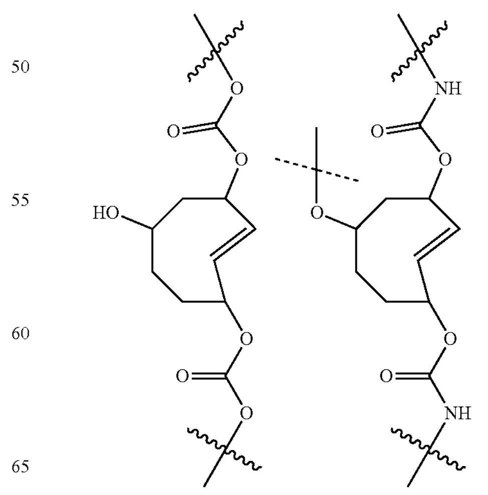

-continued
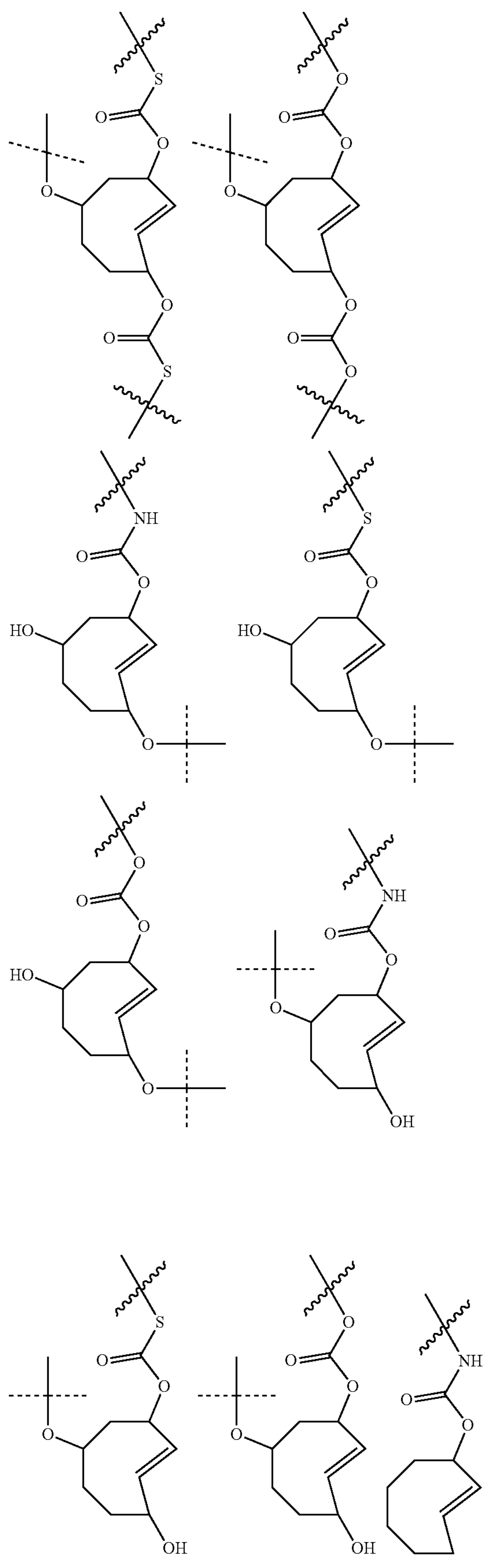
-continued
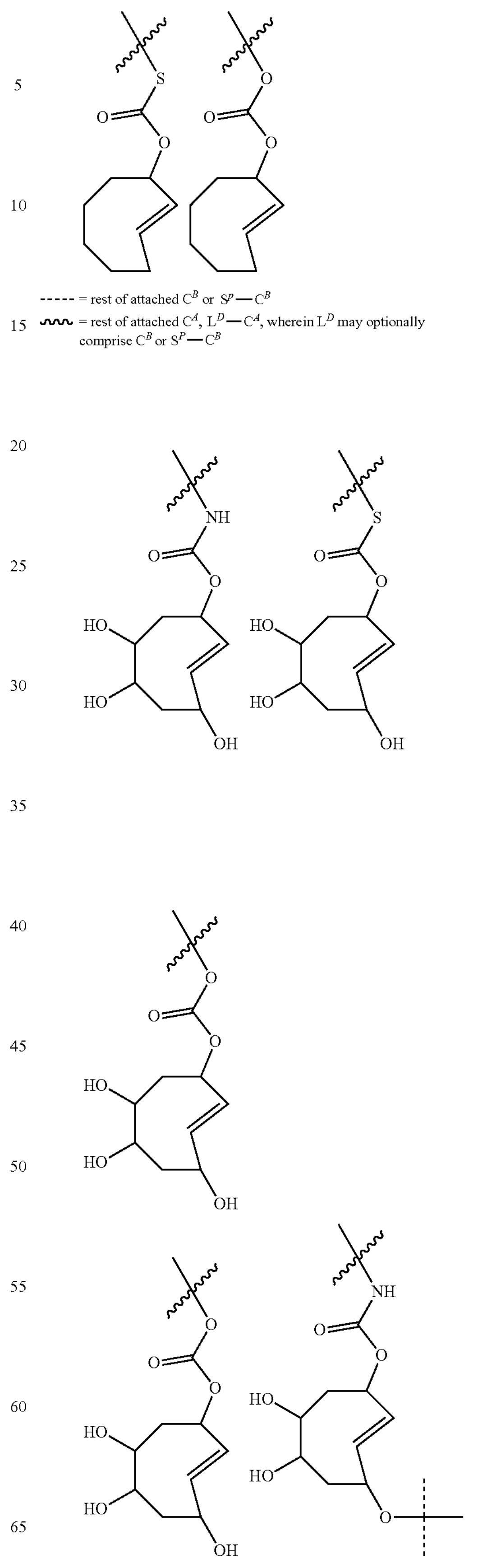
- - - - - = rest of attached $C^B$ or $S^P$—$C^B$
∿∿∿ = rest of attached $C^A$, $L^D$—$C^A$, wherein $L^D$ may optionally comprise $C^B$ or $S^P$—$C^B$ -continued
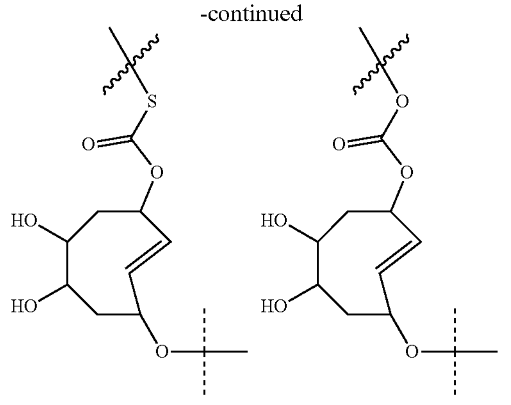
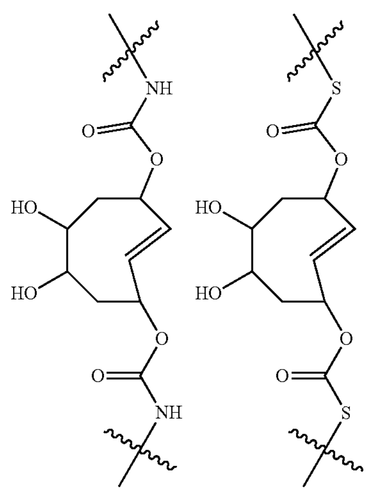
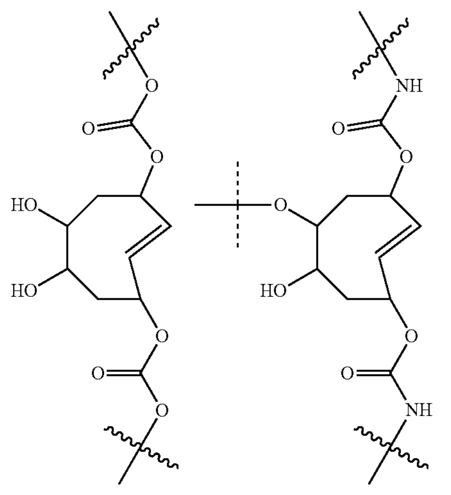
-continued
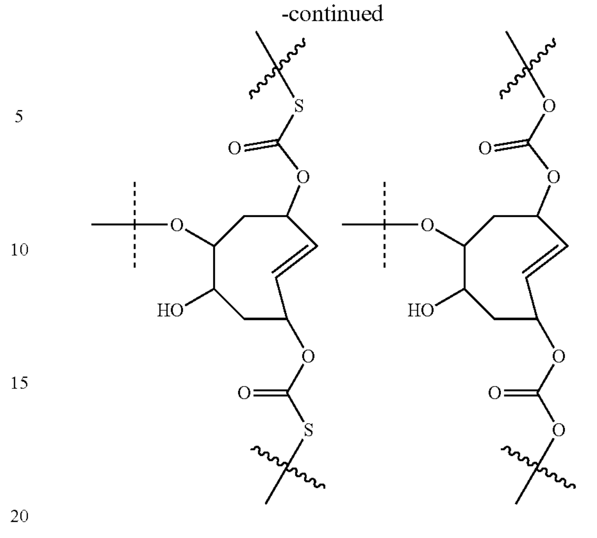
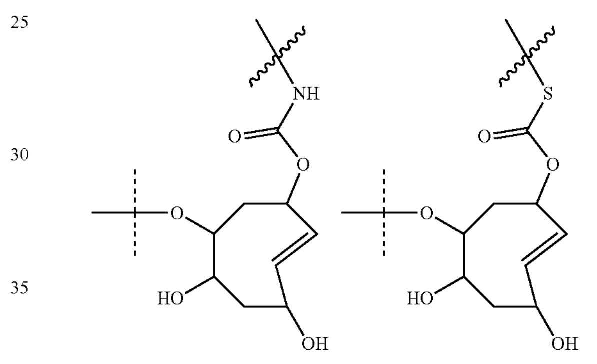
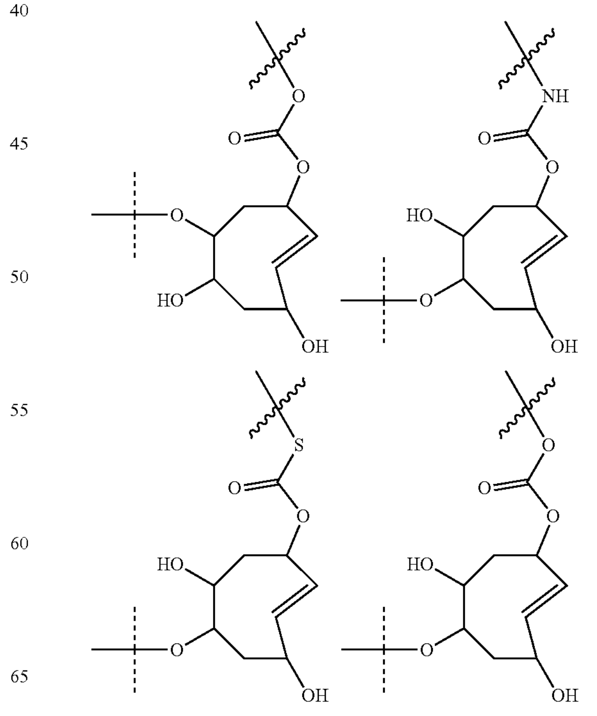

-continued
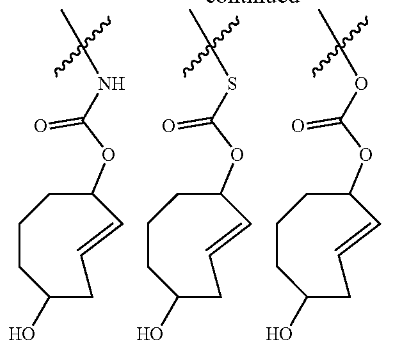
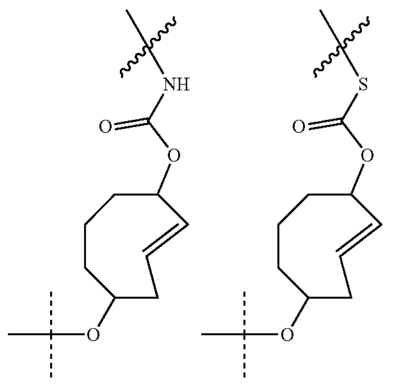
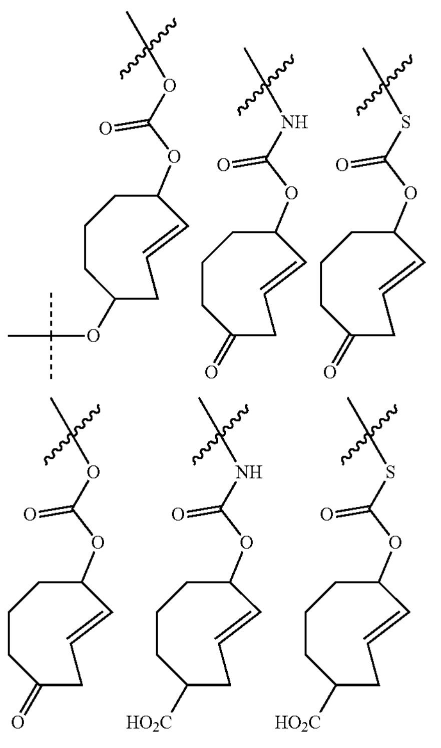
-continued
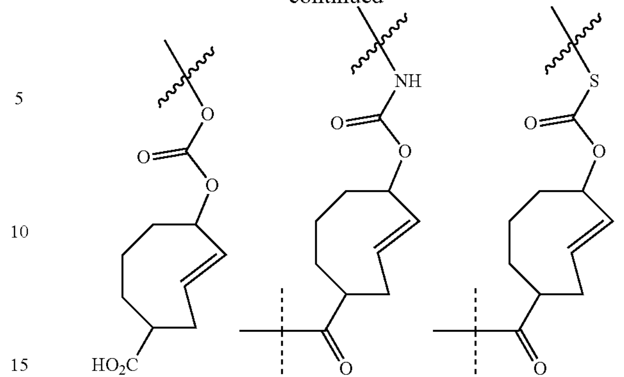
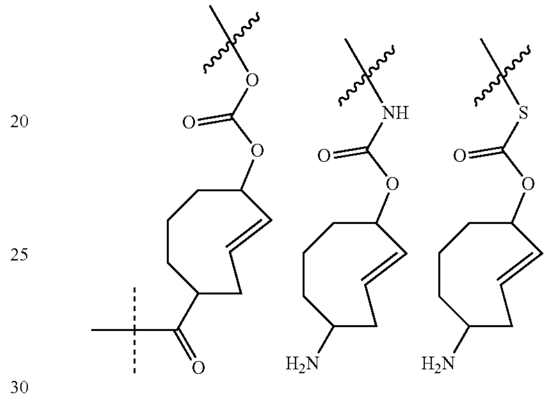
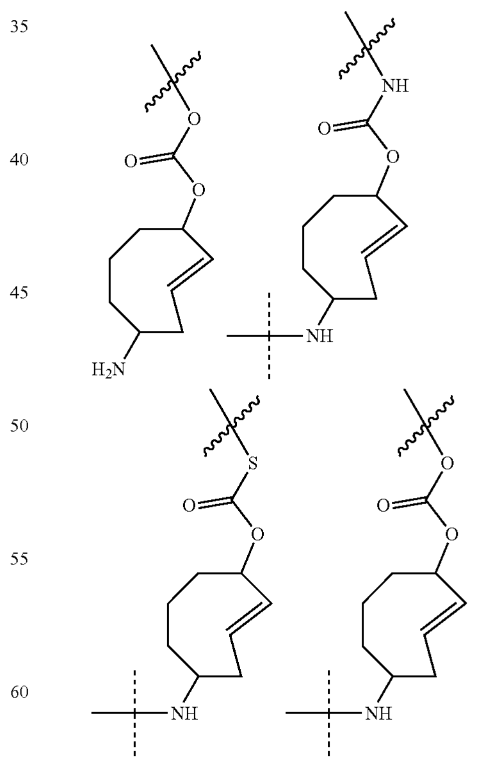
- - - - - = rest of attached $C^B$ or $S^P$—$C^B$
∿∿∿ = rest of attached $C^A$, $L^D$—$C^A$, wherein $L^D$ may optionally comprise $C^B$ or $S^P$—$C^B$

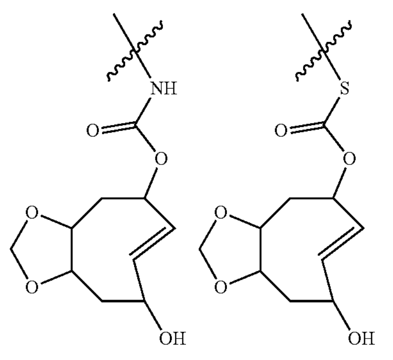
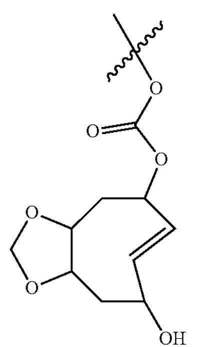
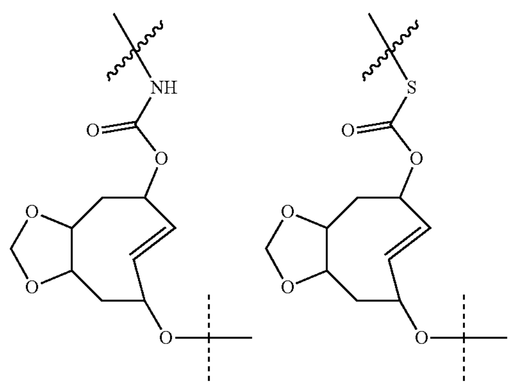
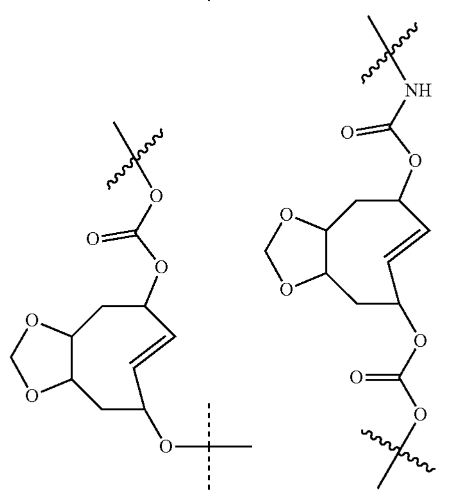
-continued
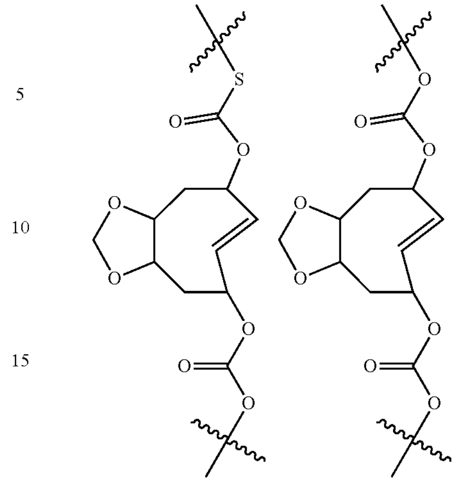
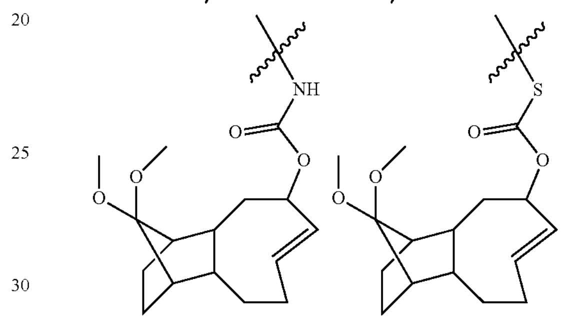
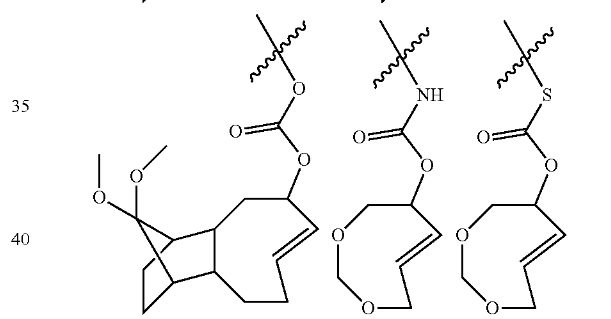
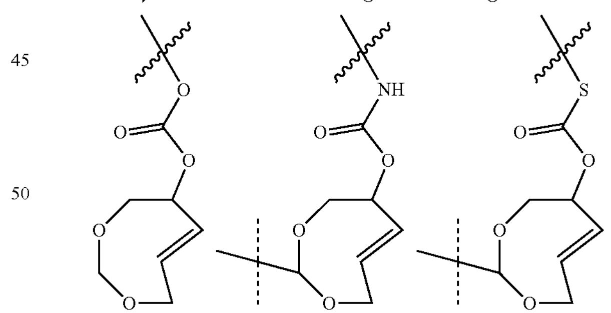
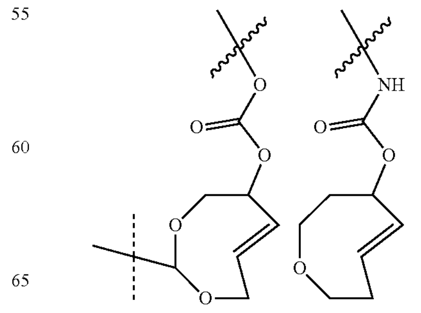

-continued
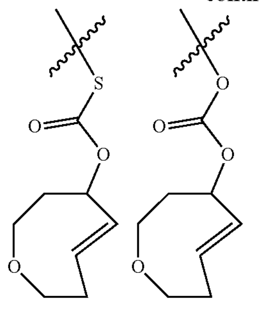
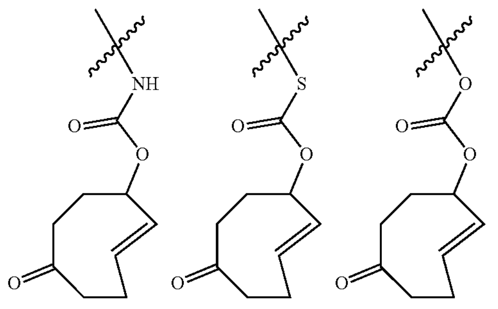
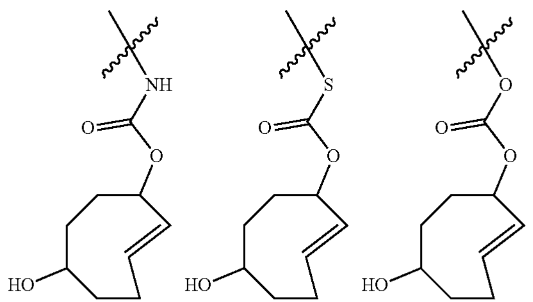
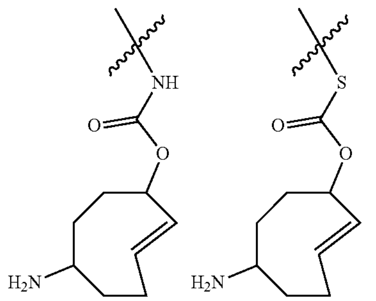
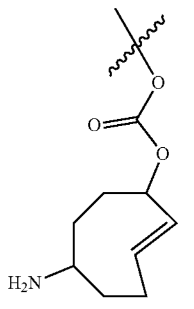
-continued
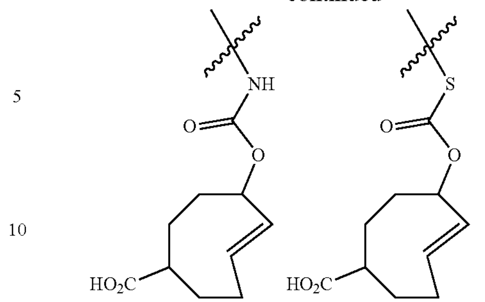
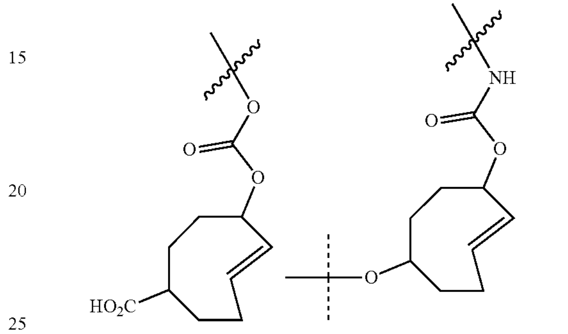
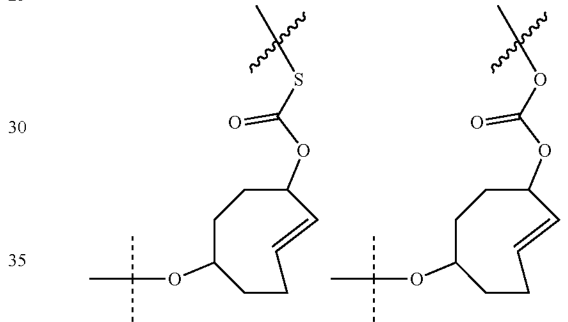
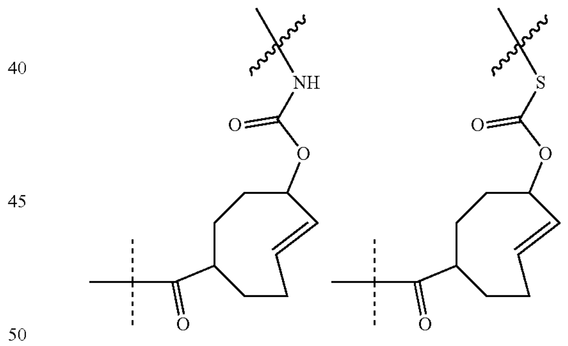
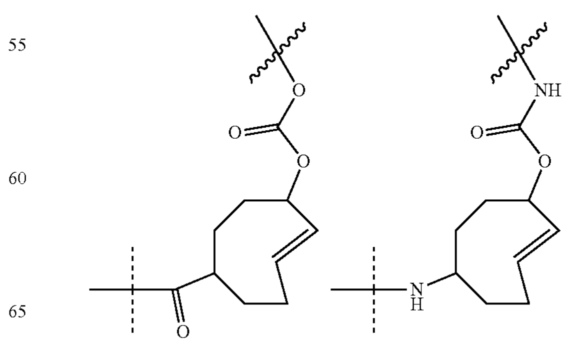

-continued

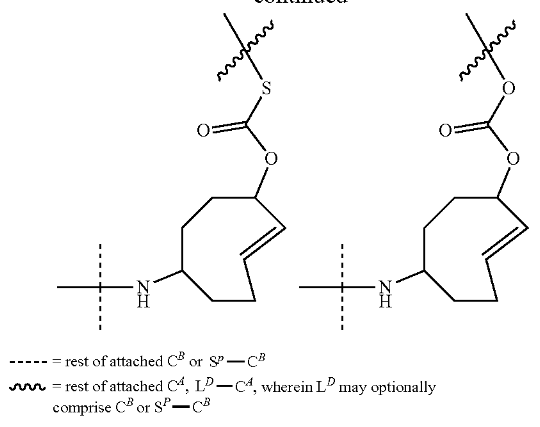

----- = rest of attached $C^B$ or $S^P$—$C^B$

= rest of attached $C^A$, $L^D$—$C^A$, wherein $L^D$ may optionally comprise $C^B$ or $S^P$—$C^B$ Preferred dienophiles, which are optimally selected for $C^A$ release believed to proceed via a strain release mechanism, are selected from the following structures:

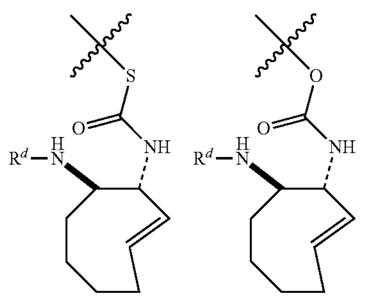

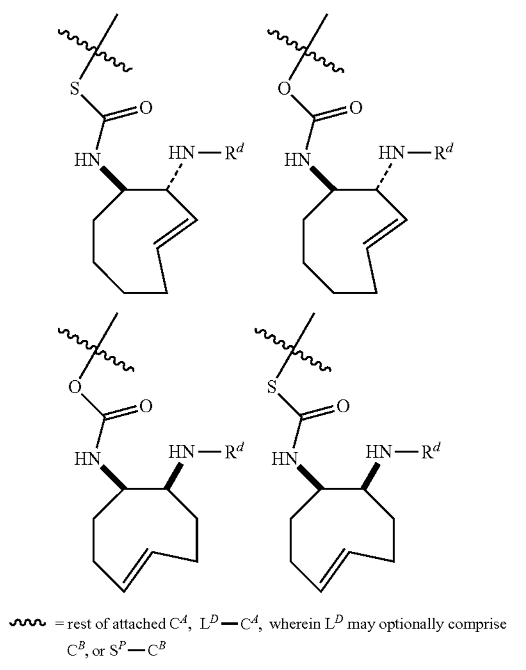

= rest of attached $C^A$, $L^D$—$C^A$, wherein $L^D$ may optionally comprise $C^B$, or $S^P$—$C^B$ In a further preferred embodiment, the dienophile is a compound selected from the following structures:

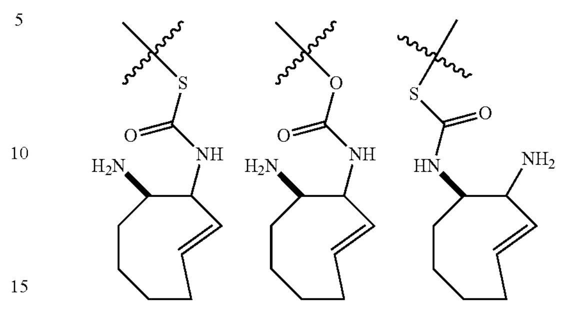

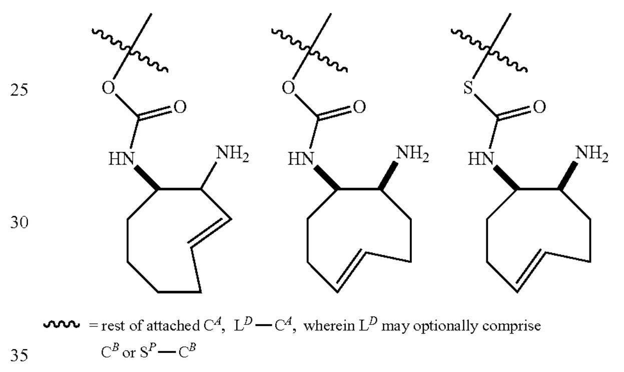

= rest of attached $C^A$, $L^D$—$C^A$, wherein $L^D$ may optionally comprise $C^B$ or $S^P$—$C^B$ In alternative embodiments, the dienophile is a compound selected from the following structures:

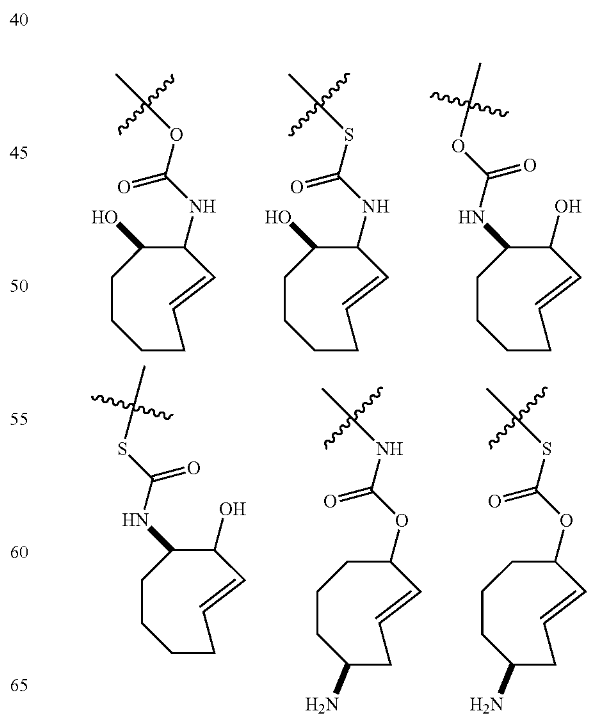

-continued

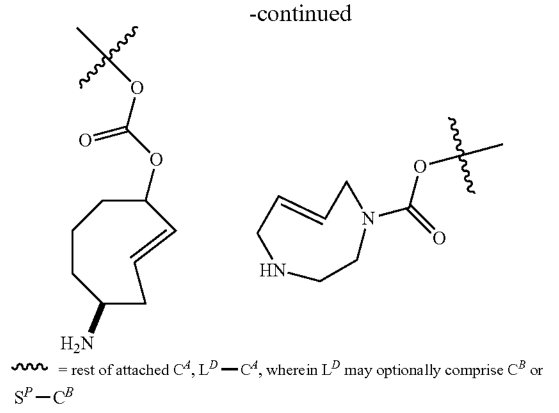

= rest of attached $C^A$, $L^D$—$C^A$, wherein $L^D$ may optionally comprise $C^B$ or $S^P$—$C^B$ The present inventors have come to the non-obvious insight, that the structure of the TCO of formula (1a), par excellence, is suitable to provoke the release of a construct linked to it, as a result of the reaction involving the double bond available in the TCO dienophile, and a diene. The features believed to enable this are (a) the nature of the rDA reaction, which involves a re-arrangement of double bonds, which can be put to use in provoking an elimination cascade; (b) the nature of the rDA adduct that bears a dihydro pyridazine group that is non-aromatic (or another non-aromatic group) and that can rearrange by an elimination reaction to form conjugated double bonds or to form an (e.g. pyridazine) aromatic group, (c) the nature of the rDA adduct that may bear a dihydro pyridazine group that is weakly basic and that may therefore catalyze elimination reactions. Alternatively, the feature believed to enable this is the change in nature of the eight membered ring of the TCO in the dienophile reactant as compared to that of the eight membered ring in the rDA adduct. The eight membered ring in the rDA adduct has significantly more conformational freedom and has a significantly different conformation as compared to the eight membered ring in the highly strained TCO prior to rDA reaction. A nucleophilic site in the dienophile prior to rDA reaction is locked within the specific conformation of the dienophile and is therefore not properly positioned to react intramolecularly and to thereby release the construct.

In contrast, and due to the changed nature of the eight membered ring, this nucleophilic site is properly positioned within the rDA adduct and will react intramolecularly, thereby releasing the construct. According to the above, but without being limited by theory, we believe that the construct release is mediated by strain-release of the TCO-dienophile after and due to the rDA reaction with the diene Activator.

It is to be emphasized that the invention is thus of a scope well beyond specific chemical structures. In a broad sense, the invention puts to use the recognition that the rDA reaction using a dienophile of formula (1a) as well as the rDA adduct embody a versatile platform for enabling provoked construct release in a bioorthogonal reaction.

Reflecting this, the invention also presents the use of the inverse electron-demand Diels-Alder reaction between a trans-cyclooctene and a tetrazine as a chemical tool for the release, in a chemical, biological, or physiological environment, of a bound substance.

The fact that the reaction is bio-orthogonal, and that many structural options exist for the reaction pairs, will be clear to the skilled person. E.g., the rDA reaction is known in the art of pre-targeted medicine. Reference is made to, e.g., WO 2010/119382, WO 2010/119389, and WO 2010/051530. Whilst the invention presents an entirely different use of the reaction, it will be understood that the various structural possibilities available for the rDA reaction pairs as used in pre-targeting, are also available in the field of the present invention.

The dienophile trigger moiety used in the present invention comprises a trans-cyclooctene ring, the ring optionally including one or more hetero-atoms. Hereinafter this eight-membered ring moiety will be defined as a trans-cyclooctene moiety, for the sake of legibility, or abbreviated as "TCO" moiety. It will be understood that the essence resides in the possibility of the eight-membered ring to act as a dienophile and to be released from its conjugated construct upon reaction. The skilled person is familiar with the fact that the dienophile activity is not necessarily dependent on the presence of all carbon atoms in the ring, since also heterocyclic monoalkenylene eight-membered rings are known to possess dienophile activity.

Thus, in general, the invention is not limited to strictly construct-substituted trans-cyclooctene. The person skilled in organic chemistry will be aware that other eight-membered ring-based dienophiles exist, which comprise the same endocyclic double bond as the trans-cyclooctene, but which may have one or more heteroatoms elsewhere in the ring. I.e., the invention generally pertains to eight-membered non-aromatic cyclic alkenylene moieties, preferably a cyclooctene moiety, and more preferably a trans-cyclooctene moiety, comprising a conjugated construct.

Other than is the case with e.g. medicinally active substances, where the in vitro or in vivo action is often changed with minor structural changes, the present invention first and foremost requires the right chemical reactivity combined with an appropriate design of the construct-conjugate. Thus, the possible structures extend to those of which the skilled person is familiar with that these are reactive as dienophiles.

It should be noted that, depending on the choice of nomenclature, the TCO dienophile may also be denoted E-cyclooctene. With reference to the conventional nomenclature, it will be understood that, as a result of substitution on the cyclooctene ring, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dienophiles according to the present invention, also in the event that substituents would formally require the opposite nomenclature. I.e., the invention relates to cyclooctene in which carbon atoms 1 and 6 as numbered below are in the E (entgegen) or trans position.

Formula (1)

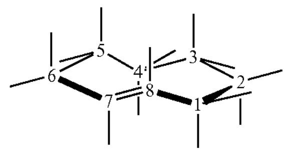

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated.

It is furthermore to be noticed that the term "comprising", used in the description and in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In several chemical formulae below reference is made to "alkyl" and "aryl." In this respect "alkyl", each independently, indicates an aliphatic, straight, branched, saturated, unsaturated and/or or cyclic hydrocarbyl group of up to ten carbon atoms, possibly including 1-10 heteroatoms such as O, N, or S, and "aryl", each independently, indicates an aromatic or heteroaromatic group of up to twenty carbon atoms, that possibly is substituted, and that possibly includes 1-10 heteroatoms such as O, N, P or S. "Aryl" groups also include "alkylaryl" or "arylalkyl" groups (simple example: benzyl groups). The number of carbon atoms that an "alkyl", "aryl", "alkylaryl" and "arylalkyl" contains can be indicated by a designation preceding such terms (i.e. $C_{1-10}$ alkyl means that said alkyl may contain from 1 to 10 carbon atoms). Certain compounds of the invention possess chiral centers and/or tautomers, and all enantiomers, diasteriomers and tautomers, as well as mixtures thereof are within the scope of the invention. In several formulae, groups or substituents are indicated with reference to letters such as "A", "B", "X", "Y", and various (numbered) "R" groups. The definitions of these letters are to be read with reference to each formula, i.e. in different formulae these letters, each independently, can have different meanings unless indicated otherwise.

In all embodiments of the invention as described herein, alkyl is preferably lower alkyl ($C_{1-4}$ alkyl), and each aryl preferably is phenyl.

Activator

The Activator comprises a Bio-orthogonal Reactive Group, wherein this Bio-orthogonal Reactive Group of the Activator is a diene. This diene reacts with the other Bio-orthogonal Reactive Group, the Trigger, and that is a dienophile (vide supra). The diene of the Activator is selected so as to be capable of reacting with the dienophile of the Trigger by undergoing a Diels-Alder cycloaddition followed by a retro Diels-Alder reaction, giving the Retro Diels-Alder adduct. This intermediate adduct then releases the construct or constructs, where this construct release can be caused by various circumstances or conditions that relate to the specific molecular structure of the retro Diels-Alder adduct. Without wishing to be bound by theory, the inventors believe that the Activator is selected such as to provoke construct release via an elimination or cascade elimination (via an intramolecular elimination reaction within the Retro Diels-Alder adduct). This elimination reaction can be a simple one step reaction, or it can be a multiple step reaction that involves one or more intermediate structures. These intermediates may be stable for some time or may immediately degrade to the thermodynamic end product or to the next intermediate structure. When several steps are involved, one can speak of a cascade reaction. In any case, whether it be a simple or a cascade process, the result of the elimination reaction is that the construct gets released from the retro Diels-Alder adduct. Without wishing to be bound by theory, the design of both components (i.e. the diene Activator and the dienophile Trigger) is such that the distribution of electrons within the retro Diels-Alder adduct is unfavorable, so that a rearrangement of these electrons must occur. This situation initiates the intramolecular (cascade) elimination reaction to take place, and it therefore induces the release of the construct or constructs. Occurrence of the elimination reaction in and Trigger release from the construct is not efficient or cannot take place prior to the Retro Diels-Alder reaction, as the Trigger-construct itself is relatively stable as such. Elimination can only take place after the Activator and the Trigger-construct have reacted and have been assembled in the retro Diels-Alder adduct.

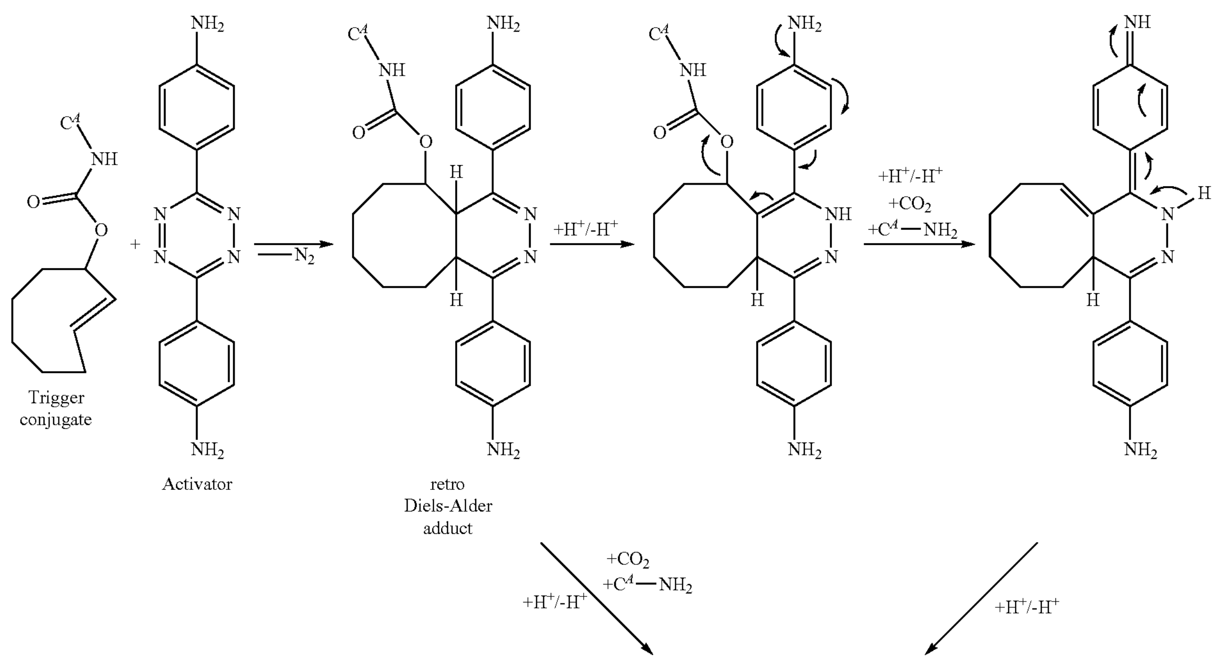

-continued
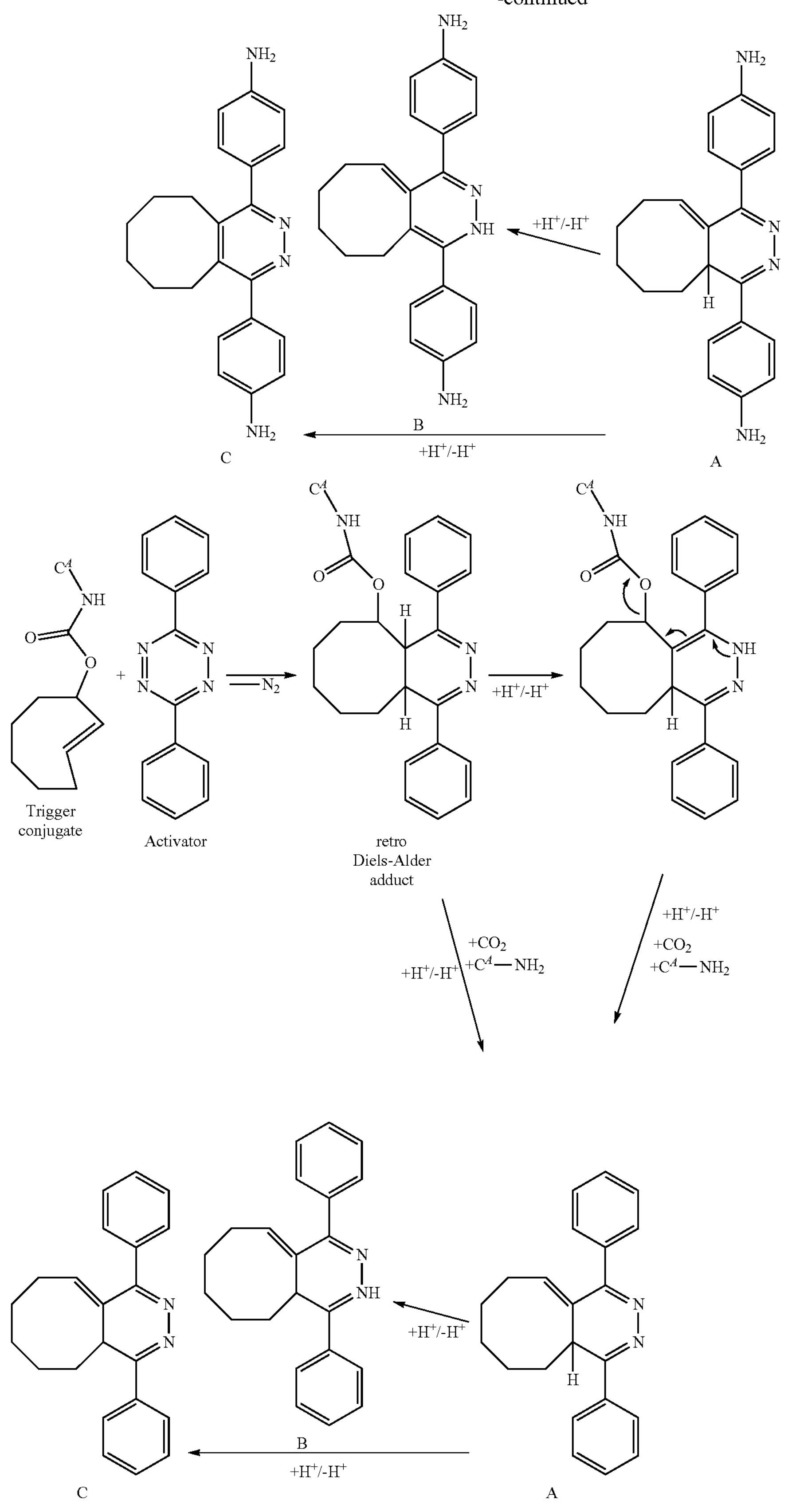

Without wishing to be bound by theory, the above two examples illustrate how the unfavorable distribution of electrons within the retro Diels-Alder adduct can be relieved by an elimination reaction, thereby releasing the construct. In one scenario, the elimination process produces end product A, where this product has a conjugation of double bonds that was not present in the retro Diels-Alder adduct yet. Species A may tautomerize to end product B, or may rearrange to form end product C. Then, the non-aromatic dihydro pyridazine ring in the retro Diels-Alder adduct has been converted to the aromatic pyridazine ring in the end product C. The skilled person will understand that the distribution of electrons in the retro Diels-Alder adduct is generally unfavorable relative to the distribution of the electrons in the end products, either species A or B or C. Thus, the formation of a species more stable than the retro Diels-Alder adduct is the driving force for the (cascade) elimination reaction. In any case, and in whatever way the process is viewed, the construct (here the amine construct-$NH_2$') is effectively expelled from the retro Diels-Alder adduct, while it does not get expelled from the Trigger-construct alone.

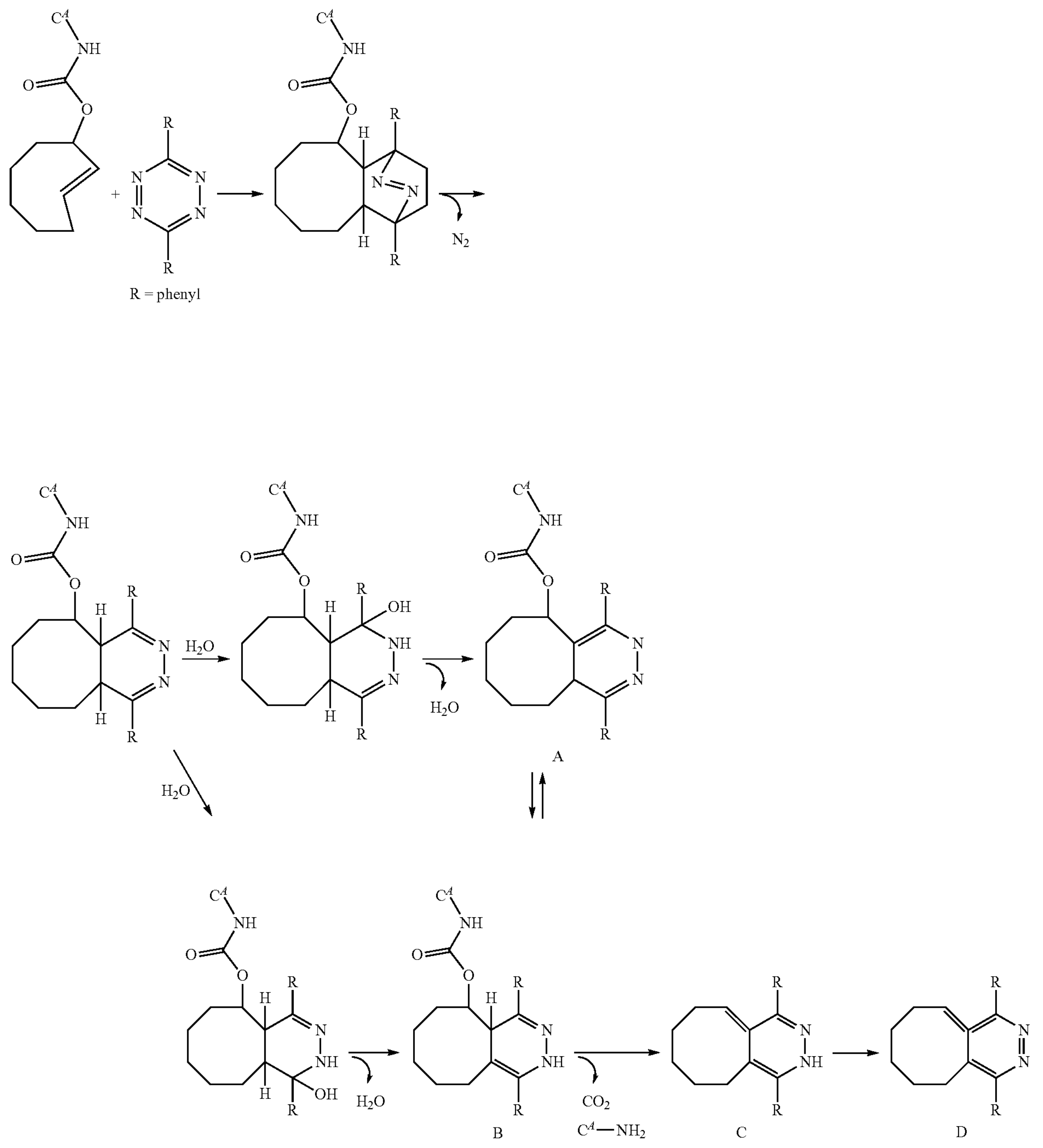

Above scheme depicts a possible alternative release mechanism for the cascade elimination, in addition to the two discussed above. Without wishing to be bound by theory, the below examples illustrates how the unfavorable distribution of electrons within the retro Diels-Alder adduct may be relieved by an elimination reaction, thereby releasing the construct. This process may evolve via various tauromerisations that are all equilibria. Here, the rDA reaction produces tautomers A and B, which can interchange into one and other. Tautomer B can lead to the elimination into product C and thereafter into D.

As discussed above, in this invention, the releasing effect of the rDA reaction is, in one embodiment, caused by an intramolecular cyclization/elimination reaction within the part of the Retro Diels-Alder adduct that originates from the TCO dienophile. A nucleophilic site present on the TCO (i.e. the dienophile, particularly from the $Y^D$ group in this Trigger, vide supra) reacts with an electrophilic site on the same TCO (particularly from the $X^D$ group in this Trigger, vide supra) after this TCO reacts with the Activator to form an rDA adduct. The part of the rDA adduct that originates from the TCO, i.e. the eight membered ring of the rDA adduct, has a different conformation and has an increased conformational freedom compared to the eight membered ring in the TCO prior to the rDA reaction, allowing the nucleophilic reaction to occur, thereby releasing the Construct $C^A$ as a leaving group. The intramolecular cyclization/elimination reaction takes place, as the nucleophilic site and the electrophilic site have been brought together in close proximity within the Retro Diels-Alder adduct, and produce a favorable structure with a low strain. Additionally, the formation of the cyclic structure may also be a driving force for the intramolecular reaction to take place, and thus may also contribute to an effective release of the leaving group, i.e. release of the $C^A$. Reaction between the nucleophilic site and the electrophilic site does not take place or is relatively inefficient prior to the Retro Diels-Alder reaction, as both sites are positioned unfavorably for such a reaction, due to the relatively rigid, conformationally restrained TCO ring. The Prodrug itself is relatively stable as such and elimination is favored only after the Activator and the Prodrug have reacted and have been assembled in a retro Diels-Alder adduct that is subject to intramolecular reaction. In a preferred embodiment the TCO ring is in the crown conformation. The example below illustrates the release mechanism pertaining to this invention.

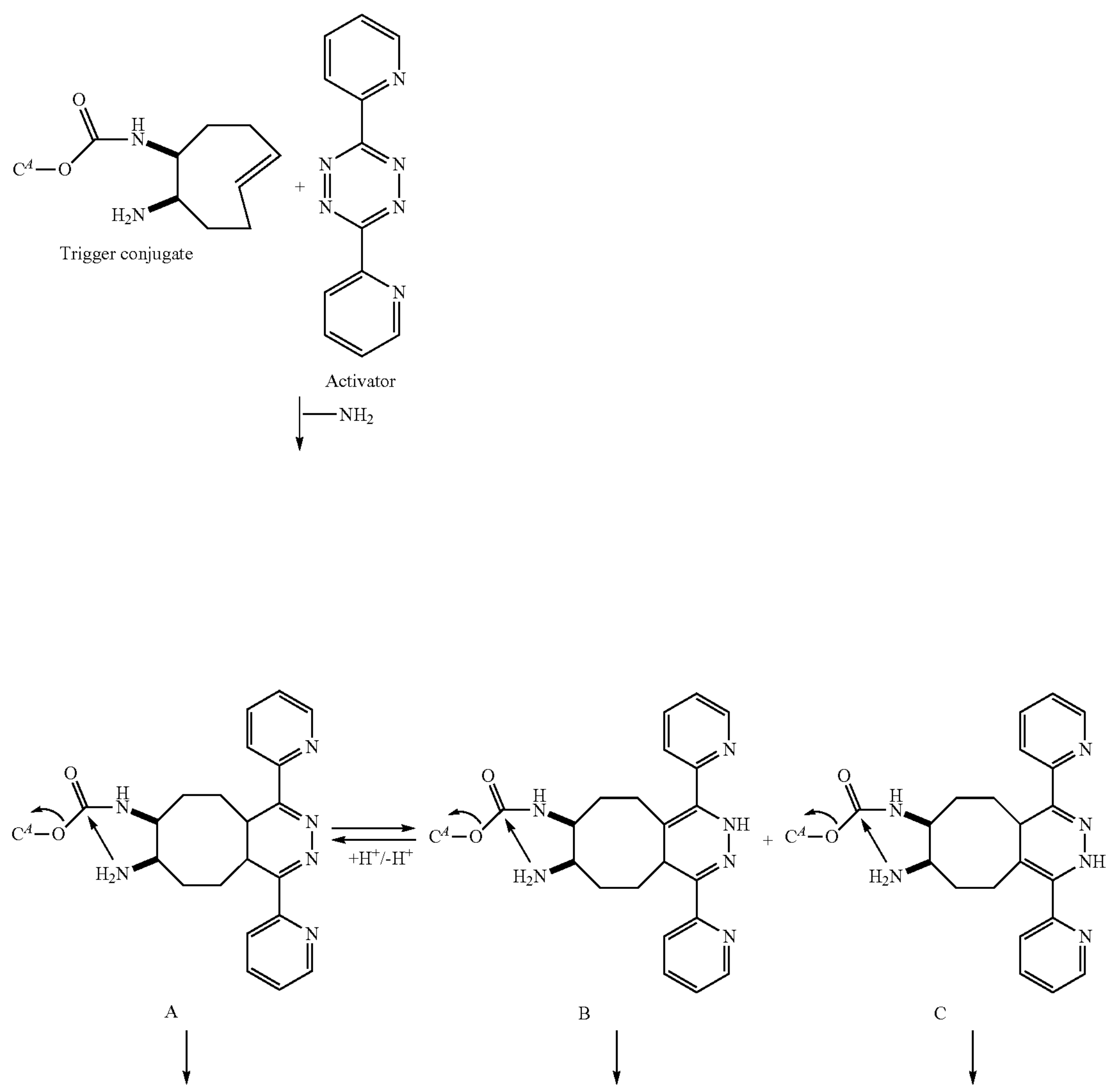

-continued

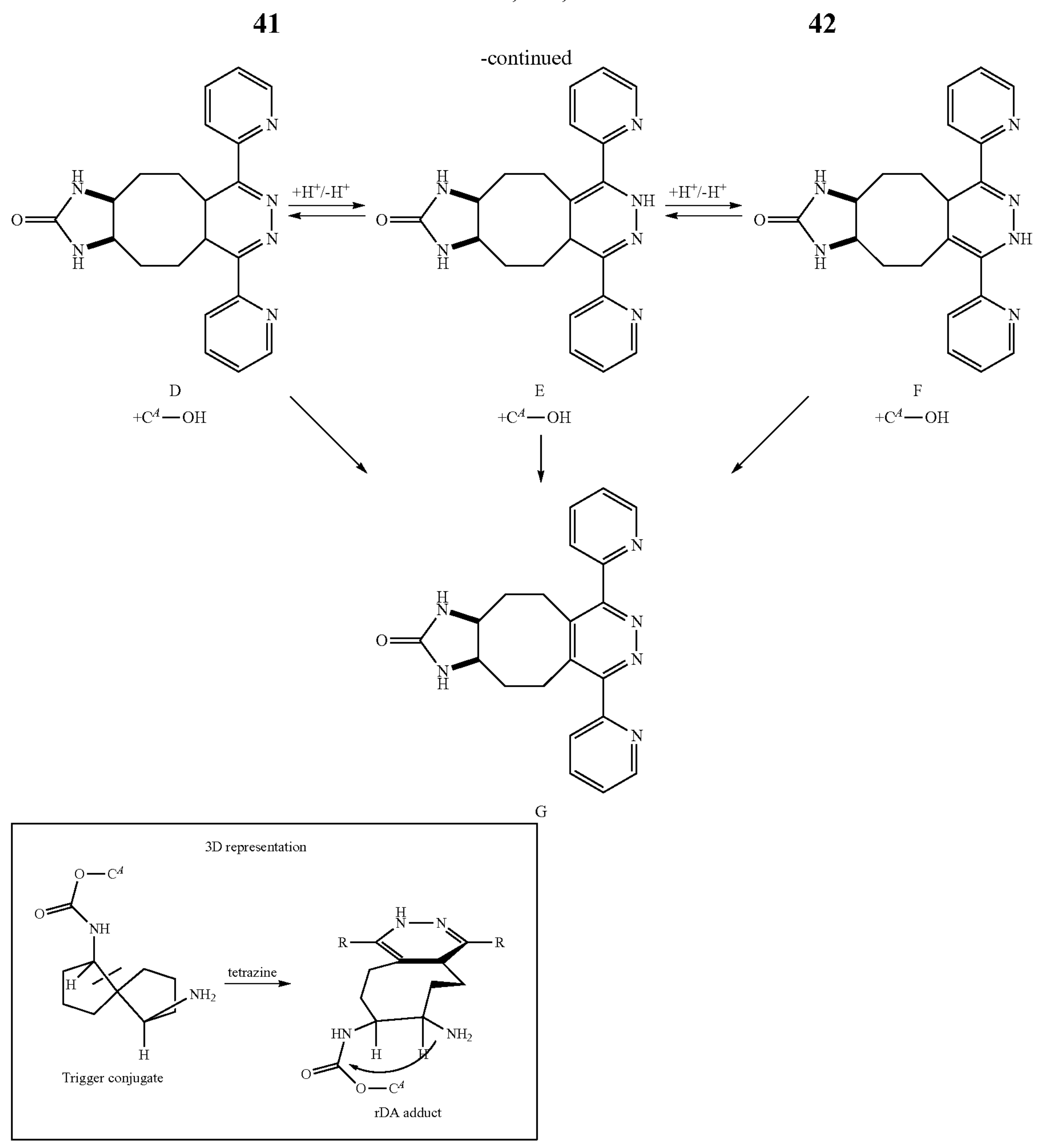

The above example illustrates how the intramolecular cyclization/elimination reaction within the retro Diels-Alder adduct can result in release of a Construct $C^A$. The rDA reaction produces A, which may tautomerize to product B and C. Structures B and C may also tautomerize to one another (not shown). rDA products A, B, and C may intramolecularly cyclize, releasing the bound drug, and affording structures D, E, and F, which optionally may oxidise to form product G. As the tautomerization of A into B and C in water is very fast (in the order of seconds) it is the inventors' belief, that Construct release occurs predominantly from structures B and C. It may also be possible that the nucleophilic site assists in expelling the Construct by a nucleophilic attack on the electrophilic site with subsequent Construct release, but without actually forming a (stable) cyclic structure. In this case, no ring structure is formed and the nucleophilic site remains intact, for example because the ring structure is short-lived and unstable and breaks down with reformation of the nucleophilic site.

Without wishing to be bound by theory, the above example illustrates how the conformational restriction and the resulting unfavorable positioning of the nucleophilic and electrophilic site in the TCO trigger is relieved following rDA adduct formation, leading to an elimination/cyclization reaction and release of the Construct.

With respect to the nucleophilic site on the TCO, one has to consider that the site must be able to act as a nucleophile under biological conditions, so for example at physiological conditions where the pH=ca. 7.4, or for example at conditions where pH-values may be somewhat higher or lower than 7.4. Preferred nucleophiles are amine, thiol or alcohol groups, as these are generally most nucleophilic in nature and therefore most effective.

The Activator is a diene. The person skilled in the art is aware of the wealth of dienes that are reactive in the Retro Diels-Alder reaction. The diene comprised in the Activator can be part of a ring structure that comprises a third double bond, such as a tetrazine (which is a preferred Activator according to the invention).

Generally, the Activator is a molecule comprising a heterocyclic moiety comprising at least 2 conjugated double bonds.

Preferred dienes are given below, with reference to formulae (2)-(4).

(2)

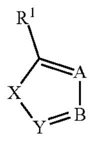

In formula (2) $R^1$ is selected from the group consisting of H, D, alkyl, aryl, $CF_3$, $CF_2$—R', OR', SR', C(=O)R', C(=S)R', C(=O)O—R', C(=O)S—R', C(=S)O—R', C(=S)S—R''', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", NR'C(=O)NR"R", NR'C(=S)NR"R" with each R' and each R" independently being H, D, aryl or alkyl; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, D, alkyl, aryl, C(=O)OR', C(=O)SR', C(=S)OR', C(=S)SR', C(=O)NR'R" with R' and R" each independently being H, D, aryl or alkyl.

(3)

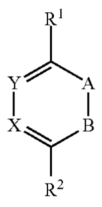

A diene particularly suitable as a reaction partner for cyclooctene is given in formula (3), wherein $R^1$ and $R^2$ each independently are selected from the group consisting of H, D, alkyl, aryl, $CF_3$, $CF_2$—R', $NO_2$, OR', SR', C(=O)R', C(=S)R', OC(=O)R''', SC(=O)R''', OC(=S)R''', SC(=S)R''', S(=O)R', $S(=O)_2R'''$, $S(=O)_2NR'R"$, C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR"R", NR'C(=S)NR"R" with each R' and each R" independently being H, D, aryl or alkyl, and R''' independently being aryl or alkyl; A is selected from the group consisting of N-alkyl, N-aryl, C=O, and CN-alkyl; B is O or S; X is selected from the group consisting of N, CH, C-alkyl, C-aryl, CC(=O)R', CC(=S)R', CS(=O)R', $CS(=O)_2R'''$, CC(=O)O—R', CC(=O)S—R', CC(=S)O—R', CC(=S)S—R', CC(=O)NR'R", CC(=S)NR'R", R' and R" each independently being H, D, aryl or alkyl and R''' independently being aryl or alkyl; Y is selected from the group consisting of CH, C-alkyl, C-aryl, N, and $N^+O^-$.

(4)

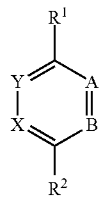

Another diene particularly suitable as a reaction partner for cyclooctene is diene (4), wherein $R^1$ and $R^2$ each independently are selected from the group consisting of H, D, alkyl, aryl, $CF_3$, $CF_2$—R', NO, $NO_2$, OR', SR', CN, C(=O)R', C(=S)R', OC(=O)R''', SC(=O)R''', OC(=S)R''', SC(=S)R''', S(=O)R', $S(=O)_2R'''$, $S(=O)_2OR'$, $PO_3R'R"$, $S(=O)_2NR'R"$, C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR"R", NR'C(=S)NR"R" with each R' and each R" independently being H, D, aryl or alkyl, and R''' independently being aryl or alkyl; A is selected from the group consisting of N, C-alkyl, C-aryl, and $N^+O^-$; B is N; X is selected from the group consisting of N, CH, C-alkyl, C-aryl, CC(=O)R', CC(=S)R', CS(=O)R', $CS(=O)_2R'''$, CC(=O)O—R', CC(=O)S—R', CC(=S)O—R', CC(=S)S—R', CC(=O)NR'R", CC(=S)NR'R", R' and R" each independently being H, D, aryl or alkyl and R''' independently being aryl or alkyl; Y is selected from the group consisting of CH, C-alkyl, C-aryl, N, and $N^+O^-$.

(5)

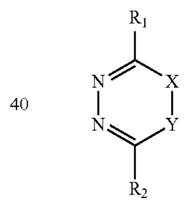

(6)

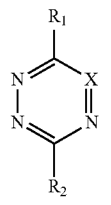

(7)

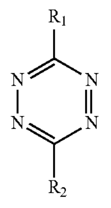

According to the invention, particularly useful dienes are 1,2-diazine, 1,2,4-triazine and 1,2,4,5-tetrazine derivatives, as given in formulas (5), (6) and (7), respectively.

The 1,2-diazine is given in (5), wherein $R^1$ and $R^2$ each independently are selected from the group consisting of H, D, alkyl, aryl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R'', NR'C(=S)NR''R'' with each R' and each R'' independently being H, D, aryl or alkyl, and R''' independently being aryl or alkyl; X and Y each independently are selected from the group consisting of O, N-alkyl, N-aryl, C=O, CN-alkyl, CH, C-alkyl, C-aryl, CC(=O)R', CC(=S)R', CS(=O)R', CS(=O)$_2$R''', CC(=O)O—R', CC(=O)S—R', CC(=S)O—R', CC(=S)S—R', CC(=O)NR'R'', CC(=S)NR'R'', with R' and R'' each independently being H, D, aryl or alkyl and R''' independently being aryl or alkyl, where X—Y may be a single or a double bond, and where X and Y may be connected in a second ring structure apart from the 6-membered diazine. Preferably, X—Y represents an ester group (X=O and Y=C=O; X—Y is a single bond) or X—Y represents a cycloalkane group (X=CR' and Y=CR''; X—Y is a single bond; R' and R'' are connected), preferably a cyclopropane ring, so that R' and R'' are connected to each other at the first carbon atom outside the 1,2-diazine ring.

The 1,2,4-triazine is given in (6), wherein $R^1$ and $R^2$ each independently are selected from the group consisting of H, D, alkyl, aryl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R'', NR'C(=S)NR''R'' with each R' and each R'' independently being H, D, aryl or alkyl, and R''' independently being aryl or alkyl; X is selected from the group consisting of CH, C-alkyl, C-aryl, CC(=O)R', CC(=S)R', CS(=O)R', CS(=O)$_2$R''', CC(=O)O—R', CC(=O)S—R', CC(=S)O—R', CC(=S)S—R', CC(=O)NR'R'', CC(=S)NR'R'', R' and R'' each independently being H, D, aryl or alkyl and R''' independently being aryl or alkyl.

The 1,2,4,5-tetrazine is given in (7), wherein $R^1$ and $R^2$ each independently are selected from the group consisting of H, D, alkyl, aryl, $CF_3$, $CF_2$—R', NO, $NO_2$, OR', SR', CN, C(=O)R', C(=S)R', OC(=O)R''', SC(=O)R''', OC(=S)R''', SC(=S)R''', S(=O)R', S(=O)$_2$R''', S(=O)$_2$OR', $PO_3$R'R'', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R'', NR'C(=S)NR''R'' with each R' and each R'' independently being H, D, aryl or alkyl, and R''' independently being aryl or alkyl.

Electron-deficient 1,2-diazines (5), 1,2,4-triazines (6) or 1,2,4,5-tetrazines (7) are especially interesting as such dienes are generally more reactive towards dienophiles. Di-tri- or tetra-azines are electron deficient when they are substituted with groups or moieties that do not generally hold as electron-donating, or with groups that are electron-withdrawing. For example, $R^1$ and/or $R^2$ may denote a substituent selected from the group consisting of H, D, alkyl, $NO_2$, F, Cl, $CF_3$, CN, COOR, CONHR, $CONR_2$, COR, $SO_2$R, $SO_2$OR, $SO_2NR_2$, $PO_3R_2$, NO, 2-pyridyl, 3-pyridyl, 4-pyridyl, 2,6-pyrimidyl, 3,5-pyrimidyl, 2,4-pyrimidyl, 2,4 imidazyl, 2,5 imidazyl or phenyl, optionally substituted with one or more electron-withdrawing groups such as $NO_2$, F, Cl, $CF_3$, CN, COOR, CONHR, CONR, COR, $SO_2$R, $SO_2$OR, $SO_2NR_2$, $PO_3R_2$, NO, Ar, wherein R is H, D or $C_1$-$C_6$ alkyl, and Ar stands for an aromatic group, particularly phenyl, pyridyl, or naphthyl.

The 1,2,4,5-tetrazines of formula (7) are most preferred as Activator dienes, as these molecules are most reactive in retro Diels-Alder reactions with dienophiles, such as the preferred TCO dienophiles, even when the $R^1$ and/or $R^2$ groups are not necessarily electron withdrawing, and even when $R^1$ and/or $R^2$ are in fact electron donating. Electron donating groups are for example OH, OR', SH, SR', $NH_2$, NHR', NR'R'', NHC(=O)R'', NR'C(=O)R'', NHC(=S)R'', NR'C(=S)R'', $NHSO_2$R'', NR'$SO_2$R'' with R' and R'' each independently being alkyl or aryl groups. Examples of other electron donating groups are phenyl groups with attached to them one or more of the electron donating groups as mentioned in the list above, especially when substituted in the 2-, 4- and/or 6-position(s) of the phenyl group.

According to the invention, 1,2,4,5-tetrazines with two electron withdrawing residues, or those with one electron withdrawing residue and one residue that is neither electron withdrawing nor donating, are called electron deficient. In a similar way, 1,2,4,5-tetrazines with two electron donating residues, or those with one electron donating residue and one residue that is neither electron withdrawing nor donating, are called electron sufficient. 1,2,4,5-Tetrazines with two residues that are both neither electron withdrawing nor donating, or those that have one electron withdrawing residue and one electron donating residue, are neither electron deficient nor electron sufficient.

The 1,2,4,5-tetrazines can be asymmetric or symmetric in nature, i.e. the $R^1$ and $R^2$ groups in formula (7) may be different groups or may be identical groups, respectively. Symmetric 1,2,4,5-tetrazines are more convenient as these Activators are more easily accessible via synthetic procedures.

We have tested several 1,2,4,5-tetrazines with respect to their ability as Activator to release a model construct (e.g. benzyl amine, phenol) from a Trigger-construct conjugate, and we have found that tetrazines that are electron deficient, electron sufficient or neither electron deficient nor electron sufficient are capable to induce the construct release. Furthermore, both symmetric as well as asymmetric tetrazines were effective.

Electron deficient 1,2,4,5 tetrazines and 1,2,4,5-tetrazines that are neither electron deficient nor electron sufficient are generally more reactive in retro Diels-Alder reactions with dienophiles (such as TCOs), so these two classes of 1,2,4,5-tetrazines are preferred over electron sufficient 1,2,4,5-tetrazines, even though the latter are also capable of inducing Trigger release in Trigger-construct conjugates.

EXAMPLES

In the following paragraphs specific examples of 1,2,4,5-tetrazine Activators according to the second embodiment of this invention will be highlighted by defining the $R^1$ and $R^2$ residues in formula (7).

Symmetric electron deficient 1,2,4,5-tetrazines with electron withdrawing residues are for example those with $R^1$=$R^2$=H, D, 2-pyridyl, 3-pyridyl, 4-pyridyl, 2,4-pyrimidyl, 2,6-pyrimidyl, 3,5-pyrimidyl, 2,3,4-triazyl or 2,3,5-triazyl. Other examples are those with $R^1$=$R^2$=phenyl with COOH or COOMe carboxylate, or with CN nitrile, or with $CONH_2$, $CONHCH_3$ or $CON(CH_3)_2$ amide, or with $SO_3H$ or $SO_3Na$ sulfonate, or with $SO_2NH_2$, $SO_2NHCH_3$ or $SO_2N(CH_3)_2$ sulfonamide, or with $PO_3H_2$ or $PO_3Na_2$ phosphonate substituents in the 2-, 3- or 4-position of the phenyl group, or in the 3- and 5-positions, or in the 2- and 4-positions, or in the 2,- and 6-positions of the phenyl group. Other substitution patterns are also possible, including the use of different substituents, as long as the tetrazine remains symmetric. See below for some examples of these structures.

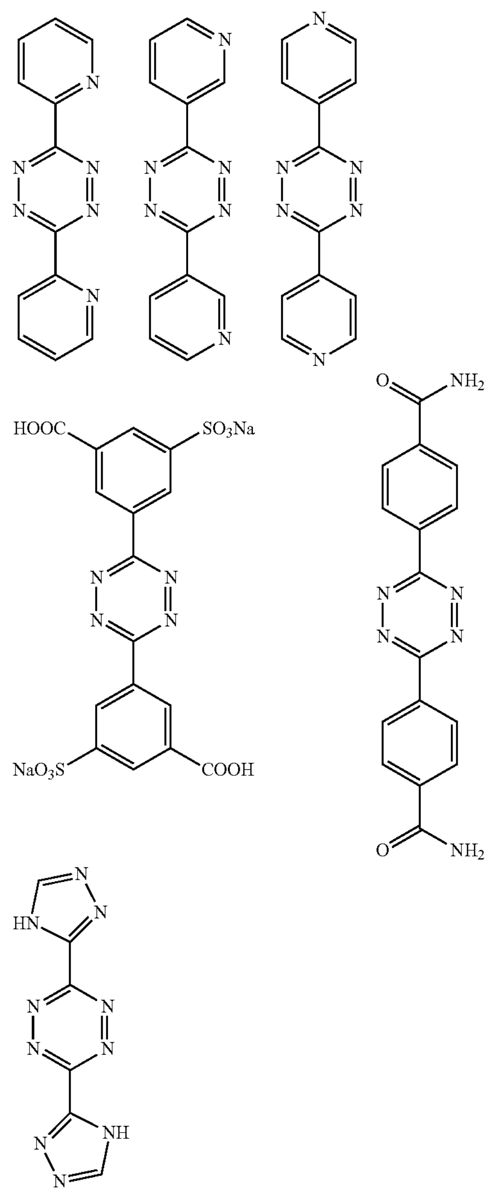

Symmetric electron sufficient 1,2,4,5-tetrazines with electron donating residues are for example those with $R^1=R^2=OH$, OR', SH, SR', $NH_2$, NHR', $NR'_2$, NH—CO—R', NH—SO—R', NH—$SO_2$—R', 2-pyrryl, 3-pyrryl, 2-thiophene, 3-thiophene, where R' represents a methyl, ethyl, phenyl or tolyl group. Other examples are those with $R^1=R^2$=phenyl with OH, OR', SH, SR', $NH_2$, NHR', $NR'_2$, NH—CO—R', NR"—CO—R', NH—SO—R' or NH—$SO_2$—R' substituent(s), where R' represents a methyl, ethyl, phenyl or tolyl group, where R" represents a methyl or ethyl group, and where the substitution is done on the 2- or 3- or 4- or 2- and 3- or 2- and 4- or 2- and 5- or 2- and 6- or 3- and 4- or 3- and 5- or 3-, 4- and 5-position(s). See below for some examples of these structures.

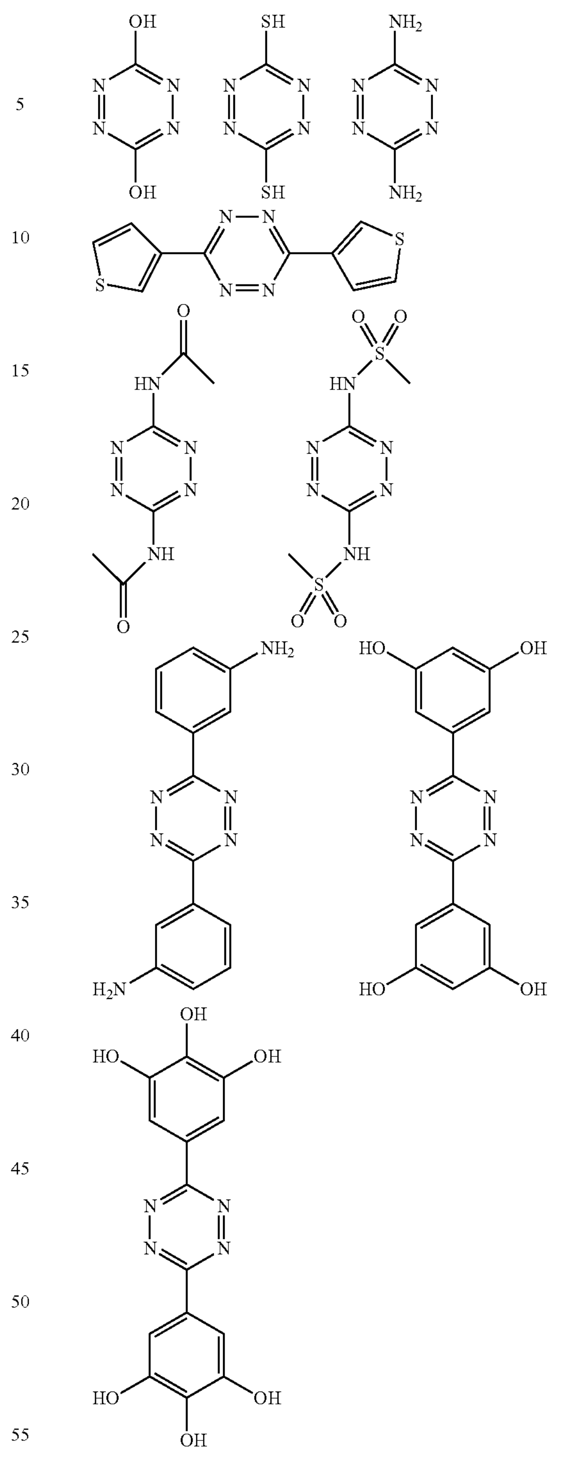

Symmetric 1,2,4,5-tetrazines with neither electron withdrawing nor electron donating residues are for example those with $R^1=R^2$=phenyl, methyl, ethyl, (iso)propyl, 2,4-imidazyl, 2,5-imidazyl, 2,3-pyrazyl or 3,4-pyrazyl. Other examples are those where $R^1=R^2$-a hetero(aromatic) cycle such as a oxazole, isoxazole, thiazole or oxazoline cycle. Other examples are those where $R^1=R^2$=a phenyl with one electron withdrawing substituent selected from COOH, COOMe, CN, $CONH_2$, $CONHCH_3$, $CON(CH_3)_2$, $SO_3H$, $SO_3Na$, $SO_2NH_2$, $SO_2NHCH_3$, $SO_2N(CH_3)_2$, $PO_3H_2$ or $PO_3Na_2$ and one electron donating substituent selected from OH, OR', SH, SR', $NH_2$, NHR', $NR'_2$, NH—CO—R', NR"—CO—R', NH—SO—R' or NH—$SO_2$—R' substituent(s), where R' represents a methyl, ethyl, phenyl or tolyl group and where R" represents a methyl or ethyl group. Substitutions can be done on the 2- and 3-, 2- and 4-, 2,- and 5-, 2- and 6, 3- and 4-, and the 3- and 5-positions. Yet other examples are those where $R^1$=$R^2$=a pyridyl or pyrimidyl moiety with one electron donating substituent selected from OH, OR', SH, SR', $NH_2$, NHR', $NR'_2$, NH—CO—R', NR"—CO—R', NH—SO—R' or NH—$SO_2$—R' substituents, where R' represents a methyl, ethyl, phenyl or tolyl group and where R" represents a methyl or ethyl group. See below for some examples.

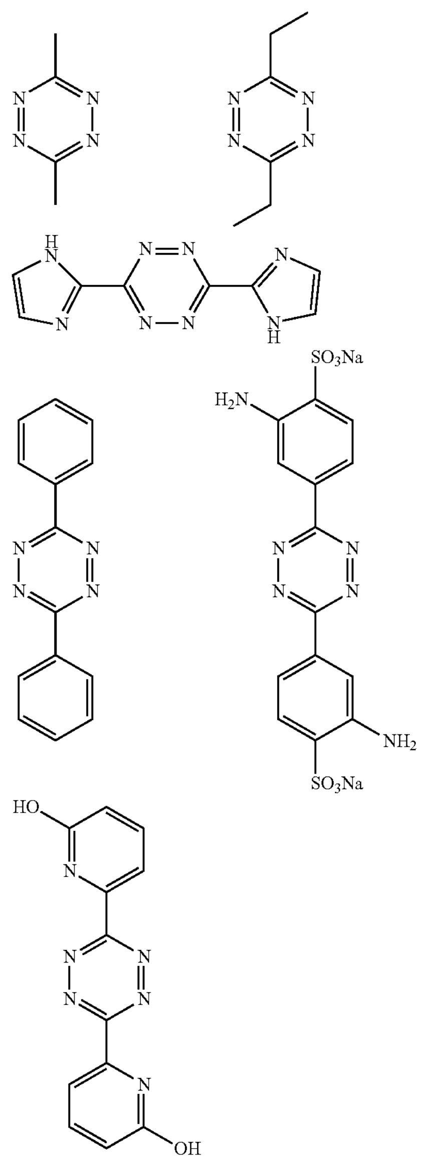

In case asymmetric 1,2,4,5-tetrazines are considered, one can choose any combination of given $R^1$ and $R^2$ residues that have been highlighted and listed above for the symmetric tetrazines according to formula (7), provided of course that $R^1$ and $R^2$ are different. Preferred asymmetric 1,2,4,5-tetrazines are those where at least one of the residues $R^1$ or $R^2$ is electron withdrawing in nature. Find below some example structures drawn.

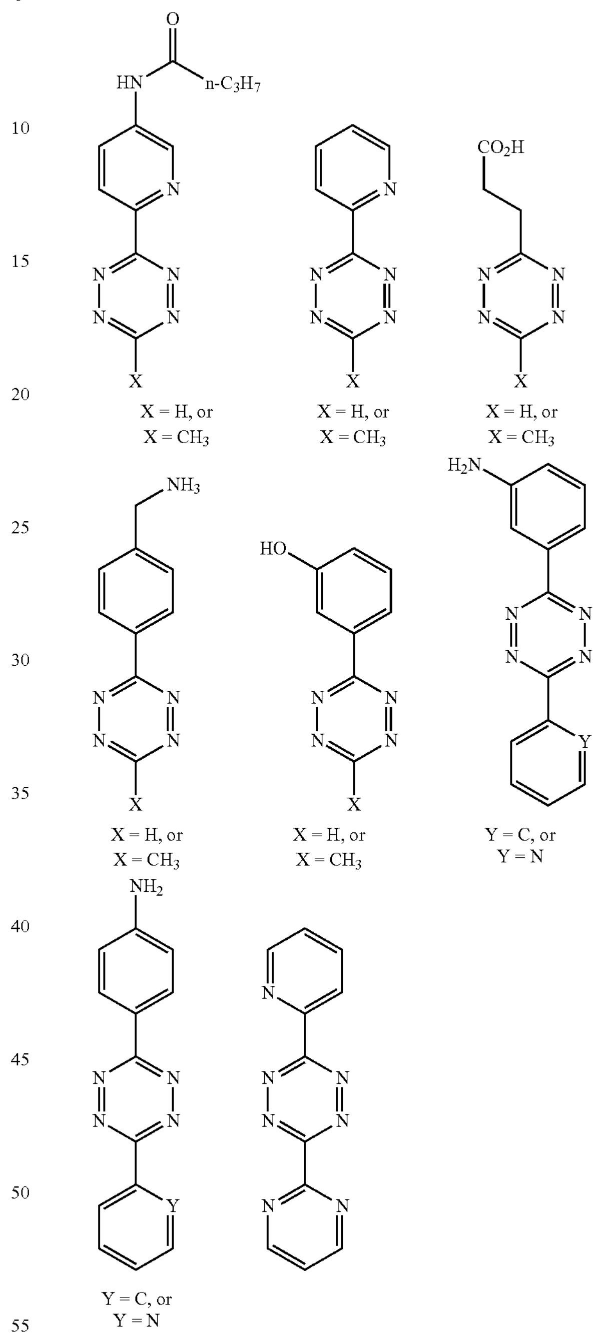

X = H, or X = $CH_3$

X = H, or X = $CH_3$

X = H, or X = $CH_3$

X = H, or X = $CH_3$

X = H, or X = $CH_3$

Y = C, or Y = N

Y = C, or Y = N

Further Considerations Regarding the Activator

Preferred Activators are 1,2-diazines, 1,2,4-triazines and 1,2,4,5-tetrazines, particularly 1,2,4,5-tetrazines, are the preferred diene Activators. In the below, some relevant features of the Activator will be highlighted, where it will also become apparent that there are plentiful options for designing the right Activator formulation for every specific application.

According to one aspect of the invention, the Activator, e.g. a 1,2,4,5-tetrazine, has useful and beneficial pharmacological and pharmaco-kinetic properties, implying that the Activator is non-toxic or at least sufficiently low in toxicity, produces metabolites that are also sufficiently low in toxicity, is sufficiently soluble in the applicable chemical, biological, or physiological solutions, can be applied in aqueous or other formulations that are routinely used in pharmaceutics, and has the right log D value where this value reflects the hydrophilic/hydrophobic balance of the Activator molecule at physiological pH. As is known in the art, log D values can be negative (hydrophilic molecules) or positive (hydrophobic molecules), where the lower or the higher the log D values become, the more hydrophilic or the more hydrophobic the molecules are, respectively. Log D values can be predicted fairly adequately for most molecules, and log D values of Activators can be tuned by adding or removing polar or a polar groups in their designs. Find below some Activator designs with their corresponding calculated log D values (at pH=7.4). Note that addition of methyl, cycloalkylene, pyridine, amine, alcohol or sulfonate groups or deletion of phenyl groups modifies the log D value, and that a very broad range of log D values is accessible.

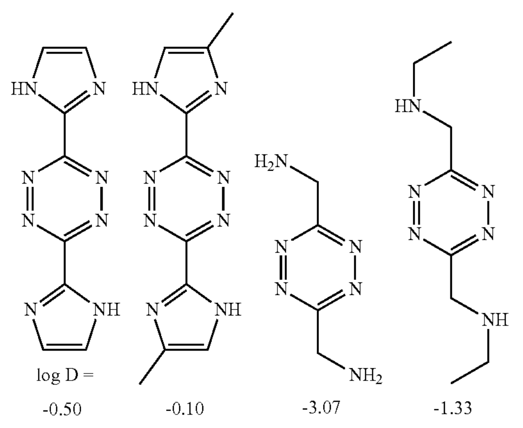

log D =

-0.50 -0.10 -3.07 -1.33

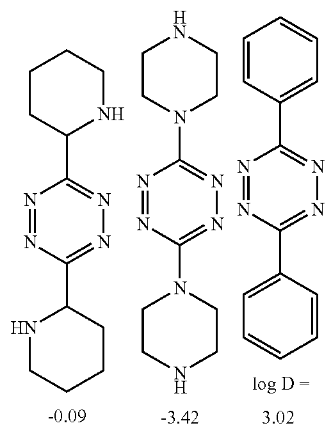

log D =

-0.09 -3.42 3.02

-continued

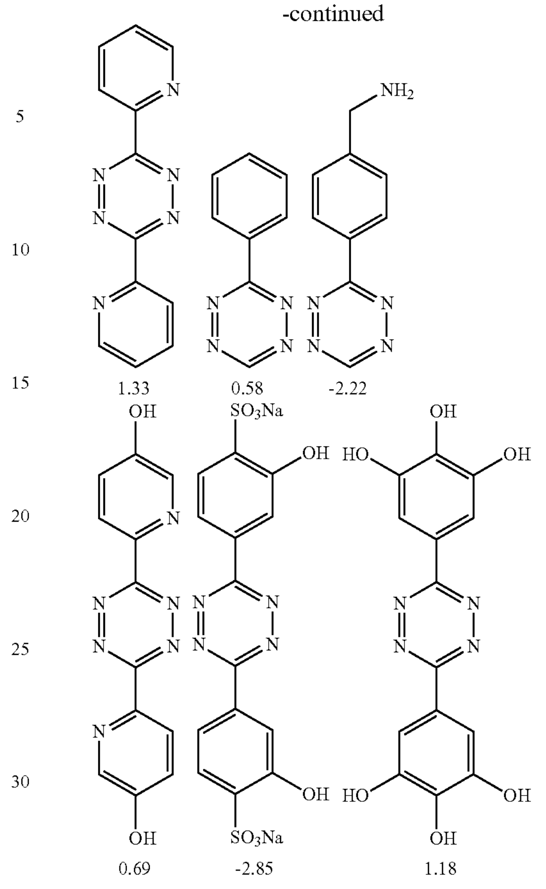

1.33 0.58 -2.22

0.69 -2.85 1.18

The given log D numbers have been calculated from a weighed method, with equal importance of the 'VG' (Viswanadhan, V. N.; Ghose, A. K.; Revankar, G. R.; Robins, R. K., J. Chem. Inf. Comput. Sci., 1989, 29, 163-172), 'KLOP' (according to Klopman, G.; Li, Ju-Yun.; Wang, S.; Dimayuga, M.: J. Chem. Inf. Comput. Sci., 1994, 34, 752) and 'PHYS' (according to the PHYSPROP© database) methods, based on an aqueous solution in 0.1 M in $Na^+/K^+Cl^-$.

The Activator according to the invention has an appropriate reactivity towards the Trigger-construct, and this can be regulated by making the diene, particularly the 1,2,4,5-tetrazines, sufficiently electron deficient. Sufficient reactivity will ensure a fast retro Diels-Alder reaction with the Trigger-construct as soon as it has been reached by the Activator.

The Activator according to the invention may be multimeric, so that multiple diene moieties may be attached to a molecular scaffold, particularly to e.g. multifunctional molecules, carbohydrates, polymers, dendrimers, proteins or peptides, where these scaffolds are preferably water soluble. Examples of scaffolds that can be used are (multifunctional) polyethylene glycols, poly (propylene imine) (PPI) dendrimers, PAMAM dendrimers, glycol-based dendrimers, heparin derivatives, hyaluronic acid derivatives or serum albumin proteins such as HSA. Furthermore, the Activator may be conjugated to resins, especially solid phase synthesis resins, such as polystyrene.

With respect to application in a cellular environment, depending on the position of the Trigger-construct (e.g. inside the cell or outside the cell) the Activator is designed to be able to effectively reach this Trigger-construct. Therefore, the Activator can for example be tailored by varying its log D value, its reactivity or its charge. The Activator may even be engineered with a targeting agent (e.g. a protein, a peptide and/or a sugar moiety), to achieve spatial control over the activation. In case a targeting agent is applied, it is preferred that it is a simple moiety (i.e. a short peptide or a simple sugar).

According to the invention, a mixture of different Activators can be applied. This may be relevant for regulation of the release profile of the Construct.

Preferred activators with Triggers based on the cascade mechanism are:

(8a)

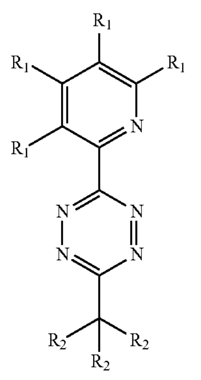

(8b)

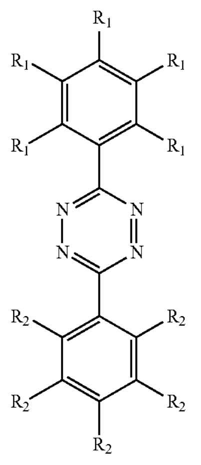

The 1,2,4,5-tetrazine given in Formula (8a) and (8b), wherein each $R^1$ and each $R^2$ independently are selected from the group consisting of H, D, alkyl, aryl, $CF_3$, $CF_2$—R', $NO_2$, OR', SR', C(═O)R', C(═S)R', OC(═O)R''', SC(═O)R''', OC(═S)R''', SC(═S)R''', S(═O)R', $S(═O)_2R'''$, $S(═O)_2NR'R''$, C(═O)O—R', C(═O)S—R', C(═S)O—R', C(═S)S—R', C(═O)NR'R'', C(═S)NR'R'', NR'R'', NR'C(═O)R'', NR'C(═S)R'', NR'C(═O)OR'', NR'C(═S)OR'', NR'C(═O)SR'', NR'C(═S)SR'', OC(═O)NR'R'', SC(═O)NR'R'', OC(═S)NR'R'', SC(═S)NR'R'', NR'C(═O)NR''R'', NR'C(═S)NR''R'' with each R' and each R'' independently being H, D, aryl or alkyl, and R''' independently being aryl or alkyl.

Other preferred activators with Triggers based on the cascade mechanism are:

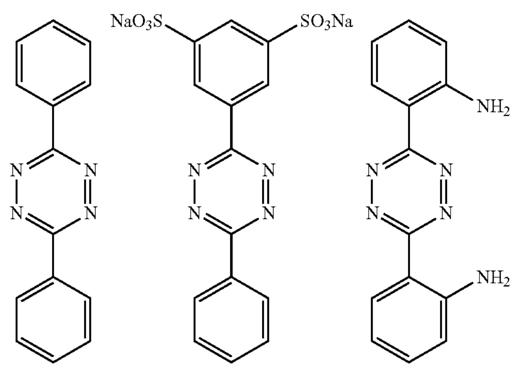

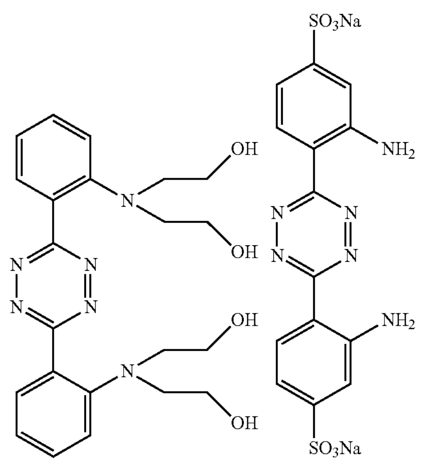

-continued
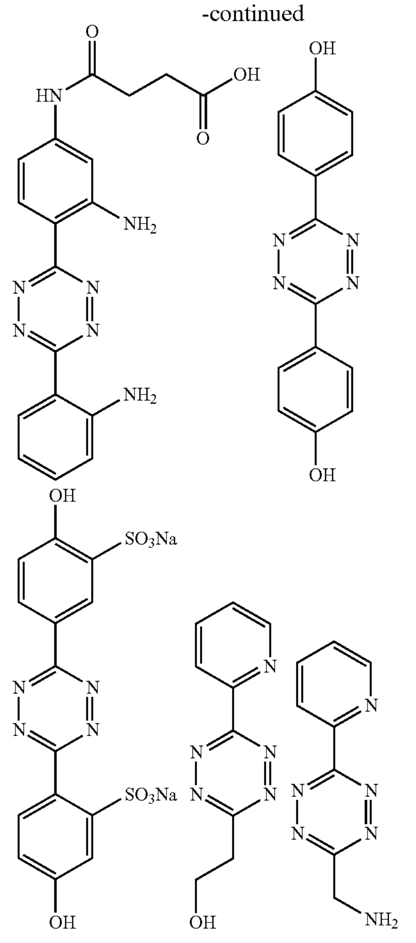
-continued
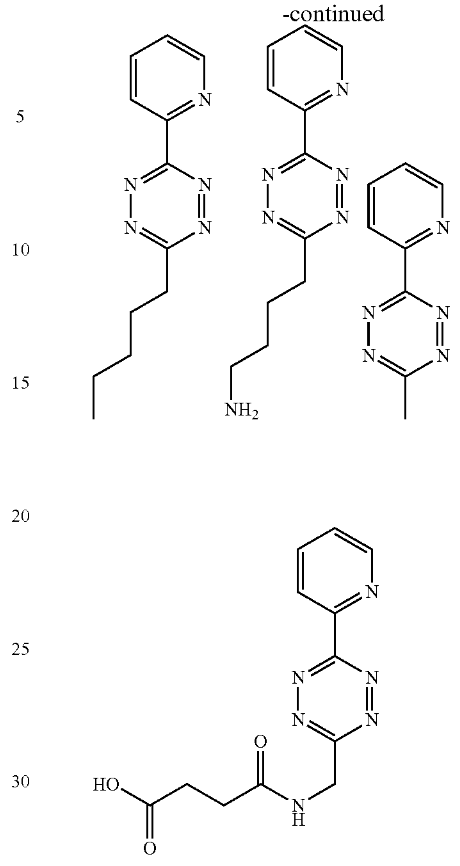
Further preferred activators with Triggers based on the strain release mechanism are
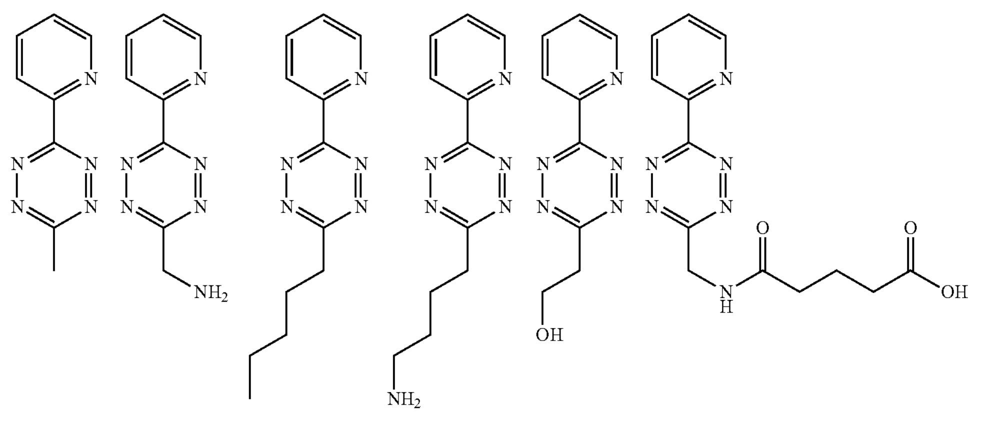

-continued
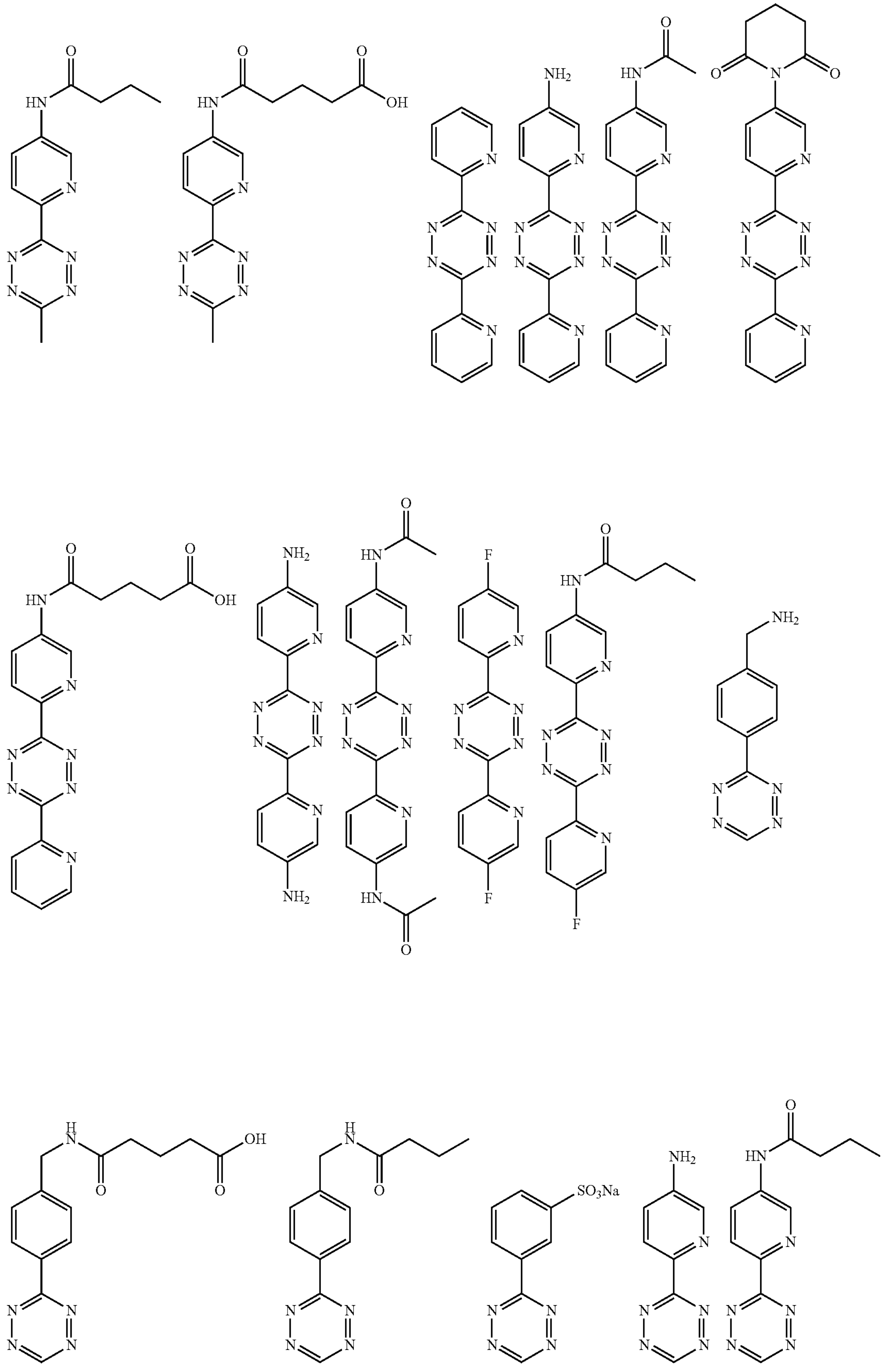

-continued
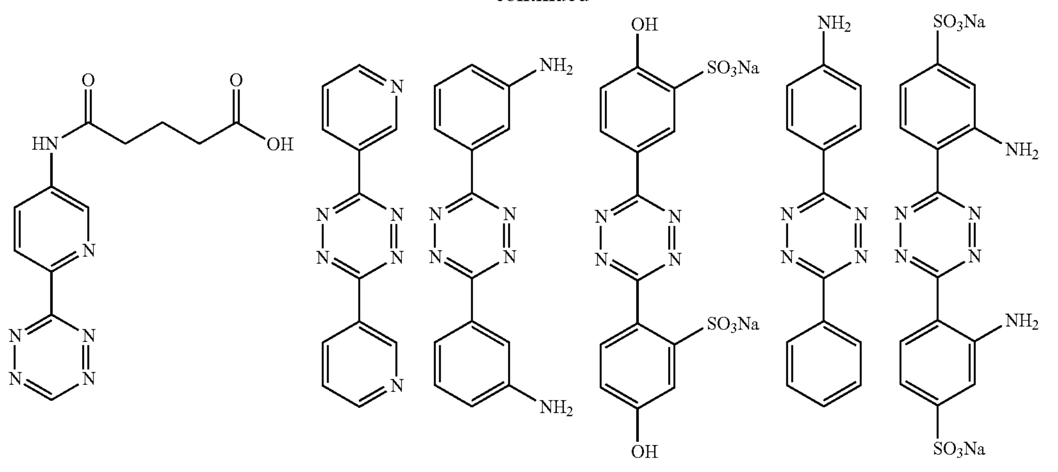
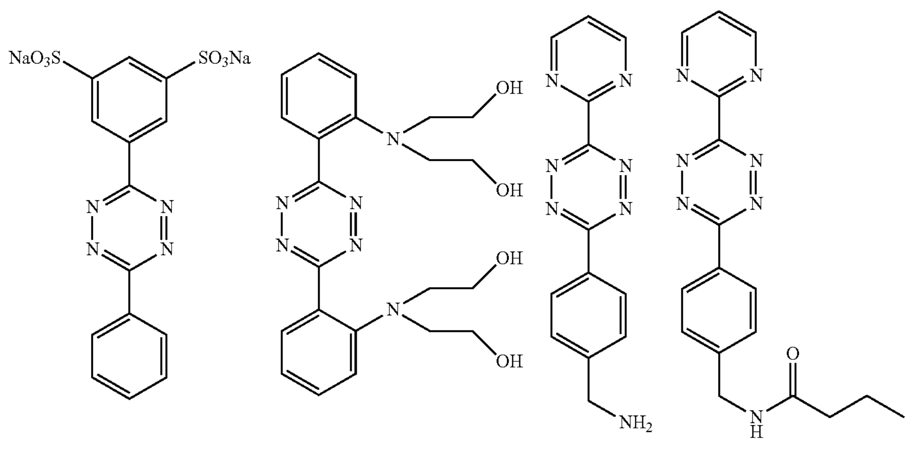
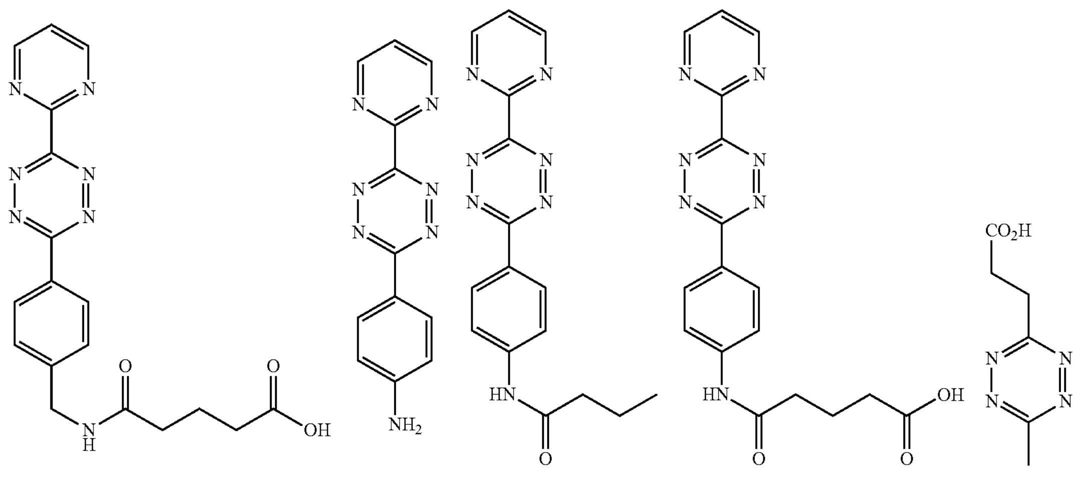

-continued
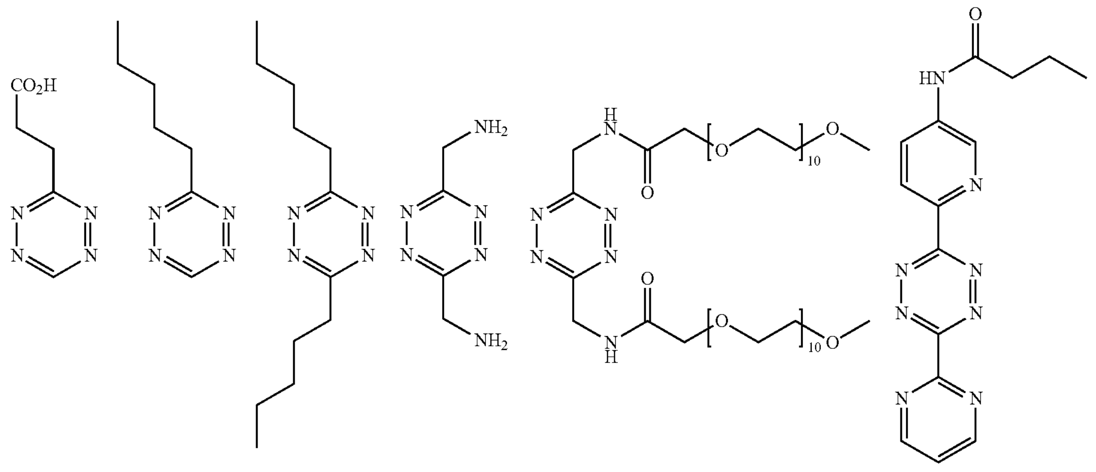
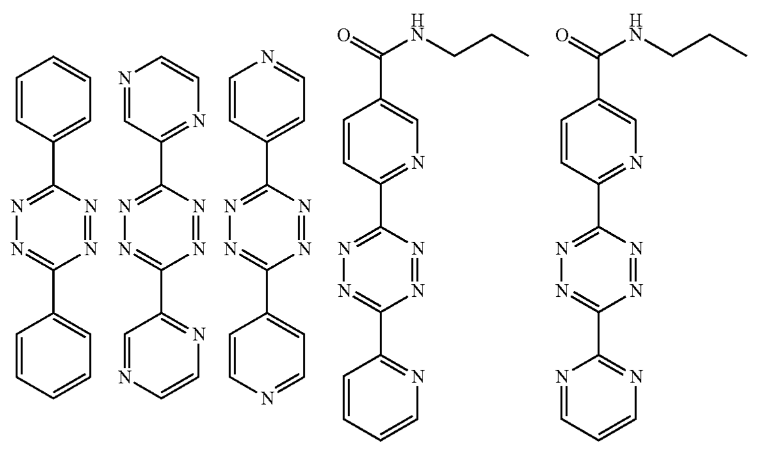
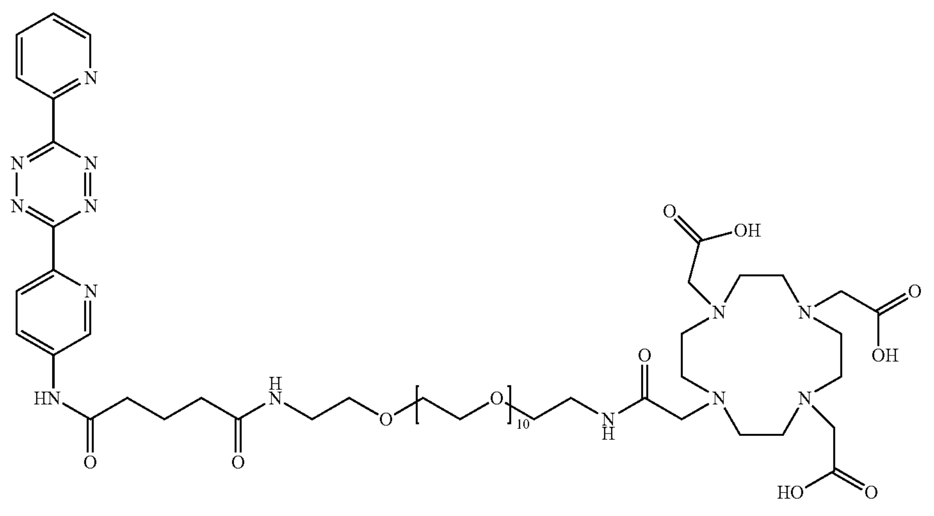

-continued

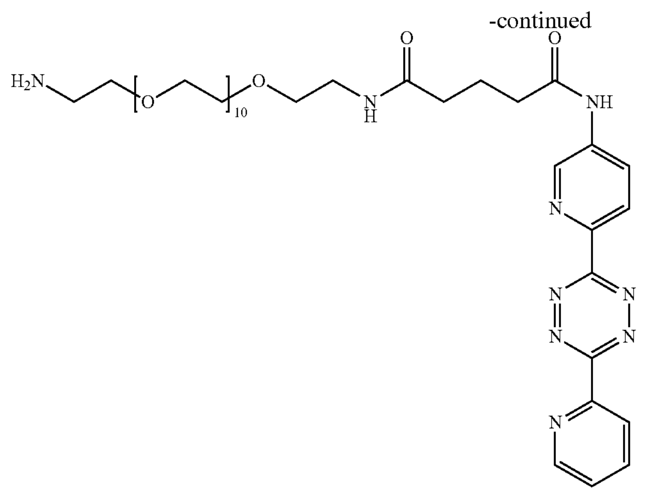

The Activator can have a link to a desired moiety such as a peptide, protein, carbohydrate, PEG, or polymer. Preferably, these Activators for use with Triggers based on the cascade mechanism satisfy one of the following formulae:

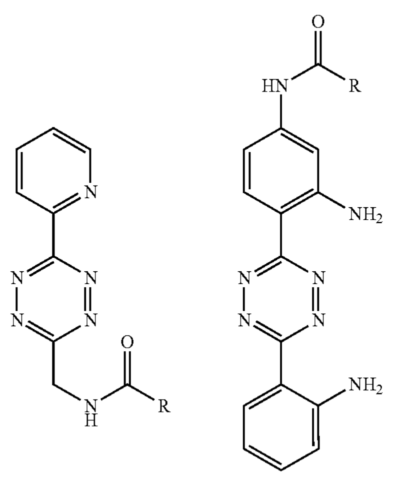

R = (link to) peptide, protein, carbohydrate, PEG, polymer

Preferably, these Activators for use with Triggers based on the strain release mechanism, satisfy one of the following formulae:

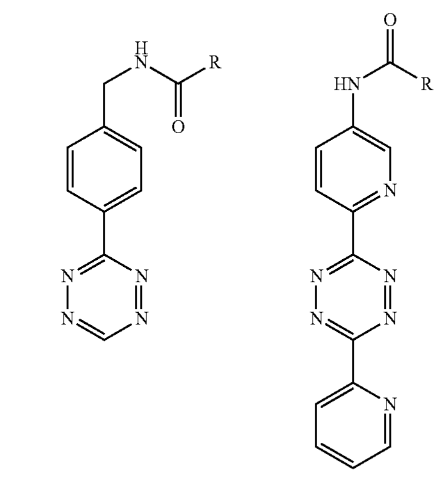

R = (link to) peptide, protein, carbohydrate, PEG, polymer

Synthesis routes to the above activators are readily available to the skilled person, based on standard knowledge in the art. References to tetrazine synthesis routes include Lions et al, *J. Org. Chem.,* 1965, 30, 318-319; Horwitz et al, *J. Am. Chem. Soc.,* 1958, 80, 3155-3159; Hapiot et al, *New. J. Chem.,* 2004, 28, 387-392, Kaim et al, *Z. Naturforsch.,* 1995, 50b, 123-127.

Construct-Trigger

A Construct-Trigger comprises a conjugate of the Construct or Constructs $C^A$ and the Trigger $T^R$. Optionally the Trigger is further linked to Construct or Constructs $C^B$.

The general formula of the Construct-Trigger is shown below in Formula (9a) and (9b).

(9a)

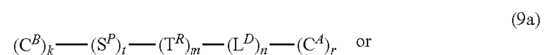

or (9b)

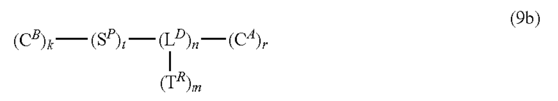

$C^A$ is Construct A, $C^B$ is Construct B, $S^P$ is spacer; $T^R$ is Trigger, and $L^D$ is linker.

$k, n, t \geq 0; m, r \geq 1.$ Formula (9a)

$k, t \geq 0; m, n, r \geq 1.$ Formula (9b)

It will be understood that the Construct $C^A$ can optionally be attached to the TCO derivative through a linker $L^D$ or a self-immolative linker $L^D$, or a combination thereof, and which may consist of multiple (self-immolative, or non immolative) units.

In the Trigger-Construct conjugate, the Construct $C^A$ and the Trigger $T^R$—the TCO derivative-can be directly linked to each other. They can also be bound to each other via a linker or a self-immolative linker $L^D$. It will be understood that the invention encompasses any conceivable manner in which the dienophile Trigger is attached to the Construct $C^A$. The same holds for the attachment of an Construct $C^B$ to the Trigger. Methods of affecting conjugation, e.g. through reactive amino acids such as lysine or cysteine in the case of proteins, are known to the skilled person.

It will be understood that the Construct $C^A$ is linked to the TCO in such a way that the Construct $C^A$ is eventually capable of being released after formation of the retro Diels-Alder adduct. Generally, this means that the bond between the Construct $C^A$ and the TCO, or in the event of a linker, the bond between the TCO and the linker $L^D$, or in the event of a self-immolative linker $L^D$, the bond between the linker and the TCO and between the Construct $C^A$ and the linker, should be cleavable. Predominantly, the Construct $C^A$ and the optional linker is linked via a hetero-atom, preferably via O, N, NH, or S. The cleavable bond is preferably selected from the group consisting of carbamate, thiocarbamate, carbonate, ether, ester, amine, amide, thioether, thioester, sulfoxide, and sulfonamide bonds.

It will be understood that formula 1a and 1b describe the Trigger and describe how the Trigger is attached to $C^A$, $C^B$, $L^D$, $S^P$, but that species $C^A$, $C^B$, $L^D$, $S^P$ are not part of the Trigger and should be viewed as separate entities, as can be seen in e.g. Scheme 1 and formula 9.

The Combination of and Reaction Between the Construct-Trigger and the Activator

Note that in cases of release of amine functional Constructs $C^A$ these can be e.g. primary or secondary amine, aniline, imidazole or pyrrole type of drugs, so that the Construct can be varying in leaving group character. Release of Constructs with other functionalities may also be possible (e.g. thiol functionalized Construct), in case corresponding hydrolytically stable TCO-Construct conjugates are applied. The drawn fused ring products may or may not tautomerize to other more favorable tautomers.

Hereunder, some nonlimiting model combinations of TCO-Construct conjugates and tetrazine Activators illustrate the possibilities for cascade elimination induced model Construct $C^A$ release from the retro Diels-Alder adduct. The Construct, whether or not via a linker, is preferably attached to a carbon atom that is adjacent to the double bond in the TCO ring.

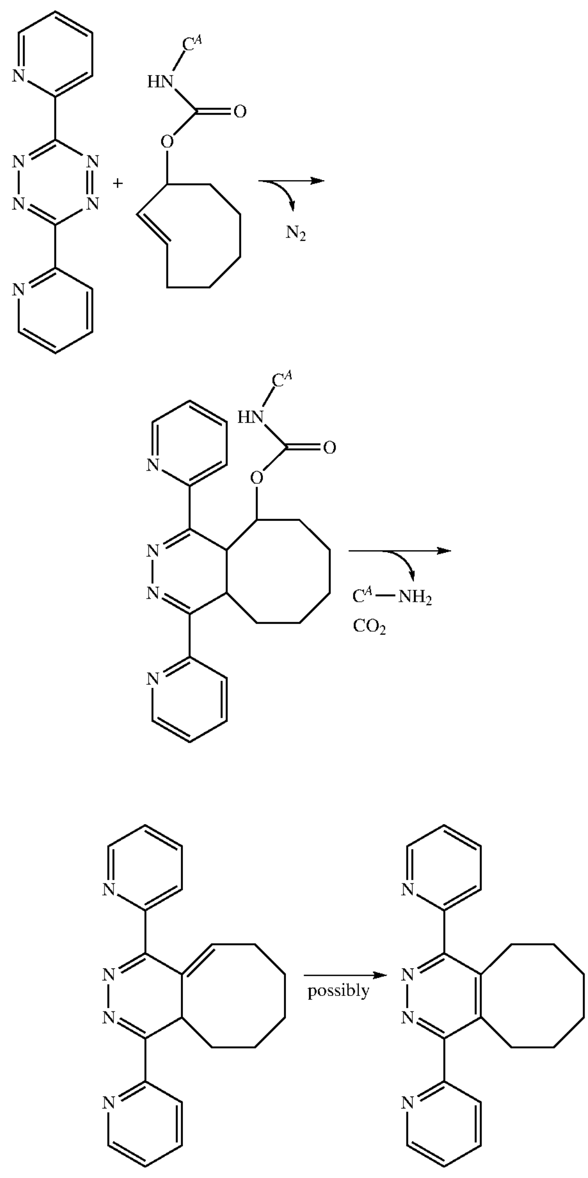

The above example of urethane (or carbamate) substituted TCOs gives release of an amine functional Construct from the adduct. The tetrazine Activator is symmetric and electron deficient.

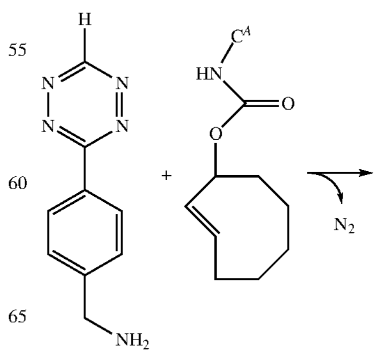

-continued

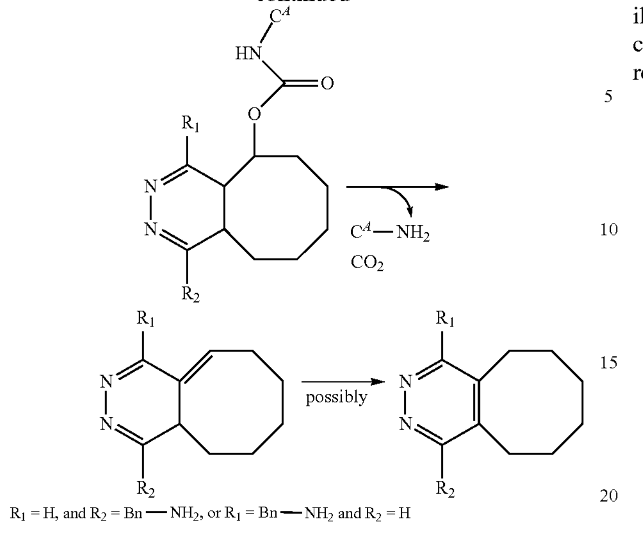

The above examples of urethane (or carbamate) substituted TCOs gives release of an amine functional Construct from the adduct. The tetrazine Activator is asymmetric and electron deficient. Note that use of an asymmetric tetrazine leads to formation of retro Diels-Alder adduct regiomers, apart from the stereoisomers that are already formed when symmetric tetrazine are employed.

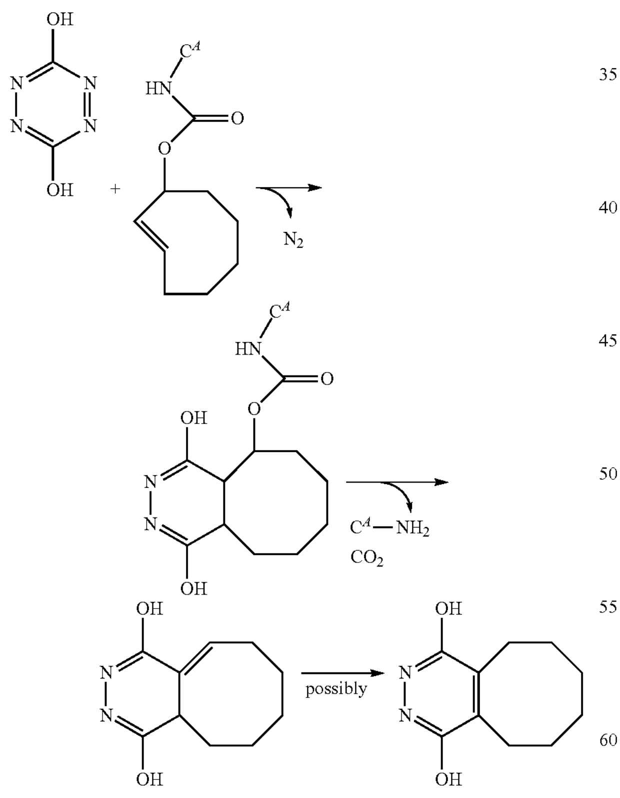

The above example of urethane (or carbamate) TCOs gives release of an amine functional Construct from the adduct. The tetrazine Activator is symmetric and electron sufficient.

The following schemes depict non-limiting examples illustrative for the various strain release mechanisms that can be made to apply on the basis of the choice for the rDA reaction for activating a Trigger-Construct conjugate.

embodiment 1

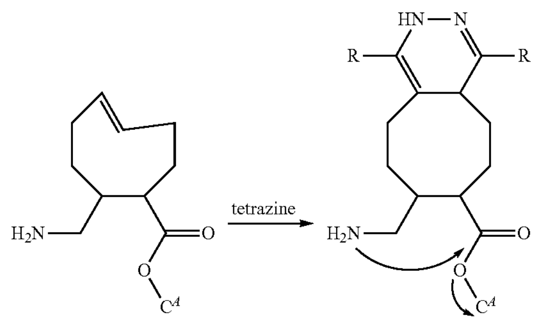

alternative:

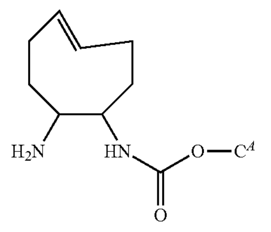

embodiment 2

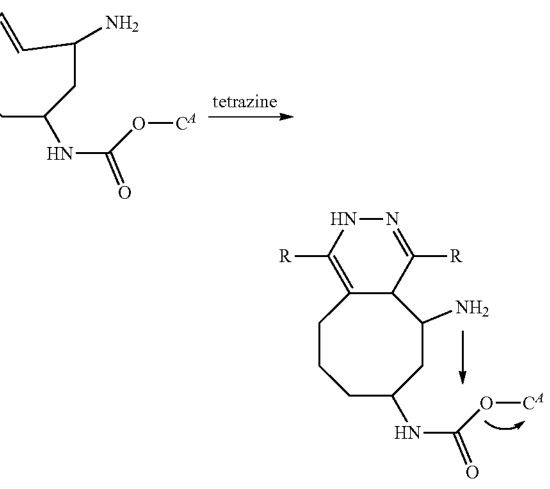

alternative:

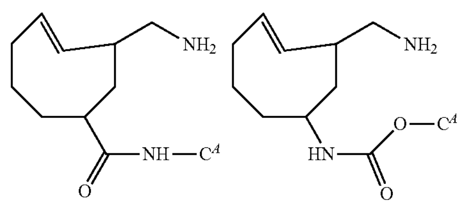

embodiment 3

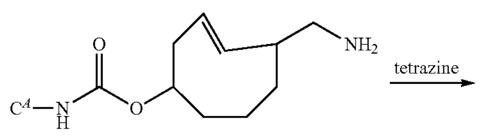

-continued

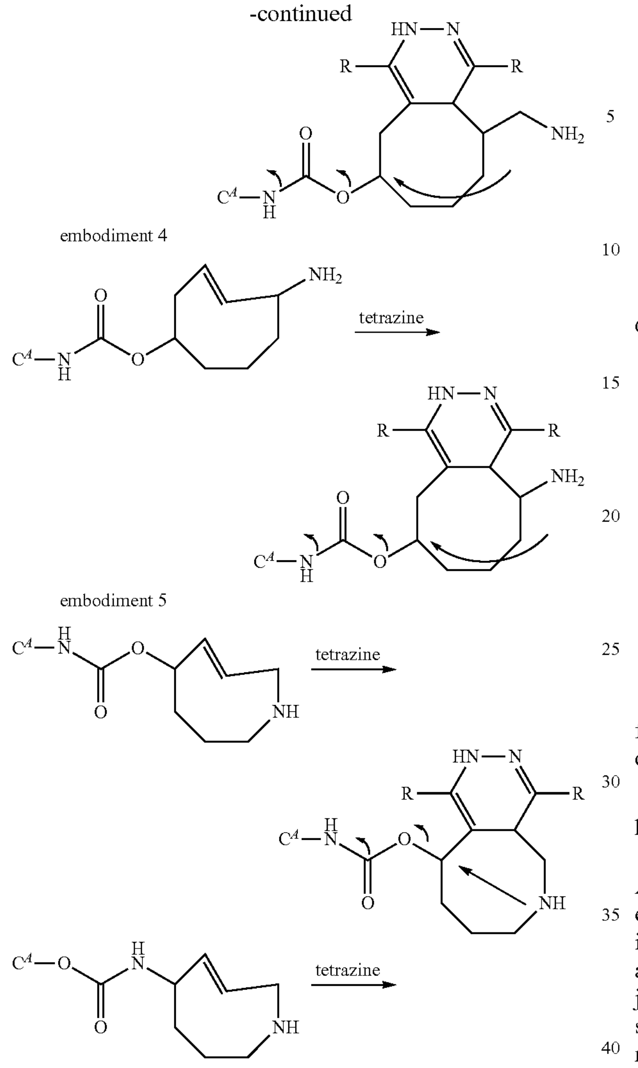

-continued embodiment 6

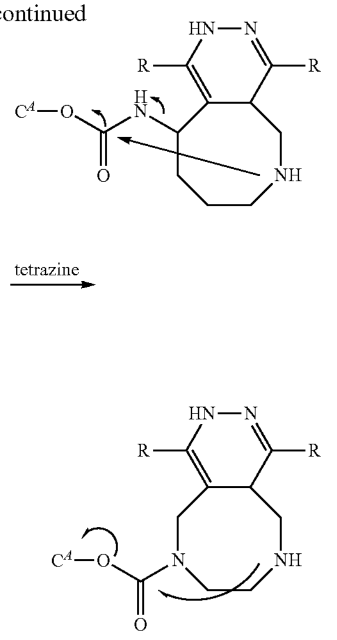

The invention includes in one aspect a Trigger which functions as a protective or masking group for use in organic/peptide/protein/bio-/surface/solid-phase chemistry.

Therein, with reference to formula 9a and 9b: k is preferably 0.

Selective removal of the Trigger via reaction with the Activator unmasks the construct. Exemplary chemical moieties that can be protected and selectively deprotected include, but are not limited to, amines, thiols, hydroxyl, aminooxy groups. Furthermore, the Activator may be conjugated to a resin, especially solid-phase synthesis resins, such as polystyrene, or to a bead. Thus circumventing the need for solution phase purification after the deprotection step.

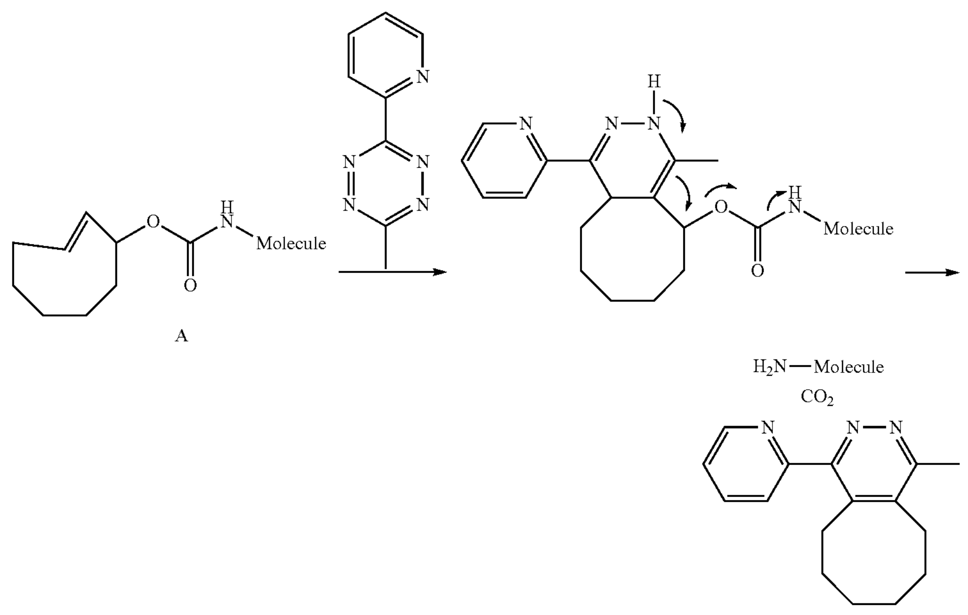

A

-continued

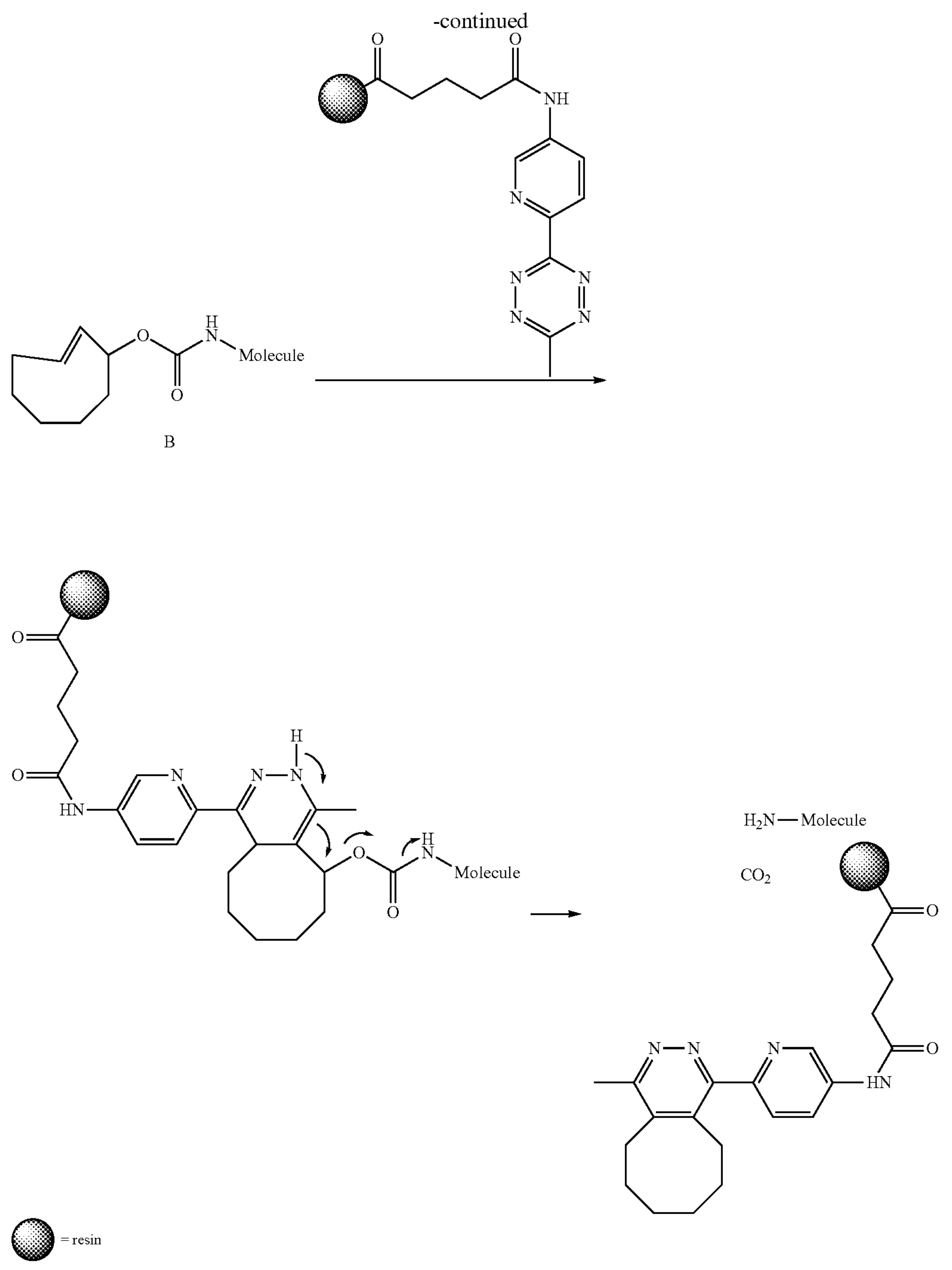

B

In the case of biomolecules such as proteins the Trigger can be introduced after the protein has been formed or during protein synthesis by means of genetically incorporating a Trigger-modified amino acid. There have been many studies demonstrating the incorporation of unnatural amino acids in proteins, including TCO and tetrazine (e.g. Chalker et al. Acc Chem Res, Vol. 44, No. 9, 2011, 730-741). In this way one can for example conduct bioconjugation chemistry elsewhere on the molecule, after which the TCO-masked amino acid can be unveiled and selectively manipulated. This so-called "Tag-and-Modify" approach thus allows for multiple and different post-translational modifications on a single protein and can be extended to controlled assembly and fragmentation of complex materials, proteins, cells, tissues. Examples of masked amino acid derivatives, which can be used in such as approach are shown below. Compound A is the amino acid cysteine of which the thiol functionality is masked by TCO. After release of TCO the thiol can be used in conjugation reactions. In addition to achieving selectivity, the ability to mask and unmask a thiol enables stabilization of thiol containing proteins against undesired oxidation and disulfide formation. Compound B is amino acid lysine conjugated via its e-amine moiety to a TCO. Compound C is the amino acid lysine conjugated via its e-amine moiety to a TCO-masked aminooxy functionality. After unmasking this aminooxy can be selectively conjugated to aldehyde and ketone derivatives.

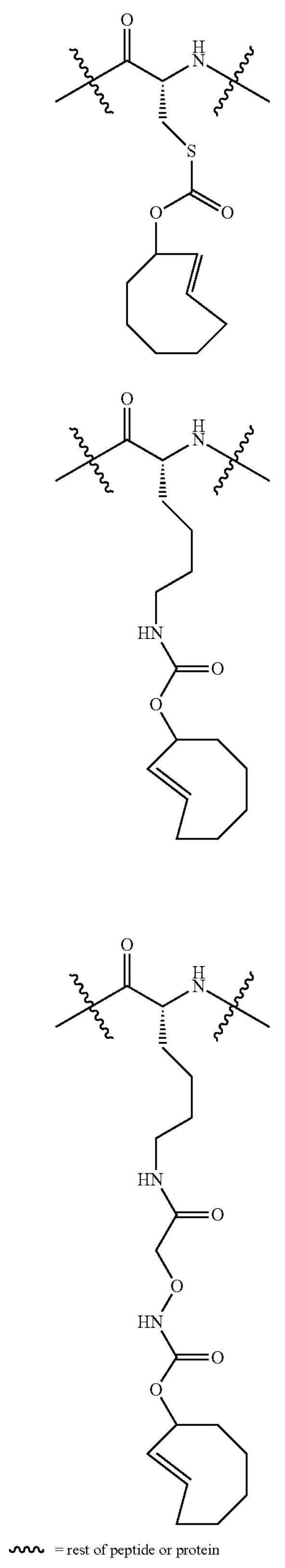

In a similar embodiment depicted below the TCO mask is used to stabilize protein formulations in e.g. stock solutions to prevent aggregation and precipitation. For this purpose the TCO is functionalized with $C^B$ being an hydrophilic moiety such as a PEG (or e.g. a carbohydrate moiety), and one or multiple TCO-$C^B$ groups are conjugated to the protein (being $C^A$) via e.g. lysine residues. At the time of use, the protein solution is contacted with the Activator yielding the unmasked parent protein $C^A$. Also here it may be advantageous to use an Activator that is conjugated to solid phase synthesis resins or a bead, thus circumventing the need for solution phase purification after the unmasking step.

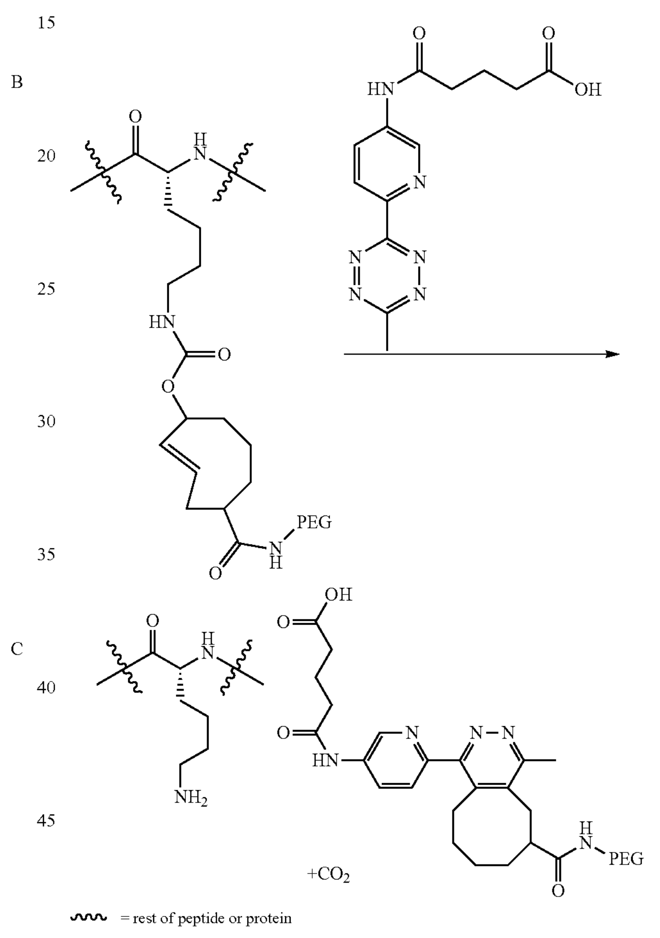

In another embodiment the Trigger is used as a chemically cleavable mask in the patterning or etching of surfaces with application in e.g. spatially controlled cell and tissue culture, or for (e.g. protein, DNA) microarray assembly. Selective removal of the mask reveals e.g. free amine or thiol moieties (comprised in $C^A$), which can be used for further modifications, such as the conjugation of cell adhering peptides in the case surfaces for cell culture. For example, the TCO can be used as cleavable linker between a surface or surface-coated gel and cell-interacting moieties, such as integrin binders, for use in cell culture. After cell culture on this surface or in this 3D the cells can be removed from the surface or the surface-coated gel by mild cleavage of the TCO, instead of resorting to harsh trypsinization, or physical force.

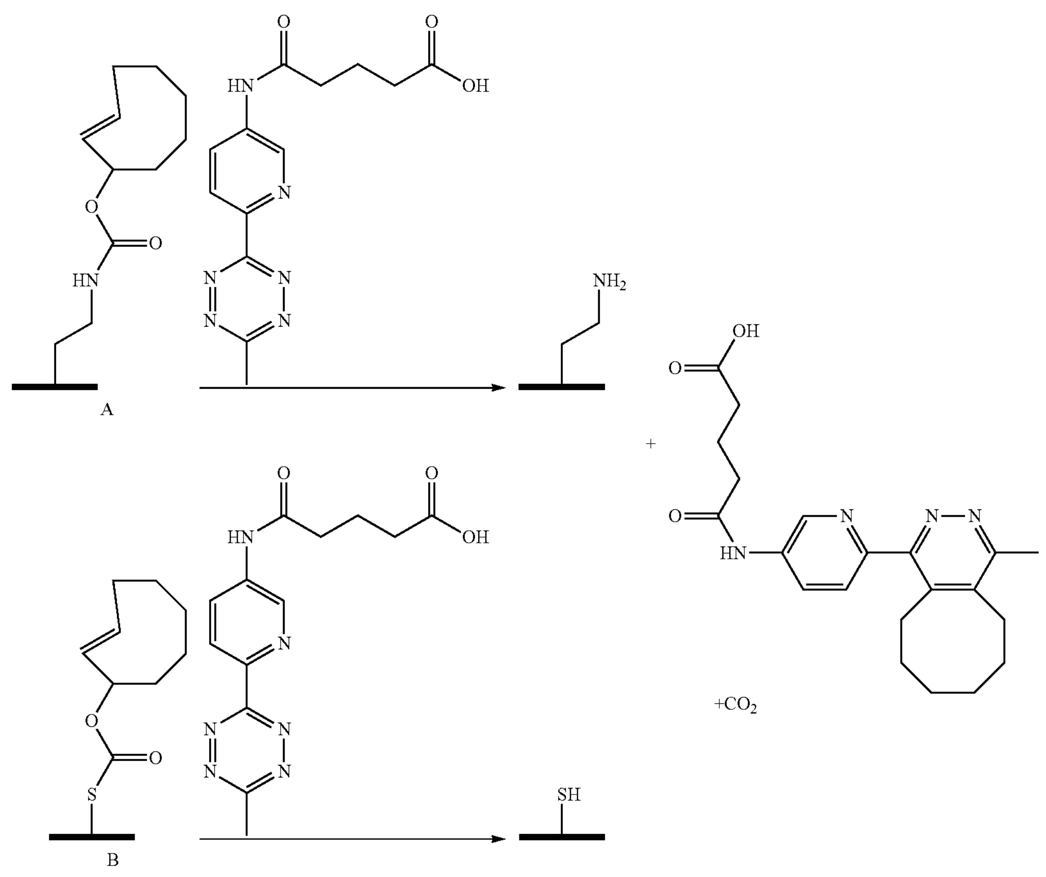

In an alternative embodiment the TCO mask is used to spatially and or temporally control the action of biomolecules in vitro or in vivo. For example, the action of a particular enzyme in an in vitro assay can be controlled by using an enzyme that has been deactivated through conjugation to one or more TCO masks, followed by contacting the enzyme with the Activator followed by release of the TCO mask and, affording the parent, active enzyme ($C^A$). Another example, useful in chemical biology, is the TCO-protection of certain amino acid residues in a protein against enzymatic action such as phosphorylation by kinase, allowing spatial and temporal control over the phosphorylation after Activator addition. Alternatively, phospho amino acids in phosphoproteins can be masked by TCO to be revealed at desired time by use of the Activator, as shown in a similar approach using light activatable masks by Rothman et al (2005) J. Am. Chem. Soc, 127, 847.

In another aspect of the invention the Trigger is used as a cleavable linker in "catch and release" systems, such as those used in chemical biology. Therein, with reference to formula 9a and 9b: k is preferably 1.

One application of these linkers is in the purification of proteins tagged with a biotinylated Activity Based Probes (ABP). Biotinylated ABPs are often used for enrichment of captured enzymes, for instance, by pull-down with streptavidin-coated beads. The main disadvantages of this approach, however, are that the conditions to liberate the captured proteins from the beads are harsh (boiling of the sample, all or not in the presence of unmodified biotin) and that, beside the target proteins, both endogenously biotinylated proteins and (denatured) streptavidin can end up in the sample. In addition the presence of the biotin complicates MS/MS analysis. Furthermore, in another application, this concept can be used to capture and release whole cells with e.g. antibodies conjugated to e.g. a bead or solid support for example for the purpose of further analysis with FACS, requiring healthy intact cells. Several groups have developed linker systems that can be incorporated in the ABP, or alternatively in a bioorthogonal reagent for two-step ABPP, and that can be cleaved in a chemoselective manner after affinity pull-down. Examples include the disulfide, diazabenzene, and bisaryl hydrazine cleavable linkers (Willems L. I. et al. (2011) Acc. Chem. Res. 44, 718-729). However, these linkers have a limited bioorthogonality. In below scheme several embodiment examples are shown of the use of the rDA Trigger for this application. In addition to the enhanced bioorthogonality this method also offers the opportunity to introduce a new label or affinity tag or to preserve a synthetic handle for further modification, through the binding of the tetrazine activator to the TCO.

Example A1 depicts the capturing of an enzyme by a ABP conjugated to biotin via a TCO linker. The complex is subsequently bound and isolated by streptavidin coated beads, after which the linker is cleaved by the Activator, and the enzyme, comprising the ABP linked to the rDA residue is released. In Example A2, the same concept is used with a reversed Trigger, leading to traceless release of the ABP-enzyme complex. Example B depicts an analogous 2 step ABP approach where the enzyme is captured by an ABP functionalized with an azide moiety. The complex is subsequently reacted with a cyclooctyne moiety, which is linked to a biotin via a TCO linker. It has been shown in Weissleder Angewandte Chemie 2011 that the TCO/tetrazine pair can be used orthogonally to and in the presence of the azide-octyn pair. In Example C the cyclooctyne-TCO-biotin probe approach described in B) is used to capture a specific piece of protein, which has metabolically incorporated an azide-modified aminoacid. Example D depicts the capturing of cells using magnetic beads conjugated to antibodies via the Trigger. After binding and isolation using magnetic action, the cells are detached under mild conditions by adding the Activator. Example E depicts an alternative to the general approach in Examples A-D where the TCO combines the function of the biotin tag with the function of releasable linker. In this example, target cells are first bound by TCO-modified antibodies, followed by addition of tetrazine-coated beads. Suitably chosen tetrazine-TCO pairs that function via the strain release mechanism will give a release with a half life of >2 h and given the required reaction time of <10 minutes thus allow enough time for isolation of the bead-cell complex before the complex releases the cell automatically through release of the linker. The TCO used in this example is an example of a TCO that functions via the strain release mechanism and gives $C^A$ release with a half life of >2 h, largely independent of the type of tetrazine, provided the tetrazine reacts with the TCO within ca 10 min. The feature believed to enable slow release in the strain release mechanism is the aliphatic nature of the leaving group $C^A$, in the case a aliphatic hydroxyl.

A1

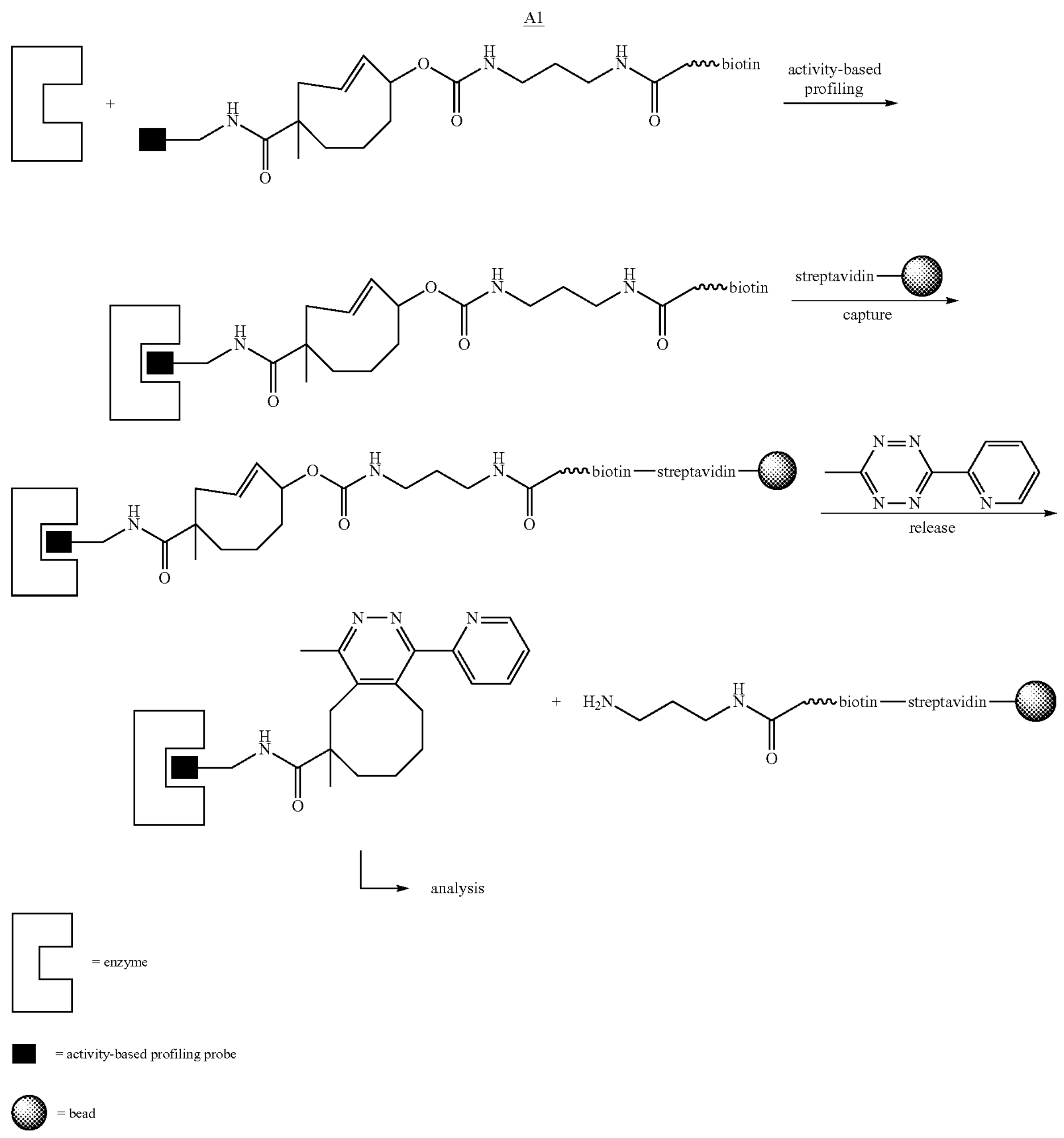

A2
release
B
activity-based profiling
capture
release

-continued
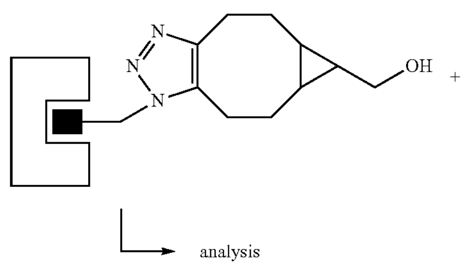
+
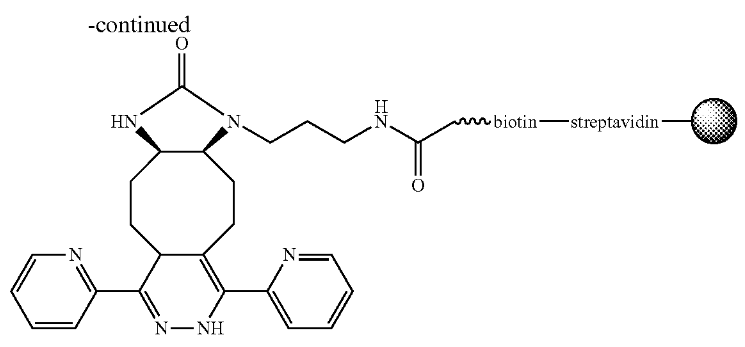
C
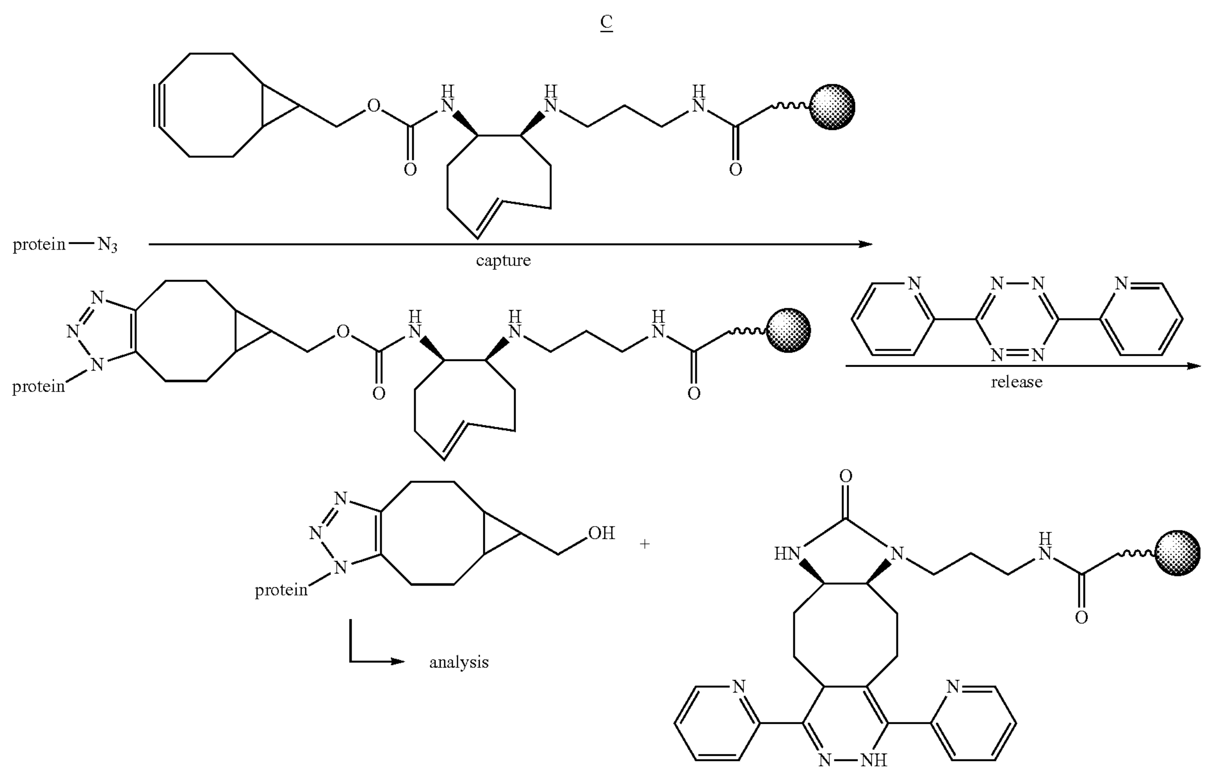
D
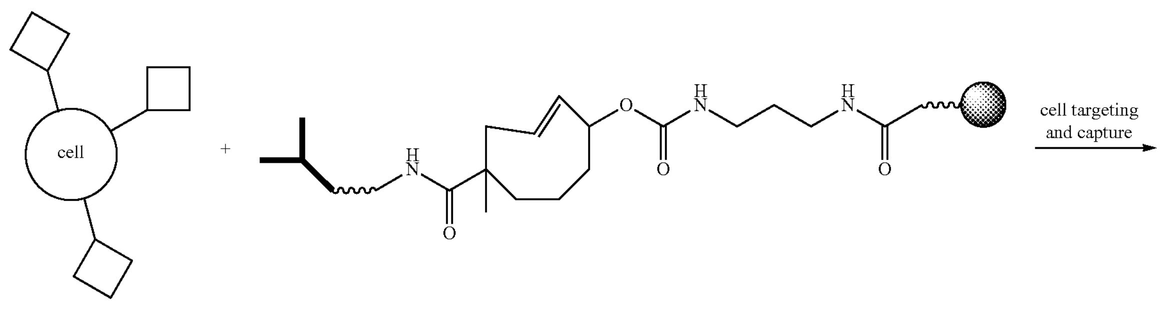

-continued
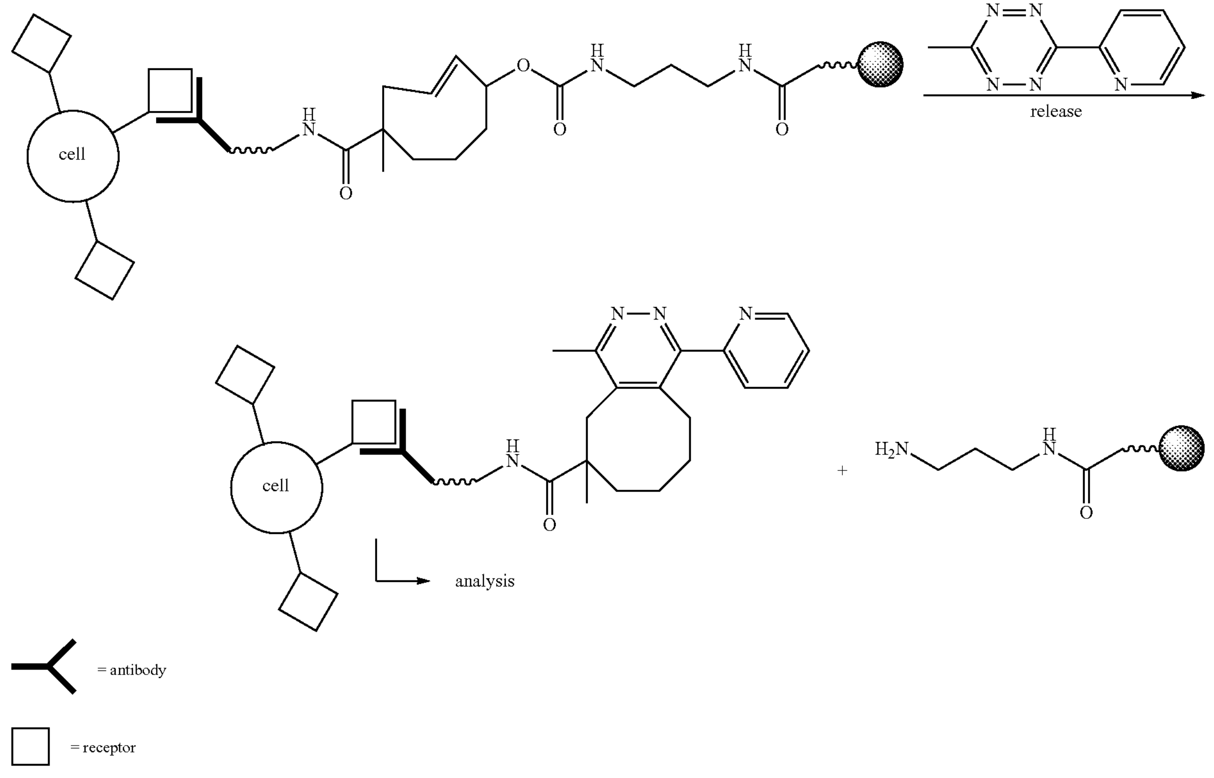
E
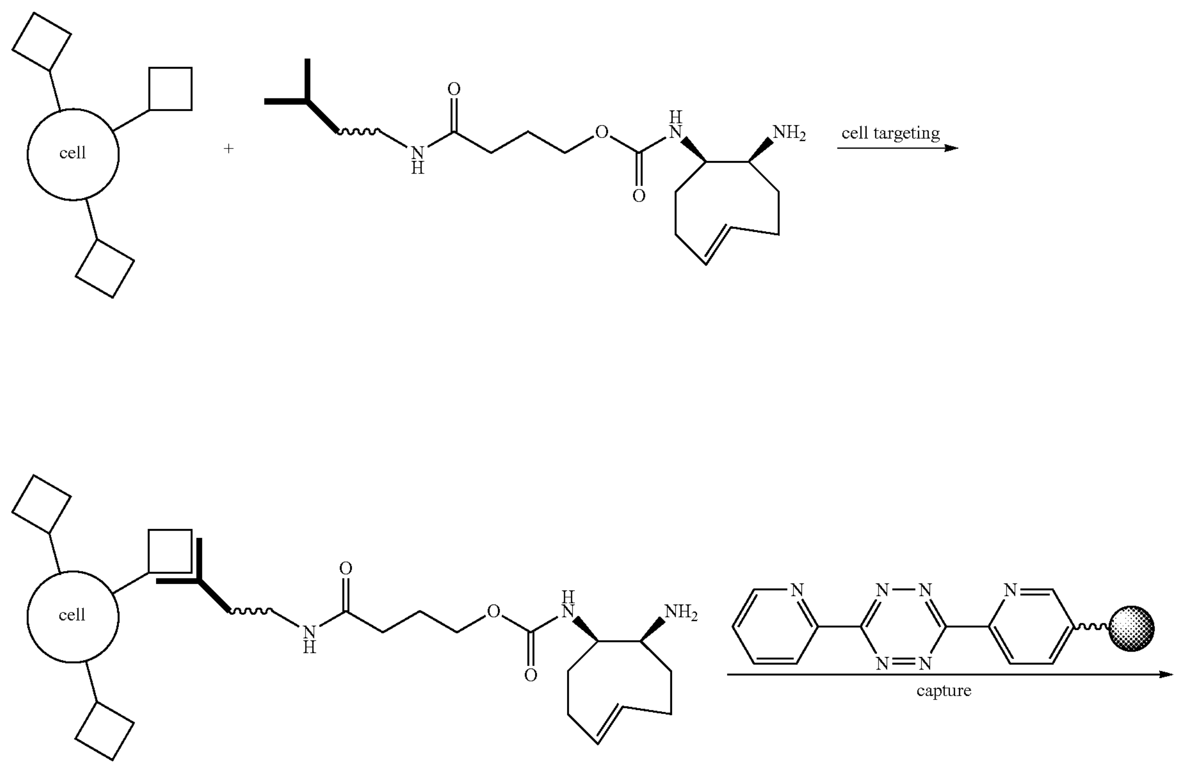

-continued

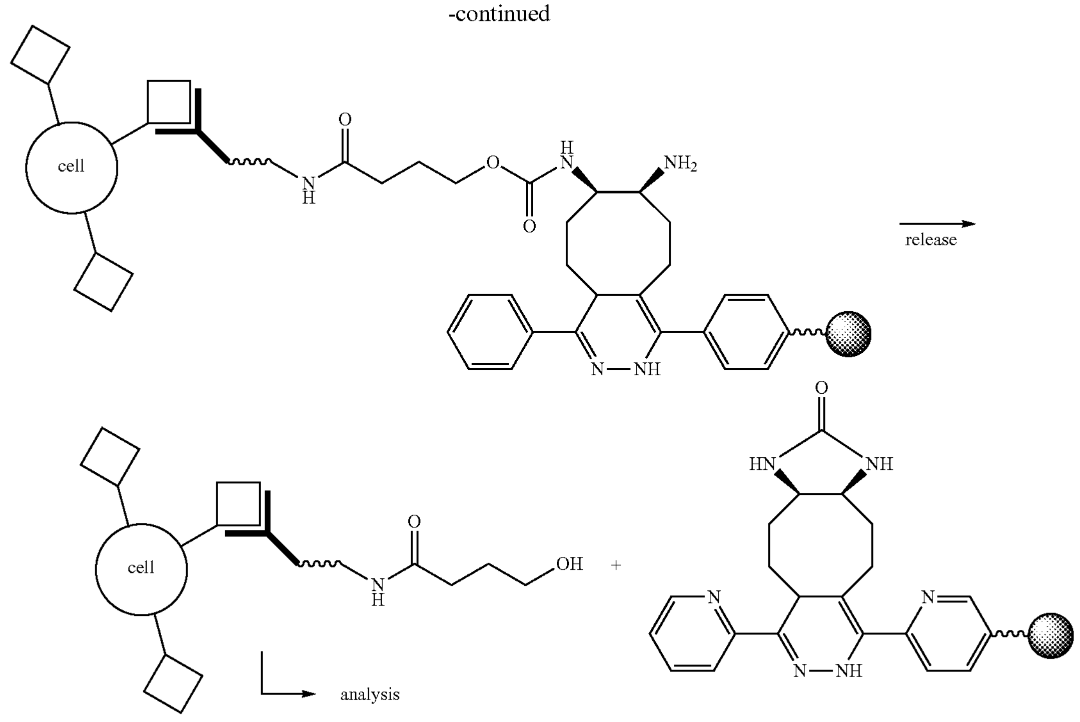

An alternative aspect of the invention comprises the Trigger as a chemoselective cleavable linker between a solid support and a solid support-bound substance.

Therein, with reference to formula 9a and 9b: k is preferably 1.

In one embodiment, the Trigger is used as cleavable linker in solid phase synthesis. Solid-phase synthesis methods have been used in organic synthesis over the last decades, first for peptides, then for oligonucleotides, followed by other organic molecules. This development was accompanied by the development of various cleavable linkers for the detachment of molecules from the solid support resin. Examples include linkers that can be cleaved by acids, bases, fluoride ion, or photochemical reactions (Maruta et al. Tetrahedron Letters 47 (2006) 2147-2150; Shabat et al. Chem. Eur. J 2004, 10, 2626). An alternative bioorthogonal approach may expand the scope of compatible functionalities. Here a solid phase synthesis resin, such as polystyrene, is functionalized with TCO Triggers upon which the molecule of interest, for example a peptide, is synthesized. After the synthesis is complete, the Activator is added which reacts with the Trigger releasing the product (e.g. peptide) from the resin-bound Trigger into solution.

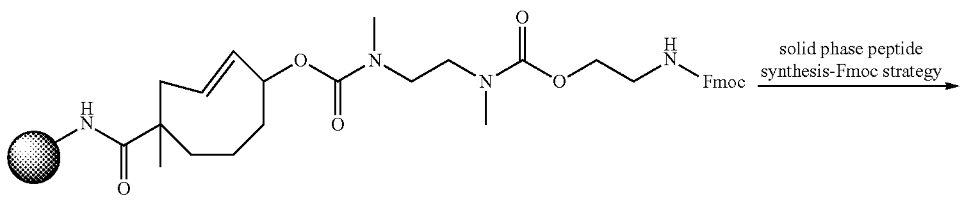

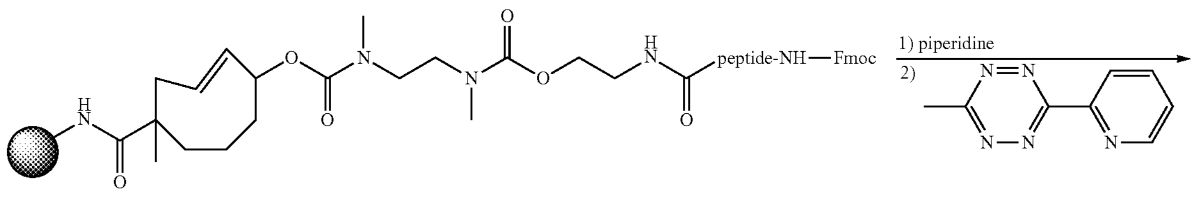

-continued
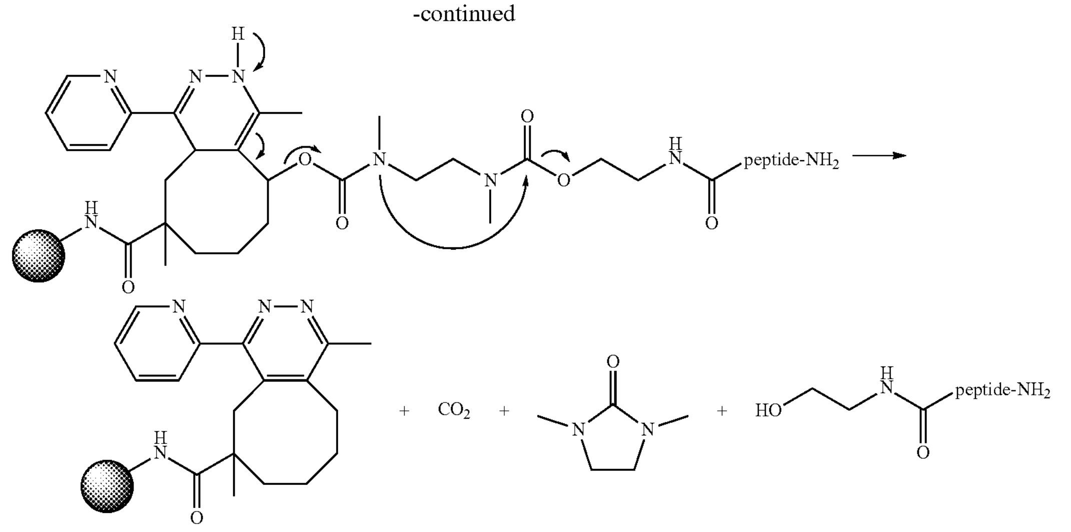
Alternative Solid-Phase Synthesized Compounds:
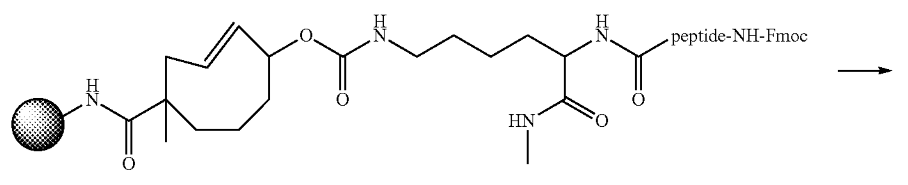
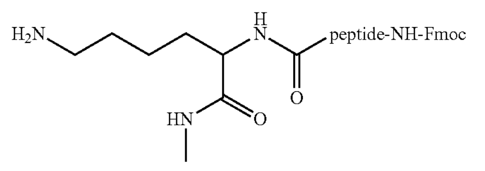
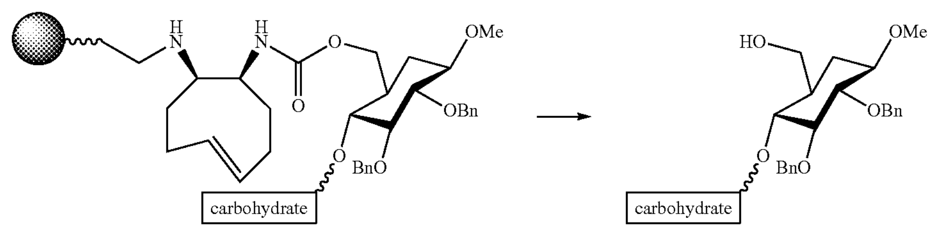

An alternative embodiment, shown directly below, comprises the selective release and activation of a surface-bound chemical reagent in a cartridge or a lab on a chip device.

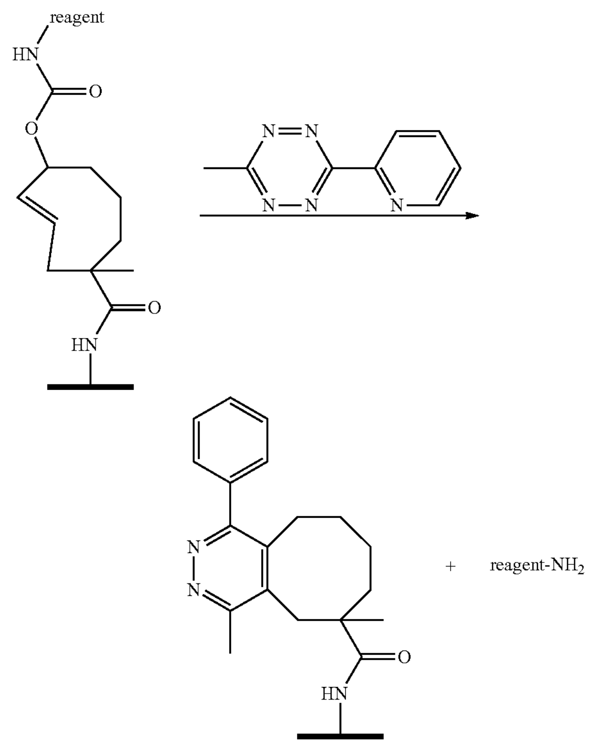

In yet another aspect the Trigger functions as a cleavable linker for reversible biomolecule crosslinking, and/or and immobilization, followed by release. Applications in chemical biology include a) the use of two proteins linked together via TCO, and their studying their action in e.g. a cellular environment before and after TCO cleavage; b) cleavage of a protein-TCO-targeting agent conjugate in cells to release the protein from a particular subcellular domain; c) cleavage of a protein-targeting agent-TCO conjugate in cells to target the protein to a particular subcellular domain (see Lim Acc Chem Res 2011).

In one embodiment the Trigger is used as cleavable linker in a biomolecule biotinylation agent for application in biomolecule detection, isolation and purification. Thus, use is made of biomolecule-reactive Trigger-biotin conjugates for the cleavable (reversible) attachment of biotin to peptides, proteins (for example cell surface proteins), glycoproteins, DNA and other biomolecules. The cleavable linker allows mild detachment of the bound biomolecule after affinity purifying biotinylated proteins using immobilized avidin or streptavidin. With reference to the scheme directly below, Probe A is useful for biotinilation of lysine residues in proteins. With R=$SO_3Na$ the agent will remain charged and in the extracellular space and is especially useful for labeling cell membrane proteins. Probe B is an aminooxy-biotin reagent and probe C is a hydrazide-biotin reagent and as such B and C are useful for biotinylating glycoproteins and other molecules that have oxidizable polysaccharides groups. Compounds D-F are a photoactivatable reagent that enables biotinylation of nucleic acids and other molecules that do not have readily available amine or sulfhydryl groups for coupling. When exposed to strong ultraviolet or visible light, the aryl azide group of D-F converts to a reactive nitrene that readily reacts to form covalent bonds with a variety of chemical groups, such as nucleic acids. Compound G enables simple and efficient reversible biotinylation of antibodies, cysteine-containing peptides and other thiol-containing molecules. Compound H is a reagent that enables proteins to be temporarily labeled at sulfhydryl sites for later photo-induced covalent attachment and transfer of biotinylation to an interacting protein, thereby tagging the previously unknown interacting protein(s) for affinity purification, detection, analysis (e.g. mass spectrometry, electrophoresis or sequencing).

A

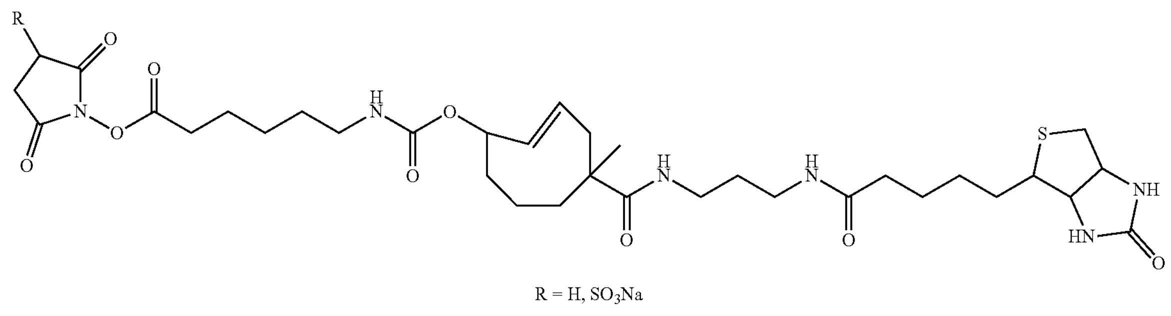

R = H, $SO_3Na$

B

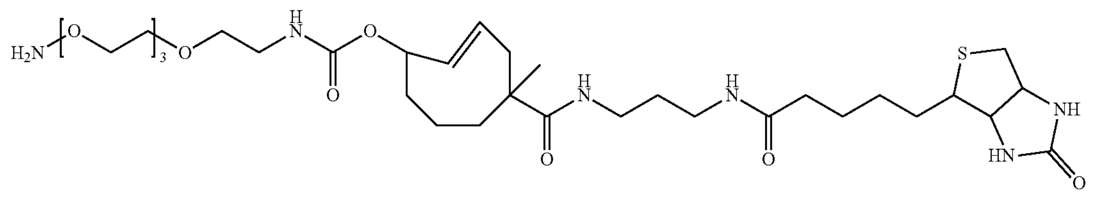

-continued
C
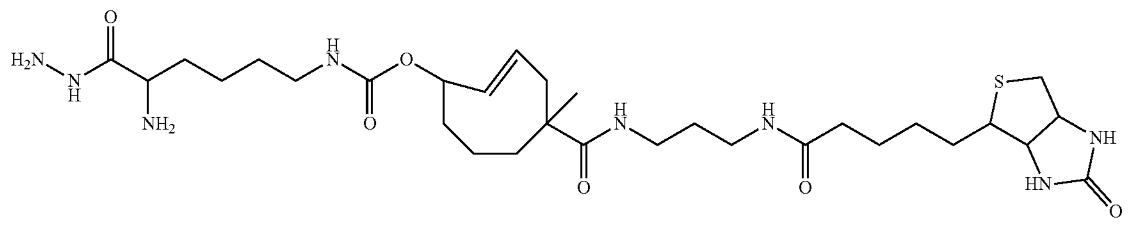
D
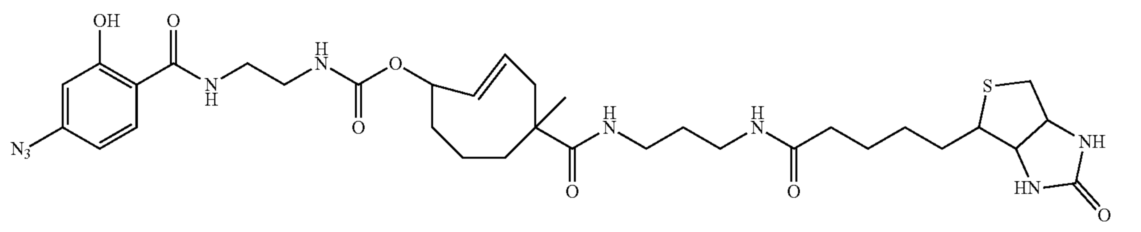
E
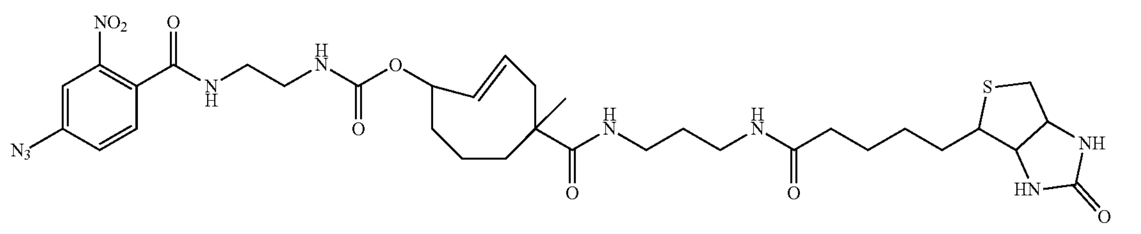
F
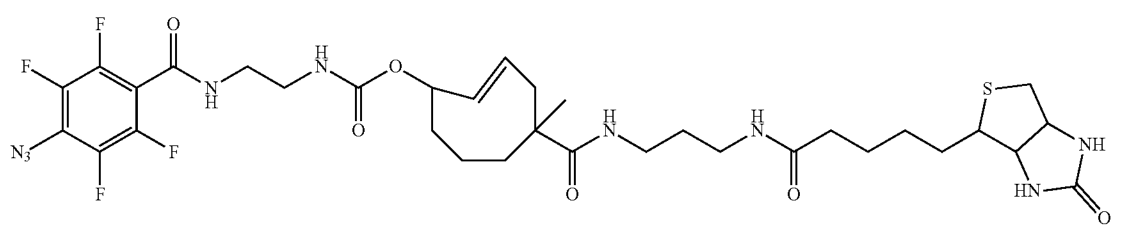
G
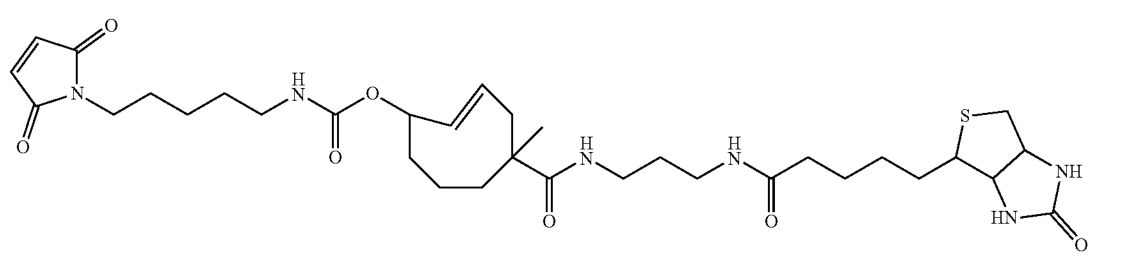
H
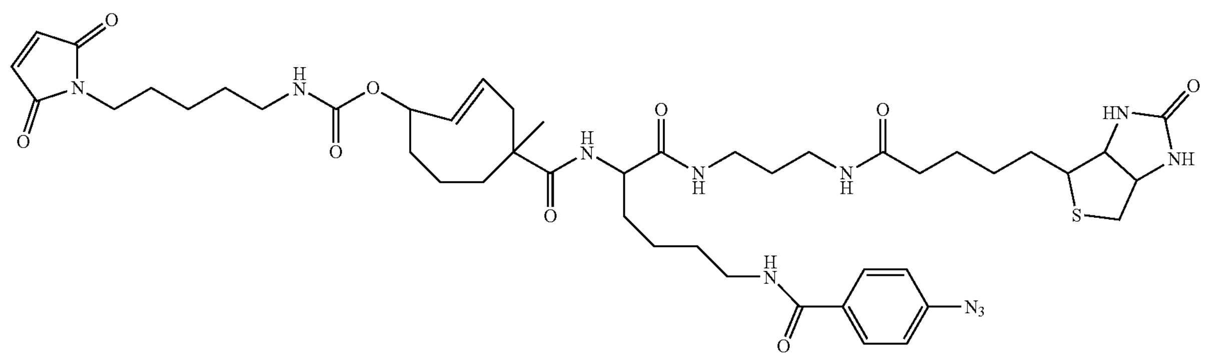

In another embodiment the Trigger is used as cleavable linker in a crosslinker between two biomolecules for e.g. application in biomolecule detection, immobilization, isolation and purification, in particular with respect to biomolecule interactions. Examples include crosslinking of cell surface proteins prior to cell lysis and immunoprecipitation, fixing of protein interactions to allow identification of weak or transient protein interactions, fixing of tissues for immunostaining. 1-step bioconjugations, and immobilization of proteins onto eg amine-coated surfaces. Thus, use is made of biomolecule-reactive bifunctional crosslinkers containing a cleavable Trigger for the cleavable (reversible) attachment of biomolecules such as peptides, glycoproteins, DNA to one another. Such as linker can for example be used in a "shotgun" approach to capture interaction complexes. When using lysine reactive moieties, the reagent will crosslink any and all interacting molecules whose respective lysine residues come within the spacer length of the crosslinker. Subsequently, a particular interaction complex is detected after crosslinking and (usually) cell lysis by immunoprecipitation or by administering a specific antibody or other probe for one of the target molecules in the complex. With reference to the scheme directly below, compound A is an homobifunctional lysine-reactive crosslinker, useful for the crosslinking of for example two proteins. Compound B is a cleavable heterobifunctional amine-reactive photocrosslinker, useful with molecules where no amine residue is available or accessible (even DNA, polysaccharides and other molecules). These heterobifunctional linkers enable "two-step" reactions in which "bait" proteins can be labeled, added to a cell and light-activated to crosslink at the desired time (e.g., upon cell stimulation when the interaction of interested is presumed to occur), followed by isolation and mild cleavage through the Trigger. Compound C is a cleavable homobifunctional thiol reactive crosslinker for covalent but reversible conjugation between e.g. proteins or peptide cysteines. Compound D is a cleavable heterobifunctional thiol and amine reactive crosslinker for covalent but reversible conjugation between e.g. proteins or peptide cysteines and lysines. Compound E is a cleavable modification reagent for aminoacids, allowing a temporary change in protein charge.

A

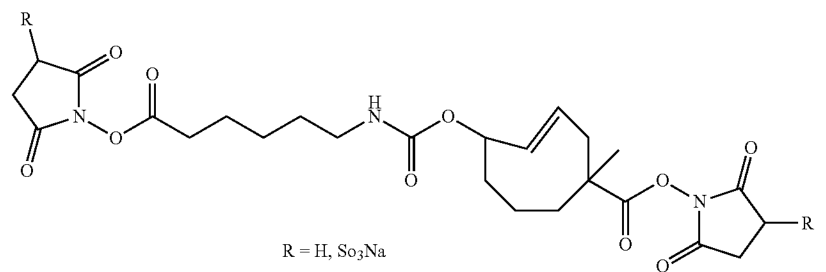

R = H, $So_3Na$

B

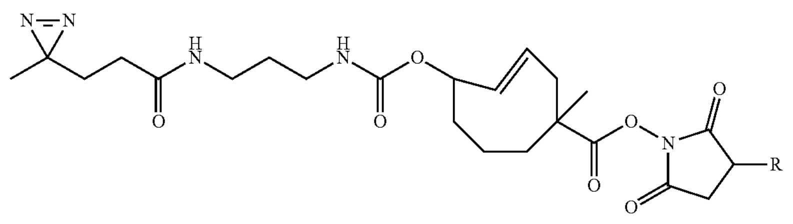

C

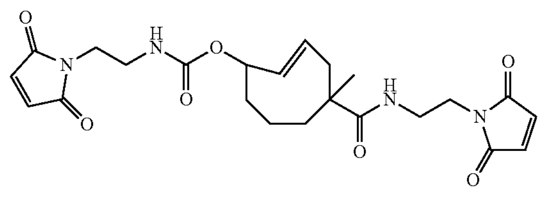

D

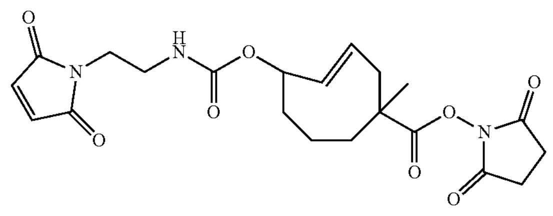

E

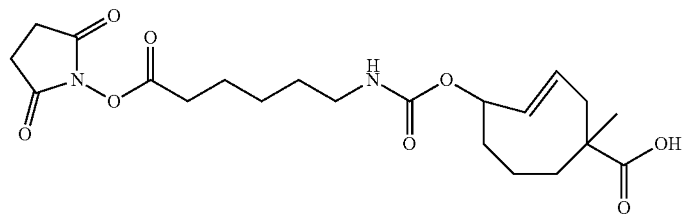

In another aspect the Trigger is used as in a radiolabeling kit, as shown in the scheme directly below. Use is made of a bead linked to a $^{18}F$-labeled TCO, and a tetrazine-peptide derivative is added, which reacts with the TCO affording $^{18}F$-tetrazine-TCO-peptide. With reference to formula 9, k is preferably 1.

A

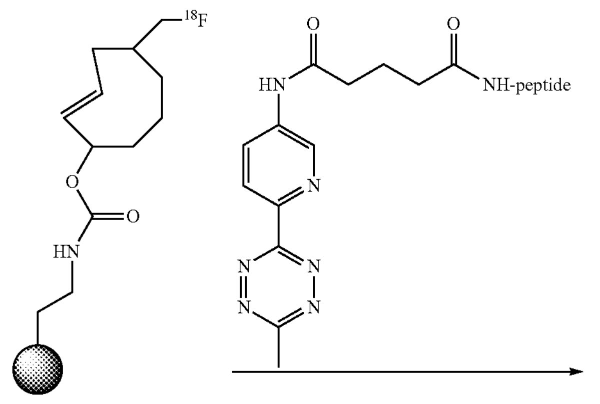

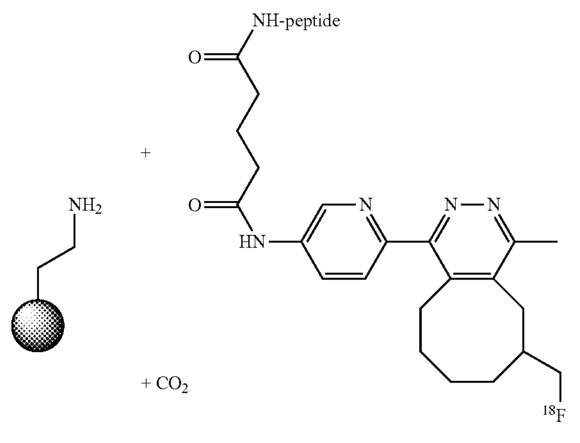

In another aspect the Trigger is used in a diagnostic kit, see directly below. With reference to formula 9, k is preferably 1. Immobilized (e.g. in a 96-well plate) TCO conjugated to one or more quenched fluorophores is contacted with a sample containing an unknown amount of tetrazine moieties. These tetrazines have been previously incorporated in a biomolecule as amino acid residue in a metabolic engineering experiment, or alternatively the sample contains e.g. tetrazine-based pesticide. Reaction of the tetrazine with the TCO effects release and dequenching of the fluorophores, allowing readout via e.g. UV absorption.

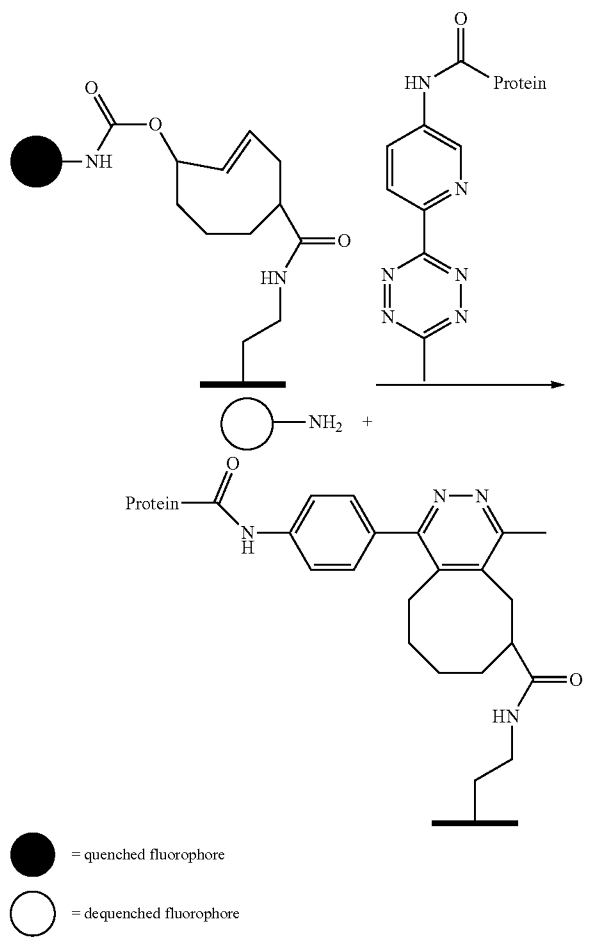

Constructs $C^A$ and $C^B$

The Constructs to be used in the present invention include but are not limited to small molecules, organic molecules, metal coordination compounds, inorganic molecules, organometallic molecules, biomolecules, drugs, polymers, resins (e.g. polystyrene, agarose) particles (e.g. beads, magnetic beads, gold, silica-based, polymer, glass, iron oxide particles, micro- and nanoparticles, such as liposomes, polymersomes), gels, surfaces (e.g. glass slides, chips, wavers, gold, metal, silica-based, polymer, plastic, resin), cells, biological tissues, pathogens (viruses, bacteria, fungi, yeast). The Constructs may for example comprise a combination of the aforementioned Constructs.

Examples of biomolecules include: carbohydrates, peptides, peptoids, lipids, proteins, enzymes, oligonucleotides, DNA, RNA, PNA, LNA, aptamers, hormones, toxins, steroids, cytokines, antibodies, antibody fragments (e.g. Fab2, Fab, scFV, diabodies, triabodies, VHH), antibody (fragment) fusions (e.g. bi-specific and trispecific mAb fragments).

Spacers

Spacers $S^P$ include but are not limited to polyethylene glycol (PEG) chains varying from 2 to 200, particularly 3 to 113 and preferably 5-50 repeating units. Other examples are biopolymer fragments, such as oligo- or polypeptides or polylactides, or carbohydrates. Further preferred examples are shown in the examples.

Further Embodiment 1

With reference to formula (1a) and (1b) for Triggers that function via cascade-mediated release or elimination (i.e.

cascade mechanism), when p=1 and n=1 it is preferred that $L^D$ is linked to $T^R$ via N or NH or O or S or an aliphatic or aromatic carbon, wherein these atoms are part of the linker; and when p=1 and n=0 it is preferred that $C^A$ is linked to $T^R$ via N or NH or O or S or an aliphatic or aromatic carbon, wherein these atoms are part of $C^A$. It is further preferred that said N and NH and O and S moieties comprised in $L^D$ or $C^A$ are bound to an aliphatic or aromatic carbon of $L^D$ or $C^A$.

With reference to formula (1a) and (1b) for Triggers that function via cascade-mediated release or elimination (i.e. cascade mechanism), when p=0 and n=1 it is preferred that $L^D$ is linked to $T^R$ via S or O, wherein these atoms are part of the linker; and when p=0 and n=0 it is preferred that $C^A$ is linked to $T^R$ via S or O, wherein these atoms are part of $C^A$. It is further preferred that said S and O moieties comprised in $L^D$ or $C^A$ are bound to an aliphatic or aromatic carbon or carbonyl or thiocarbonyl of $L^D$ or $C^A$.

With reference to formula (1a) and (1b) for Triggers that function via cascade-mediated release or elimination (i.e. cascade mechanism), in particular embodiments when $X^D$ is S—C(O)-$(L^D)_n$-$(C^A)$, O—C(S)-$(L^D)_n$-$(C^A)$, S—C(S)-$(L^D)_n$-$(C^A)$ and n 1 it is preferred that $L^D$ is linked to $T^R$ via N or NH or O or S or an aliphatic or aromatic carbon, wherein these atoms are part of the linker; and when n=0 it is preferred that $C^A$ is linked to $T^R$ via N or NH or O or S or an aliphatic or aromatic carbon, wherein these atoms are part of $C^A$. It is further preferred that said N and NH and O and S moieties comprised in $L^D$ or $C^A$ are bound to an aliphatic or aromatic carbon of $L^D$ or $C^A$.

Further Embodiment 2

Further preferred activators for use with Triggers based on the cascade mechanism are:

(8c)

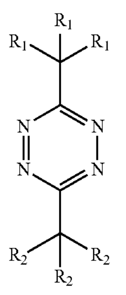

(8d)

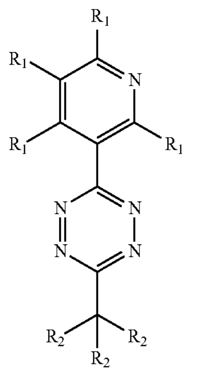

-continued (8e)

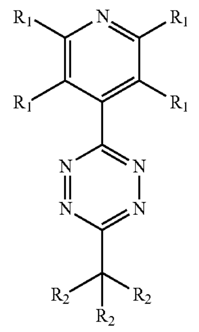

(8f)

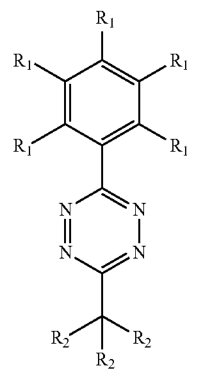

(8g)

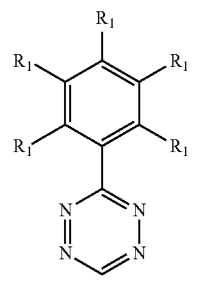

The 1,2,4,5-tetrazine given in Formula (8c-g), wherein each $R^1$ and each $R^2$ independently are selected from the group consisting of H, alkyl, aryl, $CF_3$, $CF_2$—R', $NO_2$, OR', SR', C(═O)R', C(═S)R', OC(═O)R''', SC(═O)R''', OC(═S)R''', SC(═S)R''', S(═O)R', $S(═O)_2R'''$, $S(═O)_2$ NR'R", C(═O)O—R', C(═O)S—R', C(═S)O—R', C(═S) S—R', C(═O)NR'R", C(═S)NR'R", NR'R", NR'C(═O) R", NR'C(═S)R", NR'C(═O)OR", NR'C(═S)OR", NR'C (═O)SR", NR'C(═S)SR", OC(═O)NR'R", SC(═O) NR'R", OC(═S)NR'R", SC(═S)NR'R", NR'C(═O) NR"R", NR'C(═S)NR"R" with each R' and each R" independently being H, aryl or alkyl, and R''' independently being aryl or alkyl.

Other preferred activators for use with Triggers based on the cascade mechanism are:
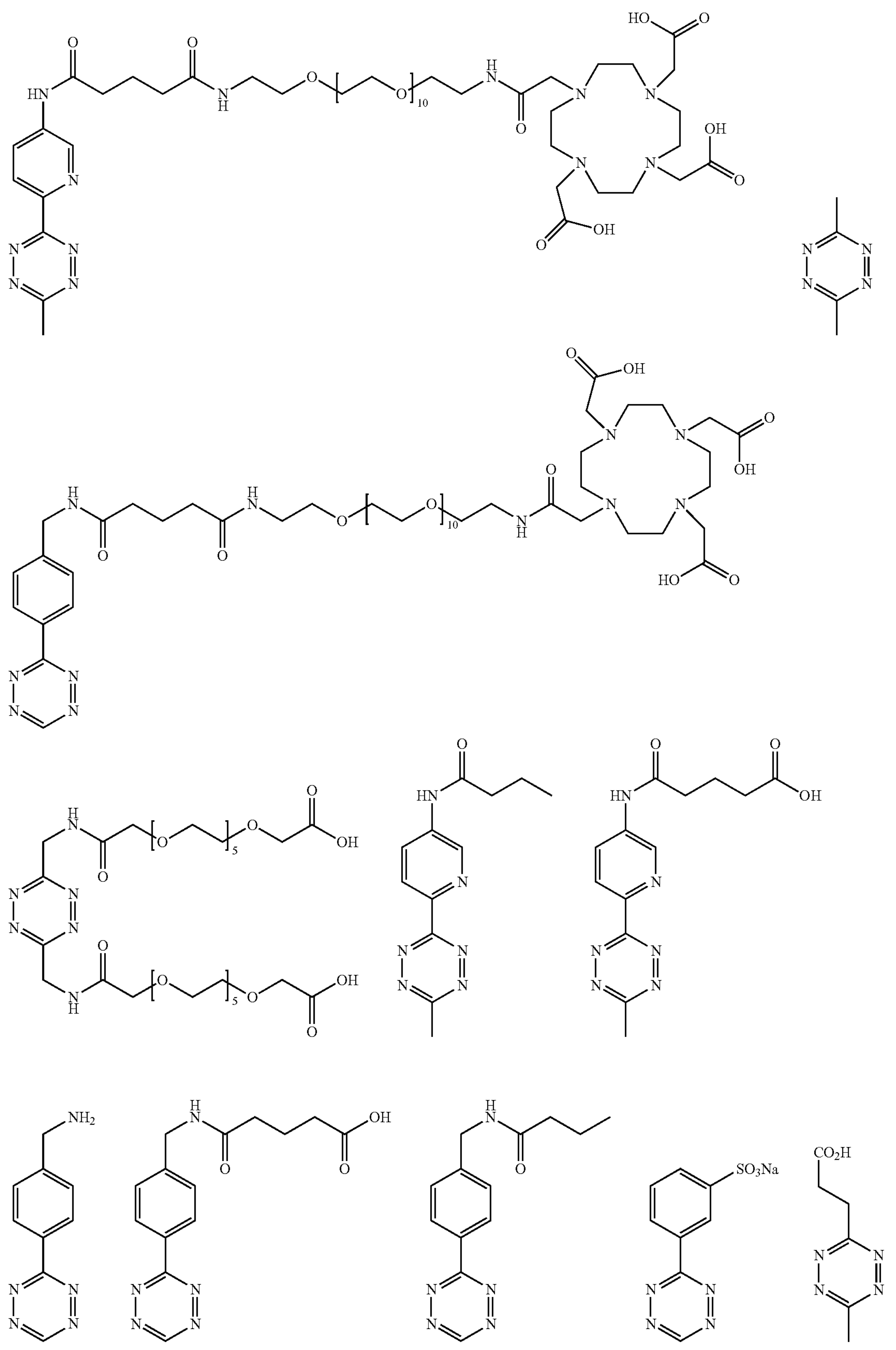

-continued
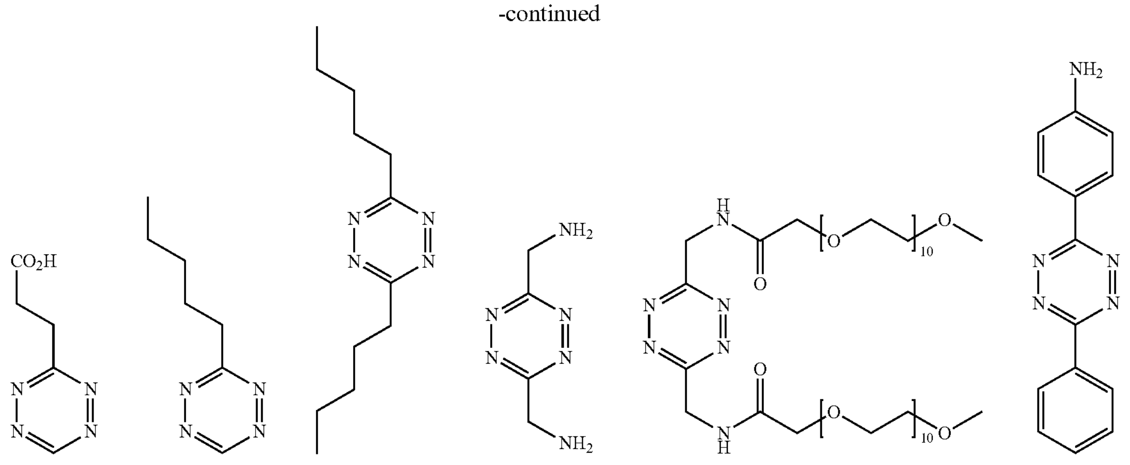
Other preferred activators for use with Triggers based on the strain release mechanism are:
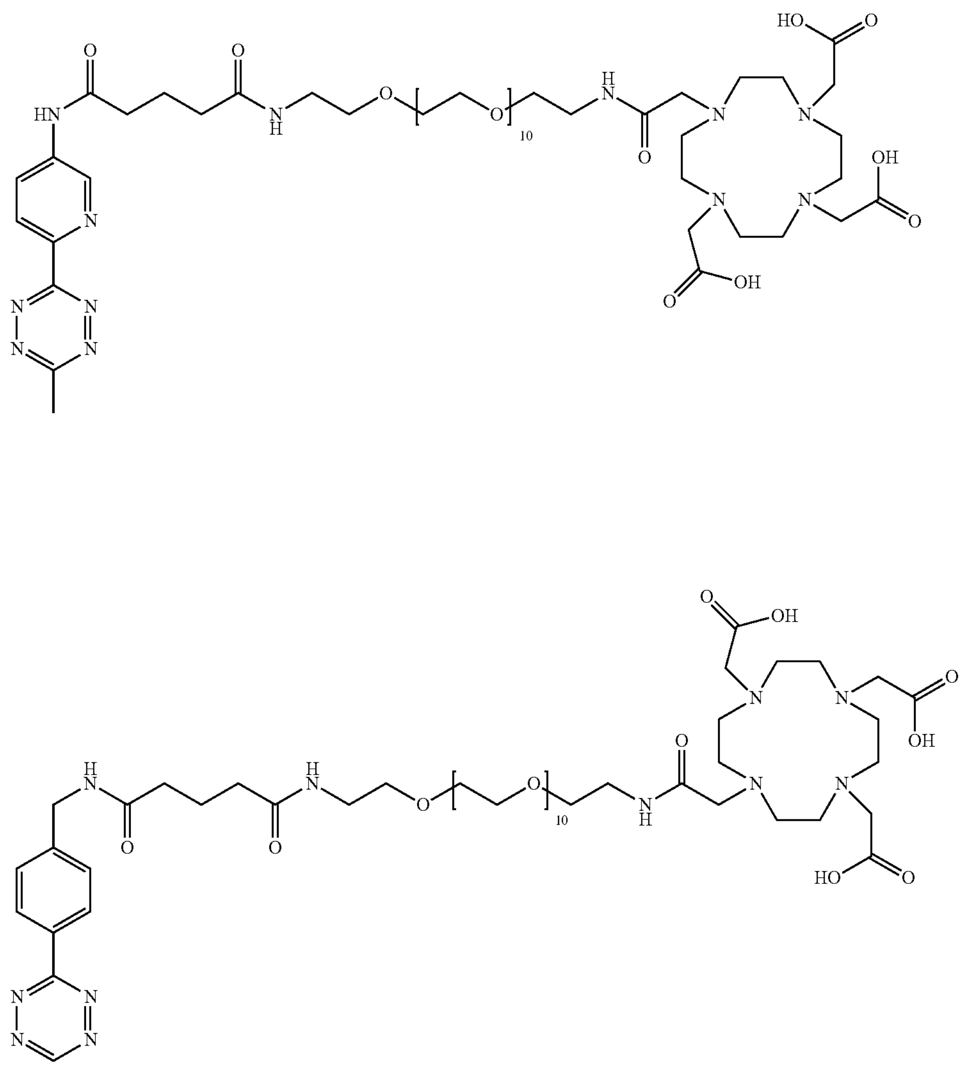

The Activator can have a link to a moiety such as a peptide, protein, carbohydrate, PEG, or polymer, resin, particle, gel, surface.

Preferably, Activators for use with Triggers based on the cascade mechanism and with a link to said moiety satisfy one of the following formulae:

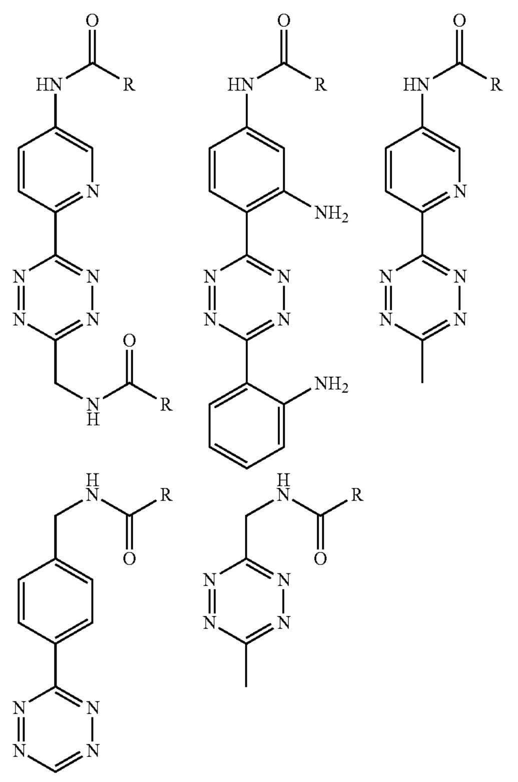

R = (link to) peptide, protein, carbohydrate, PEG, polymer, resin, particle, gel, surface Preferably, Activators for use with Triggers based on the strain release mechanism and with a link to said moiety satisfy one of the following formulae:

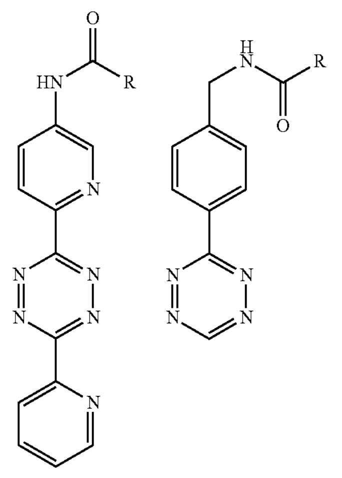

R = (link to) peptide, protein, carbohydrate, PEG, polymer, resin, particle, gel, surface Further Embodiment 3

Some embodiments satisfy the one of the following formulas:

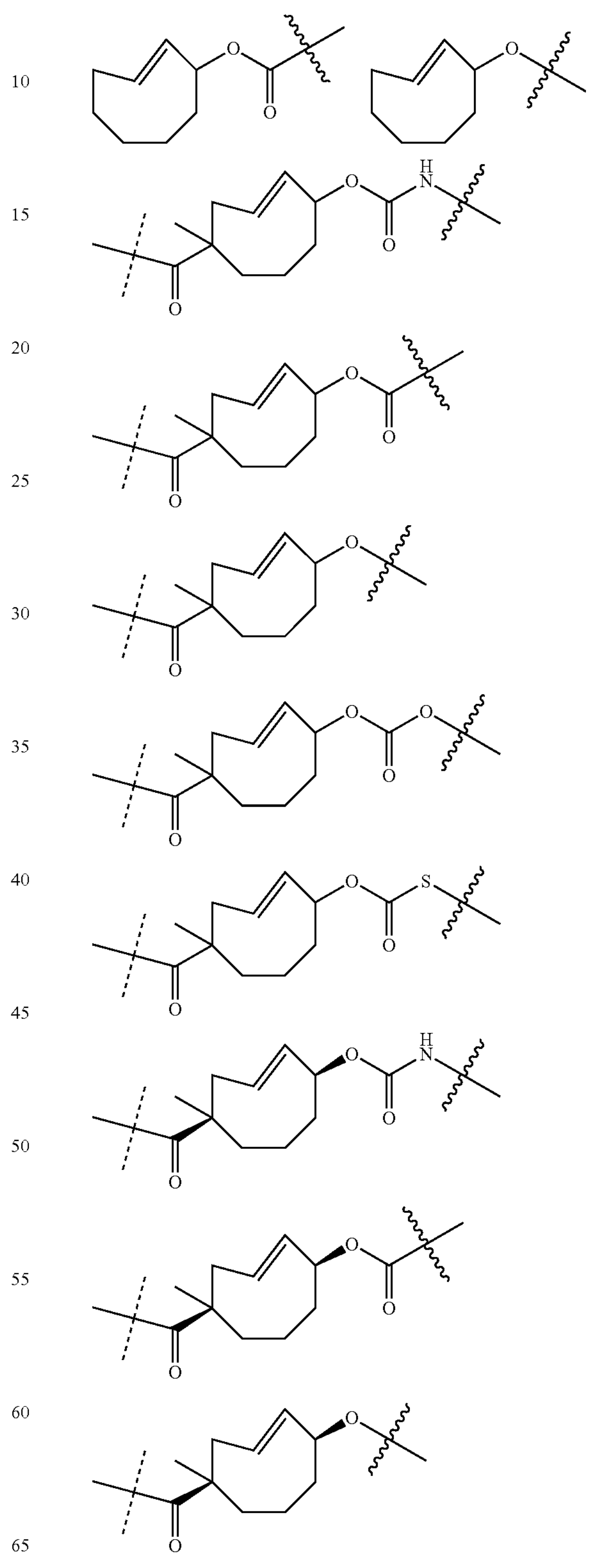

-continued
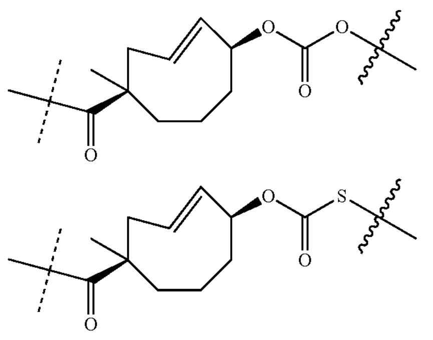
= rest of attached $C^B$ or $S^P$-$C^B$
= rest of attached $C^A$ or $L^D$-$C^A$
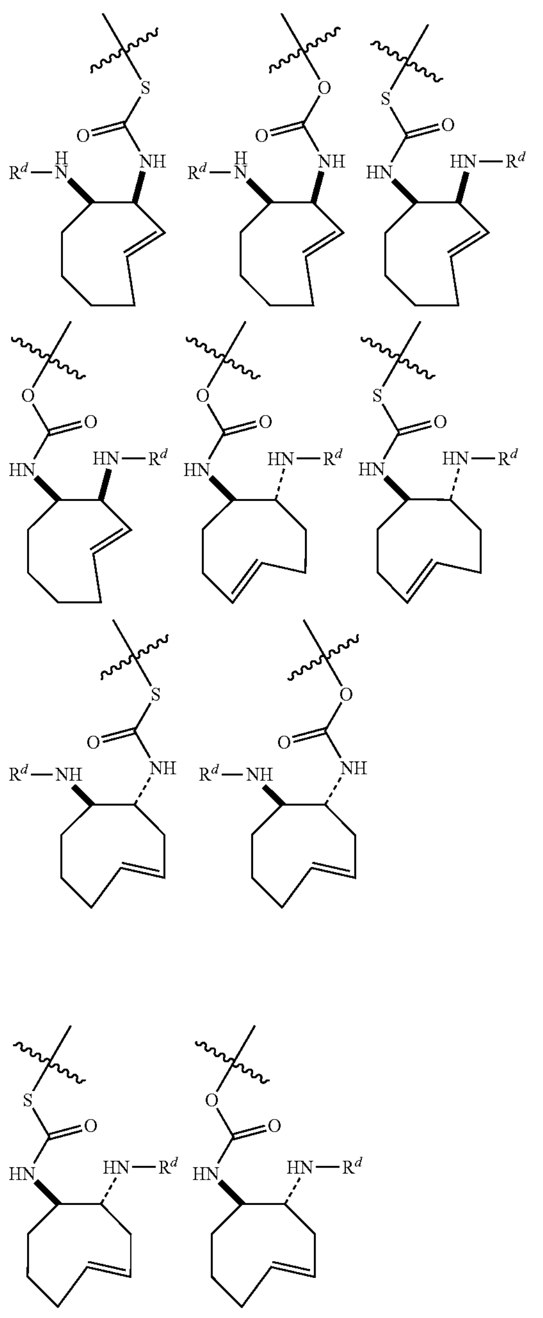
-continued
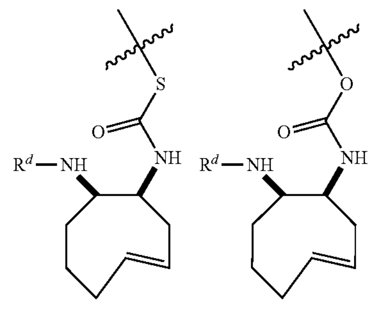
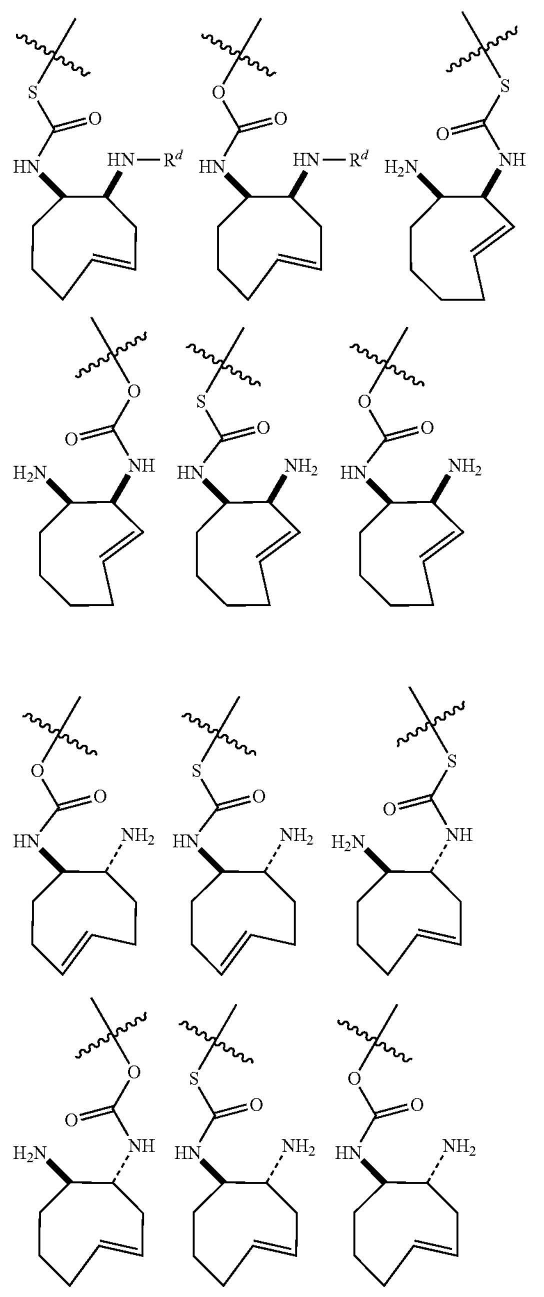

-continued

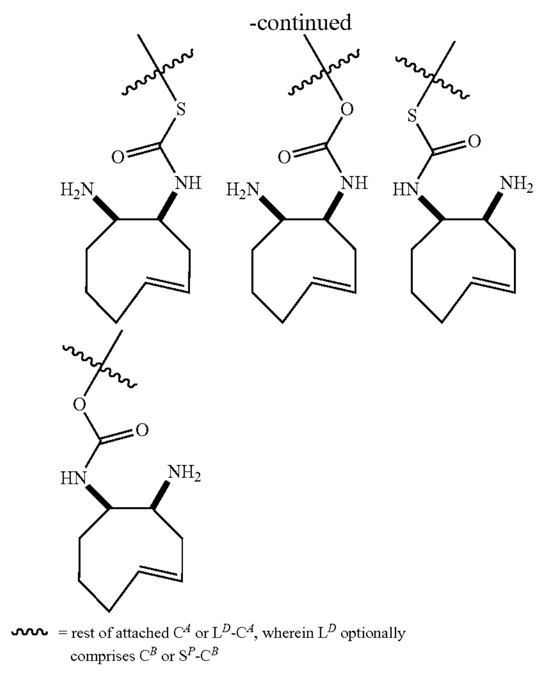

= rest of attached $C^A$ or $L^D$-$C^A$, wherein $L^D$ optionally comprises $C^B$ or $S^P$-$C^B$

EXAMPLES

The following examples demonstrate the invention or aspects of the invention, and do not serve to define or limit the scope of the invention or its claims.

Methods. $^1$H-NMR and $^{13}$C-NMR spectra were recorded on a Varian Mercury (400 MHz for $^1$H-NMR and 100 MHz for $^{13}$C-NMR) spectrometer at 298 K. Chemical shifts are reported in ppm downfield from TMS at room temperature. Abbreviations used for splitting patterns are s=singlet, t=triplet, q=quartet, m=multiplet and br=broad. IR spectra were recorded on a Perkin Elmer 1600 FT-IR (UATR). LC-MS was performed using a Shimadzu LC-10 AD VP series HPLC coupled to a diode array detector (Finnigan Surveyor PDA Plus detector, Thermo Electron Corporation) and an Ion-Trap (LCQ Fleet, Thermo Scientific). Analyses were performed using a Alltech Alltima HP Cis 3 column using an injection volume of 1-4 μL, a flow rate of 0.2 mL min-1 and typically a gradient (5% to 100% in 10 min, held at 100% for a further 3 min) of $CH_3CN$ in $H_2O$ (both containing 0.1% formic acid) at 25° C. Preparative RP-HPLC ($CH_3CN/H_2O$ with 0.1% formic acid) was performed using a Shimadzu SCL-10A VP coupled to two Shimadzu LC-8A pumps and a Shimadzu SPD-10AV VP UV-vis detector on a Phenomenex Gemini 5 Cis 110A column. Size exclusion (SEC) HPLC was carried out on an Agilent 1200 system equipped with a Gabi radioactive detector. The samples were loaded on a Superdex-200 10/300 GL column (GE Healthcare Life Sciences) and eluted with 10 mM phosphate buffer, pH 7.4, at 0.35-0.5 mL/min. The UV wavelength was preset at 260 and 280 nm. The concentration of antibody solutions was determined with a NanoDrop 1000 spectrophotometer (Thermo Fisher Scientific) from the absorbance at 322 nm and 280 nm, respectively.

Materials. All reagents, chemicals, materials and solvents were obtained from commercial sources, and were used as received: Biosolve, Merck and Cambridge Isotope Laboratories for (deuterated) solvents; and Aldrich, Acros, ABCR, Merck and Fluka for chemicals, materials and reagents. All solvents were of AR quality.

General Examples

The invention can be exemplified with the same combinations of TCO and diene as included in applications WO2012156919A1 (e.g. Examples 9-14) and WO2012156920A1 (e.g. Examples 8-11), except that a Construct as defined hereinbefore is taken in lieu of a drug as disclosed therein.

Example 1

Synthesis of Tetrazine Activators

For previously synthesized tetrazines see WO2012156919A1 and WO2012156920A1. Bis-pyridyl-tetrazine-NHS derivative was described in J. Nucl. Med. 2013, 54,1989-1995.

3,6-dibenzyl-1,2,4,5-tetrazine (4)

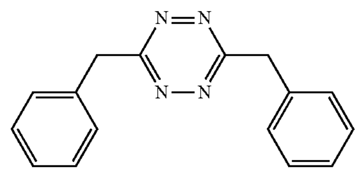 [SMILES: c1ccc(Cc2nnc(Cc3ccccc3)nn2)cc1]

Hydrazine hydrate (2.43 mL, 50.0 mmol) was added to a solution of benzyl cyanide (1.16 mL, 10.0 mmol) and $ZnI_2$ (160 mg, 0.5 mmol) in DMF (20 mL) and the solution was stirred overnight at 60° C. under argon. $NaNO_2$ (3.45 g, 50.0 mmol in 10 mL $H_2O$) was added dropwise to the suspension at room temperature. 1M HCl (ca. 80 mL) was added until gas formation stopped and pH=2. The mixture was extracted with $CH_2Cl_2$ (3×80 mL) and the combined organic fractions were dried with $Na_2SO_4$ and concentrated. 4 was obtained after silica gel column chromatography (EtOAc/heptanes, 1/20) as purple oil. Yield: 0.64 g (2.44 mmol, 45%). $^1$H NMR (400 MHz, $CDCl_3$): δ 7.38-7.26 (m, 8H), 3.75 (s, 4H) ppm. $^{13}$C NMR (400 MHz, $CDCl_3$): δ 129.9, 129.1, 128.0, 127.9, 23.6 ppm. No MS data available due to poor ionization.

Synthesis of 3,6-diisopropyl-1,2,4,5-tetrazine (5)

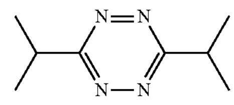

Hydrazine hydrate (13.2 mL, 312 mmol) was added to isobutyronitrile (3.59 mL, 40.0 mmol) and $ZnI_2$ (0.64 g, 2.0 mmol) and the mixture was stirred overnight at 60° C. under argon. $NaNO_2$ (13.45 g, 200 mmol in 200 mL $H_2O$) was added dropwise to the light colored suspension at room temperature over a cold-water bath. 1M HCl (ca. 400 mL) was added to the pink solution until gas formation stopped and pH=2. The mixture was extracted with $CH_2Cl_2$ (4×100 mL) and the combined organic fractions were dried with $Na_2SO_4$ and concentrated. 5 was obtained after silica gel column chromatography (EtOAc/hexanes, 1/9) as volatile purple oil. Yield: 3.6 g (21.4 mmol, quantitative yield). Rf:

0.25 (EtOAc/hexanes, 1/9). $^1$H NMR (400 MHz, $CDCl_3$): δ 3.63 (sep, J=7.2 Hz, 2H), 1.52 (d, J=7.0 Hz, 12H) ppm. $^{13}$C NMR (400 MHz, $CDCl_3$): δ 173.8, 34.2, 21.3 ppm. ESI-MS [M+H$^+$]: calc: 167.13 Da, found: 167.08 Da.

3,6-dimethyl-1,2,4,5-tetrazine (8)

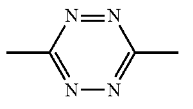

Acetamidine hydrochloride (3.97 mg; 42.0 mmol) was dissolved in water (20 mL), and hydrazine hydrate (4.0 mL; 84.0 mmol) was added. The mixture was stirred at 20° C. under an atmosphere of argon for 5 h. Water (20 mL) was added, followed by sodium nitrite (14.4 g; 210 mmol). The reaction mixture was cooled on an icebath and acidified to pH=3 by careful addition of acetic acid (15.0 g; 250 mmol). The dark pink, aqueous solution was extracted with dichloromethane (2 times 50 mL), and the combined organic layers were washed with 1 M hydrochloric acid (50 mL), dried over magnesium sulfate, and the solvent was removed by evaporation. The product was obtained as dark red crystals (750 mg; 33%). $^1$H-NMR ($CDCl_3$): δ=3.04 (s, 6H) ppm. $^{13}$C-NMR ($CDCl_3$): δ=167.2, 21.0 ppm. GC-MS: m/z=+110 M$^+$(calcd 110.06 for $C_4H_6N_4$).

3-methyl-6-(pyridin-3-yl)-1,2,4,5-tetrazine (10)

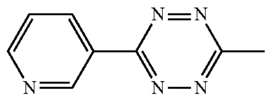

Hydrazine hydrate (2.68 mL, 55.2 mmol) was added to 3-cyanopyridine (500 mg, 4.8 mmol), acetamidine hydrochloride (2.00 g, 21.2 mmol) and sulfur (78 mg, 2.4 mmol) and the mixture was stirred overnight under argon at room temperature. The reaction mixture was concentrated and suspended in a mixture of THF (10 mL) and AcOH (12 mL) over a cold-water bath. $NaNO_2$ (2.76 g, 40.0 mmol in 10 mL $H_2O$) was added dropwise and the mixture was stirred for another 5 minutes. $H_2O$ (80 mL) and $CHCl_3$ (100 mL) were added and the layers were separated. The organic layer was washed with $H_2O$ (2×100 mL), dried with $Na_2SO_4$ and concentrated. Silica gel column chromatography (acetone/hexanes, 1/4) yielded 10 contaminated with a small amount of the bis-pyridyl side product. Recrystallization from EtOAc yielded 10 as long needles (70 mg, 0.40 mmol, 8%). Concentration of the EtOAc filtrate yielded another crop (170 mg) of almost pure 10. $^1$H NMR (400 MHz, $CDCl_3$): δ 9.80 (dd, $J_1$=0.8 Hz, $J_2$=1.9 Hz), 8.88-8.84 (m, 2H), 7.55 (m, 1H), 3.14 (s, 3H) ppm. $^{13}$C NMR (400 MHz, $CDCl_3$): δ 168.0, 163.1, 153.2, 149.3, 135.1, 127.9, 123.9, 21.3 ppm. ESI-MS [M$^+$H$^+$]calc: 174.08 Da, found: 174.08 Da.

3-methyl-6-(pyridin-4-yl)-1,2,4,5-tetrazine (11)

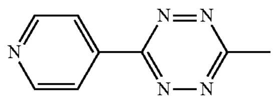

Hydrazine hydrate (2.68 mL, 55.2 mmol) was added to 4-cyanopyridine (500 mg, 4.8 mmol), acetamidine hydrochloride (2.00 g, 21.2 mmol) and sulfur (78 mg, 2.4 mmol) and the mixture was stirred overnight under argon at room temperature. The reaction mixture was concentrated and suspended in a mixture of THF (10 mL) and AcOH (12 mL) over a cold-water bath. $NaNO_2$ (2.76 g, 40.0 mmol in 10 mL $H_2O$) was added dropwise and the mixture was stirred for another 5 minutes. $H_2O$ (80 mL) and $CHCl_3$ (100 mL) were added and the layers were separated. The organic layer was washed with $H_2O$ (2×100 mL), dried with $Na_2SO_4$ and concentrated. Silica gel column chromatography (acetone/hexanes, 1/4) yielded 11 with a ca. 20% contamination of a thiadiazole compound. The crude material (220 mg) was recrystallized from diisopropylether to yield 11 as pink crystals. Yield: 135 mg (0.78 mmol, 16%). Rf: 0.07 (acetone/hexanes, 1/4). $^1$H NMR (400 MHz, $CDCl_3$): δ 8.91 (dd, $J_1$=1.5 Hz, $J_2$=4.7 Hz, 2H), 8.44 (dd, $J_1$=1.8 Hz, $J_2$=4.5 Hz, 2H), 3.17 (s, 3H) ppm. $^{13}$C NMR (400 MHz, $CDCl_3$): δ 168.5, 163.0, 151.1, 139.2, 121.2, 21.4 ppm. ESI-MS [M$^+$H$^+$]: calc: 174.08 Da, found: 174.08 Da.

3-methyl-6-(3-methylpyridin-2-yl)-1,2,4,5-tetrazine (12)

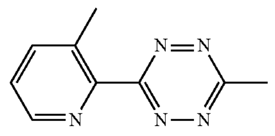

Hydrazine hydrate (2.76 mL, 56.2 mmol) was added to 3-methylpicolinonitrile (0.57 g, 4.8 mmol), acetamidine hydrochloride (2.00, 21.2 mmol) and sulfur (155 mg, 4.8 mmol) and the mixture was stirred under argon at room temperature for 40 hours. EtOH (10 mL) was added and the mixture was filtered. The filtrate was concentrated and suspended in a mixture of THF (10 mL) and AcOH (12 mL) over a cold-water bath. $NaNO_2$ (2.76 g, 40.0 mmol in 10 mL $H_2O$) was added dropwise and the mixture was stirred for another 5 minutes. $H_2O$ (80 mL) and $CHCl_3$ (100 mL) were added and the layers were separated. The organic layer was washed with $H_2O$ (2×100 mL), dried with $Na_2SO_4$ and concentrated. Silica gel column chromatography (acetone/hexanes, 1/4) yielded 12 as purple liquid. Yield: 110 mg (0.59 mmol, 12%). $^1$H NMR (400 MHz, $CDCl_3$): δ 8.73 (dd, $J_1$=0.8 Hz, $J_2$=4.6 Hz, 1H), 7.76 (ddd, $J_1$=0.8 Hz, $J_2$=1.5, $J_3$=7.8 Hz, 1H), 7.43 (dd, $J_1$=4.7 Hz, $J_2$=7.8 Hz, 1H), 3.17 (s, 3H), 2.60 (s, 3H) ppm. $^{13}$C NMR (400 MHz, $CDCl_3$): δ 167.3, 166.0, 149.8, 148.0, 139.7, 134.5, 125.2, 21.4, 19.8 ppm. ESI-MS [M$^+$H$^+$]calc: 188.09 Da, found: 188.08 Da.

3-methyl-6-phenyl-1,2,4,5-tetrazine (14)

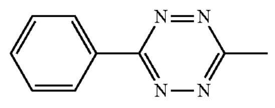

Hydrazine hydrate (3.24 mL, 66.7 mmol) was added to benzonitrile (600 mL, 5.8 mmol), acetamidine hydrochloride (2.41 g, 25.5 mmol) and sulfur (94 mg, 2.9 mmol) and the mixture was stirred overnight under argon at room temperature. The reaction mixture was concentrated and suspended in a mixture of THF (10 mL) and AcOH (12 mL) over a cold-water bath. $NaNO_2$ (3.33 g, 28.3 mmol in 10 mL $H_2O$) was added dropwise and the mixture was stirred for another 5 minutes. $H_2O$ (50 mL) and $CHCl_3$ (100 mL) were added and the layers were separated. The organic layer was washed with $H_2O$ (2×70 mL), dried with $Na_2SO_4$ and concentrated. Silica gel column chromatography (acetone/hexanes, 1/4) yielded 14 with some contamination (ca. 75 mg). The crude product could not be purified by recrystallization from numerous solvents. $^1H$ NMR (400 MHz, $CDCl_3$): δ 8.59 (dd, $J_1$=1.6 Hz, $J_2$=8.2 Hz, 2H), 7.68-7.60 (m, 2H), 7.50-7.46 (m, 1H), 3.10 (s, 3H) ppm. $^{13}C$ NMR (400 MHz, $CDCl_3$): δ 167.3, 164.2, 132.6, 131.8, 129.3, 127.9, 21.2 ppm. MALDI-TOF-MS: $[M^+H^+]$: calc: 173.08 Da, found 173.30 Da.

Example 2

TCO Synthesis

The following TCO constructs have been prepared according to WO2012156920A1:

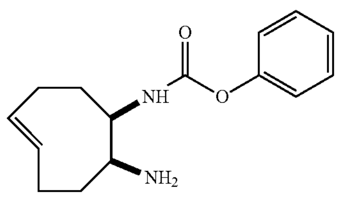

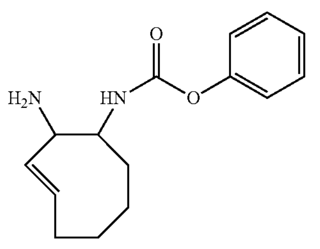

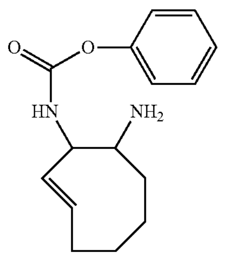

-continued

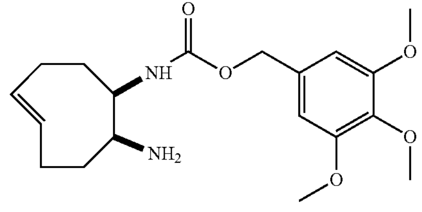

3-PNP-TCO was synthesized following WO2012156919A1.

Axial-TCO-1-Doxorubicin

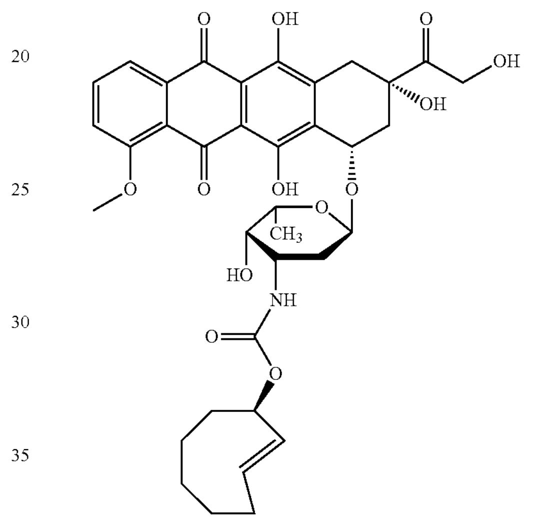

The synthesis of Axial-TCO-1-Doxorubicin is described in WO2012156919A1.

TCO-3-Doxorubicin

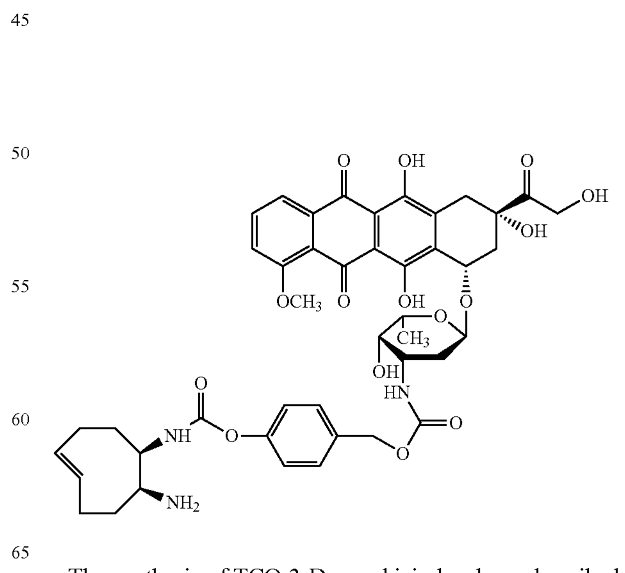

The synthesis of TCO-3-Doxorubicin has been described in WO2012156920A1.

Synthesis of (E)-cyclooct-2-enyl naphthalen-1-ylmethylcarbamate

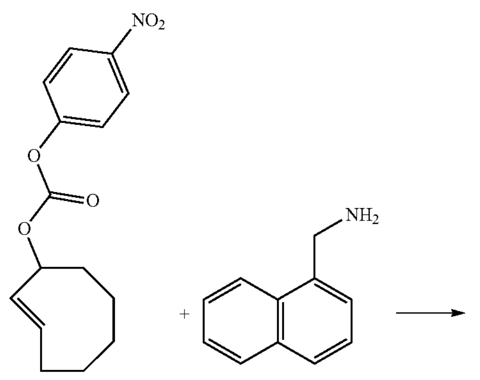

3-PNP-TCO (41.9 mg; $1.44*10^{-4}$ mol) was dissolved in dichloromethane (1.5 mL), and DIPEA (55.7 mg; $4.32*10^{-4}$ mol) and 1-naphthylmethylamine (27.2 mg; $1.73*10^{-4}$ mol) were added. The reaction mixture was stirred at 20° C. under and atmosphere of argon and slowly turned yellow. After 20 h the solvent was removed by evaporation in vacuo, and the mixture was redissolved in dichloromethane and washed with subsequently, 1 M aqueous sodium hydroxide (5 times 2.5 mL) and 1 M aqueous citric acid (2 times 1.5 mL). The organic layer was dried over sodium sulfate, filtered, and evaporated to dryness. The product was further purified by preparative RP-HPLC, and isolated by lyophilization, to yield a white powder (32.0 mg; 72%). $^{1}$H-NMR ($CDCl_3$): δ=8.04 (d, 1H), 7.89 (d, 1H), 7.81 (d, 1H), 7.54 (m, 2H), 7.45 (m, 2H), 5.79 (m, 1H), 5.56 (d, 1H), 5.40 (m, 1H), 5.03 (br. s, 1H), 4.85 (m, 2H), 2.44 (m, 1H), 2.2-1.6 (br. m, 6H), 1.43 (m, 1H), 1.02 (m, 1H), 0.79 (m, 1H) ppm. $^{13}$C-NMR ($CDCl_3$): δ=131.7, 131.4, 128.8, 128.5, 126.5, 126.4, 125.9, 125.4, 123.5, 74.2, 43.2, 40.7, 35.9, 29.1, 29.0, 24.1 ppm. FT-IR (ATR): ν=3322, 2927, 2857, 1692, 1533, 1258, 1070, 1025, 987 $cm^{-1}$. LC-MS: m/z=+310.25 $[M^{+}H]^{+}$(calcd 309.17 for $C_{20}H_{23}NO_2$).

Axial-(E)-cyclooct-2-en-1-yl 4-nitrobenzoate

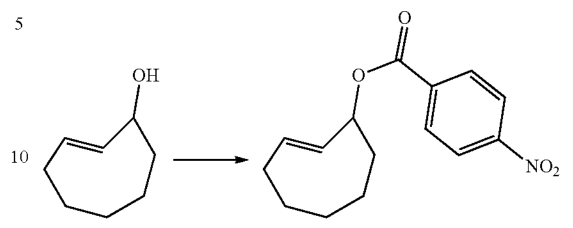

Axial-(E)-cyclooct-2-en-1-ol (152 mg, 1.20 mmol) was dissolved in 10 mL dichloromethane. 4-(N,N-dimethylamino)pyridine (306 mg, 2.50 mmol) was added and the solution was cooled in an ice-bath. A solution of 4-nitrobenzoyl chloride (201 mg, 1.08 mmol) in 5 mL dichloromethane was added in portions over a 5 min period. The solution was stirred for 3 days. The solvent was partially removed by rotary evaporation. The remaining solution (a few mL) was chromatographed on 19 g silica, using dichloromethane as the eluent. The product fractions were rotary evaporated yielding a colourless solid (144 mg, 0.52 mmol, 48%).

$^{1}$H-NMR ($CDCl_3$): δ 8.4-8.2 (m, 4H), 5.9 (m, 1H), 5.6 (m, 2H), 2.2 (dd, 1H), 2.5 (m, 1H), 2.15-1.7 (m, 6H), 1.55 (m, 1H), 1.2 (dt, 1H), 0.9 (dt, 1H).

Equatorial-(E)-cyclooct-2-en-1-yl 4-nitrobenzoate

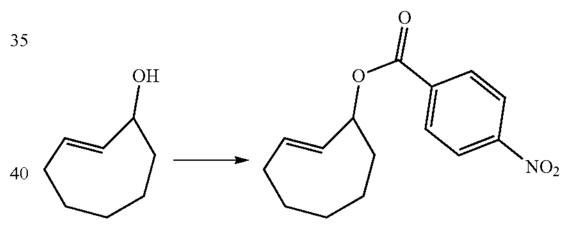

Equatorial-(E)-cyclooct-2-en-1-ol (154 mg, 1.22 mmol) was dissolved in 10 mL dichloromethane. 4-(N,N-dimethylamino)pyridine (300 mg, 2.46 mmol) was added and the solution was cooled in an ice-bath. A solution of 4-nitrobenzoyl chloride (268 mg, 1.44 mmol) in 5 mL dichloromethane was added in portions over a 5 min period. The solution was stirred for 4 days. The solvent was removed by rotary evaporation and the residue was chromatographed on 19 g silica, using dichloromethane as the eluent. The product fractions were rotary evaporated yielding a colourless solid.

$^{1}$H-NMR ($CDCl_3$): δ 8.4-8.1 (m, 4H), 5.9 (m, 1H), 5.7 (m, 1H), 5.4 (m, 1H), 2.5 (m, 1H), 2.3 (m, 1H), 2.1-1.8 (m, 3H), 2.8-2.4 (m, 4H), 1.8-1.4 (m, 4H), 1.0-0.8 (m, 1H).

(E)-3-phenoxycyclooct-1-ene

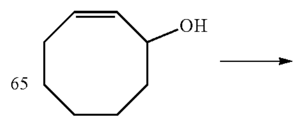

-continued

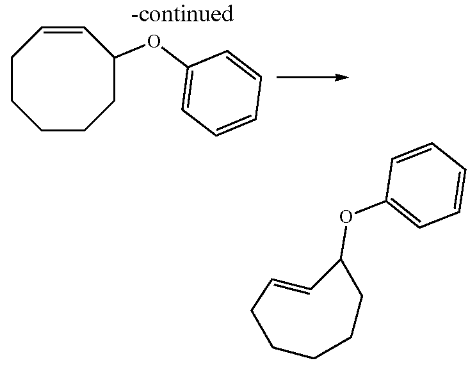

Cyclooct-2-en-1-ol (5.002 g, 39.64 mmol) was dissolved in 100 mL THF. Phenol (3.927 g, 41.78 mmol) was added to the solution. Triphenylphosphine (10.514 g, 40.01 mmol) was added and the resulting solution was cooled in an ice-bath. A solution of diethyl azodicarboxylate (6.975 g, 40.01 mmol) in 50 mL THF was added over a 30 min period. The reaction mixture was stirred for 24 h and then rotary evaporated. The residue was stirred with heptane, the mixture was filtered and the filtrate was rotary evaporated. The residue was chromatographed on 50 g silica, using heptane as eluent. Product fractions were rotary evaporated and the residue was stirred with methanol until homogeneous, then filtered, and rotary evaporated. The residue was purified by Kugelrohr distillation to yield the product as an oil (3.5 g, 17.33 mmol, 44%).

3-phenoxycyclooctene (5.5 g, 27.23 mmol) was dissolved in heptane—ether (ca.1/2). The solution was irradiated for 7 days while the solution was continuously flushed through a 42 g silver nitrate impregnated silica column (containing ca. 4.2 g silver nitrate). The column was rinsed twice with TBME, then with TBME containing 5% methanol, then with TBME containing 10% MeOH. The product fractions were washed with 100 mL 15% ammonia (the same ammonia being used for each fraction), then dried and rotary evaporated. The column material was stirred with TBME and 15% ammonia, then filtered, and the layers were separated. The organic layer was dried and rotary evaporated. The first two TBME fractions were combined, and all other fractions were separately rotary evaporated, then examined for the presence of the product (none of the fractions contained a pure trans-cyclooctene isomer, however). The product fractions were combined and chromatographed on 102 g silica, using heptane as the eluent. The first fractions yielded the pure minor (believed to be axial) isomer as an oil (144 mg, 0.712 mmol, 2.6%). The next fractions contained a mixture of minor and major isomer. Pure major (believed to be equatorial) isomer was eluted last, yielding a colourless solid (711 mg, 3.52 mmol, 13%).

(Z)-3-phenoxycyclooct-1-ene: $^1$H-NMR ($CDCl_3$): δ 7.25 (m, 2H), 6.9 (m, 3H), 5.7 (m, 1H), 5.5 (m, 1H), 5.1 (m, 1H), 2.5-2.0 (m, 3H), 1.3-1.9 (m, 7H).

(E)-3-phenoxycyclooct-1-ene (axial isomer): $^1$H-NMR ($CDCl_3$): δ 7.25 (m, 2H), 6.9 (m, 3H), 5.9 (m, 1H), 5.6 (m, 1H), 4.9 (s, 1H), 2.4 (m, 1H), 2.2 (m, 1H), 2.0-0.8 (m, 8H)

(E)-3-phenoxycyclooct-1-ene (equatorial isomer): $^1$H-NMR ($CDCl_3$): δ 7.25 (m, 2H), 6.9 (m, 3H), 5.9 (m, 1H), 5.55 (m, 1H), 4.8 (m, 1H), 2.45-2.25 (m, 2H), 2.05-1.4 (m, 6H), 1.0-0.8 (m, 2H)

Axial (E)-cyclooct-2-en-1-yl 2-phenylacetate

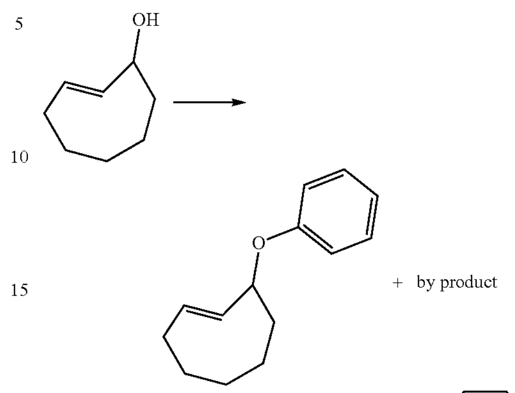

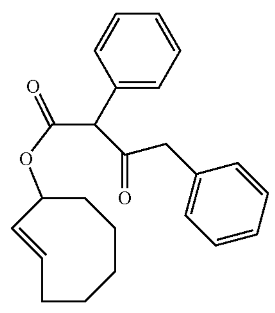

Axial (E)-cyclooct-2-en-1-ol (102 mg, 0.81 mmol) was dissolved in 7.5 mL dichloromethane with 4-(N,N-dimethylamino)pyridine (303 mg, 2.70 mmol). A solution of phenylacetyl chloride (155 mg, 1.00 mmol) in 2.5 mL dichloromethane was added in portions over a 5 min period to the ice-cooled solution. The reaction mixture was stirred for 4 days, then washed with water. The aqueous layer was extracted with 10 mL dichloromethane. The combined organic layers where dried and rotary evaporated, followed by chromatography yielding a colourless powder (22 mg) which was identified as the depicted byproduct.

Axial-(E)-3-(benzyloxy)cyclooct-1-ene

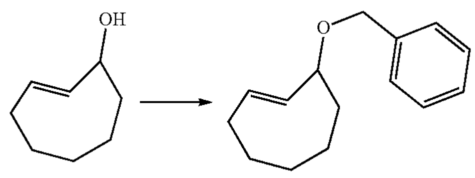 [SMILES: OC1/C=C/CCCCC1 ; C1=C/C(OCc2ccccc2)CCCCC/1]

Axial (E)-cyclooct-2-en-1-ol (131 mg, 1.04 mmol) was dissolved in 5 mL THF. Sodium hydride (60% dispersion in oil, 80 mg, 2 mmol) was added. The mixture was stirred for 5 min, then heated at 55° C. for 1 h, and then stirred at rt for 4 h. Benzyl bromide (210 μL, 300 mg, 1.9 mmol) was added in 5 small portions. The reaction mixture was stirred for 4 days, after which 10 mL water was added carefully. The mixture was extracted with 2×10 mL dichloromethane and the successive organic layers were washed with 10 mL water, dried and rotary evaporated. The residue was heated at ca. 40° C. under high vacuum in order to remove most of the benzyl bromide. The residue was purified by chromatography on 20 g silica using heptane as eluent, followed by elution with toluene. The latter solvent eluted the product. The product fractions were rotary evaporated, leaving a colourless oil, which contained traces of dibenzyl ether (69 mg, 0.32 mmol, 31%).

$^{1}$H-NMR ($CDCl_3$): δ 7.4-7.2 (m, 5H), 6.0 (m, 1H), 5.45 (d, 1H), 4.7-4.4 (dd, 2H), 4.2 (s, 1H), 2.5 (m, 1H), 2.2-1.8 (m, 4H), 1.7-1.5 (m, 3H), 1.3-1.1 (m, 1H), 0.8 (m, 1H)

Axial-(E)-2,5-dioxopyrrolidin-1-yl 5-((((2,5-dioxopyrrolidin-1-yl)oxy)carbonyl)oxy)-1-methylcyclooct-3-enecarboxylate TCO-2

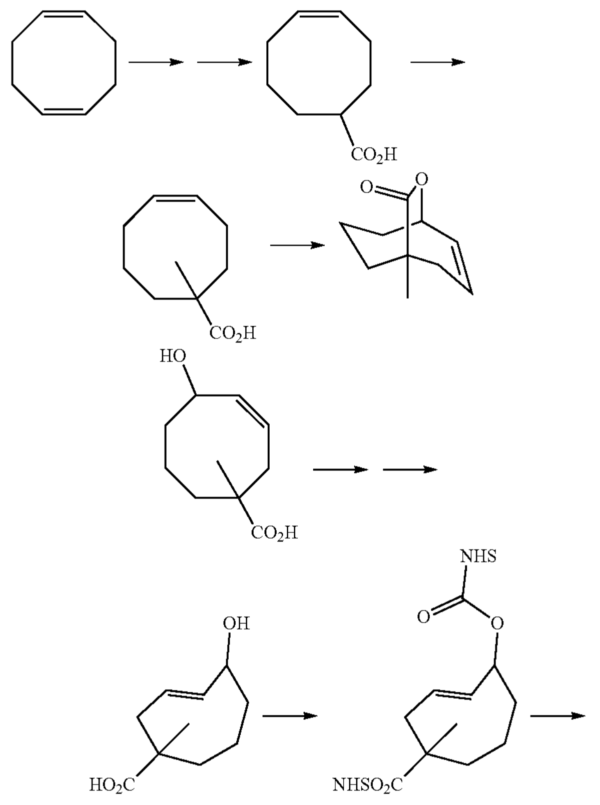

(Z)-5-bromocyclooct-1-ene

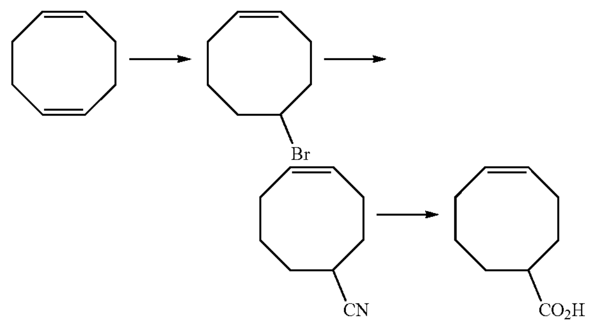

1,5-cyclooctadiene (225 mL, 1.83 mol) was added to ice-cooled 310 mL 33% hydrogen bromide in acetic acid over a 30 min period at ca. 10° C. The mixture was stirred for 2 days, then 300 mL water was added, and the mixture was extracted with 2×300 mL pentane containing some TBME. The successive organic layers were washed with 75 mL water and with 75 mL sodium bicarbonate solution. Drying and rotary evaporation left 325 g residue which was used as such in the next step.

(Z)-cyclooct-4-enecarbonitrile

A mixture of 700 mL DMSO and sodium cyanide (117.3 g, 2.39 mol) was heated to 90° C. The bromide obtained above was added over a 4 h period at 90-96° C. The mixture was subsequently heated at 98° C. for 16 h, then it was cooled and 200 mL water was added during this cooling process. The mixture was extracted with 3×300 mL pentane containing some TBME. Washing with 50 mL water, drying and rotary evaporation resulted in 170 g residue which was used as such in the next step. See J. Org. Chem. 1988, 53, 1082 for a similar procedure.

(Z)-cyclooct-4-enecarboxylic acid

The product obtained above was treated with 100 mL ethanol, 160 mL 35% hydrogen peroxide, and 400 mL 30% sodium hydroxide solution, via the method described by D. Hartley in J. Chem. Soc. 1962, 4722. After acidification, further workup and Kugelrohr distillation, the distillate (94.4 g) appeared to be mainly the starting nitrile.

This distillate, combined with ca. 25 g of the solid residue from the Kugelrohr distillation, was stirred with 400 mL ethanol. Potassium hydroxide (155 g, 2.35 mol) was added, and the mixture was cooled with cold water (reaction mixture attained 40° C.). When the temperature had dropped to 25° C., 35 mL water was added, followed by the portion-wise addition of 140 mL 35% hydrogen peroxide (foaming, temperature around 30° C.). After the addition was complete and the temperature had dropped, the cooling-bath was removed and replaced by a heating mantle. The mixture was warmed up slowly, resulting in an exothermal reaction and foaming. Hereby the temperature gradually reached 63° C. (some cooling was necessary). When the temperature had decreased to 55° C., 100 mL 30% sodium hydroxide solution was added. The mixture was then heated for 4 h, while distilling off ca. 350 mL of solvent. Another 30 mL 30% sodium hydroxide solution was added and the mixture was heated under reflux for 10 h. The reaction mixture was cooled to rt, 400 mL heptane was added and the layers were separated. The organic layer was washed with a small amount of water. The combined aqueous layers were acidified with conc. hydrochloric acid and extracted with 3×250 mL TBME. Drying, rotary evaporation and Kugelrohr distillation gave 109.77 g of the desired acid (0.713 mol, 39% yield based on 1,5-cyclooctadiene).

(Z)-1-methylcyclooct-4-enecarboxylic acid

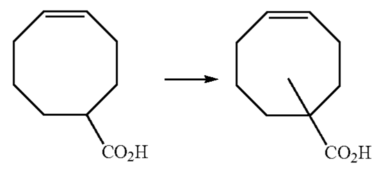

A mixture of diisopropylamine (90.2 g, 0.893 mol) and 300 mL THF was cooled below −20° C. n-Butyllithium in hexanes (2.5 N, 360 mL, 0.900 mol) was added in a slow stream, keeping the temperature below −20° C. The solution was stirred for 15 min, then cooled to −50° C. (Z)-cyclooct-5-enecarboxylic acid (54.0 g, 0.351 mol), dissolved in 150 mL THF, was added over a 20 min period at temperatures between −50 and −25° C. The mixture was stirred for an additional 40 minutes, allowing the temperature to rise to −5° C. The mixture was subsequently heated for 3 h at 50° C., then cooled to −50° C. Iodomethane (195.5 g, 1.377 mol) was added over a 20 min period at temperatures between −50 and −30° C. The mixture was stirred overnight, heated for 1 h at 40° C., then rotary evaporated in order to remove most of the solvents. Toluene (250 mL) was added to the residue, followed by 500 mL dilute hydrochloric acid. The layers were separated and the organic layer was washed with 100 mL 2 N hydrochloric acid. The successive aqueous layers were extracted with 2×250 mL toluene. The organic layers were dried and rotary evaporated. The residue was purified by Kugelrohr distillation to yield 59.37 g of the methylated acid (0.353 mol, 100%), which was sufficiently pure to be used as such in the next step.

$^1$H-NMR ($CDCl_3$): δ 5.75-5.60 (m, 1H), 5.55-5.40 (m, 1H), 2.4-1.5 (m, 10H), 1.27 (s, 3H).

$^{13}$C-NMR ($CDCl_3$): δ 185.5 (C═O), 131.9 (═CH), 126.5 (═CH), 46.2, 35.3, 32.3, 27.1 ($CH_3$), 26.1, 24.8, 24.7.

rel(1R,5R)-5-methyl-9-oxabicyclo[3.3.2]dec-7-en-10-one

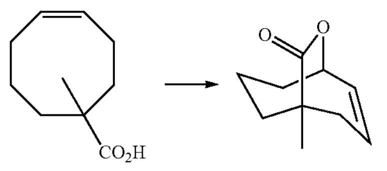

To a mixture of the methylated acid (42.0 g, 0.25 mol), 300 mL dichloromethane, and 300 mL water sodium bicarbonate was added (68.9 g, 0.82 mol). The mixture was stirred for 10 min, then it was cooled in ice. A mixture of potassium iodide (125.2 g, 0.754 mol) and iodine (129 g, 0.508 mol) was added over a 1 h period in 6 equal portions. The reaction mixture was stirred for 3½ h. Sodium bisulfite was added slowly, until the dark colour had disappeared. The layers were separated and the cloudy aqueous layer was extracted with 2×250 mL dichloromethane. Drying and rotary evaporation gave the desired iodolactone.

$^1$H-NMR ($CDCl_3$, product signals): δ 5.65-5.5 (m, 2H), 4.8 (dt, 1H), 3.95 (dt, 1H), 2.6-1.95 (m, 8H).

The iodolactone was dissolved in 250 mL toluene, and DBU (65.2 g, 0.428 mol) was added. The mixture was allowed to stand overnight, after which it was heated under reflux for 75 min (NMR indicated full conversion). After cooling the reaction mixture, it was washed with 150 and 100 mL water. The successive aqueous layers were extracted with 250 mL toluene. The organic layers were dried and rotary evaporated and the residue was purified by Kugelrohr distillation to yield 38.86 g of the bicyclic olefin (0.234 mol, 94%, containing a trace of toluene).

$^1$H-NMR ($CDCl_3$): δ 5.95-5.85 (m, 1H), 5.45-5.35 (dm, 1H), 5.05 (bs, 1H), 2.5-2.3 (m, 1H), 2.2-2.0 (m, 2H), 1.95-1.6 (m, 5H), 1.27 (s, 3H).

$^{13}$C-NMR ($CDCl_3$): δ 177.2 (C═O), 129.1 (═CH), 127.9 (═CH), 79.2 (CH), 45.2, 43.0, 31.9, 29.5 ($CH_3$), 26.6, 24.0.

(Z)-methyl 5-hydroxy-1-methylcyclooct-3-enecarboxylate

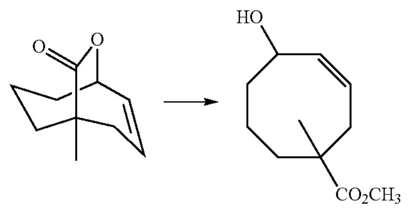

The bicyclic olefin obtained above (38.86 g, 0.234 mol), plus another batch of 1.5 g bicyclic olefin, was stirred for 64 h at 25-30° C. with 250 mL methanol and potassium bicarbonate (100.0 g, 1.0 mol). Another 50.0 g potassium bicarbonate (0.5 mol) was added because NMR indicated the presence of ca. 35% starting olefin. The mixture was stirred for an additional 64 h, but the amount of starting material remained unchanged. Filtration, washing with methanol and rotary evaporation of the filtrate gave a residue, which was chromatographed on 200 g silica using dichloromethane as the eluent. The starting olefin eluted first, then a mixture of starting olefin and product eluted. Further elution with dichloromethane/methanol gave 6.69 g of product, contaminated with ca. 15% of starting olefin, and then 17.53 g of pure product (total 0.117 mmol, 48%).

$^1$H-NMR ($CDCl_3$): δ 5.6-5.5 (m, 1H), 5.35-5.25 (m, 1H), 5.0-4.85 (m, 1H), 3.63 (s, 3H), 2.90 (d, 1H, OH), 2.35-1.90 (m, 5H), 1.75-1.45 (m, 3H), 1.20 (s, 3H).

$^{13}$C-NMR ($CDCl_3$): δ 178.8 (C═O), 132.7 (═CH), 129.0 (═CH), 68.0 (CH), 52.0 ($CH_3$), 46.1, 35.9, 33.7, 30.4, 26.8, 24.7 ($CH_3$).

(E)-methyl 5-hydroxy-1-methylcyclooct-3-enecarboxylate

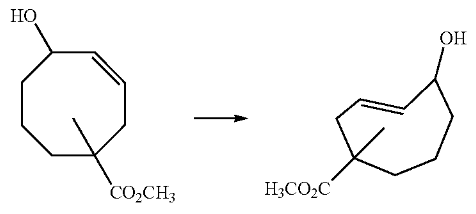

The two portions of hydroxy ester obtained above, plus 2.29 g of hydroxy ester from another experiment (total amount 26.51 g, 133.8 mmol) were mixed with 25.0 g methyl benzoate and heptane/ether (ca. 4/1). The solution was irradiated, the irradiated solution being continuously flushed through a silver nitrate impregnated silica column (213.6 g, containing ca. 126 mmol silver nitrate). During the irradiation process some solvent was lost due to evaporation; this solvent was replaced by ether. The irradiation and flushing were stopped when the irradiated solution contained hardly any starting material. The silica column was successively flushed with 600 mL TBME, 500 mL TBME/5% methanol, 500 mL TBME/10% methanol, and 500 mL TBME/20% methanol. The first 3 eluates were rotary evaporated. The first eluate contained methyl benzoate and the starting hydroxy ester in a ca. 2/3 ratio. The fourth eluate was washed with 300 mL 10% ammonia solution, then dried and rotary evaporated (axial/equatorial ratio of the trans-cycloctene was ca. 5/4). The residues from the second and third eluate were combined, dissolved in TBME and washed with the ammonia layer of above. Drying and rotary evaporation gave a residue which consisted of the axial/equatorial isomers of the trans-cycloctene in a ratio of ca. 5/4. The residual column material was stirred with TBME, 100 mL water and the ammonia layer of above. Filtration, layer separation, drying and rotary evaporation gave a residue. The process was repeated twice to give a residue which consisted of the axial/equatorial isomers of the trans cycloctenes in a ratio of ca. 1/7. All fractions of the trans cyclooctenes were combined to give a total yield of 19.1 g (96.5 mmol, 72%).

Note: The axial/equatorial assignment is based on the stereochemistry of the hydroxy group, in similar fashion as for trans-cycloocten-2-ol. In both isomers the hydroxy and methylester substituents are positioned cis relative to each other. In the axial isomer, these cis-positioned substituents are both in the axial position.

$^1$H-NMR ($CDCl_3$) (mixture of isomers): axial isomer: δ 5.8 (m, 1H), 5.35 (m, 1H), 4.2 (m, 1H), 3.72 (s, 3H), 2.7 (m, 1H), 2.3-1.7 (m, 6H), 1.5 (m, 1H), 1.3 (m, 1H), 1.19 (s, 3H). $^{13}$C-NMR ($CDCl_3$): δ 177.6 (C═O), 136.1 (═CH), 132.3 (═CH), 74.8 (CH), 51.5 ($CH_3$), 47.5, 46.0, 39.9, 38.9, 34.8 ($CH_3$), 31.0.

$^1$H-NMR ($CDCl_3$) (mixture of isomers): equatorial isomer: δ 6.05 (m, 1H), 5.6 (dd, 1H), 4.45 (bs, 1H), 3.62 (s, 3H), 2.35-1.7 (m, 8H), 1.5 (m, 1H), 1.08 (s, 3H). $^{13}$C-NMR ($CDCl_3$): δ 180.7 (C═O), 135.2 (═CH), 130.3 (═CH), 69.6 (CH), 52.1 ($CH_3$), 44.9, 44.7, 38.3, 30.9, 29.8, 18.3 ($CH_3$).

Axial-(E)-5-hydroxy-1-methylcyclooct-3-enecarboxylic acid

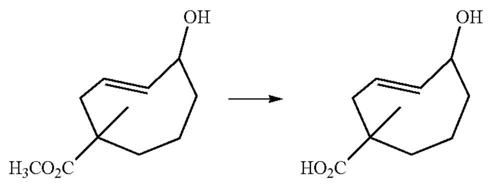

A solution of 1.60 g potassium hydroxide in 5 mL water was added over a 5 min period to a water-cooled solution of the trans-cyclooctene ester isomer mixture (0.49 g, 2.47 mmol, ratio of the axial/equatorial isomer ca. 2½/1) in 11 mL methanol. The solution was stirred for 18 h at 28° C. 15 mL water was added and the mixture was extracted with 2×30 mL TBME. The combined organic layers were washed with 10 mL water, then dried and rotary evaporated to give the non-hydrolyzed equatorial ester. The combined aqueous layers were treated with 30 mL TBME, and then with 4.5 g citric acid. The layers were separated and the aqueous layer was extracted with 30 mL TBME. The organic layers were dried and rotary evaporated at 55° C. to afford 0.34 g (1.85 mmol, 75%) of the pure axial isomer of the trans-cyclooctene acid.

$^1$H-NMR ($CDCl_3$): δ 6.15-5.95 (m, 1H), 5.6 (d, 1H), 4.45 (bs, 1H), 2.4-1.7 (m, 7H), 1.6 (dd, 1H), 1.18 (s, 3H).

$^{13}$C-NMR ($CDCl_3$): δ 185.4 (C═O), 134.8 (═CH), 130.7 (═CH), 69.8 (CH), 44.8, 38.2, 31.0, 29.8 ($CH_2$), 18.1 ($CH_3$).

Note: The hydrolysis of the axial/equatorial ester appears to be extremely selective. Whereas the axial isomer hydrolyzes surprisingly easily at rt, the major isomer remains unaffected, thus enabling an straightforward separation between both isomers (the equatorial isomer hydrolyzes upon overnight heating at ca. 60° C.). In both isomers the hydroxy and carboxylic substituents are positioned cis relative to each other. In the axial isomer, these cis-positioned substituents are both in the axial position.

Axial-(E)-2,5-dioxopyrrolidin-1-yl 5-((((2,5-dioxopyrrolidin-1-yl)oxy)carbonyl)oxy)-1-methylcyclooct-3-enecarboxylate TCO-2

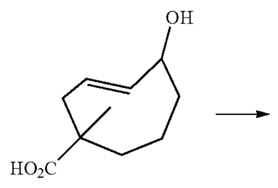

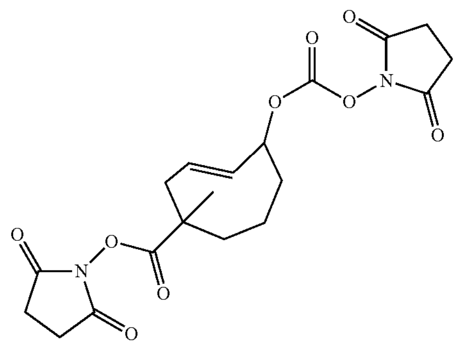

To a solution of Axial-(E)-5-hydroxy-1-methylcyclooct-3-enecarboxylic acid obtained above (375 mg, 2.04 mmol) in 10.1 g acetonitrile there was added N,N-diisopropylethylamine (1.95 g, 15.07 mmol), followed by N,N'-disuccinimidyl carbonate (2.25 g, 8.79 mmol). The mixture was stirred for 3 days at rt, and subsequently rotary evaporated at 55° C. The residue was chromatographed on 20 g silica, elution being done with dichloromethane, followed by elution with dichloromethane containing some TBME. The latter solvent mixture eluted the product. The product fractions were combined and rotary evaporated. The resulting residue was stirred with TBME until a homogeneous suspension was obtained. Filtration and washing gave 400 mg of product.

$^1$H-NMR ($CDCl_3$): δ 6.15-6.0 (m, 1H), 5.6 (dd, 1H), 5.25 (bs, 1H), 2.8 (2s, 8H), 2.5-1.85 (m, 8H), 1.25 (s, 3H).

Axial-TCO-2-Doxorubicin

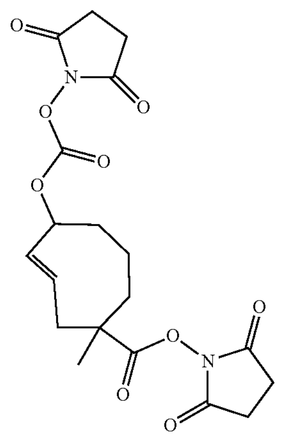

+

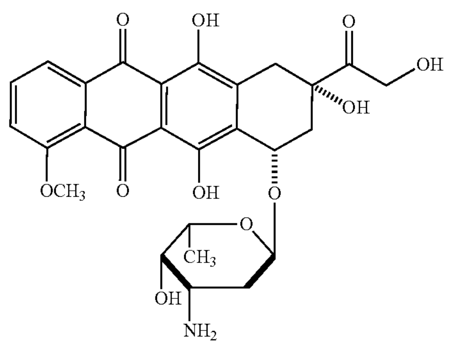

-continued

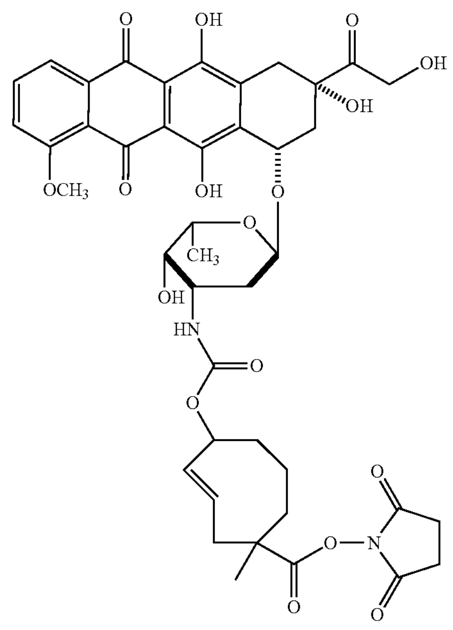

Doxorubicin hydrochloride (133 mg; 2.30*10$^{-4}$ mol) and TCO-2 (97.0 mg; 2.30*10$^{-4}$ mol) were dissolved in DMF (5 mL), and DIPEA (148 mg; 1.15*10$^{-3}$ mol) was added. The solution was stirred under an atmosphere of argon at 20° C. for 18 h. Acetonitrile (6.5 mL), formic acid (0.2 mL), and water (6.5 mL), were added and the suspension was filtered. The filtrate was purified by preparative RP-HPLC (50 v % acetonitrile in water, containing 0.1 v % formic acid). The product was isolated by lyophilization, dissolved in chloroform (3 mL), and precipitated in diethyl ether (20 mL), to yield 134 mg of an orange powder (68%). $^1$H-NMR ($CDCl_3$): Q=13.97 (s, 1H), 13.22 (s, 1H), 8.03 (d, J=7.9 Hz, 1H), 7.78 (t, J=8.0 Hz, 1H), 7.38 (d, J=8.6 Hz, 1H), 5.85 (m, 1H), 5.59 (m, 1H), 5.51 (s, 1H), 5.29 (s, 1H). 5.16 (d, J=8.4 Hz, 1H), 5.12 (s, 1H), 4.75 (d, J=4.8 Hz, 2H), 4.52 (d, J=5.8 Hz, 1H), 4.15 (q, J=6.5 Hz, 1H), 4.08 (d, J=3.6 Hz, 3H), 3.87 (m, 1H), 3.69 (m, 1H), 3.26 (d, J=18.8 Hz, 1H), 3.00 (m, 2H), 2.81 (s, 4H), 2.4-1.7 (br. m, 13H), 1.62 (s, 2H), 1.30 (d, J=6.5 Hz, 3H), 1.23 (s, 3H) ppm. $^{13}$C-NMR ($CDCl_3$): Q=213.89, 187.07, 186.68, 174.30, 169.27, 161.03, 156.15, 155.64, 154.66, 135.73, 135.49, 133.58, 131.70, 131.10, 120.88, 119.83, 118.43, 111.58, 111.40, 100.73, 72.09, 69.65, 67.28, 65.54, 56.67, 46.87, 44.38, 35.75, 34.00, 30.49, 30.39, 30.20, 25.61, 17.92, 16.84 ppm. LC-MS: m/z=+873.42 [$M^+Na]^+$, −849.58 [M−H]$^-$ (calcd 850.28 for $C_{42}H_{46}N_2O_{17}$).

(E)-2,5-dioxopyrrolidin-1-yl 1-methyl-5-(((2-(5-(2-oxohexahydro-1H-thieno[3,4-d]imidazol-4-yl)pentanamido)ethyl)carbamoyl)oxy)cyclooct-3-enecarboxylate TCO-2-Biotin

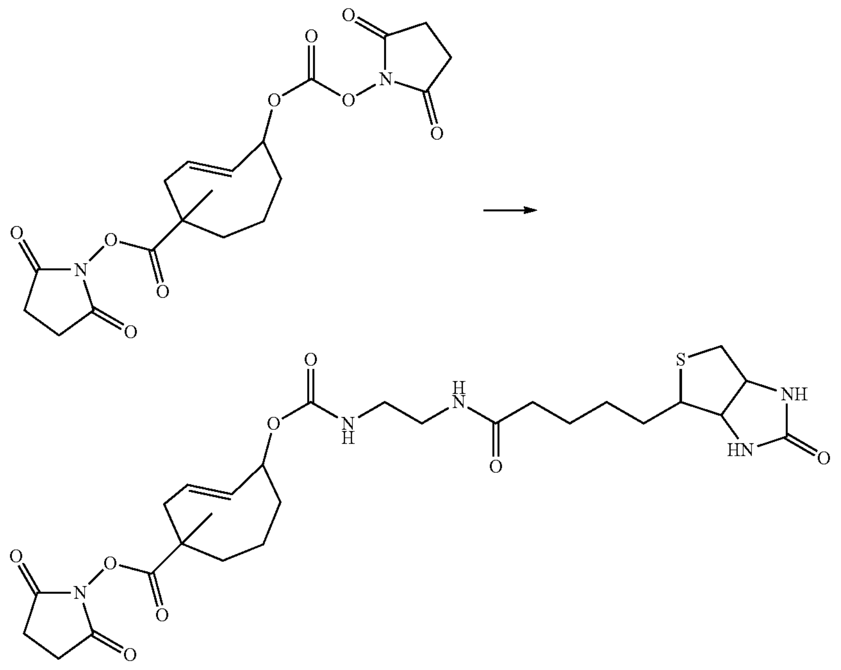

N-(2-aminoethyl)-5-(2-oxohexahydro-1H-thieno[3,4-d]imidazol-4-yl)pentanamide

A mixture of biotin (3.0 g, 12.30 mmol) and 40 mL DMF was heated for 30 min at 60-63° C. The suspension was allowed to cool to 48° C., and N,N'-carbonyldiimidazole (2.40 g, 14.8 mmol) was added in one portion. Within a few minutes the suspension turned into a solution, and then into a thick suspension again after 5-10 minutes. The suspension was added to ethylenediamine (17.0 g, 0.283 mol) in 20 mL DMF. The resulting solution was rotary evaporated at 65° C. in order to remove the excess of ethylenediamine and most of the DMF. The residue (15-20 mL) was stirred for 3 days with 100 mL TBME, resulting in a homogeneous suspension. Filtration, stirring of the solid with 50 mL TBME for 2 h, filtration and drying gave 3.484 g of the biotin-ethylenediamine adduct (12.16 mmol, 99%), which was used as such in the next step.

$^1$H-NMR (DMSO-$d_6$): δ 7.75 (bs, 1H), 6.4 (bs, 1H), 6.3 (bs, 1H), 4.3 (bs, 1H), 4.1 (bs, 1H), 3.1 (t, 2H), 2.8 (m, 1H), 2.55 (m, 2H), 2.05 (t, 2H), 1.7-1.2 (m, 6H). Some other signals were obscured by water and DMSO signals.

(E)-2,5-dioxopyrrolidin-1-yl 1-methyl-5-(((2-(5-(2-oxohexahydro-1H-thieno[3,4-d]imidazol-4-yl)pentanamido)ethyl)carbamoyl)oxy)cyclooct-3-enecarboxylate N,N-diisopropylethylamine (122 mg, 0.94 mmol) was added to a solution of (E)-2,5-dioxopyrrolidin-1-yl 5-((((2,5-dioxopyrrolidin-1-yl)oxy)carbonyl)oxy)-1-methylcyclooct-3-enecarboxylate (TCO-2) (100 mg, 0.237 mmol; axial isomer) in 4.12 g DMF, followed by the addition of the biotin-ethylenediamine adduct obtained above (100 mg, 0.237 mmol). The mixture was stirred at rt for 3 days, and subsequently evaporated under high vacuum at ca. 40° C. The residue was dissolved in some dichloromethane, then TBME was added while stirring. A precipitate resulted which was removed by vacuum filtration. The filtrate was rotary evaporated and the residue was stirred with TBME. Filtration left a solid, which was combined with the first obtained solid. The mixture was stirred with dichloromethane, and then filtered. The filtrate was rotary evaporated and the residue was stirred overnight with TBME. Filtration gave 25 mg of the product (0.042 mmol, 17%).

$^1$H-NMR ($CDCl_3$): δ 6.76 (bs, 1H), 6.46 (bs, 1H), 6.0-5.5 (m, 3H), 5.16 (bs, 1H), 4.50 (m, 1H), 4.33 (m, 1H), 3.5-3.0 (m, H), 3.0-1.3 (m) and 2.82 (s) (H), 1.25 (s, 3H).

Example 3

Tetrazine Induced Release of Doxorubicin from TCO-1-Doxorubicin

The tetrazines featured in FIG. 1 were tested with respect to their ability to release doxorubicin from TCO-2-doxorubicin. The relative release yield for each tetrazine is given in FIG. 1 (+++=highest).

PBS/MeCN (1 mL, 3/1), preheated at 37° C. and TCO-2-doxorubicin (10 μL of a 2.5 mM solution in DMSO, 1 eq.) were added to a preheated injection vial. Tetrazine (10 μL of a 25 mM solution in DMSO, 10 eq.) was added and the vial was vortexed. After incubation for 1 hour at 37° C., the vial was placed in LC-MS autosampler at 10° C. LC-MS analysis was performed using a 5% to 100% $H_2O$/MeCN gradient over 11 minutes with a C18 reverse-phase column at 35° C.

A control sample containing only TCO-2-doxorubicin (1 eq), as well as a sample containing only doxorubicin (1 eq.), was analyzed under the same conditions. All tetrazine containing samples were measured twice and the doxorubicin control sample was run after every three other samples during an overnight program. The peak area of released dox was divided by the peak area of TCO-2-doxorubicin or doxorubicin reference signals and multiplied by 100 to calculate the percentage of release. The calculated percentage of release was corrected when it was observed that the TCO-2-doxorubicin was not fully converted to inv-DA adduct(s). This was done by quantification of remaining dox-TCO, but full conversion was almost always observed. Peak areas (used for doxorubin quantification) were determined at λ=470-500 nm where characteristic doxorubicin absorption takes place and peak integration was done by hand.

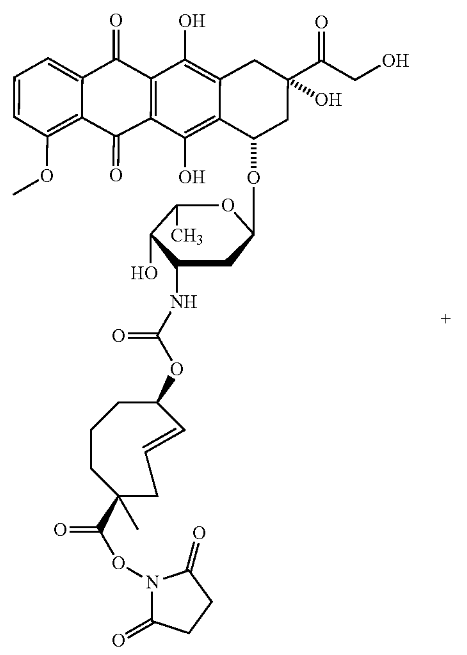

+

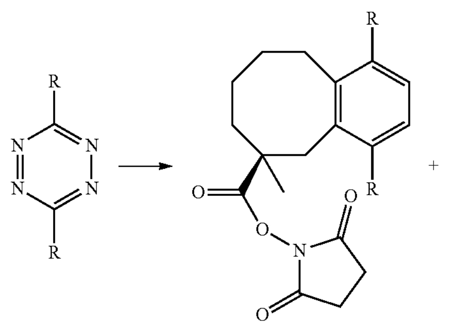

+

-continued

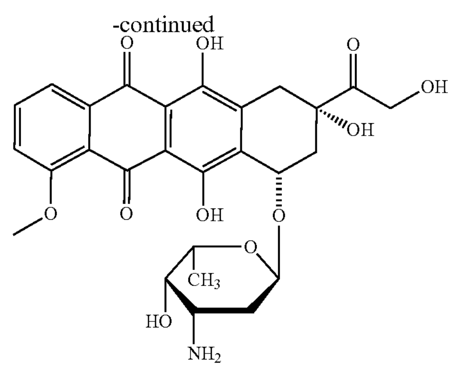

Example 4

In a similar fashion as Example 3, the release of doxorubicin from TCO-1-doxorubucin as induced by tetrazines 1,8,9 in PBS/ACN and in serum was measured. From Table 1 it is clear that tetrazine 8 affords the highest release and that the release yields are retained when testing in serum.

Serum Experiments were Conducted as Follows:

TCO-1-doxorubucin ($6.25\times10^{-8}$ mol) was dissolved in DMSO (0.050 mL), and PBS (0.475 mL) was added slowly in aliquots of 0.010 mL, followed by mouse serum (0.475 mL). A portion of this mixture (0.200 mL) was equilibrated at 37° C., and a solution of tetrazine ($1.25\times10^{-7}$ mol) in DMSO (0.005 mL) was added, and the solution was thoroughly mixed and incubated at 37° C. in the dark for 4 h. Subsequently, cold MeCN (0.200 mL) was added, followed by centrifugation at 13400 rpm for 5 min. The supernatant was used for further analysis by HPLCMS/PDA analysis to determine the release of doxorubicin.

TABLE 1

Doxorubicin release (%) from Axial-TCO-1-Doxorubicin following addition of 10 equiv. tetrazine 1,9,8 in 25% MeCN in PBS or 50% serum at 37° C.; measured with LCMS at 4 h (n = 3).

| Probe | PBS/MeCN (3/1) | Serum |
|---|---|---|
| 1 | 7 ± 3 | 12 ± 1 |
| 9 | 55 ± 4 | 46 ± 3 |
| 8 | 79 ± 3 | 75 ± 4 |
| -[a] | 0 | 0 |

[a]no release of doxorubicin from Axial-TCO-1-Doxorubicin at 37° C. in PBS (72 h) and serum (24 h).

Example 5

TCO as a Protecting Group

The feasibility to use the TCO group as a protective group in chemistry was studied by testing the stability of a range of TCO derivatives as model compounds under various conditions, and following the deprotection upon reaction with a tetrazine derivative under these conditions. The results in Tables 2-4 support the versatility of the TCO-based protecting group and at the same time demonstrate that in addition to aromatic and aliphatic carbamates also carbonates and aromatic and aliphatic esters and ethers are effectively cleaved from the TCO upon tetrazine reaction. In addition to amines, also hydroxy and carboxylic acids were effectively protected and subsequently unmasked in a range of challenging conditions that are typical of standard chemical transformations.

Typical Example for Testing the Stability of a TCO Compound

The TCO stock solution (10 μL 25 mM; $2.5*10^{-7}$ mol) was added to a solution of the specific condition (100 L). The mixture was stirred at the specific condition for a certain amount of time, and then the fate of the TCO compound was monitored by HPLC-MS/PDA analysis and/or GC-MS analysis, and an estimation of its stability was made.

Typical Example for Testing the Feasibility of the Deprotection

The TCO stock solution (10 μL 25 mM in acetonitrile; $2.5*10^{-7}$ mol) was added to a solution of the specific condition (100 uL). A solution of 3,6-dimethyl-1,2,4,5-tetrazine (8, 20 uL 25 mM in acetonitrile; $5.0*10^{-7}$ mol) was added, and the mixture was stirred at the specific condition for a certain amount of time. The reaction was monitored by HPLC-MS/PDA analysis and/or GC-MS analysis, and the percentage of deprotection was estimated.

Conditions:

A) in acetonitrile with 5 equivalents of pyridine per TCO at 20° C.
B) in acetonitrile with 5 equivalents of DIPEA per TCO at 20° C.
C) in acetonitrile with 5 equivalents of piperidine per TCO at 20° C.
D) in acetonitrile with 5 equivalents of n-butylamine per TCO at 20° C.
E) in acetonitrile with 5 equivalents of 2-mercaptoethanol per TCO at 20° C.
F) in tetrahydrofuran with 5 equivalents of triphenylphosphine per TCO at 20° C.
G) in acetonitrile with 5 equivalents of DCC per TCO at 20° C.
H) in acetonitrile with 5 equivalents of PyBOP per TCO at 20° C.
I) in acetonitrile with 1 v % of formic acid at 20° C.
J) in chloroform at 20° C.
K) in chloroform with 1 v % of formic acid at 20° C.
L) in chloroform with 1 v % of trifluoroacetic acid at 20° C.
M) in chloroform with 10 v % of trifluoroacetic acid at 20° C.
N) in chloroform with 33 v % of trifluoroacetic acid at 20° C.
Z) in 25% acetonitrile in water at 20° C.

TABLE 2

| TCO | Condition | Stability of TCO | Deprotection (%) | Deprotected product |
|---|---|---|---|---|
| 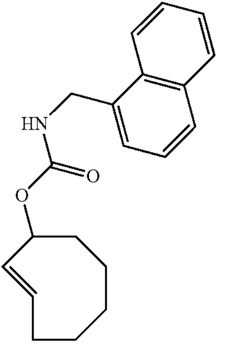 axial isomer | A) for 1 h<br>B) for 1 h<br>C) for 1 h<br>D) for 1 h<br>E) for 1 h<br>F) for 1 h<br>G) for 1 h<br>H) for 1 h<br>I) for 1 h<br>J) for 1 h<br>K) for 1 h<br>L) for 1 h<br>M) for 1 h<br>Z) for 1 h | stable<br>stable<br>stable<br>stable<br>stable<br>stable<br>stable<br>stable<br>stable<br>stable<br>stable<br>stable<br>stable<br>stable | 87<br>58<br>48<br>47<br>67<br>75<br>74<br>74<br>93<br>73<br>98<br>99<br>99<br>85 | 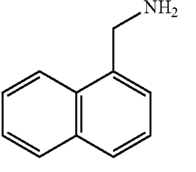 [SMILES: NCc1cccc2ccccc12] |
| 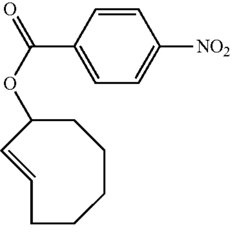 axial isomer | A) for 1 h<br>B) for 1 h<br>G) for 1 h<br>I) for 1 h<br>Z) for 1 h | stable<br>ca. 2% hydrolysis<br>stable<br>stable<br>stable | 68<br>83<br>89<br>95<br>80 | 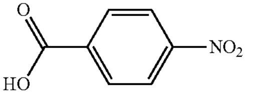 [SMILES: O=C(O)c1ccc([N+](=O)[O-])cc1] |
| 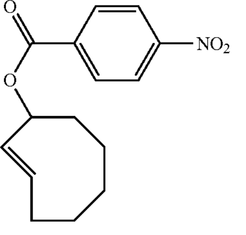 equatorial isomer | Z) for 1 h | stable | 66 | 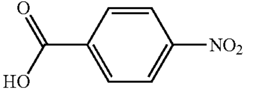 [SMILES: O=C(O)c1ccc([N+](=O)[O-])cc1] |

TABLE 2-continued

| TCO | Condition | Stability of TCO | Deprotection (%) | Deprotected product |
|---|---|---|---|---|
| 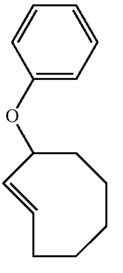<br>axial isomer | A) for 1 h<br>B) for 1 h<br>G) for 1 h<br>I) for 1 h<br>Z) for 1 h | stable<br>stable<br>stable<br>stable<br>stable | 42<br>92<br>80<br>92<br>87 | 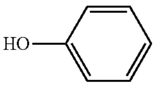 |
| 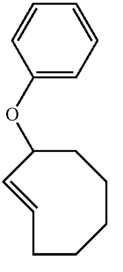<br>equatorial isomer | Z) for 1 h | stable | 72 | 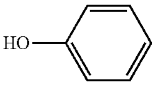 |

TABLE 3

| TCO | Condition | Stability of TCO | Deprotection (%) | Deprotected product |
|---|---|---|---|---|
| 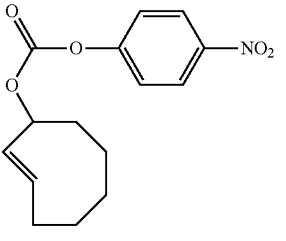<br>axial isomer | A) for 1 h<br>B) for 1 h<br>G) for 1 h<br>I) for 1 h<br>Z) for 1 h | stable<br>19% hydrolysis<br>stable<br>stable<br>stable | 64<br>90<br>72<br>97<br>70 | 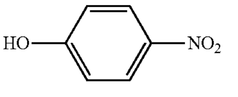 |
| 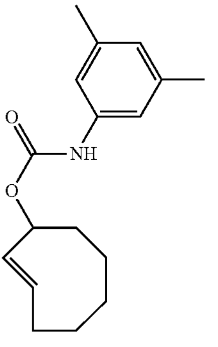<br>axial isomer | A) for 1 h<br>B) for 1 h<br>G) for 1 h<br>I) for 1 h | stable<br>stable<br>stable<br>stable | 14<br>4<br>61<br>97 | 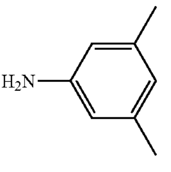 |

TABLE 3-continued

| TCO | Condition | Stability of TCO | Deprotection (%) | Deprotected product |
|---|---|---|---|---|
| 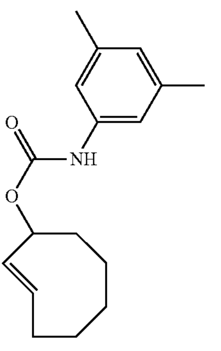 equatorial isomer | A) for 1 h<br>B) for 1 h<br>G) for 1 h<br>I) for 1 h | stable<br>stable<br>stable<br>stable | 55<br>39<br>91<br>97 | 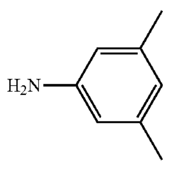 |
| 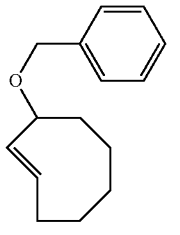 axial isomer | J) for 1 h<br>Z) for 1 h | stable<br>stable | 70<br>54 | 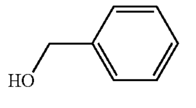 |
| 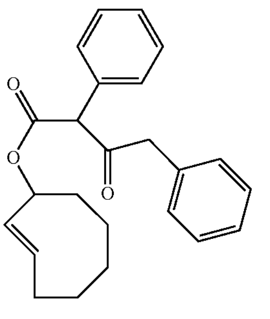 axial isomer | J) for 1 h<br>Z) for 1 h | stable<br>stable | 95<br>70 | 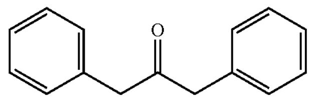 [SMILES: O=C(Cc1ccccc1)Cc1ccccc1] |

TABLE 4

| TCO | Condition* | Stability of TCO | Deprotection (%) | Deprotected product |
|---|---|---|---|---|
| 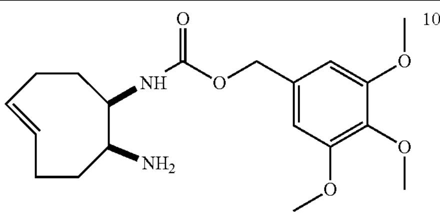 | 10% MeCN in $H_2O$ for 5 day | stable | 0% | 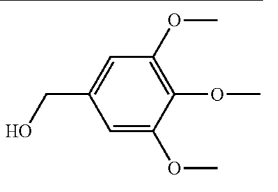 |
| | 0.1 M $NH_4OAc$ buffer, pH = 7.0 for 5 day | stable | 0% | |
| | 0.1 M HCOOH buffer, pH = 2.0 for 2 day | stable | 0% | |
| | 0.1 M $NH_3$ buffer, pH = 11 for 5 day | <5% cyclization | 87% | |
| | 10% MeCN in $H_2O$ at | <5% | 50% | |

TABLE 4-continued

| TCO | Condition* | Stability of TCO | Deprotection (%) | Deprotected product |
|---|---|---|---|---|
| | 70° C. for 5 day | cyclization | | |
| | 0.1 M $NH_4OAc$ buffer, pH = 8.0 for 8 day | stable | 0% | |
| | 0.1 M $NH_4OAc$ buffer, pH = 9.0 for 8 day | stable | 25% | |
| | 0.1 M $NH_4OAc$ buffer, pH = 10.0 for 8 day | stable | 81% | |
| 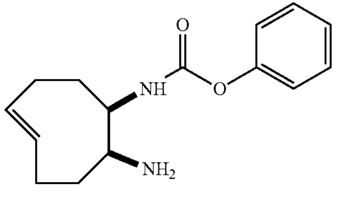 | 0.1 M $NH_4OAc$ $t_{1/2}$ = 80 h buffer, pH = 7.0 | $t_{1/2}$ = 80 h | $t_{1/2}$ = 140 min | 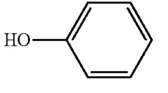 |
| | 0.1 M $NH_4OAc$ $t_{1/2}$ = 17 h buffer, pH = 8.0 | $t_{1/2}$ = 17 h | $t_{1/2}$ = 25 min | |
| | 0.1 M $NH_4OAc$ $t_{1/2}$ = 5.3 h buffer, pH = 9.0 | $t_{1/2}$ = 5.3 h | $t_{1/2}$ = 4.6 min | |
| | with 5 eq. of pyridine in MeCN for 16 h | 2.6% cyclization | 71.7% | |
| | with 5 eq. of DIPEA in MeCN for 16 h | 6.7% cyclization | 98.8% | |
| | with 5 eq. of PyBOP in MeCN for 16 h | 5.9% cyclization | 24.4% | |
| | with 5 eq. of HCOOH in MeCN for 16 h | 1.9% cyclization | 33.9% | |
| 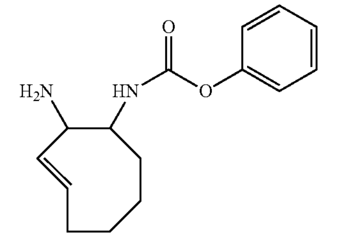 | in PBS buffer | $t_{1/2}$ = 65 h | $t_{1/2}$ = 70 min | 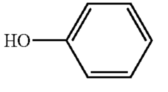 |
| 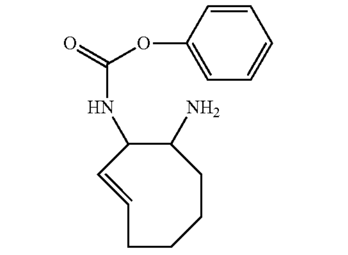 | in PBS buffer | $t_{1/2}$ = 29 h | $t_{1/2}$ = 100 min | 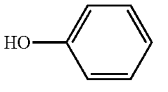 |

*): study is performed at 20° C., unless stated otherwise

Example 6

TCO as a Protecting Group

In this example the use of the TCO group as a protective group in chemistry is demonstrated in the synthesis of 6-aminohexyl phenylcarbamate from 6-amino-1-hexanol. Direct reaction of 6-amino-1-hexanol with phenyl isocyanate proceeds with the amine instead of the hydroxy affording 1-(6-hydroxyhexyl)-3-phenylurea instead of the desired 6-aminohexyl phenylcarbamate (see 1st reaction below). However, protection the amine of 6-amino-1-hexanol with 3-PNP-TCO followed by reaction with phenyl isocyanate and removal of the TCO group affords 6-aminohexyl phenylcarbamate in good yield.

Reaction Between 6-amino-1-hexanol and phenyl isocyanatate

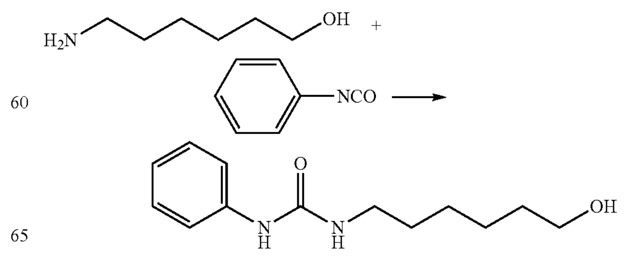

To a solution of 6-amino-1-hexanol (50.2 mg; $4.21*10^{-4}$ mol) in chloroform (1 mL) was added a solution of phenyl isocyanate (65 mg; $5.46*10^{-4}$ mol) in chloroform (1 mL). The resulting suspension was stirred at 20° C. under an atmosphere of argon for 45 min. Then, diethyl ether was added, and the mixture was thoroughly mixed. The product was isolated by filtration, and dried in vacuo. Yield: 91.7 mg of a white powder (92%). $^1$H-NMR (DMSO-d6): δ=8.35 (s, 1H), 7.37 (d, 2H), 7.20 (t, 2H), 6.87 (t, 1H), 6.09 (t, 1H), 4.33 (t, 1H), 3.38 (q, 2H), 3.06 (q, 2H), 1.42 (m, 4H), 1.29 (m, 4H) ppm. $^{13}$C-NMR (DMSO-d6): δ=155.16, 140.58, 128.58, 120.83, 117.50, 60.64, 38.97, 32.51, 29.80, 26.28, 25.26 ppm. FT-IR (ATR): ν=3319, 2938, 2857, 1633, 1560, 1065, 731, 621, 613 $cm^{-1}$. LC-MS: m/z=+237.25 $[M^+H]^+$ (calcd 236.15 for $C_{13}H_{20}N_2O_2$).

N-Protection of 6-amino-1-hexanol Using the TCO Group

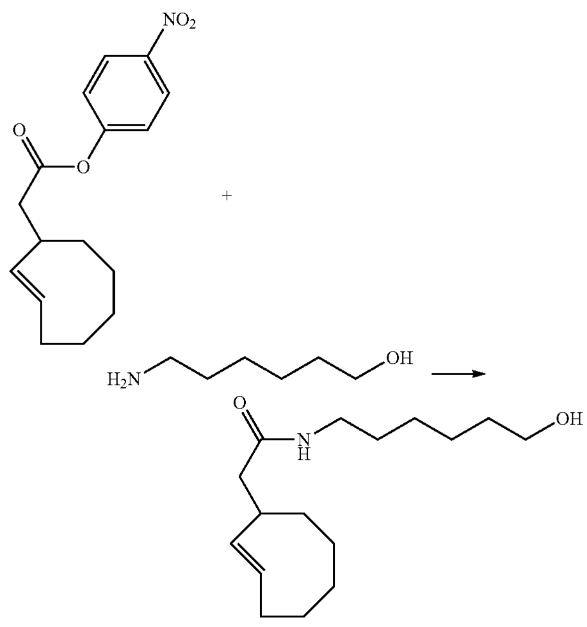

3-PNP-TCO (20.2 mg; $6.93*10^{-5}$ mol) was dissolved in dichloromethane (1 mL), and DIPEA (26.8 mg; $2.08*10^{-4}$ mol) and 6-amino-1-hexanol (9.75 mg; $8.32*10^{-5}$ mol) were added. The reaction mixture was stirred at 20° C. under and atmosphere of argon and slowly turned yellow. After 7 h the solvent was removed by evaporation in vacuo, and the mixture was redissolved in chloroform and washed with subsequently, 1 M aqueous sodium hydroxide (3 times 1.5 mL) and 1 M aqueous citric acid (2 times 1.5 mL). The organic layer was dried over sodium sulfate, filtered, and evaporated to dryness, to yield the product as a viscous oil: 16.7 mg (89%). $^1$H-NMR ($CDCl_3$): δ=5.81 (m, 1H), 5.52 (d, 1H), 5.32 (m, 1H), 4.76 (br. s, 1H), 3.64 (t, 2H), 3.18 (m, 2H), 2.46 (m, 1H), 2.2-1.2 (br. m, 16H), 1.06 (m, 1H), 0.81 (m, 1H) ppm. $^{13}$C-NMR ($CDCl_3$): δ=155.9, 131.6, 73.7, 62.7, 40.7, 36.0, 35.9, 32.5, 30.0, 29.1, 26.3, 25.2, 24.1 ppm. FT-IR (ATR): ν=3322, 2927, 2857, 1692, 1533, 1258, 1070, 1025, 987 $cm^{-1}$. LC-MS: m/z=+270.33 $[M^+H]^+$(calcd 269.20 for $C_{15}H_{27}NO_3$).

Derivatization of Alcohol Group with Phenyl Isocyanate

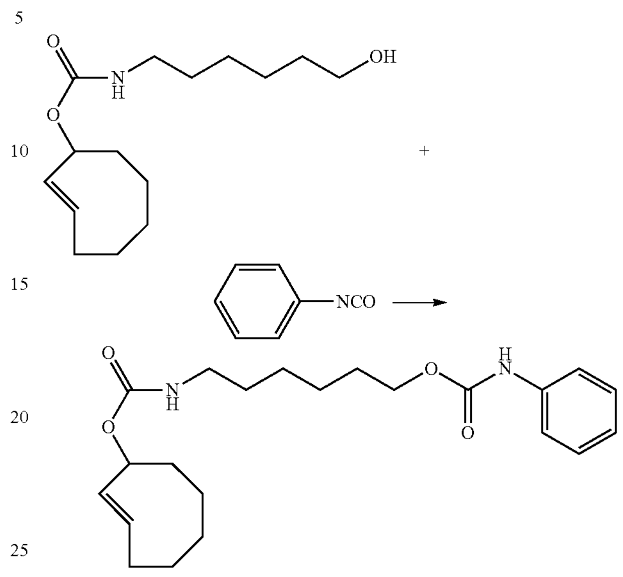

N-TCO protected 6-amino-1-hexanol (16.7 mg; $6.20*10^{-5}$ mol) was dissolved in chloroform and phenyl isocyanate (11 mg; $9.23*10^{-5}$ mol) was added, followed by dibutyltin dilaurate (0.1 mg; $1.58*10^{-7}$ mol). The mixture was stirred at 40° C. under an atmosphere of argon for 4 h, and then allowed to cool to 4° C. overnight. The crystals that had formed were removed by filtration, and the filtrate was evaporated to dryness. The crude product was recrystallized from acetonitrile to yield 16.8 mg of a white powder (70%). $^1$H-NMR ($CDCl_3$): δ=7.40 (d, 2H), 7.31 (t, 2H), 7.05 (t, 1H), 6.81 (s, 1H), 5.81 (m, 1H), 5.55 (d, 1H), 5.33 (m, 1H), 4.77 (br. s, 1H), 4.16 (q, 2H), 2.46 (m, 1H), 2.2-1.2 (br. m, 16H), 1.06 (m, 1H), 0.81 (m, 1H) ppm. $^{13}$C-NMR ($CDCl_3$): δ=155.9, 153.7, 138.1, 131.7, 131.6, 129.0, 123.2, 118.6, 73.8, 65.1, 40.7, 36.0, 35.9, 29.8, 29.1, 28.6, 26.2, 25.5, 24.1 ppm. FT-IR (ATR): ν=3367, 3351, 2930, 2856, 1707, 1693, 1530, 1236, 984 $cm^1$. LC-MS: m/z=+411.42 $[M^+Na]^+$(calcd 388.24 for $C_{22}H_{32}N_2O_4$).

Deprotection of N-TCO Protective Group

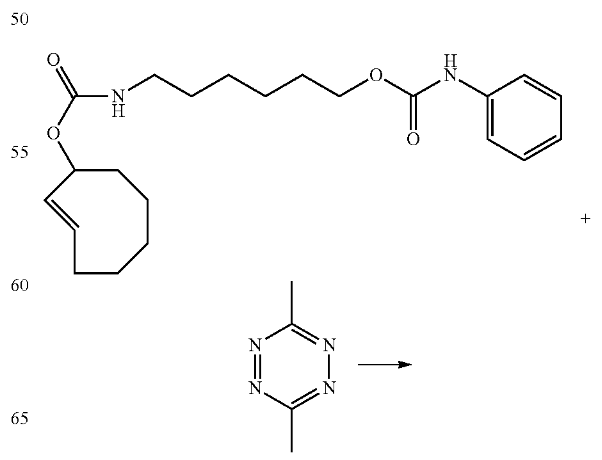

-continued

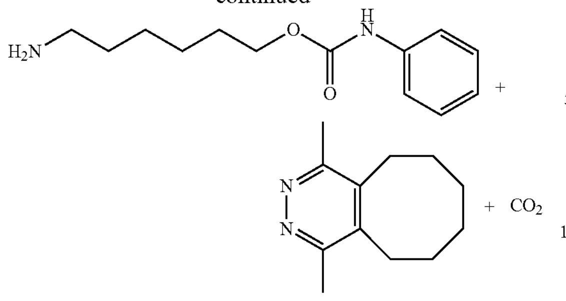

(N-TCO-6-aminohexyl) phenylcarbamate (5.61 mg; $1.44*10^{-5}$ mol) was dissolved in chloroform (0.6 mL) and trifluoroacetic acid (20 mg; $1.75*10^{-4}$ mol) was added. Subsequently, a solution of 3,6-dimethyl-1,2,4,5-tetrazine (8, 1.90 mg; $1.73*10^{-5}$ mol) in chloroform (0.1 mL) was added. The pink, homogeneous mixture was stirred at 20° C. for 40 min. According to $^1$H-NMR, more than 95% was deprotected. The reaction mixture was washed with aqueous potassium carbonate (0.5 mL 0.4 M), dried over sodium sulfate, filtered, and evaporated to dryness. The crude product was purified by preparative RP-HPLC and isolated by lyophilization to yield a white powder (2.31 mg; 68%). $^1$H-NMR (DMSO-d6): δ=9.60 (s, 1H), 7.46 (d, 2H), 7.26 (t, 2H), 6.97 (t, 1H), 4.06 (t, 2H), 2.60 (t, 2H), 1.62 (m, 2H), 1.33 (m, 6H) ppm. $^{13}$C-NMR ($CDCl_3$): δ=153.6, 139.2, 128.7, 122.2, 118.1, 73.8, 64.1, 41.5, 33.3, 28.6, 26.1, 25.4 ppm. FT-IR (ATR): ν=3343, 2939, 1707, 1542, 1448, 693 $cm^{-1}$. LC-MS: m/z=+237.17 $[M^+H]^+$(calcd 236.15 for $C_{13}H_{20}N_2O_2$).

Example 7

Use of Tetrazine Activator Bound to Solid Support in Deprotecting a TCO-Protected Molecule

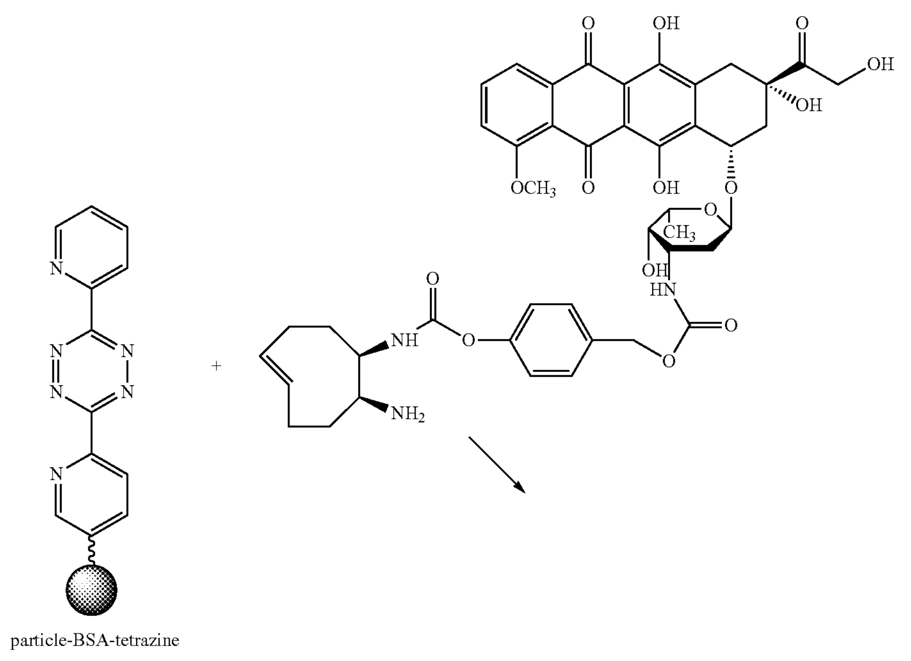
particle-BSA-tetrazine

-continued

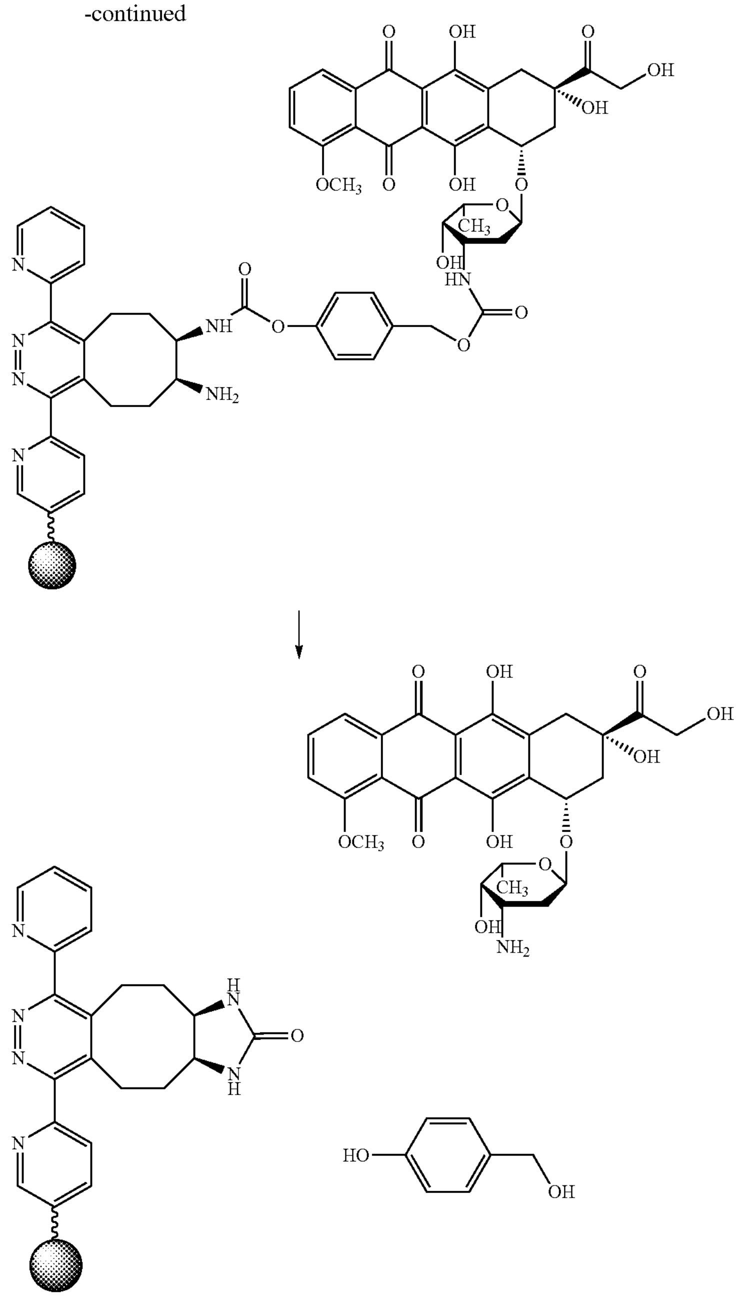

Tetrazine functionalization of a BSA-coated particle has been described in J. Nucl. Med. 2013, 54,1989-1995. Briefly, a solution of BSA (bovine serum albumin; 0.7 mg) in PBS was mixed with a 10 mg/mL solution of a bis-pyridyl-tetrazine-NHS derivative in DMF (35 μL, 30 eq. with respect to BSA) and the pH was adjusted to 9.0 with 1 M sodium carbonate buffer. The solution (125 μL total) was incubated at room temperature for 30 min then the unreacted tetrazine was removed from the solution by using a Zeba desalting spin column (7 kDa MW cut-off) pre-washed with PBS. UV measurements confirmed the presence of 12 tetrazine moieties per BSA molecule.

The eluate containing BSA-tetrazine in PBS was added to a 350 μL suspension of polystyrene beads (Polybeads, 0.5 μm, Polysciences) in $H_2O$ and the resulting suspension was incubated at +4° C. for 1 h on an end-over-end rotating mixer (10 rpm). After incubation, the suspension of beads coated with BSA-tetrazine was centrifuged at 12,000 rpm for 4 min. The supernatant was carefully removed and the pellet was resuspended in 1.5 mL PBS by using a tip sonicator at low power (Sonics VibraCell, 4×5 sec pulses, 40% of power). The centrifuging-resuspension cycle was repeated 2 times, after which the bead pellet was resuspended in 200 μL PBS and reacted with 7 nmol of TCO-protected doxorubicin (TCO-3-Doxorubin, 1 mM in DMSO).

After 5 min incubation at 37° C. in a thermomixer (350 rpm), the beads were removed by centrifugation and the supernatant was analyzed by HPLC on an Agilent Techologies system (1100 series) equipped with a fluorescence detector with $\lambda_{ex}$=485 nm and $\lambda_{em}$=590 nm. The sample was loaded on an Eclipse XDB-C18 column (5 μm, 4.6×150 $mm^2$, Agilent) which was eluted isocratically with 30% (v/v) acetonitrile in $H_2O$ containing 0.1% TFA (v/v) at 1 mL/min. HPLC analysis of the supernatant confirmed that ca. 75% of TCO-doxorubicin was bound to the beads.

Figure 2:
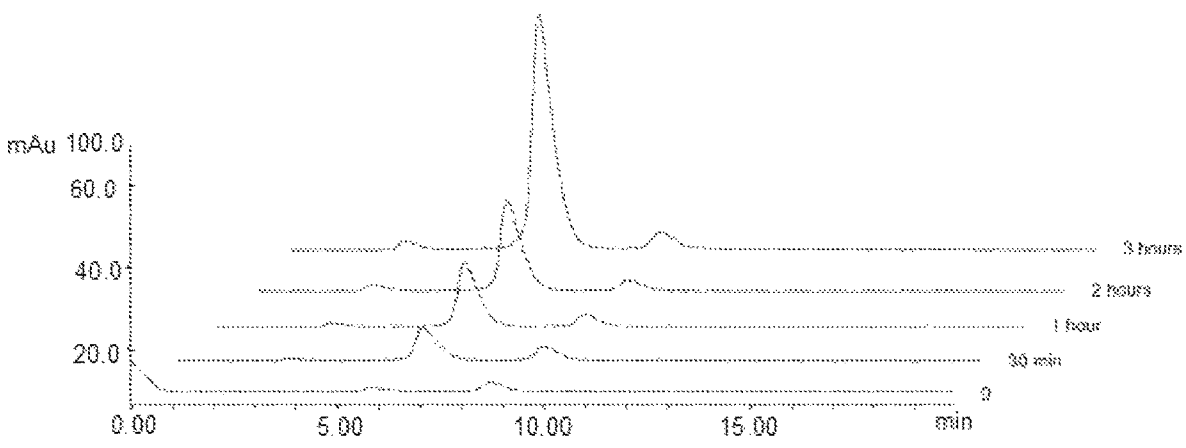
FIG. 2 presents chromatographic profiles showing release of free doxorubicin (Rt=6.2 min) from the polystyrene beads with time (>45% after 3 h; complete within 24 h).

The bead pellet was resuspended in 1.5 mL PBS and centrifuged twice to eliminate unbound TCO-doxorubicin. Subsequently, the beads were resuspended in 400 μL PBS and incubated at 37° C. At various times, aliquots of the supernatant were analyzed by HPLC. The chromatographic profiles (FIG. 2) show release of free doxorubicin (Rt=6.2 min) from the beads with time (>45% after 3 h; complete within 24 h). A small amount of TCO-doxorubicin (Rt=9.2 min) is also visible, which was present in solution already at t=0.

In comparison, when uncoated and unmodified beads were mixed with TCO-doxorubicin in the same conditions, non-specific proDox adsorption on the bead surface was observed (>95%) but no significant release of Dox was detected with time.

Example 8

Capture of Protein-TCO-Biotin with Streptavidin Beads Followed by Protein Release

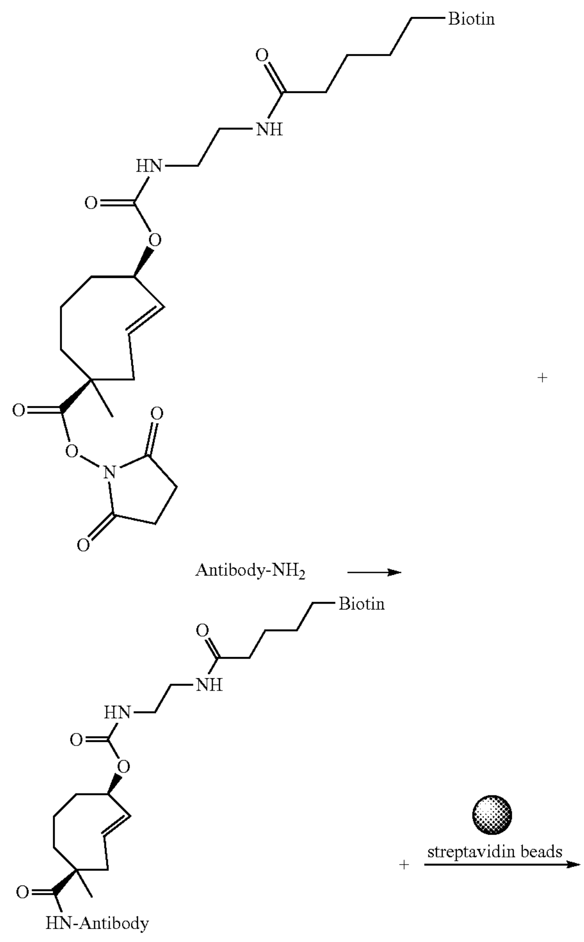

-continued

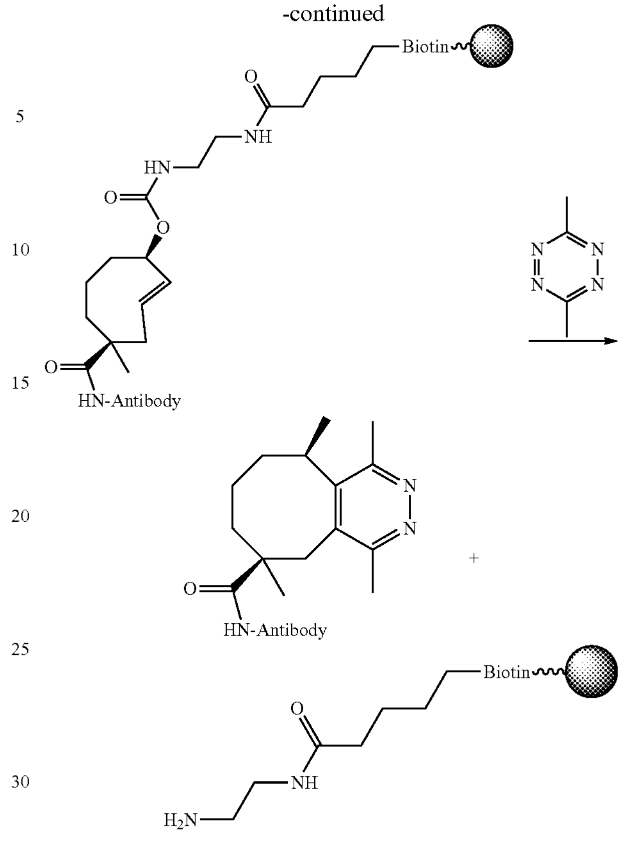

Rituximab (Rtx, 100 μg in 200 μL PBS, Roche) was radiolabeled with $^{125}$I (Perkin Elmer) in a Pierce iodination tube (5 min incubation at room temperature) followed by size exclusion (SEC) purification (2 times, 0.5 mL Zeba desalting spin cartridge, 40 kDa MWCO, Pierce). Subsequently, non-radioactive Rtx was added to the solution (making 1 mg total Rtx), the pH was adjusted to 9 with 1 M sodium carbonate buffer and TCO-2-Biotin (3 eq., 5 mg/mL in DMSO) was added. The reaction mixture (200 μL) was incubated for 2 hours at 37° C. (350 rpm), purified once by SEC cartridge and then analyzed by SEC HPLC on an Agilent 1200 system equipped with a Gaby radioactive detector and UV detector and connected to a BioSep-SEC-S-3000 column (300×7.8 mm, 5 μm particles, Phenomenex) which was eluted at 1 mL/min with 0.1 M phosphate 0.15 M NaCl pH 6.8. HPLC analysis confirmed that the $^{125}$I-Rtx-TCO-biotin solution was free of small MW radioactive impurities and showed no differences with the chromatographic behavior of $^{125}$I-Rtx (Rt=12.0 min and ca. 2% aggregates for both mAbs).

Figure 3A:
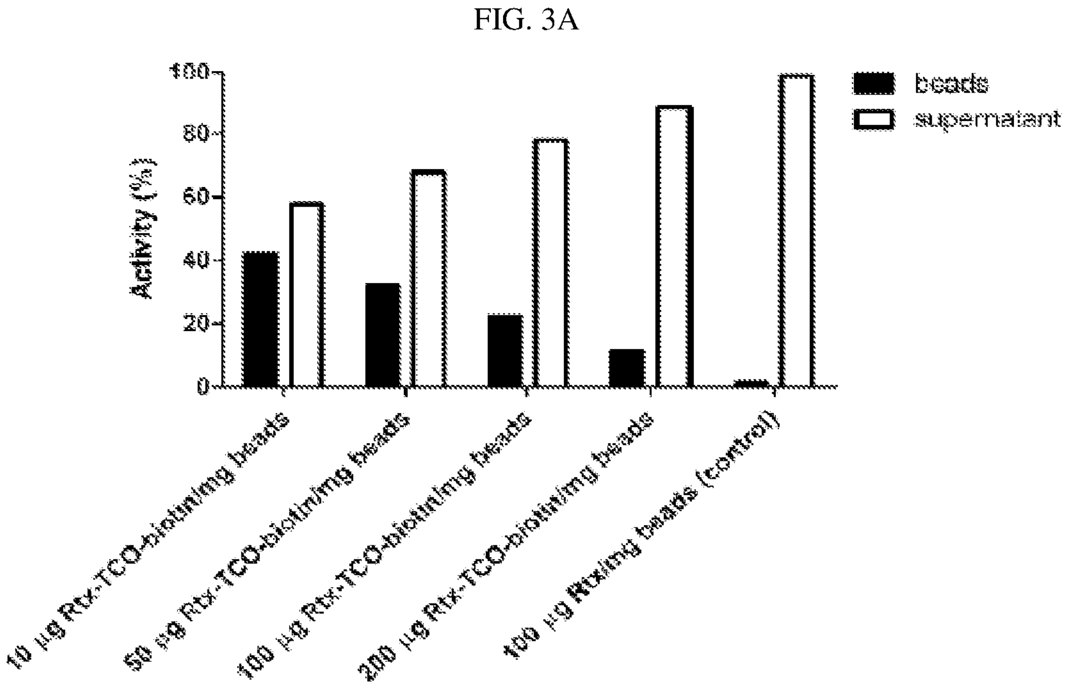
FIG. 3A shows the binding of ca. 4, 15, and 21 μg mab/mg of streptavidin beads for the samples containing 10, 50 and 100 μg $^{125}$I-Rtx-TCO-biotin, respectively.

Subsequently, various amounts of $^{125}$I-Rtx-TCO-biotin were combined with 1 mg streptavidin beads (Dynabeads MyOne Streptavidin Cl, Invitrogen) in 200 μL PBS and incubated for 1 hour at room temperature on a roller bench, to avoid bead settling. After incubation, the supernatants were removed and the beads were washed extensively with PBS. Gamma-counting (Wizard 1480, Perkin Elmer) of the beads, supernatants and washings showed the binding of ca. 4, 15, and 21 μg mab/mg beads for the samples containing 10, 50 and 100 μg $^{125}$I-Rtx-TCO-biotin, respectively (FIG. 3A). Incubation with higher amounts of $^{125}$I-Rtx-TCO-biotin (200 μg mab/mg beads) did not improve the mab-biotin loading, probably due to bead saturation. On the contrary, after 1 hour incubation almost no radioactivity was bound to the beads incubated with 5 $^{125}$I-Rtx.

Figure 3B:
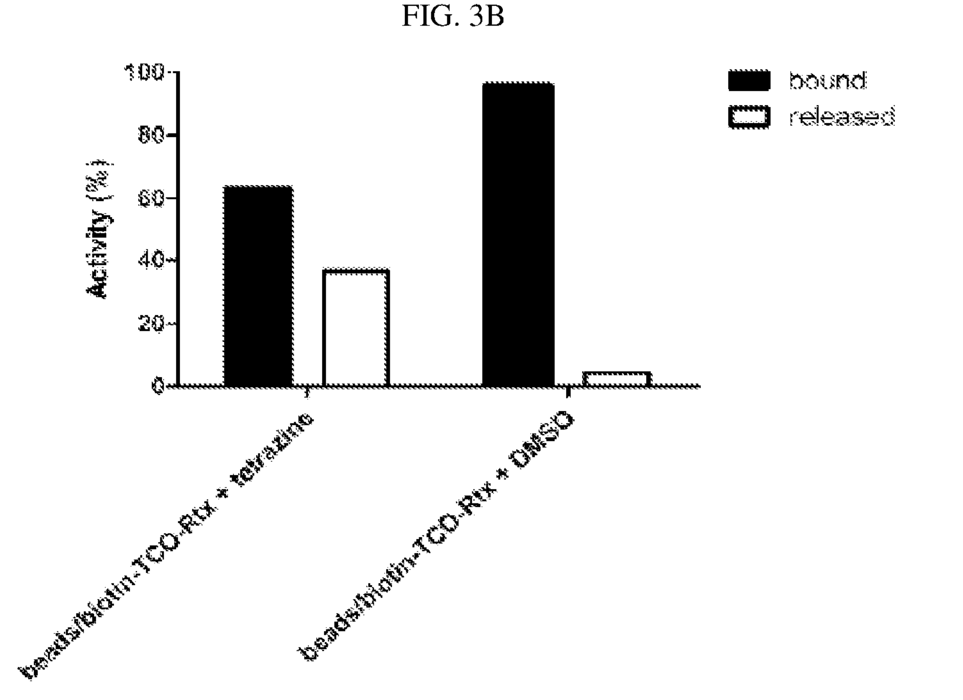
FIG. 3B shows the release of 37% of the bead-bound radioactivity from the beads treated with 3,6-dimethyl-1,2,4,5-tetrazine while only 4% activity was found in the supernatant of the beads treated with DMSO alone measured by gamma counting.
Figure 4:
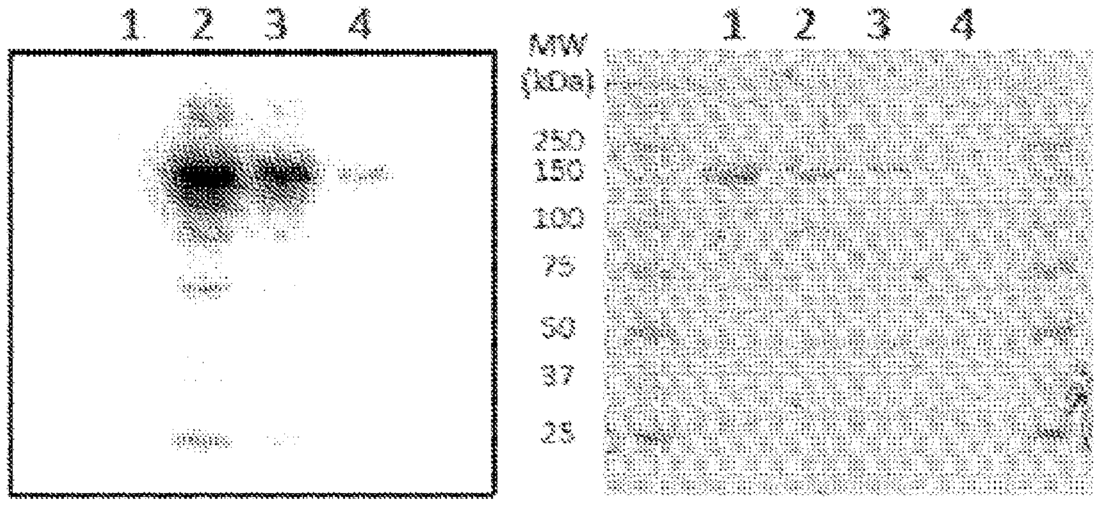
FIG. 4 presents Radiogram (left panel) and protein stain (right panel: homogeneous 7% Phastgel, GE Healthcare Life Sciences) of SDS-PAGE Analysis: Lane 1—unmodified rituximab (Trx); Lane 2—$^{125}$I-Trx; Lane 3—the supernatant of streptavidin beads loaded with $^{125}$I-Rtx-TCO-biotin and treated with 3,6-dimethyl-1,2,4,5-tetrazine (8); and Lane 4—the supernatant of streptavidin beads loaded with $^{125}$I-Rtx-TCO-biotin and treated with DMSO.

The bead suspension containing 21 μg $^{125}$I-Rtx-TCO-biotin/mg beads (1 mL in PBS) was divided in two aliquots and reacted with a large excess of 3,6-dimethyl-1,2,4,5-tetrazine (8, $1.5\times10^3$ eqs with respect to Rtx) in DMSO (5 μL) or with DMSO alone (control) and incubated for 1 hour at room temperature on a roller bench. After incubation, gamma counting of the beads and supernatant showed the release of 37% of the bead-bound radioactivity from the beads treated with 3,6-dimethyl-1,2,4,5-tetrazine while only 4% activity was found in the supernatant of the beads treated with DMSO alone (FIG. 3B). SDS-PAGE confirmed that the activity in the supernatant was due to the release of $^{125}$I-Rtx from the beads (FIG. 4), thus confirming cleavage of the Rtx-TCO-biotin linker upon reaction with the 3,6-dimethyl-1,2,4,5-tetrazine.

Example 9

Antibody Masking by Modification with (E)-Cyclooct-2-En-1-Yl NHS Carbonate, and Subsequent Antibody Activation by Reaction with Tetrazine Activator

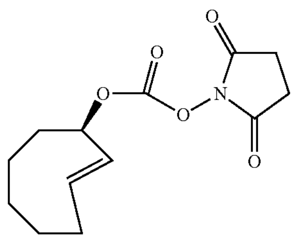

Antibody Conjugation with Axial-(E)-cyclooct-2-en-1-yl NHS Carbonate

The synthesis of Axial-(E)-cyclooct-2-en-1-yl NHS carbonate has been described in WO2012156919A1. A solution of CC49 (8 mg/mL, 62.5 μL) in PBS was added with 6.2 μL DMF and the pH was adjusted to 9 with 1 M sodium carbonate buffer. Subsequently, axial-(E)-cyclooct-2-en-1-yl NHS carbonate freshly dissolved in dry DMF was added (5 μg/μL, 40 mol eq. with respect to CC49) and the resulting solution was incubated for 3 hr at room temperature, under gentle shaking and in the dark. After incubation the reaction mixture was diluted to 500 μL with PBS and unreacted TCO was eliminated by means of a Zeba desalting spin column (40 kDa MW cut-off, Pierce) pre-equilibrated with PBS. The concentration of the obtained mAb solution was measured by UV-Vis (Nanodrop) and the purity and integrity of the product were assessed by SDS-PAGE. The conjugation yield was determined with a tetrazine titration. The DOTA-tetrazine derivative was radiolabeled with carrier-added $^{177}$Lu as previously described (Rossin et al., Angew Chem Int Ed, 2010, 49, 3375-3378). The TCO-modified mAb (25 μg) was reacted with a known excess of $^{177}$Lu-DOTA-tetrazine in PBS (50 μL). After 10 min incubation at 37° C., the reaction mix was added with non-reducing sample buffer and analyzed by SDS-PAGE. After gel electrophoresis, the radioactivity distribution in each lane was assessed with phosphor imager. The reaction yields between $^{177}$Lu-DOTA-tetrazine and the CC49-TCO construct was estimated from the intensity of the radioactive mAb band with respect to the total radioactivity in the lane. With this procedure an average of 20 TCO moieties per CC49 molecule was found (50% conjugation yield).

CC49 and CC49-TCO Radiolabeling

The unmodified CC49 was radiolabeled with $^{125}$I with the Bolton-Hunter procedure according to the manufacturer instruction. Briefly, ca. 40 MBq sodium [$^{125}$I]iodide was diluted with 50 μL PBS and added with 1 μL Bolton-Hunter reagent (SHPP, Pierce) solution in DMSO (0.1 μg/μL) and 25 μL chloramine-T (Sigma-Aldrich) solution in PBS (4 mg/mL). The solution was mixed for 10-20 sec, then 5 μL DMF and 100 μL toluene were added. After vortexing, the organic phase containing $^{125}$I—SHPP was transferred into a glass vial and dried at room temperature under a gentle stream of $N_2$. 30 μg CC49 in PBS (50 μL) were then added to the $^{125}$I—SHPP coated glass vial and the pH was adjusted to 9 with 1M sodium carbonate buffer pH 9.6. The vial was incubated at room temperature under gentle agitation for ca. 60 min then the $^{125}$I-mAb labeling yield was evaluated with radio-ITLC (47%). The crude $^{125}$I-mAb was purified through Zeba Desalting spin columns (40 kDa MW cut-off, Pierce) pre-equilibrated with saline solution and the radiochemical purity of the obtained $^{125}$I-labeled CC49 was greater than 98%, as determined by radio-ITLC and radio-HPLC.

The CC49 carrying 20 TCO moieties per molecules was reacted with DOTA-tetrazine (1 mol eq. with respect to mAb) which was previously radiolabeled with non-carrier-added $^{177}$Lu as described (Rossin et al., *Angew Chem Int Ed,* 2010, 49, 3375-3378). After 10 min incubation 91% radiochemical purity for the $^{177}$Lu-labeled CC49-TCO by radio-HPLC and the reaction mixture was used without further purification.

Antibody Activation Experiments

In this example we show that by over-modifying CC49 with TCO we can significantly reduce the ability of the mAb to bind its target in vitro and that by reacting the over-modified CC49-TCO construct with tetrazine 9 the target binding capability is restored. The mAb re-activation upon reaction with the tetrazine indicates TCO release following the electronic cascade mediated elimination mechanism.

Figure 5A:
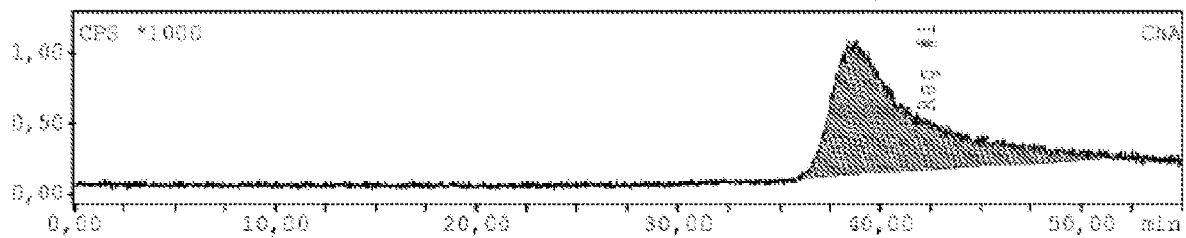
FIG. 5A and FIG. 5B present size exclusion radio-chromatograms of $^{125}$I-CC49 and $^{125}$I-CC49 bound to bovine submaxillary mucin type I-S (BSM), respectively.
Figure 5B:
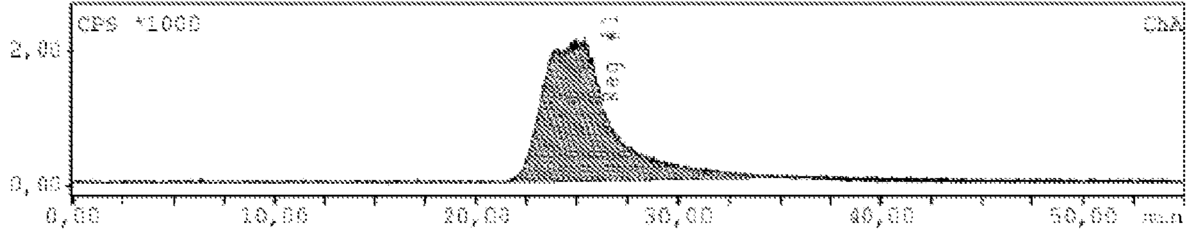

The capability of CC49 constructs to bind their target was evaluated by using an immunoreactivity assay modified from a previously described method (Lewis et al., Bioconjug Chem, 2006, 17, 485-492). Briefly, the radiolabeled mAb constructs (1 μg) were reacted with a 20-fold molar excess of bovine submaxillary mucin type I-S(BSM; Sigma-Aldrich) in 1% BSA solution (100 μL). After 10 min incubation at 37° C. the mixtures were analyzed by radio-HPLC using a Superdex-200 column (GE Healthcare Biosciences) eluted with PBS at 0.35 mL/min. In these conditions non-TCO-modified $^{125}$I-CC49 eluted from the column in a broad peak with a 39 min retention time (FIG. 5A). As expected, after incubation with BSM the $^{125}$I activity eluted from the column in a peak corresponding to a higher MW species (25 min retention time), confirming the binding of $^{125}$I-CC49 to BSM (100% immunoreactivity; FIG. 5B).

Figure 6A:
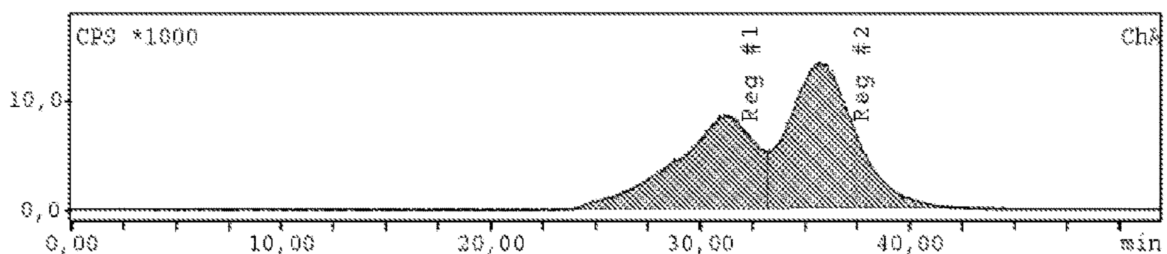
FIG. 6A presents size exclusion radio-chromatograms of $^{177}$Lu-CC49-TCO and $^{177}$Lu-CC49-TCO in the presence of bovine submaxillary mucin type I-S(BSM) (FIG. 6B) before and after 1 hour (FIG. 6C) reaction with tetrazine 9
Figure 6B:
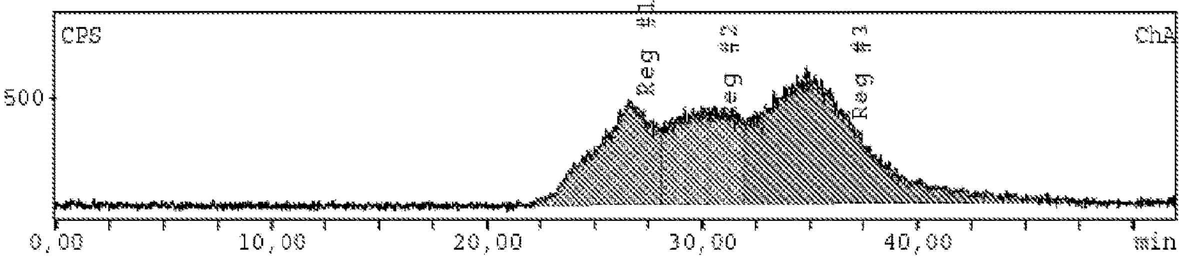

When the $^{177}$Lu-labeled CC49 carrying 20 TCO moieties per molecule was analyzed by radio-HPLC, the mAb eluted from the column in two broad unresolved peaks with 31 min and 36 min retention times, accounting for 43% and 57% of the total mAb-related activity, respectively (FIG. 6A). This behavior suggests over-modification of CC49 with TCO groups. In fact, the change of MW after conjugation is relatively small and not likely to cause a 3 min change in retention time (from 39 to 36 min) between CC49 and CC49-TCO. Therefore, the shorter retention in the column is more likely due to conformational changes caused by the 20 TCO moieties attached to the mAb. Also, the broad peak eluting from the column at 31 min is a sign of mAb aggregation. As a consequence, after incubating the $^{177}$Lu-labeled CC49-TCO with BSM, only a small amount (ca. 20% of the total) of $^{177}$Lu activity was associated with a high MW species in the radio-chromatogram (FIG. 6B). The ca. 20% residual immunoreactivity confirms that the over-modified CC49-TCO has lost its target binding capability.

Figure 6C:
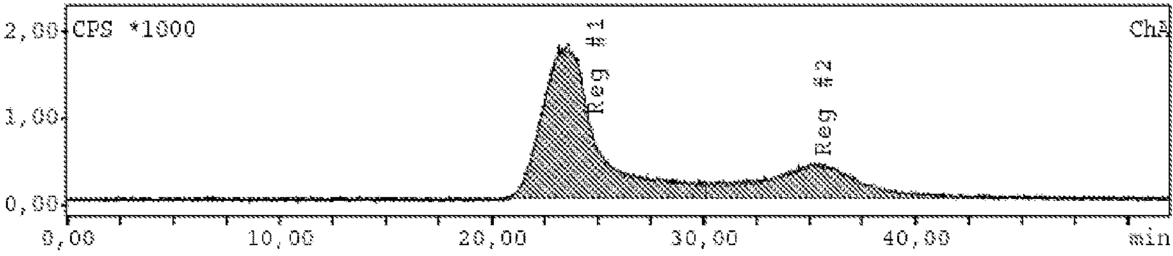

Subsequently, the $^{177}$Lu-labeled CC49-TCO was reacted with a large excess of tetrazine 7 (500-fold molar excess with respect to TCO) in PBS at 37° C. At various time points (1 hr, 4 hr and 24 hr) an aliquot of the reaction mixture (containing 1 μg mAb) was withdrawn, incubated with BSM and analyzed by radio-HPLC. As short as 1 hr after addition of tetrazine 9, the radio-chromatogram showed the disappearance of the radioactive peak attributed to CC49-TCO aggregates, a significant reduction of the peak at 36 min and the formation of an intense peak due to the formation of a $^{177}$Lu-CC49-TCO-BSM adduct ($R_t$=24 min; 72% of the total mAb-related activity; FIG. 6C).

A further slight increase in peak area was observed with time (76% after 24 hr incubation of CC49-TCO with tetrazine 9). The rapid increase in CC49 immunoreactivity following retro Diels-Alder cycloaddition between TCO and tetrazine 9 is indicative of TCO release as a result of the electronic cascade mediated elimination mechanism.

Example 10

Capture and Release of Cell

In this example, target cells are first bound by TCO-modified antibodies, followed by addition of tetrazine-coated beads. Suitably chosen tetrazine-TCO pairs that function via the strain release mechanism will give a release with a half life of >2 h and given the required reaction time of <10 minutes thus allow enough time for isolation of the bead-cell complex before the complex releases the cell automatically through release of the linker. The TCO used in this example gives $C^A$ release with a half life of >2 h at pH 7 at 37 C, largely independent of the type of tetrazine, provided the tetrazine reacts with the TCO within ca 10 min. The feature believed to enable the release at pH 7 is the aromatic nature of the leaving group $C^A$, in the case a aliphatic hydroxyl. When an aliphatic hydroyl is the leaving group in $C^A$ it is preferred to increase the pH to 9 and or increase the temperature to above 45 C, conditions which are better suited for other captured constructs.

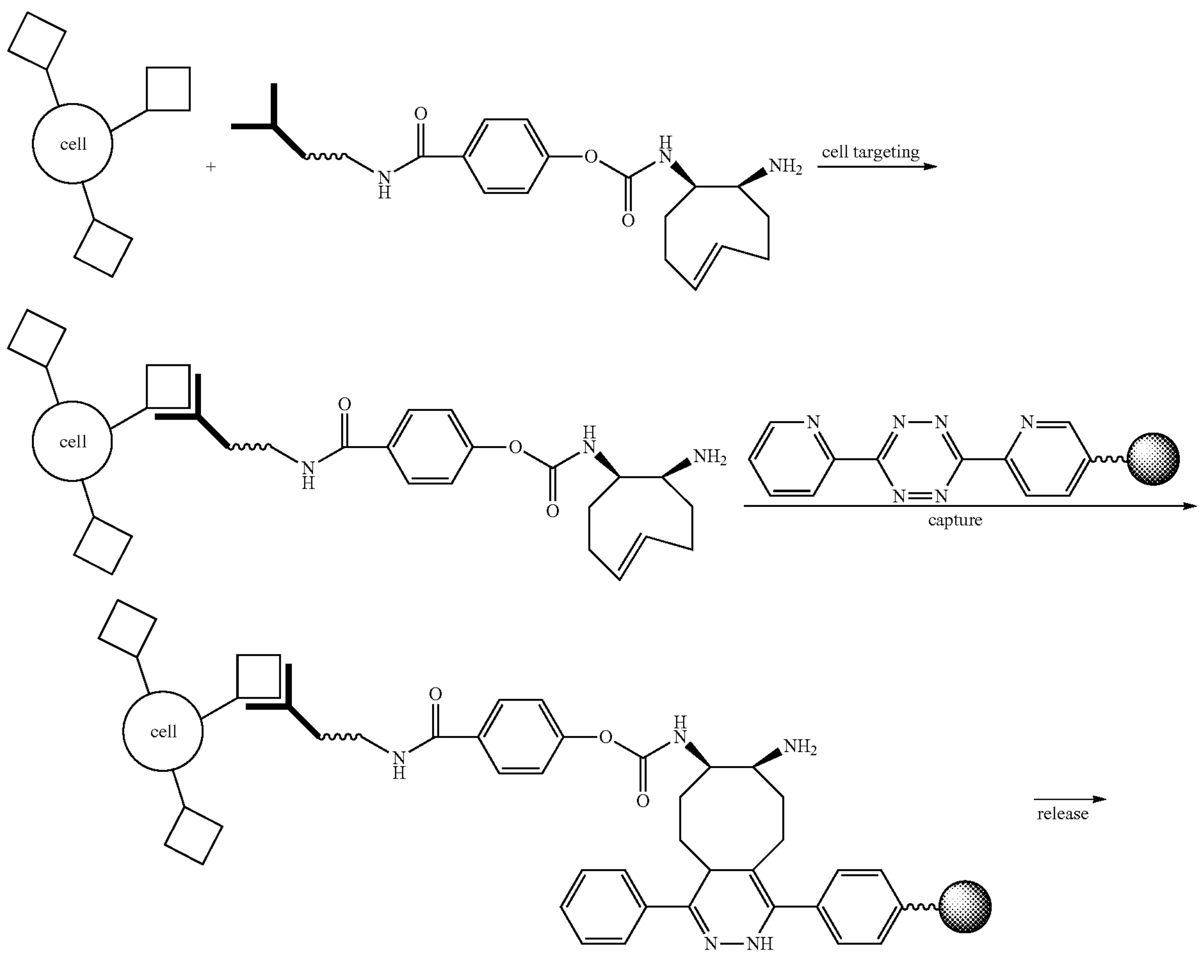

-continued

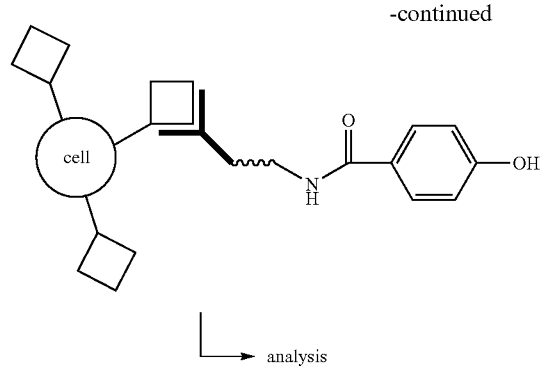

+

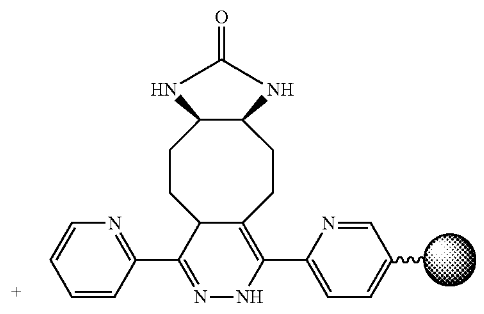

Example 11

The linkers below can be used for biomolecule (eg protein) labeling and capture using tetrazine coated beads or resin. The tetrazine moieties will react with the TCO functionalized biomolecule allowing isolation, followed by automatic biomolecule release. Suitably chosen TCOs will give a release with a half life of >2 h and given the required reaction time of <10 minutes thus allow enough time for isolation of the complex before the complex releases the biomolecule autonomically through release of the linker. For release at pH 7 and ambient temperature it is preferred to use linkers with an aromatic alcohol as leaving group from the carbamate. For applications where it is desired to delay the release it is preferred to use an aliphatic alcohol as leaving group from the carbamate and to perform the rDA reaction at pH≤8 at max 37 C. The release can subsequently be triggered by increasing the pH to 9 and/or by increasing the temperature.

A

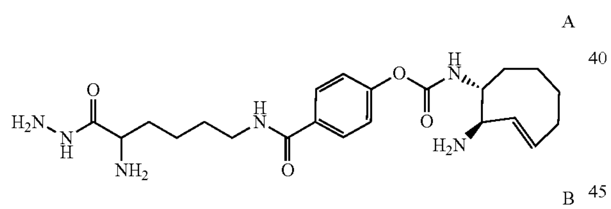

B

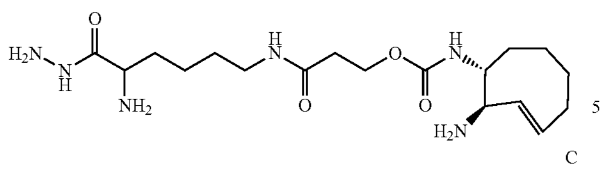

C

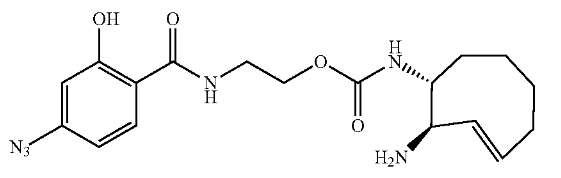

D

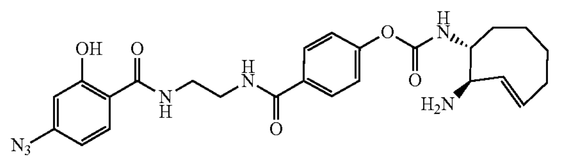

-continued

E

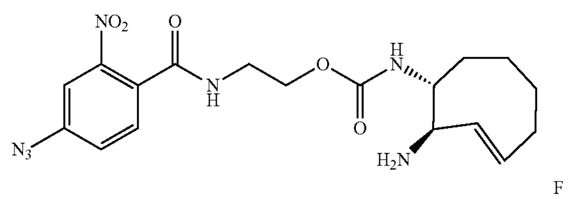

F

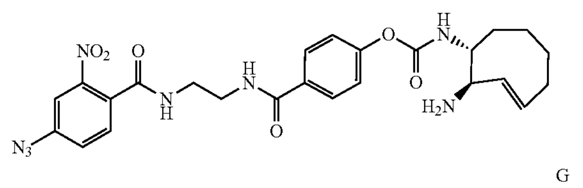

G

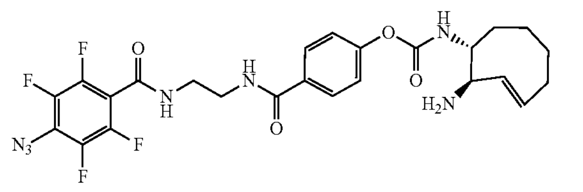

H

R = H, $SO_3Na$

Example 12

Additional TCO Building Blocks

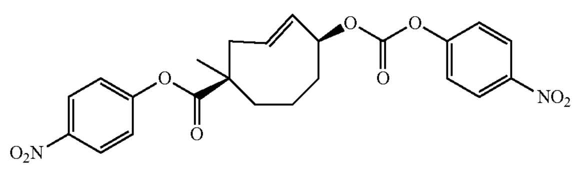

-continued

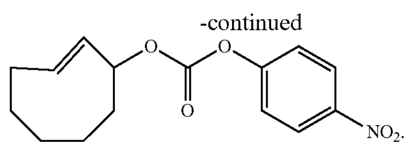

The invention claimed is:

1. A dienophile of Formula (1a):

(1a)

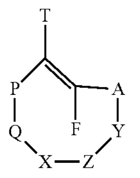

wherein A and P each independently are $CH_2$, or $CHX^D$, provided that at least one is $CHX^D$; $X^D$ is $(O—C(O))_p$-$(L^D)_n$-$(C^A)$, or O—C(S)-$(L^D)_n$-$(C^A)$; wherein n=0 or 1, wherein p=0 or 1; wherein when p=0, $L^D$ or $C^A$ is bound to the dienophile via O, S, aromatic N or aromatic NH; $L^D$ is a self-immolative linker consisting of one or more self-immolative units;

wherein each self-immolative unit is selected from the group consisting of

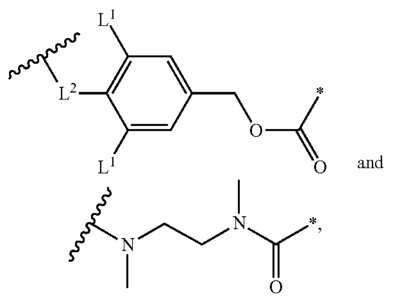

and

, wherein the wiggly line indicates a bond to $(O—C(O))_p$ or O—C(S) of $X^D$, or to a preceding self-immolative unit; wherein the asterisk indicates a bond to $C^A$ or to a further self-immolative unit;

wherein $L^2$ is O, S, NH, or NR with R being alkyl or aryl; wherein each $L^1$ is independently H or methyl;

Y, Z, X, Q each independently are selected from the group consisting of $CR^a_2$, C═O, O, and $NR^b$, with at most three of Y, Z, X, and Q being C═O, wherein two R moieties together may form a ring, and with the proviso that no adjacent pairs of atoms are present selected from the group consisting of O—O, and O—$NR^b$;

wherein each $R^a$ can independently be H, alkyl, aryl, OR', SR', S(═O)$_2$R''', S(═O)$_2$NR'R'', $SO_3H$, $PO_3H$, $NO_2$, CN, $CF_3$, $CF_2$—R', NR'R'', C(═O)R', C(═O)OH, C(═O)NR'R'', C(═S)NR'R'', NR'C(═O)—R''', NR'C(═S)—R''', NR'C(═O)O—R''', NR'C(═S)O—R''', NR'C(═O)S—R''', NR'C(═S)S—R''', OC(═O)NR'—R''', SC(═O)NR'—R''', OC(═S)NR'—R''', SC(═S)NR'—R''', NR'C(═O)NR''—R'', or NR'C(═S)NR''—R'', with each R' and each R'' independently being H, aryl or alkyl and R''' independently being aryl or alkyl;

wherein each $R^b$ is independently selected from the group consisting of H, alkyl, aryl, O-aryl, O-alkyl, OH, C(═O)NR'R'' with R' and R'' each independently being H, aryl or alkyl, and R'CO-alkyl with R' being H, alkyl, and aryl;

wherein one $R^a$ or $R^b$ is optionally bound to a construct $C^B$; and wherein the self-immolative linker $L^D$, in addition to being bound to $C^A$, is also optionally bound to a construct $C^B$; wherein T and G denote H;

wherein each $C^A$ and $C^B$ are individually selected from the group consisting of biomolecules, biomolecule-binding moieties, polymers, particles, gels, fluorophores, and radiolabels.

2. The dienophile according to claim 1, wherein p is 1.

3. The dienophile according to claim 1, wherein $X^D$ is $(O—C(O))_p$-$(L^D)_n$-$(C^A)$.

4. The dienophile according to claim 1, wherein the construct comprises a biomolecule-binding moiety selected from the group consisting of non-covalent binding moieties, and covalent binding moieties.

5. The dienophile according to claim 4, wherein the non-covalent binding moiety is biotin or an antibody.

6. The dienophile according to claim 4, wherein the covalent binding moiety is an N-hydroxysuccinimide ester, a maleimide, an azide, an alkyne, or a photoreactive group.

7. The dienophile according to claim 1, wherein the biomolecule is selected from the group consisting of carbohydrates, peptides, peptoids, lipids, proteins, oligonucleotides, DNA, RNA, PNA, LNA, aptamers, hormones, steroids, and toxins.

8. The dienophile according to claim 7, wherein the protein is an enzyme, cytokine, antibody, antibody fragment, antibody fusion, or an antibody fragment fusion.

9. The dienophile according to claim 8, wherein the antibody fragment is Fab2, Fab, scFV, a diabody, a triabody, or VHH.

10. The dienophile according to claim 1, wherein the particle is a bead, a gold particle, a silica-based particle, a glass particle, a polymer particle, an iron oxide particle, a microparticle, or a nanoparticle.

11. The dienophile according to claim 10, wherein the bead is a magnetic bead.

12. The dienophile according to claim 10, wherein the microparticle is a liposome or polymersome.

13. The dienophile according to claim 10, wherein the nanoparticle is a liposome or a polymersome.

14. The dienophile according to claim 1, wherein the polymer is a resin.

15. The dienophile according to claim 1, wherein one of the bonds PQ, QX, XZ, ZY, YA is part of a fused ring, such that two exocyclic bonds are fixed in the same plane, and provided that PQ and YA are not part of an aromatic 5- or 6-membered ring, or of a conjugated 7-membered ring; when not part of a fused ring P and A are independently $CH_2$ or $CHX^D$, provided that at least one is $CHX^D$; when part of a fused ring P and A are independently CH or $CX^D$, provided that at least one is $CX^D$; the remaining moieties Y, Z, X, and Q of the group (—Y—Z—X-Q-) being independently from each other $CR^a_2$, S, SO, $SO_2$, O, or $NR^b$, such that no adjacent pairs of atoms are present selected from the group consisting of O—O, O—$NR^b$, S—$NR^b$, O—S, O—S(O), O—S(O)$_2$, and S—S.

16. The dienophile according to claim 1, wherein the dienophile comprises a trans-cyclooctene moiety of formula (1b):

(1b)

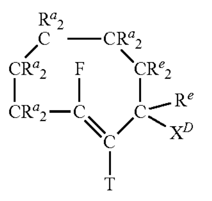

wherein $X^D$ is as defined in claim 1;

wherein, in addition to the optional presence of at most two exocyclic bonds fixed in the same plane, wherein each $R^c$ is independently selected from the group consisting of H, alkyl, aryl, OR', SR', $S(=O)_2R'''$, F, $SO_3H$, $PO_3H$, $NO_2$, CN, $CF_3$, $CF_2$—R', C(=O)R', C(=S)R', C(=O)NR'R", C(=S)NR'R", NR'C(=O)—R''', NR'C(=S)—R''', NR'C(=O)O—R''', NR'C(=S)O—R''', NR'C(=O)S—R''', NR'C(=S)S—R''', NR'C(=O)NR"—R", NR'C(=S)NR"—R", and CR'NR", with each R' and each R" independently being H, aryl or alkyl and R''' independently being aryl or alkyl;

wherein two $R^{a,e}$ moieties together may form a ring;

wherein optionally one of $R^a$ and $R^c$, or the self-immolative linker $L^D$, is bound to $C^B$.

17. A dienophile of any one of the following formulae:

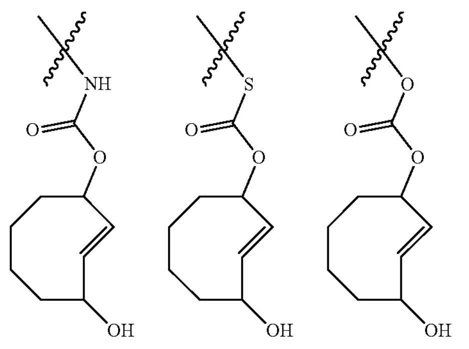

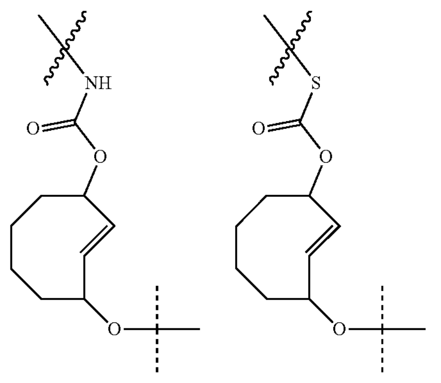

-continued

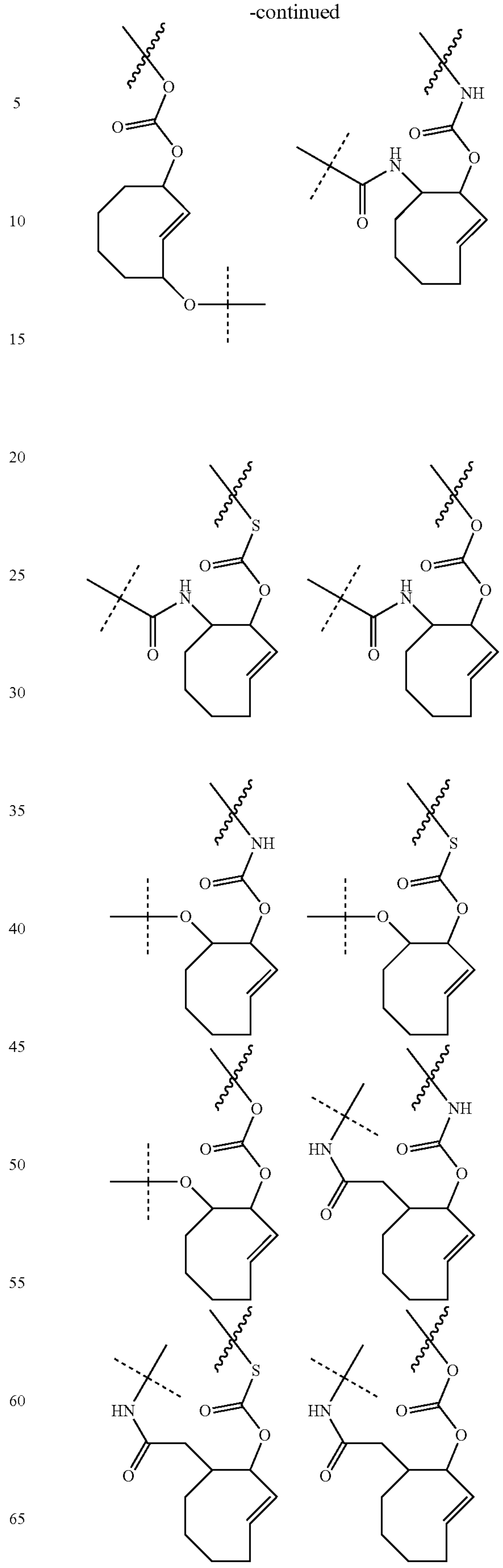

-continued
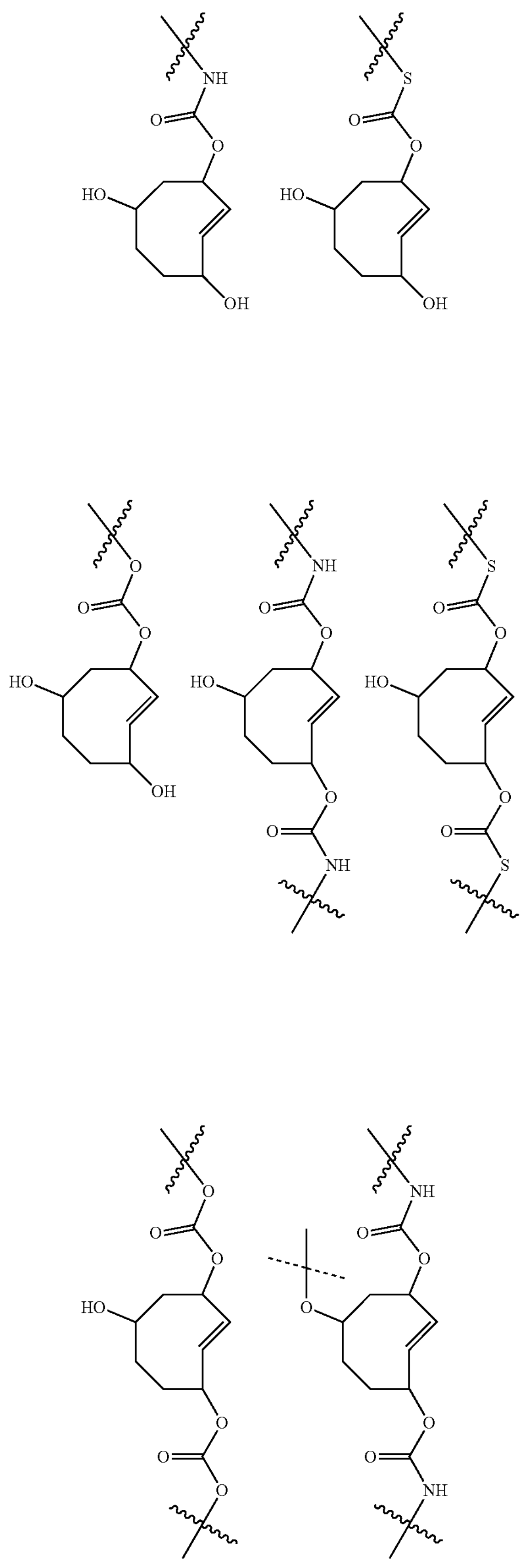
-continued
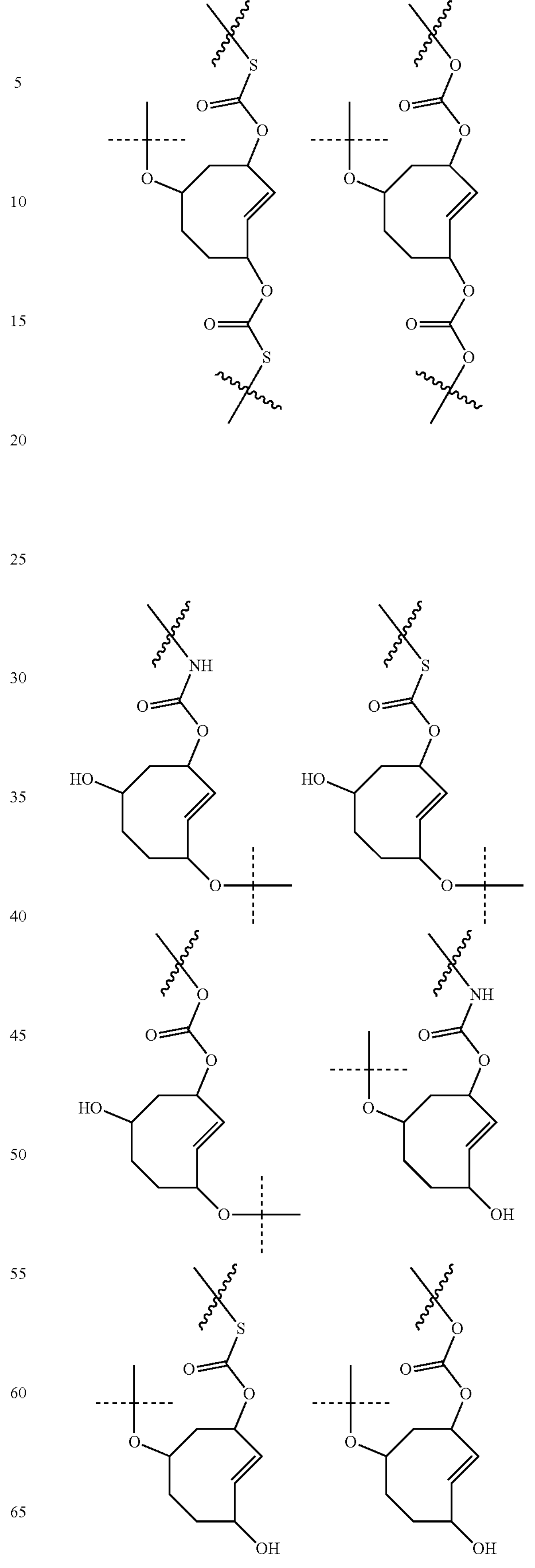

-continued
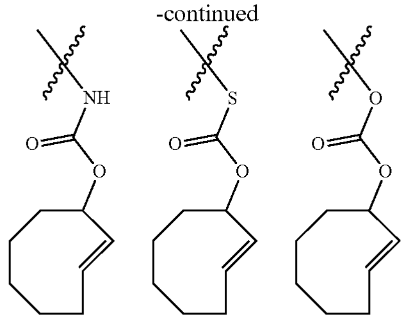
wherein the dotted line denotes a bond to the rest of $C^B$ and wherein the wavy line indicates a bond to the rest of $C^A$ or $L^D$-$C^A$, wherein $L^D$ may optionally comprise $C^B$;
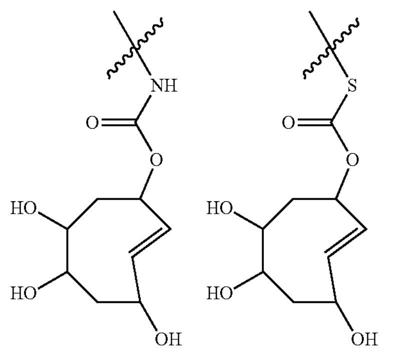
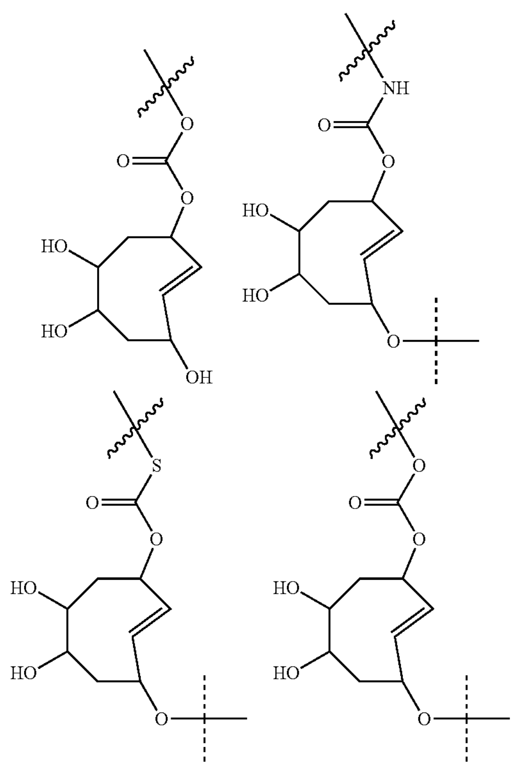
-continued
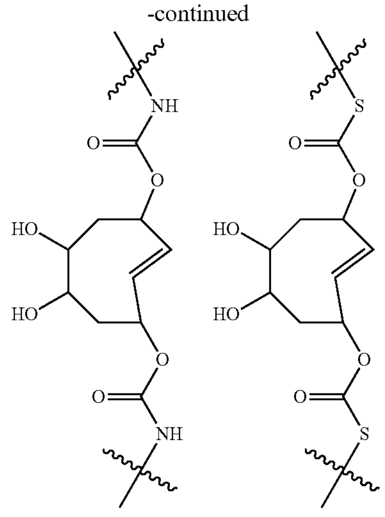
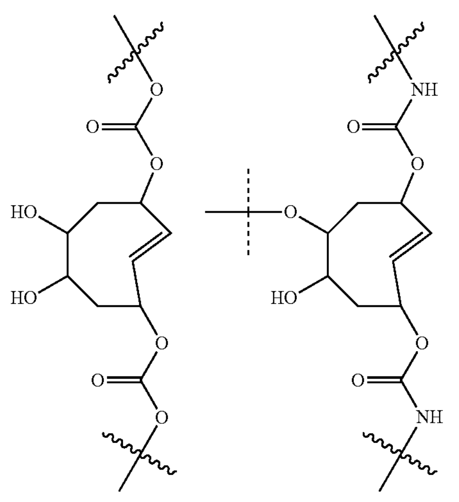
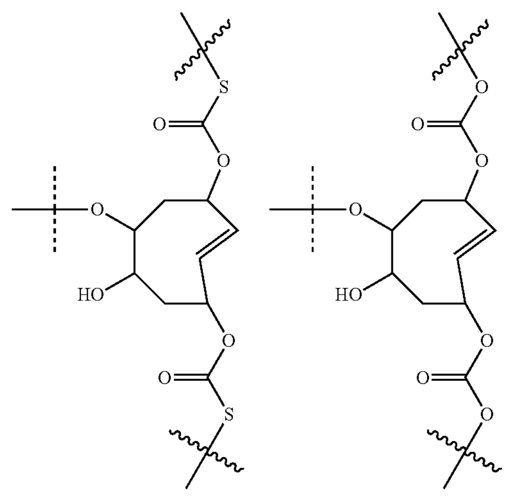

-continued
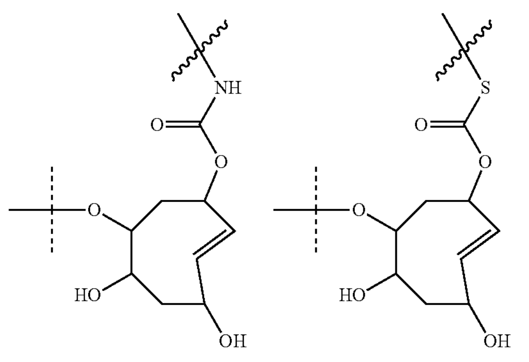
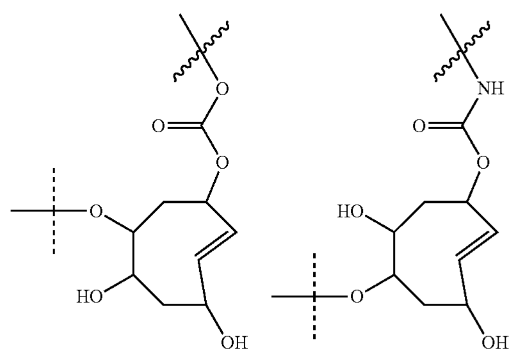
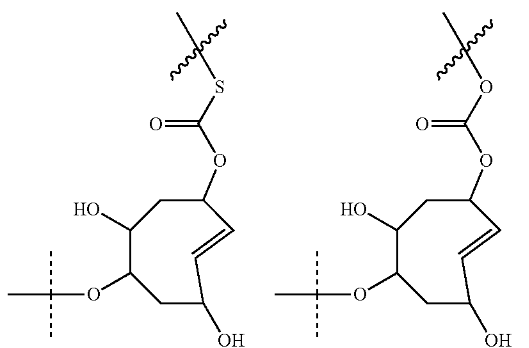
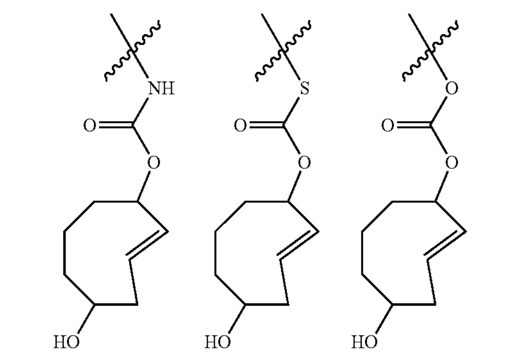
-continued
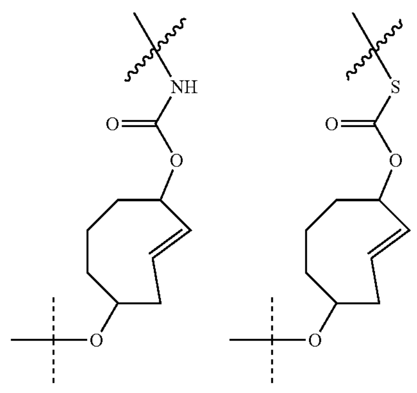
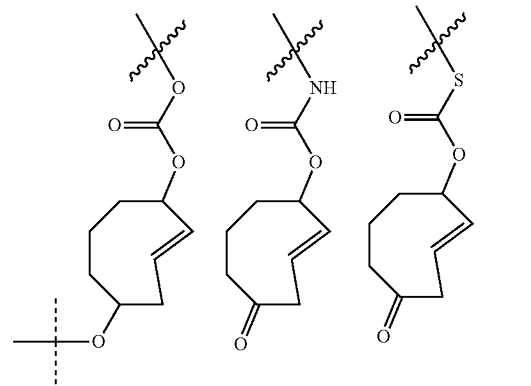
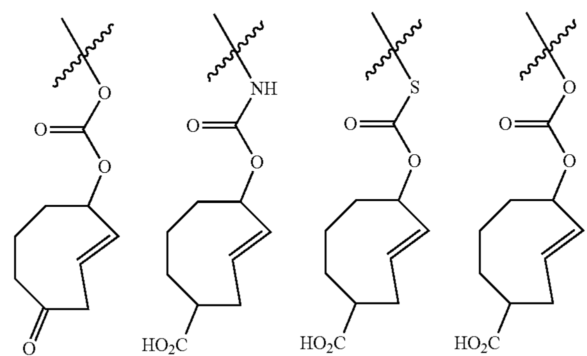
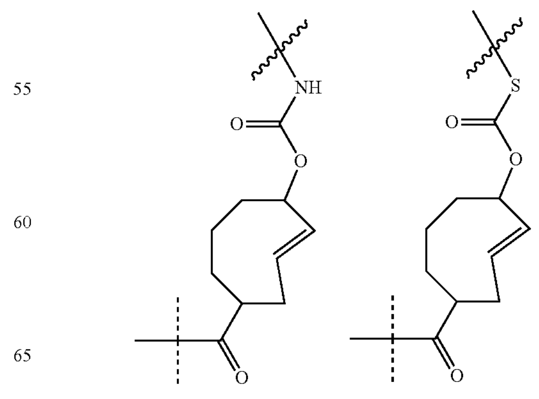

-continued
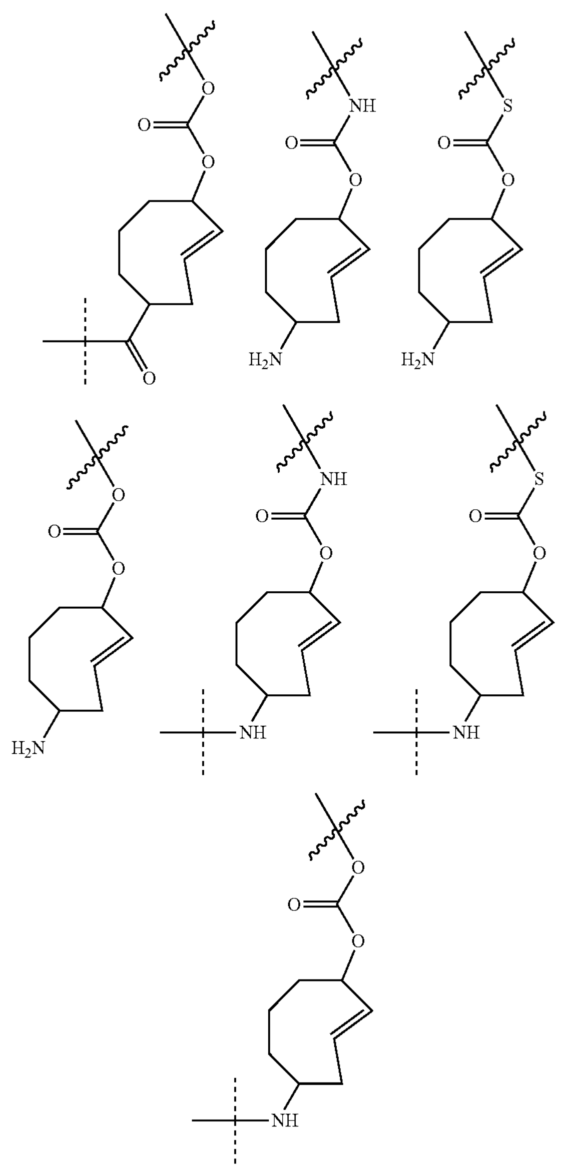
wherein the dotted line denotes a bond to the rest of $C^B$ and wherein the wavy line indicates a bond to the rest of $C^A$ or $L^D$-$C^A$, wherein $L^D$ may optionally comprise $C^B$;
-continued
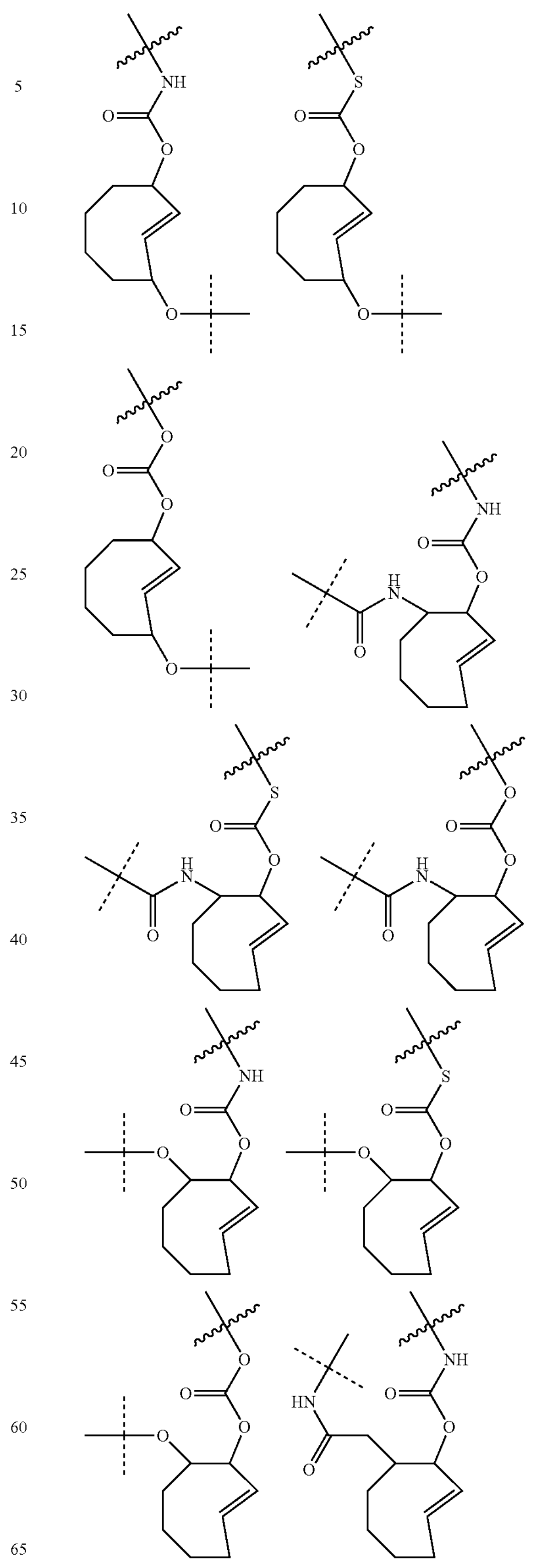

-continued
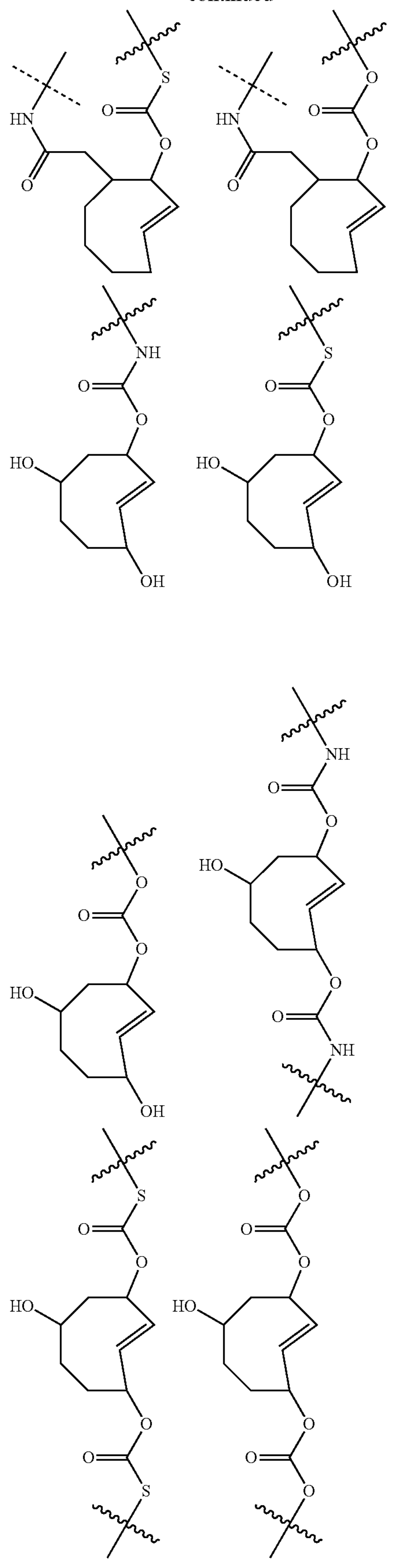
-continued
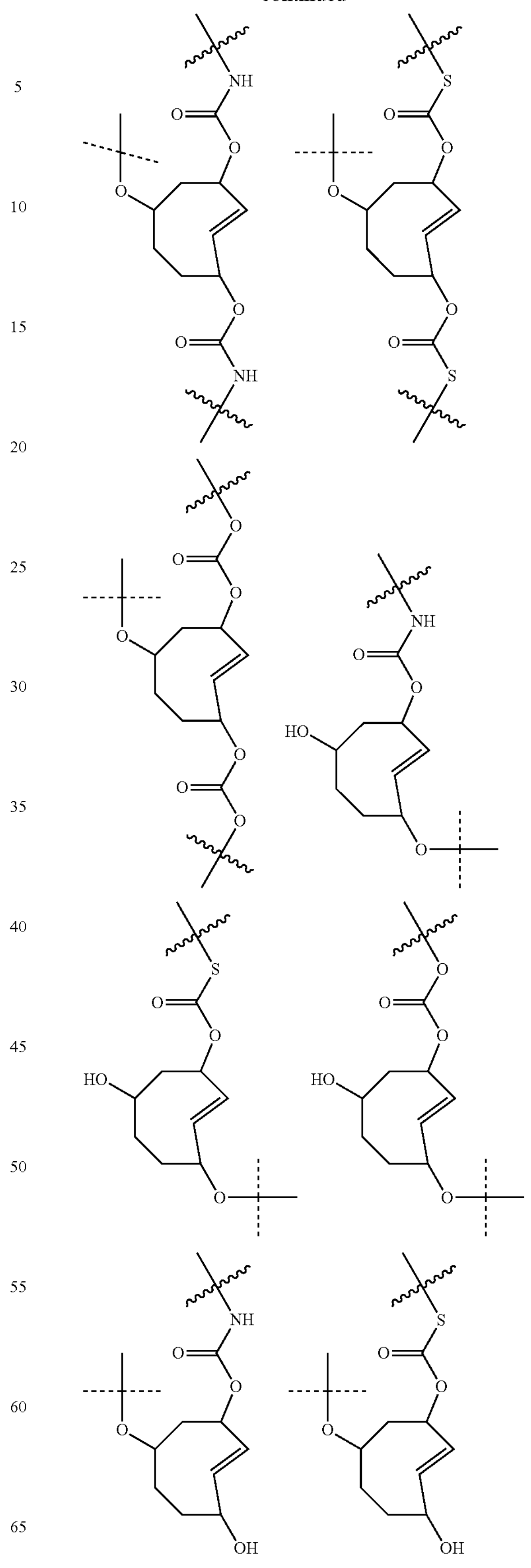

-continued
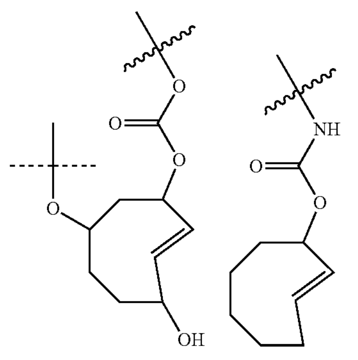
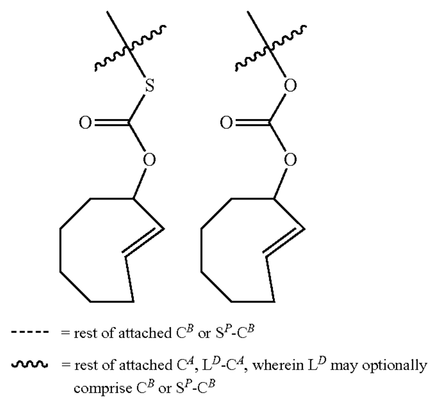
---- = rest of attached $C^B$ or $S^P$-$C^B$
∿∿ = rest of attached $C^A$, $L^D$-$C^A$, wherein $L^D$ may optionally comprise $C^B$ or $S^P$-$C^B$
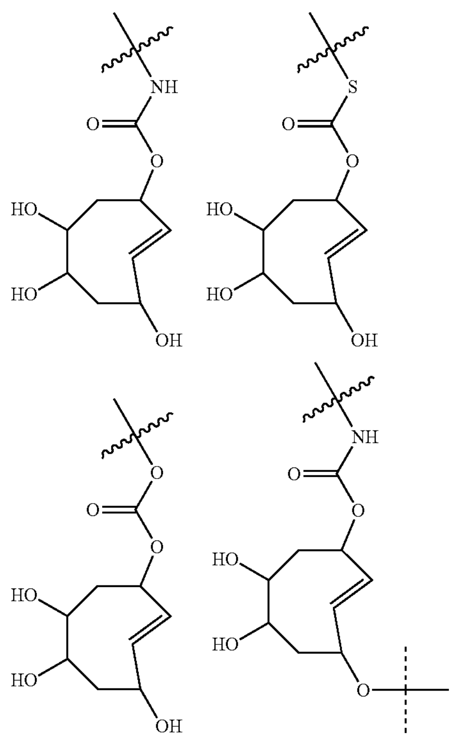
-continued
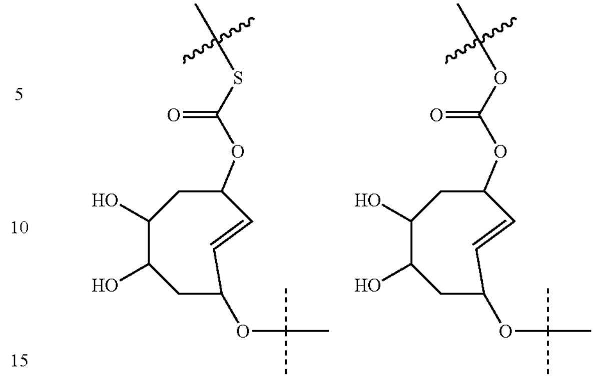
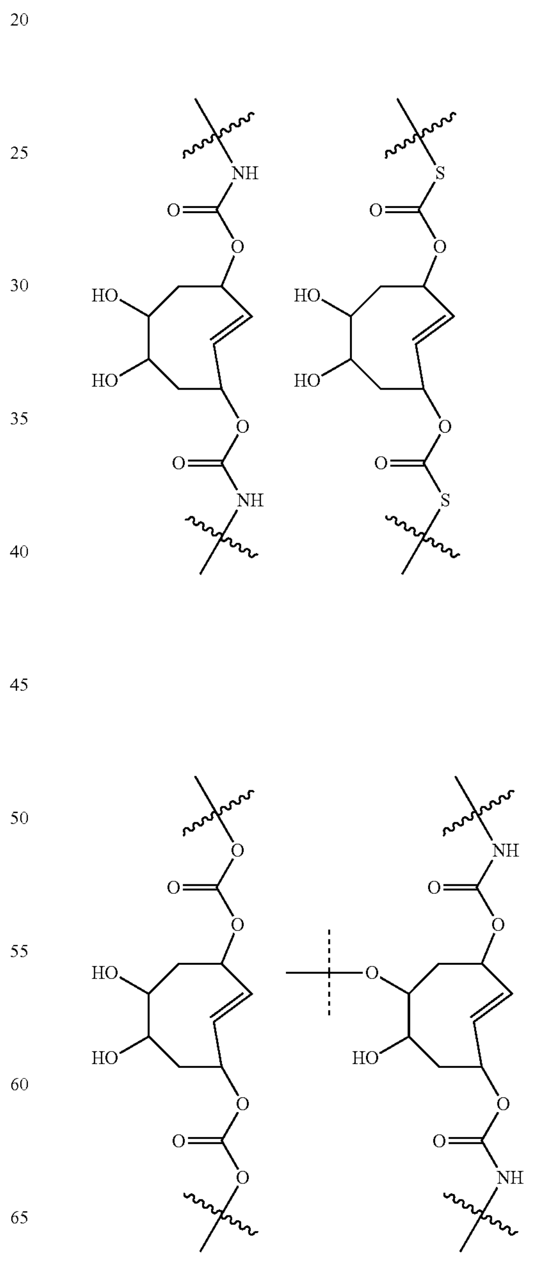

-continued
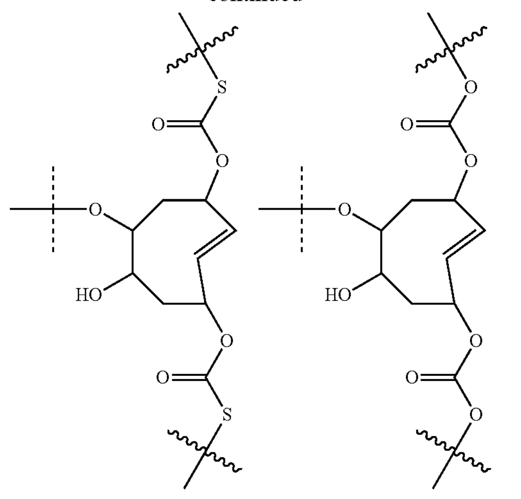
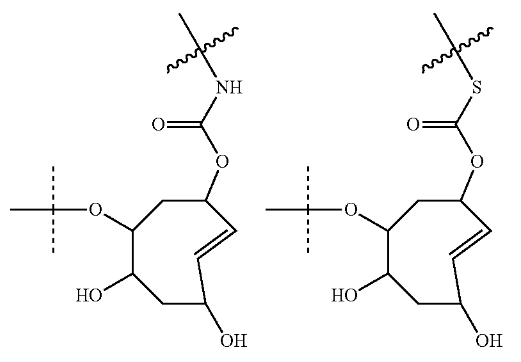
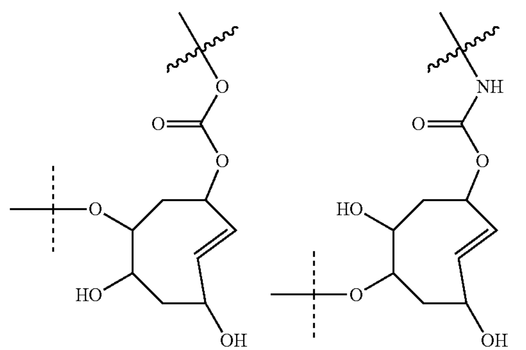
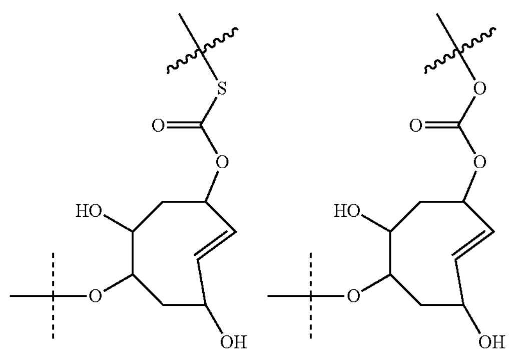
-continued
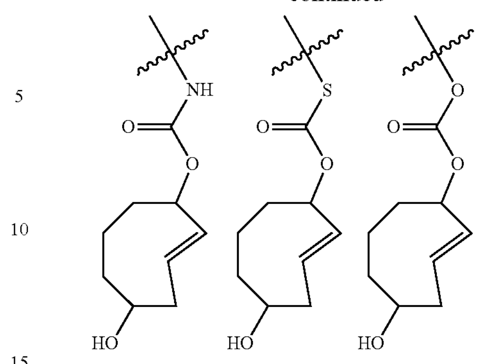
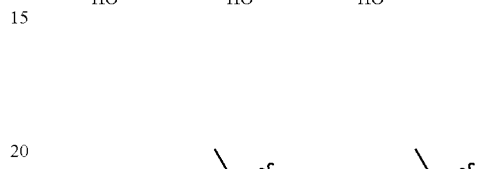
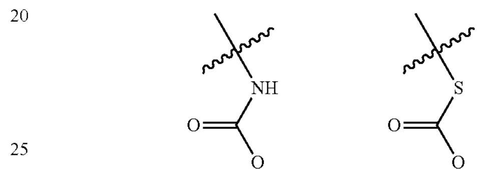
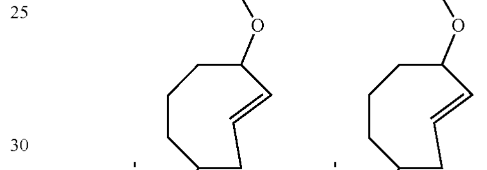
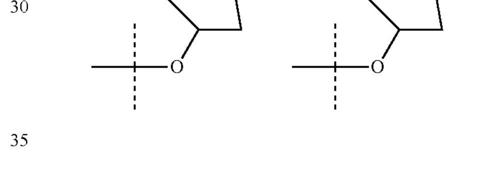
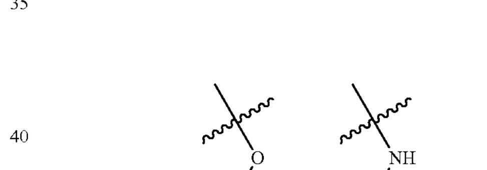
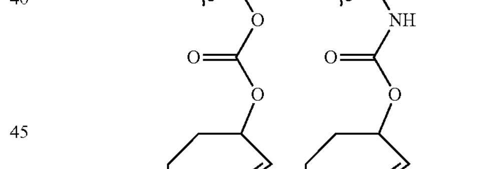
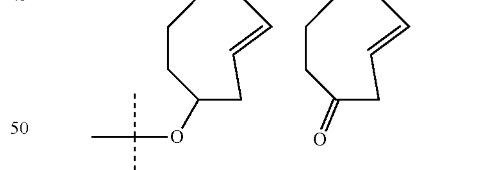
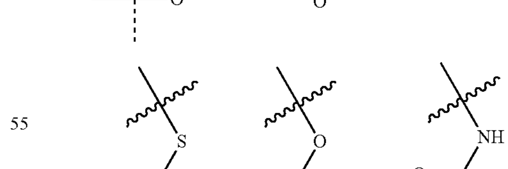
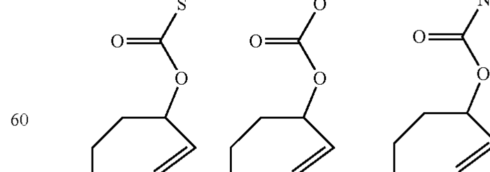
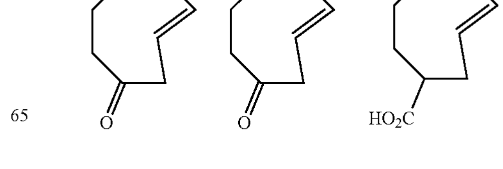

-continued
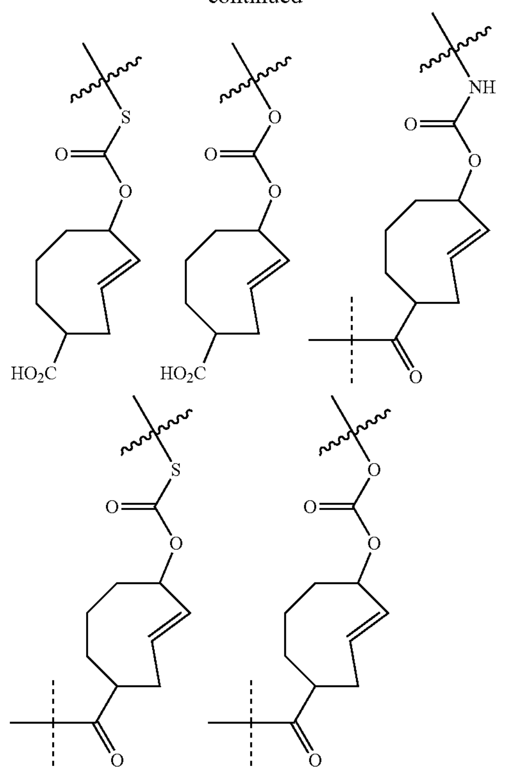
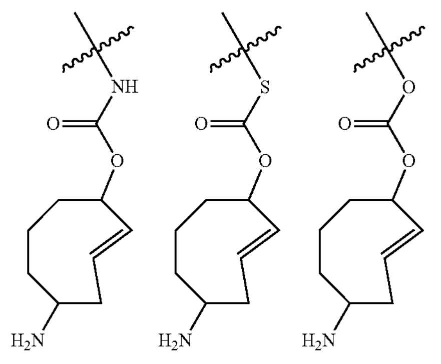
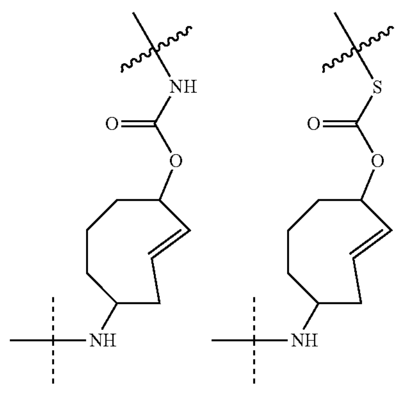
-continued
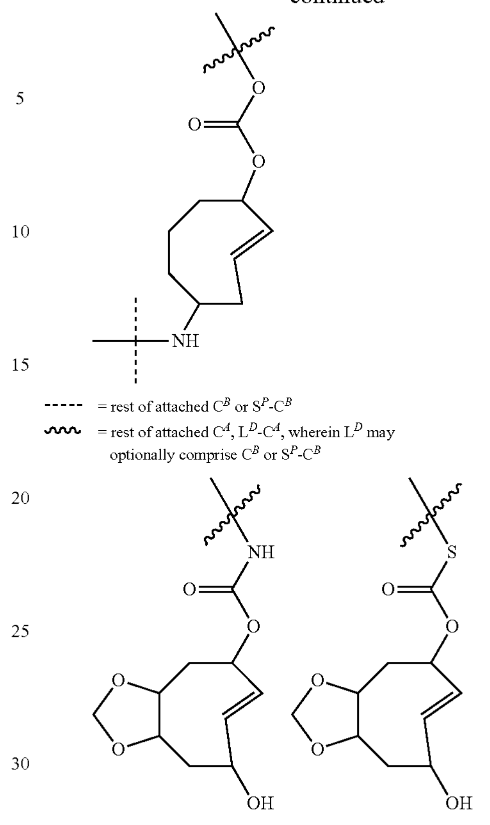
= rest of attached $C^B$ or $S^P$-$C^B$
= rest of attached $C^A$, $L^D$-$C^A$, wherein $L^D$ may optionally comprise $C^B$ or $S^P$-$C^B$
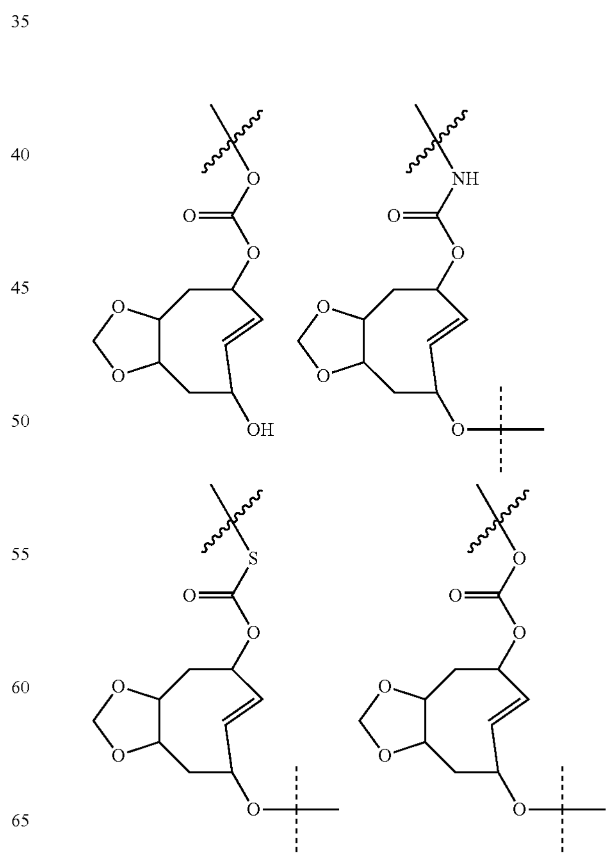

-continued
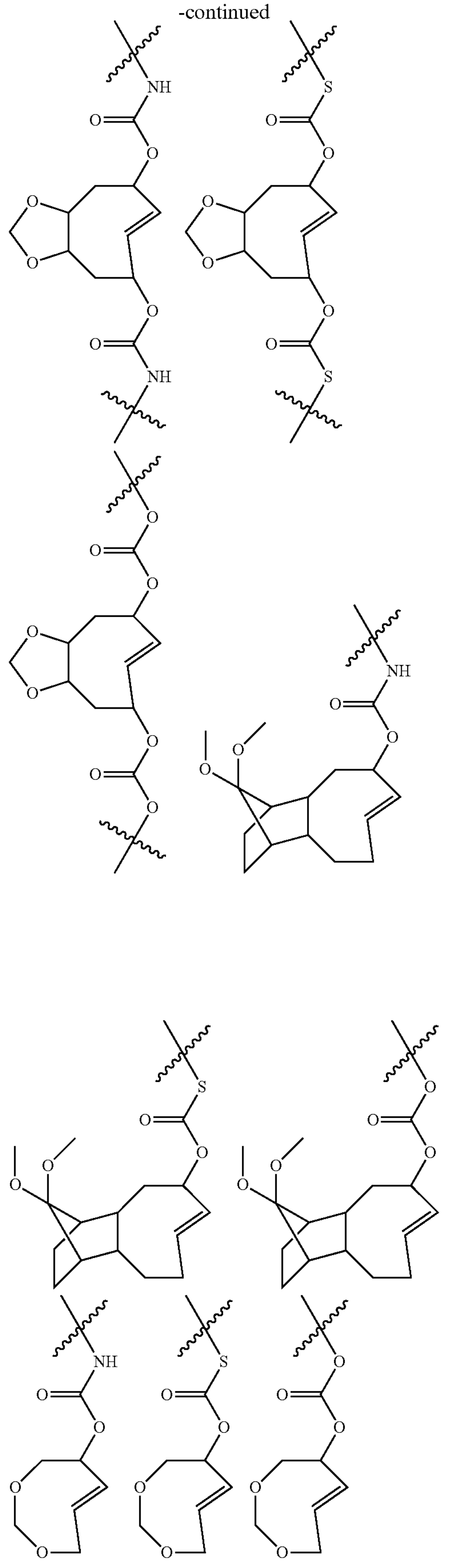
-continued
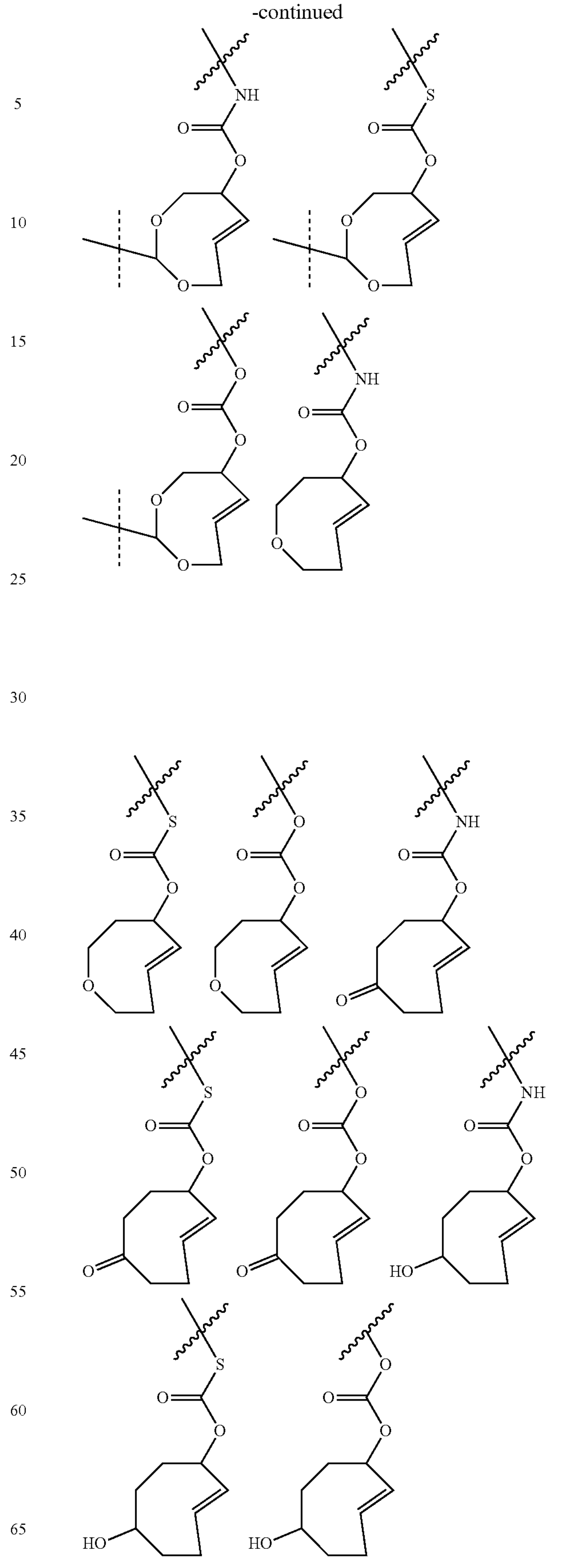

-continued

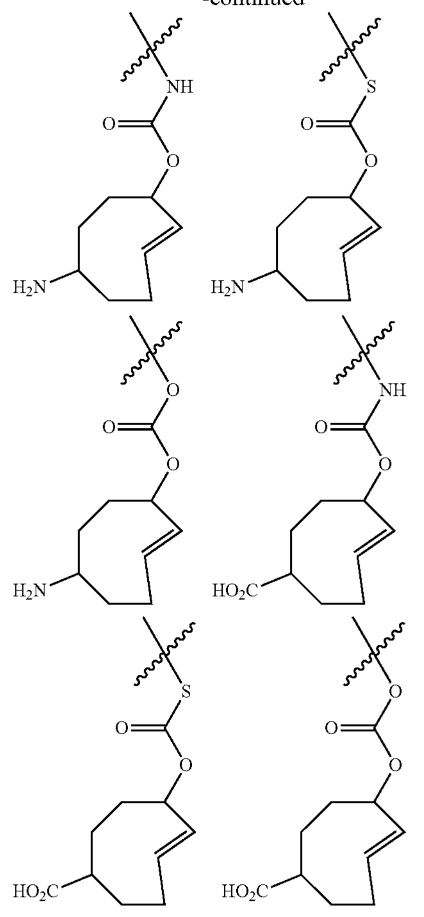

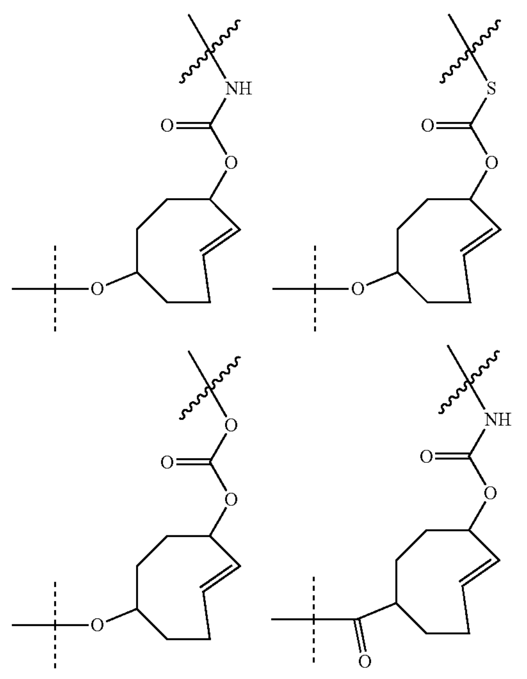

-continued

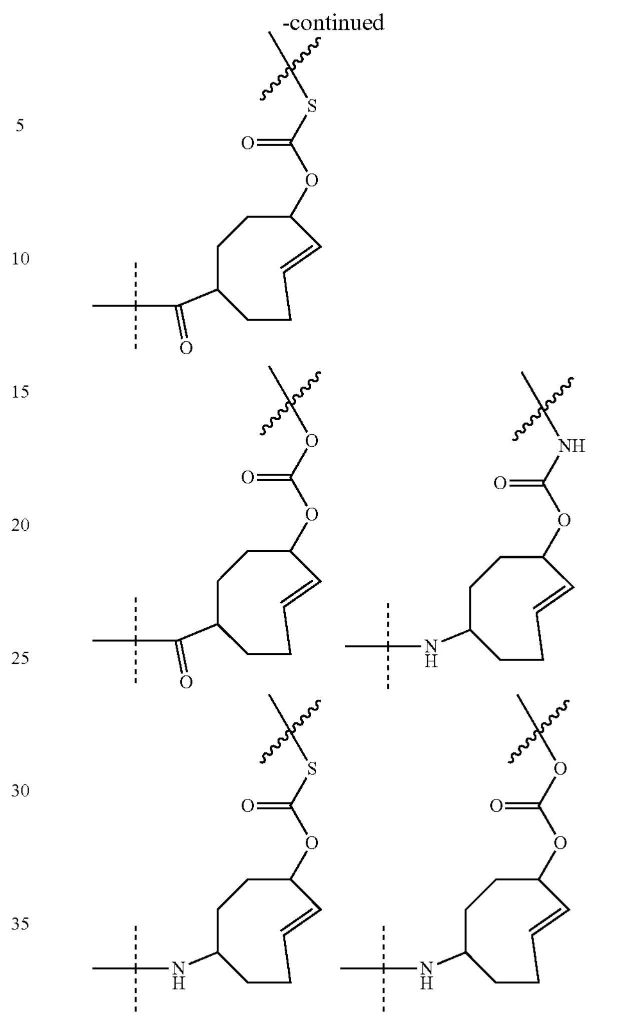

- - - - = rest of attached $C^B$ or $S^P$-$C^B$

∿∿∿ = rest of attached $C^A$, $L^D$-$C^A$, wherein $L^D$ may optionally comprise $C^B$ or $S^P$-$C^B$ wherein the dotted line denotes a bond to the rest of $C^B$ and wherein the wavy line indicates a bond to the rest of $C^A$ or $L^D$-$C^A$, wherein $L^D$ may optionally comprise $C^B$;

wherein $L^D$ is a self-immolative linker consisting of one or more self-immolative units;

wherein each self-immolative unit is selected from the group consisting of

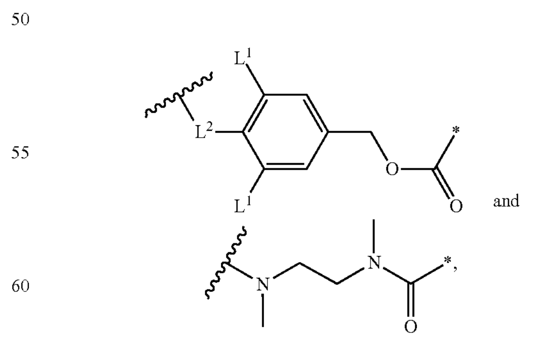

and

, wherein the wiggly line indicates a bond to $(O—C(O))_p$ or O—C(S) of $X^D$, or to a preceding self-immolative unit; wherein the asterisk indicates a bond to $C^A$ or to a further self-immolative unit;

wherein $L^2$ is O, S, NH, or NR with R being alkyl or aryl;
wherein each $L^1$ is independently H or methyl;
wherein each $C^A$ and $C^B$ are individually selected from the group consisting of biomolecules, biomolecule-binding moieties, polymers, particles, gels, fluorophores, and radio-labels.

18. The dienophile according to claim 1, which is of any one of the following formulae

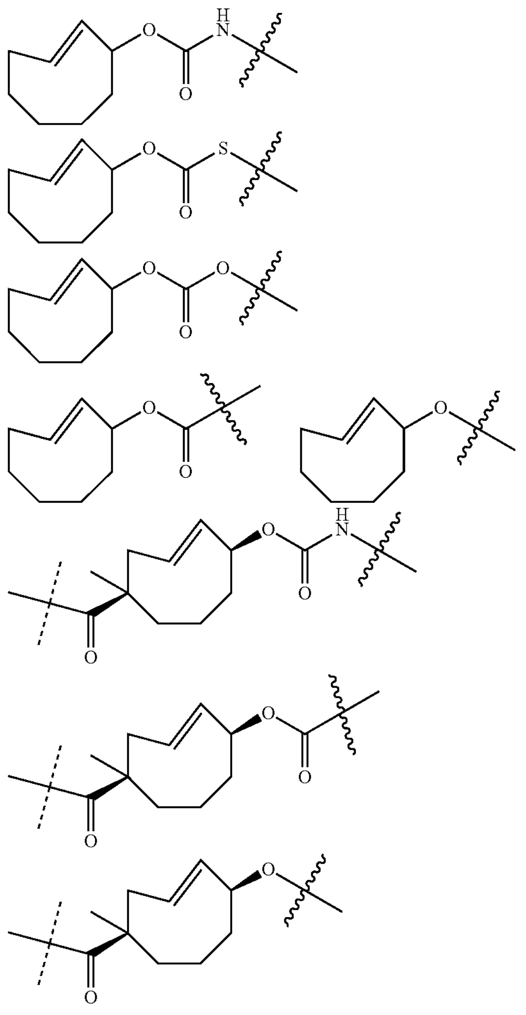

-continued

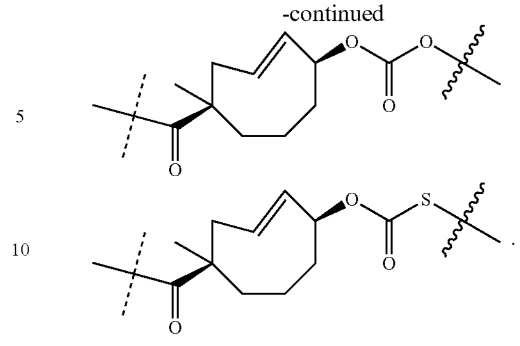

19. The dienophile according to claim 1, which is of any one of the following formulae

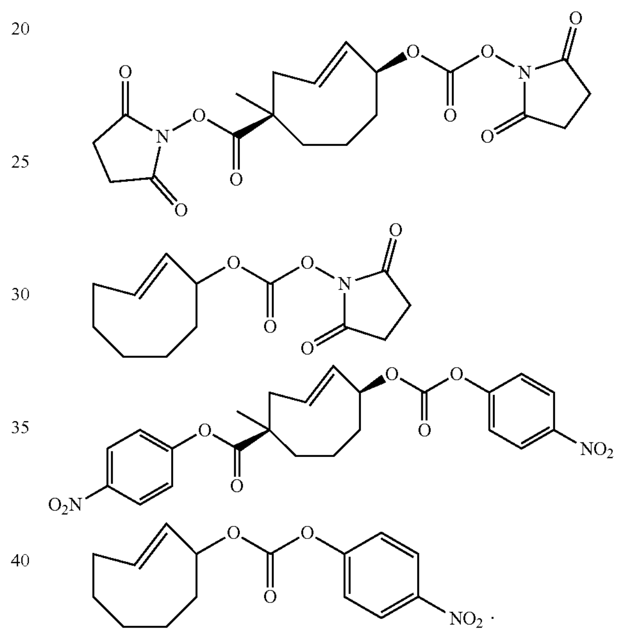

20. The dienophile according to claim 1 wherein n=0 and wherein each instance of $R^a$ and $R^b$ is bound directly to a construct $C^B$.

* * * * *